(12) United States Patent
Attar et al.

(10) Patent No.: US 12,637,509 B2
(45) Date of Patent: May 26, 2026

(54) TRISPECIFIC ANTIBODY TARGETING BCMA, GPRC5D, AND CD3

(71) Applicant: Janssen Biotech, Inc., Horsham, PA (US)

(72) Inventors: Ricardo Marcos Attar, Spring House, PA (US); Scott Ronald Brodeur, New Hope, PA (US); Rajkumar Ganesan, Thousand Oaks, CA (US); Leopoldo Luistro, Lansdale, PA (US); Ulrike Philippar, Antwerp (BE); Kodandaram Pillarisetti, King of Prussia, PA (US); Sanjaya Singh, Blue Bell, PA (US); Danlin Dan Qing Yang, Philadelphia, PA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 17/672,123

(22) Filed: Feb. 15, 2022

(65) Prior Publication Data

US 2022/0267438 A1     Aug. 25, 2022

Related U.S. Application Data

(60) Provisional application No. 63/149,921, filed on Feb. 16, 2021.

(51) Int. Cl.
 *C07K 16/28* (2006.01)
 *A61K 39/00* (2006.01)
 (Continued)

(52) U.S. Cl.
 CPC .......... *C07K 16/2803* (2013.01); *A61P 35/00* (2018.01); *C07K 14/7051* (2013.01);
 (Continued)

(58) Field of Classification Search
 CPC ........... C07K 16/2803; C07K 14/7051; C07K 2317/24; C07K 2317/33; C07K 2317/55;
 (Continued)

(56) References Cited

U.S. PATENT DOCUMENTS

| 3,832,253 | A | 8/1974 | Di Palma et al. |
| 3,854,480 | A | 12/1974 | Zaffaroni |
(Continued)

FOREIGN PATENT DOCUMENTS

| AU | 2023274132 A1 | * 12/2023 | ........... A61K 31/454 |
| CL | 2019000146 A1 | 4/2019 | |
(Continued)

OTHER PUBLICATIONS

Anasetti et al., "Advances in the prevention of graft-versus-host disease after hematopoietic cell transplatation", Transplantation, 2004, vol. 77(9)879-883.

(Continued)

*Primary Examiner* — Aurora M Fontainhas
*Assistant Examiner* — Selam Berhane
(74) *Attorney, Agent, or Firm* — BakerHostetler

(57) ABSTRACT

Provided herein are multispecific antibodies that bind to BCMA, GPRC5D and CD3 and multispecific antigen-binding fragments thereof. Also described are related polynucleotides capable of encoding the provided multispecific antibodies or multispecific antigen-binding fragments, cells expressing the provided multispecific antibodies or multispecific antigen-binding fragments, as well as associated vectors and detectably labeled multispecific antibodies or multispecific antigen-binding fragments. In addition, methods of producing and using the provided multispecific antibodies and multispecific antigen-binding fragments are described. Further provided herein are antibodies that bind to BCMA and antigen-binding fragments thereof. Also (Continued)

described are related polynucleotides capable of encoding the provided BCMA-specific antibodies or antigen-binding fragments, cells expressing the provided BCMA-specific antibodies or antigen-binding fragments, as well as associated vectors and detectably labeled BCMA-specific antibodies or antigen-binding fragments. In addition, methods of producing and using the provided BCMA-specific antibodies and antigen-binding fragments are described.

46 Claims, 69 Drawing Sheets

Specification includes a Sequence Listing.

(51) Int. Cl.
| | | |
|---|---|---|
| *A61P 35/00* | (2006.01) | |
| *C07K 14/705* | (2006.01) | |
| *C07K 14/725* | (2006.01) | |

(52) U.S. Cl.
CPC .. *A61K 2039/505* (2013.01); *A61K 2039/545* (2013.01); *C07K 2317/24* (2013.01); *C07K 2317/33* (2013.01); *C07K 2317/55* (2013.01); *C07K 2317/565* (2013.01); *C07K 2317/567* (2013.01); *C07K 2317/76* (2013.01); *C07K 2317/92* (2013.01)

(58) Field of Classification Search
CPC ........ C07K 2317/565; C07K 2317/567; C07K 2317/76; C07K 2317/92; A61P 35/00; A61K 2039/505; A61K 2039/545
See application file for complete search history.

(56) References Cited

U.S. PATENT DOCUMENTS

| | | | |
|---|---|---|---|
| 4,452,775 | A | 6/1984 | Kent |
| 4,748,034 | A | 5/1988 | de Rham |
| 5,223,409 | A | 6/1993 | Ladner et al. |
| 5,225,539 | A | 7/1993 | Winter |
| 5,239,660 | A | 8/1993 | Ooi |
| 5,403,484 | A | 4/1995 | Ladner et al. |
| 5,427,908 | A | 6/1995 | Dower et al. |
| 5,545,806 | A | 8/1996 | Lonberg et al. |
| 5,569,825 | A | 10/1996 | Lonberg et al. |
| 5,571,698 | A | 11/1996 | Ladner et al. |
| 5,580,717 | A | 12/1996 | Dower et al. |
| 5,585,089 | A | 12/1996 | Queen et al. |
| 5,639,641 | A | 6/1997 | Pedersen et al. |
| 5,693,761 | A | 12/1997 | Queen et al. |
| 5,714,352 | A | 2/1998 | Jakobovits |
| 5,885,793 | A | 3/1999 | Griffiths et al. |
| 5,969,108 | A | 10/1999 | McCafferty et al. |
| 6,150,584 | A | 11/2000 | Kucherlapati et al. |
| 6,172,197 | B1 | 1/2001 | Mccafferty et al. |
| 6,180,370 | B1 | 1/2001 | Queen et al. |
| 6,265,150 | B1 | 7/2001 | Terstappen et al. |
| 6,521,404 | B1 | 2/2003 | Griffiths et al. |
| 6,521,427 | B1 | 2/2003 | Evans |
| 6,544,731 | B1 | 4/2003 | Griffiths et al. |
| 6,555,313 | B1 | 4/2003 | Griffiths et al. |
| 6,582,915 | B1 | 6/2003 | Griffiths et al. |
| 6,593,081 | B1 | 7/2003 | Griffiths et al. |
| 6,670,127 | B2 | 12/2003 | Evans |
| 6,737,056 | B1 | 5/2004 | Presta |
| 6,818,749 | B1 | 11/2004 | Kashmiri et al. |
| 7,695,936 | B2 | 4/2010 | Carter et al. |
| 7,709,226 | B2 | 5/2010 | Foote |
| 8,236,308 | B2 | 8/2012 | Kischel et al. |
| 8,242,247 | B2 | 8/2012 | Klein et al. |
| 8,748,356 | B2 | 6/2014 | Raghunathan |
| 10,072,088 | B2 | 9/2018 | Pillarisetti et al. |
| 10,465,006 | B2 | 11/2019 | Van Den Brink et al. |
| 10,562,968 | B2 | 2/2020 | Atta et al. |
| 11,603,405 | B2 | 3/2023 | Gaudet et al. |
| 11,827,708 | B2 | 11/2023 | Obermajer et al. |
| 2002/0197266 | A1 | 12/2002 | Debinski |
| 2007/0287170 | A1 | 12/2007 | Davis et al. |
| 2009/0182127 | A1 | 7/2009 | Kjaergaard et al. |
| 2010/0015133 | A1 | 1/2010 | Igawa et al. |
| 2010/0028637 | A1 | 2/2010 | Tavsanli et al. |
| 2010/0261620 | A1 | 10/2010 | Almagro et al. |
| 2010/0286374 | A1 | 11/2010 | Kannan et al. |
| 2011/0123532 | A1 | 5/2011 | Gurney et al. |
| 2012/0149876 | A1 | 6/2012 | Von et al. |
| 2013/0195849 | A1 | 8/2013 | Spreter et al. |
| 2014/0088295 | A1 | 3/2014 | Smith et al. |
| 2014/0170149 | A1 | 6/2014 | Neijssen et al. |
| 2016/0039934 | A1 | 2/2016 | Zhukovsky et al. |
| 2016/0333095 | A1 | 11/2016 | Van et al. |
| 2017/0121420 | A1 | 5/2017 | Heidrich et al. |
| 2017/0204194 | A1 | 7/2017 | Chen et al. |
| 2018/0057597 | A1 | 3/2018 | Albrecht et al. |
| 2019/0352421 | A1 | 11/2019 | Adams et al. |
| 2019/0367612 | A1 | 12/2019 | Chaen et al. |
| 2019/0382481 | A1 | 12/2019 | Diem et al. |
| 2020/0079867 | A1 | 3/2020 | Watkins et al. |
| 2020/0190205 | A1 | 6/2020 | Adams et al. |
| 2020/0231686 | A1 | 7/2020 | Attar et al. |
| 2021/0040210 | A1 | 2/2021 | Ganesan et al. |
| 2021/0214440 | A1 | 7/2021 | Ganesan et al. |
| 2021/0284731 | A1 | 9/2021 | Ganesan et al. |
| 2022/0089731 | A1 | 3/2022 | Ganesan et al. |
| 2022/0089737 | A1 | 3/2022 | Ganesan et al. |
| 2024/0262921 | A1 | 8/2024 | Attar et al. |

FOREIGN PATENT DOCUMENTS

| | | | |
|---|---|---|---|
| CN | 107001468 | A | 8/2017 |
| CN | 112028996 | B | 1/2021 |
| EA | 202292441 | A1 | 1/2023 |
| EP | 0239400 | B1 | 8/1994 |
| EP | 2982693 | A1 | 2/2016 |
| EP | 3581651 | A1 | 12/2019 |
| EP | 3911677 | A1 | 11/2021 |
| GB | 2188638 | A | 10/1987 |
| JP | 2015-535828 | A | 12/2015 |
| JP | 2016-529882 | A | 9/2016 |
| JP | 2017-504314 | A | 2/2017 |
| JP | 2017-505121 | A | 2/2017 |
| TW | 201527323 | A | 7/2015 |
| WO | 88/01649 | A1 | 3/1988 |
| WO | 90/04036 | A1 | 4/1990 |
| WO | 90/07861 | A1 | 7/1990 |
| WO | 92/01047 | A1 | 1/1992 |
| WO | 92/22653 | A1 | 12/1992 |
| WO | 94/13804 | A1 | 6/1994 |
| WO | 98/44001 | A1 | 10/1998 |
| WO | 99/45962 | A1 | 9/1999 |
| WO | WO2000041474 | A2 | 7/2000 |
| WO | WO2001024811 | A1 | 4/2001 |
| WO | WO2001024812 | A1 | 4/2001 |
| WO | 2002/066063 | A1 | 8/2002 |
| WO | WO2002066516 | A2 | 8/2002 |
| WO | 02/43478 | A3 | 8/2003 |
| WO | 2004/111233 | A1 | 12/2004 |
| WO | 2006/028936 | A2 | 3/2006 |
| WO | WO2007042261 | A2 | 4/2007 |
| WO | 2007/059782 | A1 | 5/2007 |
| WO | 2008/119353 | A1 | 10/2008 |
| WO | WO2008119565 | A2 | 10/2008 |
| WO | WO2008119566 | A2 | 10/2008 |
| WO | WO2008119567 | A2 | 10/2008 |
| WO | 2009/018386 | A1 | 2/2009 |
| WO | 2009/080251 | A1 | 7/2009 |
| WO | 2009/080252 | A1 | 7/2009 |
| WO | 2009/080254 | A1 | 7/2009 |
| WO | 2009/085462 | A1 | 7/2009 |
| WO | WO2010037836 | A2 | 4/2010 |
| WO | WO2010037837 | A2 | 4/2010 |
| WO | WO2010037838 | A2 | 4/2010 |
| WO | WO2010051274 | A2 | 5/2010 |

(56)                References Cited

FOREIGN PATENT DOCUMENTS

| WO | WO2010093627 A2 | 8/2010 | |
| WO | WO2010104949 A2 | 9/2010 | |
| WO | 2011/131746 A2 | 10/2011 | |
| WO | 2011/143545 A1 | 11/2011 | |
| WO | 2012/162067 A2 | 11/2012 | |
| WO | 2014/047231 A1 | 3/2014 | |
| WO | 2014/093908 A2 | 6/2014 | |
| WO | 2015/095392 A1 | 6/2015 | |
| WO | 2015/181098 A1 | 12/2015 | |
| WO | 2016/090312 A1 | 6/2016 | |
| WO | WO2016090329 A2 | 6/2016 | |
| WO | 2017/223111 A1 | 12/2017 | |
| WO | WO2018017786 A3 | 1/2018 | |
| WO | 2018/052503 A1 | 3/2018 | |
| WO | WO2018147245 A1 | 8/2018 | |
| WO | 2018/237037 A2 | 12/2018 | |
| WO | WO2019060695 A1 | 3/2019 | |
| WO | WO2019154890 A1 | 8/2019 | |
| WO | 2019/220369 A2 | 11/2019 | |
| WO | 2019/224711 A2 | 11/2019 | |
| WO | 2019/224713 A2 | 11/2019 | |
| WO | 2019/224717 A2 | 11/2019 | |
| WO | 2019/224718 A2 | 11/2019 | |
| WO | WO-2020148677 A1 * | 7/2020 | ............ A61K 35/17 |
| WO | 2021/173896 A1 | 9/2021 | |
| WO | 2022/174813 A1 | 8/2022 | |

OTHER PUBLICATIONS

Atamaniuk J, Gleiss A, Porpaczy E, et al. Overexpression of G protein-coupled receptor SD in the bone marrow is associated with poor prognosis in patients with multiple myeloma. Eur J Clin Invest. 2012;42(9):953-960. doi:10.1111/j.1365-2362.2012.02679.x.

Avery DT, Kalled SL, Ellyard JI, et al. BAFF selectively enhances the survival of plasmablasts generated from human memory B cells [published correction appears in J Clin Invest. Apr. 2004;113(7):1069]. J Clin Invest. 2003;112(2):286-297. doi:10.1172/JCI200318025.

K.R. Abhinandan and Andrew C.R. Martin, "Analysis and improvements to Kabat and structurally correct numbering of antibody variable domains", 2008. Science Direct, Elsevier, Mol. Immunol. 45, 3832-3839.

Berdeja JG, Krishnan AY, Oriol A, et al., "Updated results of a phase 1, first-in-human study of talquetamab, a G protein-coupled receptor family C group 5 member D (GPRC5D) × CD3 bispecific antibody, in relapsed/refractory multiple myeloma (MM)", J Clin Oncol. 2021;39(15_suppl):8008. doi: 10.1200/JCO.2021.39.15.

Bräuner-Osborne H, Jensen AA, Sheppard PO, Brodin B, Krogsgaard-Larsen P, O'Hara P. Cloning and characterization of a human orphan family C G-protein coupled receptor GPRC5D. Biochim Biophys Acta. 2001;1518(3):237-248. doi:10.1016/s0167-4781(01)00197-x.

Bu DX, Singh R, Choi EE, et al. Pre-clinical validation of B cell maturation antigen (BCMA) as a target for T cell immunotherapy of multiple myeloma. Oncotarget. 2018;9(40):25764-25780. Published May 25, 2018. doi:10.18632/oncotarget.25359.

Carpenter RO, Evbuomwan MO, Pittaluga S, et al. B-cell maturation antigen is a promising target for adoptive T-cell therapy of multiple myeloma. Clin Cancer Res. 2013;19(8):2048-2060. doi:10.1158/1078-0432.CCR-12-2422.

Chames and Baty "Bispecific antibodies for cancer therapy" (2009) Curr Opin Drug Disc Dev 12: 276-83.

Chiu A, Xu W, He B, et al. Hodgkin lymphoma cells express TACI and BCMA receptors and generate survival and proliferation signals in response to BAFF and APRIL. Blood. 2007;109(2):729-739. doi:10.1182/blood-2006-04-015958.

Chothia et al., "Canonical Structures For the Hypervariable Regions of Immunoglobulins," *J. Mol. Biol.* 196:901 (1987).

Chothia et al., "Conformations of Immunoglobulin Hypervariable Regions," I 342:877 (1989).

Cline, "Perspectives for Gene Therapy: Inserting New Genetic Information into Mammalian Cells by Physical Techniques and Viral Vectors", *Pharmac. Ther.* vol. 29, pp. 69-92 (1985).

ClinicalTrials.gov. NCT02879695: Blinatumomab and nivolumab with or without ipilimumab in treating patients with poor-risk relapsed or refractory CD19+ precursor B-lymphoblastic leukemia. https://clinicaltrials.gov/ct2/show/NCT02879695. Accessed: Jun. 23, 2021.

Darce JR, Arendt BK, Chang SK, Jelinek DF. Divergent effects of BAFF on human memory B cell differentiation into Ig-secreting cells. J Immunol. 2007;178(9):5612-5622. doi:10.4049/jimmunol.178.9.5612.

De Groot, A. S. & Martin, W. Reducing risk, improving outcomes: bioengineering less immunogenic protein therapeutics. *Clinical immunology* 131, 189-201, doi:10.1016/j.clim.2009.01.009 (2009).

Dimopoulos MA, San-Miguel J, Belch A, et al. Daratumumab plus lenalidomide and dexamethasone versus lenalidomide and dexamethasone in relapsed or refractory multiple myeloma: updated analysis of POLLUX. Haematologica. 2018;103(12):2088-2096. doi:10.3324/haematol.2018.194282.

Drach et al., Presence of a p53 Gene Deletion in Patients with Multiple Myeloma Predicts for Short Survival after Conventional-Dose Chemotherapy (1998) Blood 92(3):802-809.

E. Meyers and W. Miller, "Optimal Alignments in linear space", Cabios, Appl. Biosci 4, 11-17 (1988).

Facon et al., (2001) Blood 97(6): 1566-1571.

Ferrara et al., "Modulation of Therapeutic Antibody Effector Functions by Glycosylation Engineering . . . ", Institute of Biotechnology, 93:851-861, 2006—Abstract.

Ferrara et al., "The Carbohydrate at Fc RIIIa Asn-162", The Journal of Biotechnol Chemistry, vol. 281, No. 8: 5032-5036, 2006.

Frigyesi I, Adolfsson J, Ali M, et al., "Robust isolation of malignant plasma cells in multiple myeloma". Blood. 2014;123(9):1336-1340. doi:10.1182/blood-2013-09-529800.

Cohen, et al., "GPRC5D is a promising marker for monitoring the tumor load and to target multiple myeloma cells", Hematology 18(6): 348-35; 2013.

Gadi et al., In vivo sensitization of ovarian tumors to chemotherapy by expression of E. coli purine nucleoside phosphorylase in a small fraction of cells, Gene Ther. 7, (2000), 1738-1743.

Gandhi UH, Cornell RF, Lakshman A, et al. Outcomes of patients with multiple myeloma refractory to CD38-targeted monoclonal antibody therapy. Leukemia, 2019;33(9):2266-2275. doi:10.1038/s41375-019-0435-7.

Gras M-P. et al. BCMAp: an integral membrane protein in the Golgi apparatus of human mature B lymphocytes, Int Immunol. 7 (1995) 1093-1106.

Gertz et al., (2005) Blood 106(8):2837-2840.

Guillerey C, Nakamura K, Pichler AC, et al. Chemotherapy followed by anti-CD137 mAb immunotherapy improves disease control in a mouse myeloma model. JCI Insight. 2019;5(14):e125932. Published Jun. 13, 2019. doi:10.1172/jci.insight.125932.

Holt et al; Trends Biotechnol. Nov. 2003; 21(11):484-90).

Huehls AM, Coupet TA, Sentman CL. Bispecific T-cell engagers for cancer immunotherapy. Immunol Cell Biol. 2015;93(3):290-296. doi:10.1038/icb.2014.93.

Inoue S, Nambu T, Shimomura T. The RAIG family member, GPRC5D, is associated with hard-keratinized structures. J Invest Dermatol. 2004; 122(3):565-573. doi:10.1046/j.0022-202X.2004.12628.x.

Jain T, Litzow MR. Management of toxicities associated with novel immunotherapy agents in acute lymphoblastic leukemia. Ther Adv Hematol. 2020;11:2040620719899897. Published Jan. 20, 2020. doi:10.1177/2040620719899897.

Johnson JI, Decker S, Zaharevitz D, et al. Relationships between drug activity in NCI preclinical in vitro and in vivo models and early clinical trials. Br J Cancer. 2001;84(10):1424-1431. doi:10.1054/bjoc.2001.1796.

Kabat et al., *Sequences of Proteins of Immunological Interest*, vol. 1, 5th ed. NIH Publication No. 91-3242 (1991).

Kalled SL. The role of BAFF in immune function and implications for autoimmunity. Immunol Rev. 2005;204:43-54. doi:10.1111/j.0105-2896.2005.00219.x.

Kamperschroer C, Shenton J, Lebrec H, Leighton JK, Moore PA, Thomas O. "Summary of a workshop on preclinical and transla-

(56)     References Cited

OTHER PUBLICATIONS tional safety assessment of CD3 bispecifics", J Immunotoxicol. 2020;17(1):67-85. doi:10.1080/1547691X.2020.1729902.

Kodama T, Kochi Y, Nakai W, et al. "Anti-GPRC5D/CD3 bispecific T-cell-redirecting antibody for the treatment of multiple myeloma", Mol Cancer Ther. 2019;18(9):1555-1564. doi:10.1158/1535-7163. MCT-18-1216.

Konno et al., "Fucose content of monoclonal antibodies can be controlled by culture medium osmolality for high antibody-dependent cellular cytotoxicity", Cytotechnology 64:249-265, (2012).

Kumar SK, Callander NS, Adekola K, et al. "Multiple Myeloma, Version 3.2021", NCCN clinical practice guidelines in oncology. J Natl Compr Canc Netw. 2020;18(12):1685-1717. Published Dec. 2, 2020. doi:10.6004/jnccn.2020.0057.

Laabi Y, Gras MP, Brouet JC, Berger R, Larsen CJ, Tsapis A. The BCMA gene, preferentially expressed during B lymphoid maturation, is bidirectionally transcribed. Nucleic Acids Res. 1994;22(7):1147-1154. doi:10.1093/nar/22.7.1147.

Laâbi Y, Gras MP, Carbonnel F, et al. A new gene, BCM, on chromosome 16 is fused to the interleukin 2 gene by a t(4;16)(q26;p13) translocation in a malignant T cell lymphoma. EMBO J. 1992;11(11):3897-3904.

Laurent SA, Hoffmann FS, Kuhn PH, et al. γ-Secretase directly sheds the survival receptor BCMA from plasma cells. Nat Commun. 2015;6:7333. Published Jun. 11, 2015. doi:10.1038/ncomms8333.

Law, et al., Preclinical and Nonclinical Characterization of HPN217: A Tri-specific T Cell Activating Construct (TriTAC) Targeting B Cell Maturation Antigen (BCMA) for the Treatment of Multiple Myeloma. Blood (2018) 132(1): 3225. Abstract.

Leong SR, Sukumaran S, Hristopoulos M, et al. An anti-CD3/anti-CLL-1 bispecific antibody for the treatment of acute myeloid leukemia. Blood. 2017;129(5):609-618. doi:10.1182/blood-2016-08-735365.

Li J, Piskol R, Ybarra R, et al. CD3 bispecific antibody-induced cytokine release is dispensable for cytotoxic T cell activity. Sci Transl Med. 2019;11(508):eaax8861. doi:10.1126/scitranslmed. aax8861.

Li J, Stagg NJ, Johnston J, et al. Membrane-proximal epitope facilitates efficient T cell synapse formation by anti-FcRH5/CD3 and is a requirement for myeloma cell killing. Cancer Cell. 2017;31(3):383-395. doi:10.1016/j.ccell.2017.02.001.

Ling J, Zhou H, Jiao Q, Davis HM. Interspecies scaling of therapeutic monoclonal antibodies: initial look. J Clin Pharmacol. 2009;49(12):1382-1402. doi:10.1177/0091270009337134.

MacCallum et al., "Antibody-Antigen Interactions: Contact Analysis and Binding Site Topography," J. Mol. Biol. 262:732 (1996).

Madry et al. (1998) "The characterization of murine BCMA gene defines it as a new member of the tumor necrosis factor receptor superfamily", Int Immunol 10(11):1693-1702.

Martin and Thornton, "Structural Families in Loops of Homologous Proteins: Automatic Classification, Modelling and Application to Antibodies," J. Mol. Biol. 263:800 (1996).

Maus MV, June CH. Zoom Zoom: racing CARs for multiple myeloma. Clin Cancer Res. 2013;19(8):1917-1919. doi:10.1158/1078-0432.CCR-13-0168.

Michels TC, Petersen KE. Multiple myeloma: diagnosis and treatment. Am Fam Physician. 2017;95(6):373-383.

Mori et al., Biotechnol Bioeng 88:901-908 (2004).

Needleman and Wunsch, J. Mol. Biol. 48, 444-453 (1970).

Ng LG, Sutherland AP, Newton R, et al. B cell-activating factor belonging to the TNF family (BAFF)-R is the principal BAFF receptor facilitating BAFF costimulation of circulating T and B cells. J Immunol. 2004;173(2):807-817. doi:10.4049/jimmunol.173. 2.807.

Novak et al., (2004) Blood 103(2):689-694.

O'Connor BP, Raman VS, Erickson LD, et al. BCMA is essential for the survival of long-lived bone marrow plasma cells. J Exp Med. 2004;199(1):91-98. doi:10.1084/jem.20031330.

Okayama and Berg, 3 Mol. Cell. Biol. 280 (1983).

Patel DR, Wallweber HJ, Yin J, et al. Engineering an APRIL-specific B cell maturation antigen. J Biol Chem. 2004;279(16):16727-16735. doi:10.1074/jbc.M312316200.

Pillarisetti K, Edavettal S, Mendonça M, et al. A T-cell-redirecting bispecific G-protein-coupled receptor class 5 member D × CD3 antibody to treat multiple myeloma. Blood. 2020;135(15):1232-1243. doi:10.1182/blood.2019003342.

Pillarisetti K, Powers G, Luistro L, et al. Teclistamab is an active T cell-redirecting bispecific antibody against B-cell maturation antigen for multiple myeloma. Blood Adv. 2020;4(18):4538-4549. doi:10.1182/bloodadvances.2020002393.

Rajkumar SV, Harousseau JL, Durie B, et al. Consensus recommendations for the uniform reporting of clinical trials: report of the International Myeloma Workshop Consensus Panel 1. Blood. 2011;117(18):4691-4695. doi:10.1182/blood-2010-10-299487.

Revets et al; Expert Opin Biol Ther. Jan. 2005; 5(1):111-24).

Rickert RC et al., Immunol Rev (2011) 244 (1): 115-133.

Ridgway, J. B., Presta, L. G. & Carter, P. 'Knobs-into-holes' engineering of antibody CH3 domains for heavy chain heterodimerization. Protein Eng 9, 617-621, doi:10.1093/protein/9.7.617 (1996).

Rodriguez-Abreu D, Bordoni A, Zucca E. Epidemiology of hematological malignancies. Ann Oncol. 2007;18 Suppl 1:i3-i8. doi:10.1093/annonc/mdl443.

Salmeron et al., (1991) J. Immunol. 147: 3047) Sanchez E, Li M, Kitto A, et al. Serum B-cell maturation antigen is elevated in multiple myeloma and correlates with disease status and survival. Br J Haematol. 2012;158(6):727-738. doi:10.1111/j.1365-2141.2012. 09241.x.

Seckinger A, Delgado JA, Moser S, et al. Target Expression, Generation, Preclinical Activity, and Pharmacokinetics of the BCMA-T Cell Bispecific Antibody EM801 for Multiple Myeloma Treatment. Cancer Cell. 2017;31(3):396-410. doi:10.1016/j.ccell.2017.02.002.

Shah N, Chari A, Scott E, Mezzi K, Usmani SZ. B-cell maturation antigen (BCMA) in multiple myeloma: rationale for targeting and current therapeutic approaches. Leukemia. 2020;34(4):985-1005. doi:10.1038/s41375-020-0734-z.

Shields et al., J Biol Chem 277:26733-26740, 2002).

Shinkawa et al., J Biol Chem 278:3466-3473, 2003).

Singh A, Dees S, Grewal IS. Overcoming the challenges associated with CD3+ T-cell redirection in cancer. Br J Cancer. 2021;124(6):1037-1048. doi:10.1038/s41416-020-01225-5.

Smith EL, Harrington K, Staehr M, et al. GPRC5D is a target for the immunotherapy of multiple myeloma with rationally designed CAR T cells. Sci Transl Med. 2019;11(485):eaau7746. doi:10.1126/scitranslmed.aau7746.

Strohl WR, Naso M. Bispecific T-cell redirection versus chimeric antigen receptor (CAR)-T cells as approaches to kill cancer cells. Antibodies (Basel). 2019;8(3):41. Published Jul. 3, 2019. doi:10.3390/antib8030041.

Tai YT, Anderson KC. Targeting B-cell maturation antigen in multiple myeloma. Immunotherapy. 2015;7(11):1187-1199. doi:10.2217/imt.15.77.

Tustian, A. D., Endicott, C., Adams, B., Mattila, J. & Bak, H. Development of purification processes for fully human bispecific antibodies based upon modification of protein A binding avidity. MAbs 8, 828-838, doi:10.1080/19420862.2016.1160192 (2016).

Usmani SZ, Berdeja JG, Madduri D, et al. Ciltacabtagene autoleucel, a B-cell maturation antigen (BCMA)-directed chimeric antigen receptor T-cell (CAR-T) therapy, in relapsed/refractory multiple myeloma (R/R MM): updated results from CARTITUDE-1. J Clin Oncol. 2021;39(15_suppl):8005. doi: 10.1200/JCO.2021.39.15_suppl.8005.

Usmani SZ, Berdeja JG, Truppel-Hartmann A, et al. KarMMa-4: Idecabtagene vicleucel (ide-cel, bb2121), a BCMA-directed CAR T-cell therapy in high-risk newly diagnosed multiple myeloma. J Clin Oncol. 2021;39(15_suppl):TPS8053. doi:10.1200/JCO.2021. 39.15_suppl.TPS8053.

Venkateshaiah SU, Bam R, Li X, Khan S, Ling W, Randal SS, Yaccoby S. GPRC5D is a cell surface plasma cell marker whose expression is high in myeloma cells and reduced following coculture with osteoclasts. Blood. 2013;122(21):3099. doi:10.1182/blood. V122.21.3099.3099.

(56)        References Cited

OTHER PUBLICATIONS

Verkleij CPM, Broekmans MEC, van Duin M, et al. Preclinical activity and determinants of response of the GPRC5DxCD3 bispecific antibody talquetamab in multiple myeloma. Blood Adv. 2021;5(8):2196-2215. doi:10.1182/bloodadvances.2020003805.

Von Kreudenstein, T. S. et al. Improving biophysical properties of a bispecific antibody scaffold to aid developability: quality by molecular design. *MAbs* 5, 646-654, doi:10.4161/mabs.25632 (2013).

Ward et al., Nature 341, 544-546 (1989).

Woo S, Jusko WJ. Interspecies comparisons of pharmacokinetics and pharmacodynamics of recombinant human erythropoietin. Drug Metab Dispos. 2007;35(9):1672-1678. doi:10.1124/dmd.107. 015248.

Xhou et al., Biotechnol Bioeng 99:652-65, 2008.

Yang SJ, The Journal of Immunology (1986) 137; 1097-1100).

Anasetti et al., "Treatment of Acute Graft-Versus-Host Disease with a Nonmitogenic Anti-CD3 Monoclonal Antibody", Transplantation, 1992, vol. 54, No. 5, pp. 844-851.

Cho et al., "BCMA-Targeting Therapy: Driving a New Era of Immunotherapy in Multiple Myeloma," Cancers, vol. 12, No. 6, 2020, pp. 29.

Holliger et al., "Diabodies: Small Bivalent and Bispecific Antibody Fragments", Proc Natl Acad Sci U S A, 1993, vol. 90, No. 14, pp. 6444-6448.

Olivier et al., "EB66 Cell Line, A Duck Embryonic Stem Cell-Derived Substrate For The Industrial Production Of Therapeutic Monoclonal Antibodies With Enhanced ADCC Activity", Mabs, 2010, vol. 2, No. 4, pp. 405-415.

Adan et al., "Flow cytometry: basic principles and applications", Crit Rev Biotechnol., 2017, vol. 37, No. 2, 163-176.

Alegre et al., "A non-activating "humanized" anti-CD3 monoclonal antibody retains immunosuppressive properties invivo", Transplantation, vol. 1994, 57,11, 1537-1543.

Altschul et al., "Basic Local Alignment Search Tool", J. Mol. Biol., 1990, vol. 215, 403-410.

Anonymous—ClinicalTrials.gov: "A Study of the Combination of Talquetamab and Teclistamab in Participants With Relapsed or Refractory Multiple Myeloma (RedirecTT-1)", Record History, NCT04586426, Jan. 28, 2021, Retrieved from the Internet, 19 pages.

Bird et al., "Single-Chain Antigen-Binding Proteins", Science, 1988, vol. 242, 423-426.

Brash et al., "Strontium Phosphate Transfection of Human Cells in Primary Culture: Stable Expression of the Simian Virus 40 Large-T-Antigen Gene in Primary Human Bronchial Epithelial Cells", Molecular and Cellular Biology, 1987, vol. 7, No. 8, 2031-2034.

Bruggemann et al., "Human antibody production in transgenic mice: expression from 100 kb of the human IgH locus", Eur. J. Immunol., 1991, vol. 21, 1323-1326.

Bruggemann et al., "Production of human antibody repertoires in transgenic mice", Current Opinion in Biotechnology, 1997, vol. 8, 455-458.

Chothia et al., "Canonical Structures for the Hypervariable Regions of Immunoglobulins", Journal of Molecular Biology, vol. 196, 1987, 901-917.

Fishwild et al., "High-avidity human IgGk monoclonal antibodies from a novel strain of minilocus transgenic mice", Nature Biotechnology, vol. 14, No. 7, 1996, 845-851.

Freshney et al., "Culture of Animal Cells: A Manual of Basic Technique, 3rd edition", Journal of Immunological Methods, 1995, vol. 183, 291-292.

Goding, "Monoclonal Antibodies: Principles and Practice", Academic Press, 1996, 59-103.

Green et al., "Antigen-specific human monoclonal antibodies from mice engineered with human Ig heavy and light chain YACs", Nature Genetics, vol. 7, 1994, 13-21.

Green, "Antibody engineering via genetic engineering of the mouse: XenoMouse strains are a vehicle for the facile generation of therapeutic human monoclonal antibodies", Journal of Immunological Methods, 1999, vol. 231, 11-23.

Green, et al., "Regulation of B Cell Development by Variable Gene Complexity in Mice Reconstituted with Human Immunoglobulin Yeast Artificial Chromosomes", J. Exp. Med., 1998, vol. 188, No. 3, 483-495.

Haskard et al., "The Production of Human Monoclonal Autoantibodies from Patients with Rheumatoid Arthritis by the EBV-Hybridoma Technique", Journal of Immunological Methods, 1984, vol. 74, 361-367.

Honegger et al., "Yet Another Numbering Scheme for Immunoglobulin Variable Domains: An Automatic Modeling and Analysis Tool", J. Mol. Biol., 2001, vol. 309, 657-670.

Hoogenboom et al., "By-passing Immunisation Human Antibodies from Synthetic Repertoires of Germline VH Gene Segments Rearranged in Vitro", J. Mol. Biol., 1992, vol. 227, 381-388.

Huang et al., "Recruitment of IRAK to the interleukin 1 receptor complex requires interleukin 1 receptor accessory protein", Proc. Natl. Acad. Sci., 1997, vol. 94, vol. 24 12829-12832.

Hudecz, "Synthesis of Peptide Bioconjugates", Methods Mol. Biol., 2005, vol. 298, 209-223.

Huse et al., "Generation of a Large Combinatorial Library of the Immunoglobulin Repertoire in Phage Lambda", Science, 1989, vol. 246, 1275-1281.

Huston et al., "Protein engineering of antibody binding sites: Recovery of specific activity in an anti-digoxin single- chain Fv analogue produced in Escherichia coli", Proc. Natl. Acad. Sci. USA, 1988, vol. 85, 5879-5883.

International Search Report from PCT/IB2020/050310 mailed Apr. 23, 2020.

International Search Report relating to corresponding International Patent Application No. PCT/ IB2019/054188, filed May 21, 2019. Date of Mailing of International Search Report: Jan. 23, 2020.

Janeway et al., "Immunobiology: The Immune System in Health and Disease", Table of Contents, 5th ed., 2001, 14pp.

Janeway et al., "Immunobiology: The Immune System in Health and Disease", Table of Contents, 6th ed., 2005, 1pp.

Johnston, "Biolistic transformation: microbes to mice", Nature, 1990, vol. 346, 776-777.

Jonker et al., "Idiotype switching of CD4-specific monoclonal antibodies can prolong the therapeutic effectivenes in spite of host-anti-mouse IgG antibodies", Eur. J. Immunol., vol. 17, 1987, 1547-1553.

Kim et al., "Synthesis of Bispecific Antibodies using Genetically Encoded Unnatural Amino Acids", J. Am. Chem. Soc., 2012, 134, 24, 9918-9921.

Kipriyanov et al., "Generation and production of engineered antibodies", Molecular Biotechnology, 2004, 26.1, 39-60.

Kirin et al., "Amino Acid and Peptide Bioconjugates of Copper(II) and Zinc(II) Complexes with a Modified N,N-Bis(2- picoly)amine Ligand", Inorganic Chemistry, 2005, vol. 44, No. 15, 5405-5415.

Knappik et al., "Fully Synthetic Human Combinatorial Antibody Libraries (HuCAL) Based on Modular Consensus Frameworks and CDRs Randomized with Trinucleotides", J. Mol. Biol., 2000, vol. 296, 57-86.

Kohler et al., "Derivation of specific antibody-producing tissue culture and tumor lines bv cell fusion", Eur. J. Immunol., 1976, vol. 6, 511-519.

Kohler et al., "The Promise of Anti-idiotype Revisited", Frontiers in Immunology, Apr. 1, 2019, vol. 10.

Krebs et al., "High-throughput generation and engineering of recombinant human antibodies", Journal of Immunological Methods, 2001, vol. 254, 67-84.

Labrijn et al., "Controlled Fab-arm exchange for the generation of stable bispecific IgG1", Nature Protocols, 2014, vol. 9, No. 10, 2450-2463.

Labrijn et al., "Efficient generation of stable bispecific IgG1 by controlled Fab-arm exchange", PNAS, 2013, vol. 110, No. 13, 5145-5150.

Labrijn et al., "Therapeutic IgG4 antibodies engage in Fab-arm exchange with endogenous human IgG4 in vivo", Nature biotechnology, vol. 27, 8, 2009, 767-771, doi: 10.1038/nbt. 1553.

Lathey et al., "Production and characterization of an anti-idiotypic antibody specific for a monoclonal antibody to glycoprotein D of herpes simplex virus", Immunology, 1986, vol. 57, 29-35.

(56)                 References Cited

OTHER PUBLICATIONS

Lefranc et al., "IMGT unique numbering for immunoglobulin and T cell receptor variable domains and Ig superfamily V-like domains", Developmental and Comparative Immunology, 2003, vol. 27, 55-77.
Lefranc et al., "IMGT®, the international ImMunoGeneTics information system®", Nucleic Acids of Research, 2009, vol. 37, 01006-01012.
Lonberg et al., "Antigen-specific human antibodies from mice comprising four distinct genetic modifications", Nature, vol. 368, 1994, 856-859.
Lonberg et al., "Human Antibodies from Transgenic Mice", International Reviews of Immunology, vol. 13, No. 1, 1995, 65-93.
Marks et al., "By-passing Immunization Human Antibodies from V-gene Libraries Displayed on Phase", J. Mol. Biol., 1991, vol. 222, 581-597.
Mendez et al., "Functional transplant of megabase human immunoglobulin loci recapitulates human antibody response in mice", Nature Genetics, vol. 15, No. 2 1997, 146-156.
Murray, "Gene Transfer and Expression Protocols", Methods in Lolecular Biology, 1991, vol. 7, 418pp.
Needleman et al., "A General Method Applicable to the Search for Similarities in the Amino Acid Sequence of Two Proteins", J. Mol. Biol., 1970, vol. 48, 443-453.
Nunez-Prado et al., "The coming of age of engineered multivalent antibodies", Drug Discovery Today, 2015, vol. 20, No. 5, 588-594.
Office Action Notice of Allowance and Fees Due (PTOL-85) dated Oct. 4, 2022 for U.S. Appl. No. 16/418,082, 1-9.
Osborn et al., "High-Affinity IgG Antibodies Develop Naturally in Ig-Knockout Rats Carrying Germline Human IgH/ IgK/IgA Loci Bearing the Rat Ch Region", J. Immunol., 2013, vol. 190, No. 4, 1481-1490.
Padlan "A Possible Procedure for Reducing the Immunogenicity of Antibody Variable Domains While Preserving Their Ligand-Binding Properties", Molecular Immunology, 1991, vol. 28, Nos. 4/5, 489-498.
Pascal., et al., "HDX Workbench: Software for the Analysis of H/D Exchange MS Data". J. Am. Soc. Mass Spectrom, 2012, vol. 23:1512-1521.
Pedersen et al., "Comparison of Surface Accessible Residues in Human and Murine Immunoglobulin Fv Domains", J. Mol. Biol., 1994, vol. 235, 959-973.
Rich et al., "Higher-throughput, label-free, real-time molecular interaction analysis." Analytical biochemistry 361.1, 2006:1-6.
Roder et al., "The EBV-Hybridoma Technique", Methods in Enzymology, 1986, vol. 121, 140-167.
Rosenberg et al., "Use of Tumor-Infiltrating Lymphocytes and Interleukin-2 in the Immunotherapy of Patients with Metastatic Melanoma", New England Journal of Medicine, 1988, vol. 319, No. 25, 1676-1680.
Sela-Culang et al., "The structural basis of antibody-antigen recognition." Frontiers in immunology 4 (2013): 302.
Sheets, et al., "Efficient construction of a large nonimmune phage antibody library: The production of high-affinity human single-chain antibodies to protein antigens", Proc. Natl. Acad. Sci., 1998, vol. 95, 6157-6162.

Shi, et al., "De Novo Selection of High-Affinity Antibodies from Synthetic Fab Libraries Displayed on Phage as plX Fusion Proteins", J. Mol. Biol., (2010), vol. 397, 385-396.
Smith et al., "Car T Cell Therapy targeting G Protein-Coupled Receptor Class C Group 5 Member D (GPRC5D), a Novel Target for the Immunotherapy of Multiple Myeloma", 2018, Blood, vol. 132, No. Supplement 1, 589.
Sugita et al., "Inhibition of T cell-mediated inflammation in uveitis by a novel anti-CD3 antibody. "Arthritis Res Ther. Jul. 2, 20175; 19(1): 176.
Thalmann, et al., "Androgen-independent Cancer Progression and Bone Metastasis in the LNCaP Model of Human Prostate Cancer", Cancer Research, (1994), vol. 54, 2577-2581.
Troy, "Remington: The Science and Practice of Pharmacy", 21st Edition, Lippincott, Williams & Wilkins, 2006, Table of Contents.
Vaughan, et al., "Human Antibodies with Sub-nanomolar Affinities Isolated from a Large Non-immunized Phage Display Library", Nature Biotechnology, (1996), vol. 14, 309-314.
Wranik, B.J., et al., "LUZ-Y, a Novel Platform for the Mammalian Cell Production of Fulllength IgG-bispecific Antibodies", Journal of Biological Chemistry, (2012), vol. 287, 52, 43331-43339.
Written Opinion of the International Searching Authority relating to corresponding International Patent Application No. PCT/IB2019/054188, filed May 21, 2019. Date of Mailing of Written Opinion: Jan. 23, 2020.
Wu et al., "An Analysis of the Sequences of the Variable Regions of Bence Jones Proteins and Myeloma Light Chains and Their Implications for Antibody Complementarity", J. Exp. Med., 1970, vol. 132, 211-250.
Www.Rockland-Inc.com: "Anti-Idiotypic Antibody Production Service", Nov. 12, 2019 (Nov. 12, 2019), XP055642733, Retrieved from the Internet: URL:https://rocklandinc. com/anti-idiotypic-antibody-production.aspx.
Yang, X.D., et al., "Eradication of Established Tumors by a Fully Human Monoclonal Antibody to the Epidermal Growth Factor Receptor without Concomitant Chemotherapy", Cancer Research, 1999, vol. 59, 1236-1243.
Ying et al., "Anti-idiotypic antibodies: biological function and structural studies.", The FASEB Journal, Federation of American Societies For Experimental Biology, Jan. 1, 1995, pp. 43-49, vol. 9(1), XP002526815.
A Study of the Combination of Talquetamab and Teclistamab in Participants With Relapsed or Refractory Multiple Myeloma (RedirecTT-1), Record History ver. 3, NCT04586426, Retrieved from https://clinicaltrials.gov/study/ NCT04586426?tab=history&a=3#version-content-panel, Jan. 21, 2021, pp. 1-18.
De Larrea et al., "Defining an Optimal Dual-Targeted CAR T-cell Therapy Approach Simultaneously Targeting BCMA and GPRC5D to Prevent BCMA Escape-Driven Relapse in Multiple Myeloma", Blood Cancer Discovery, Sep. 2020, vol. 1, pp. 146-154.
Lancman et al., "Bispecifics, trispecifics, and other novel immune treatments in myeloma", Hematology, 2020, ASH Education Program, pp. 264-271.

* cited by examiner

H929 WT

H929 GPRC5D KO

H929 BCMA KO

H929 GPRC5D/BCMA-KO

MM.1R BCMA KO

MM.1R BCMA/GPRC5D Double KO

Human Pan T D329335

Human Pan T D327645

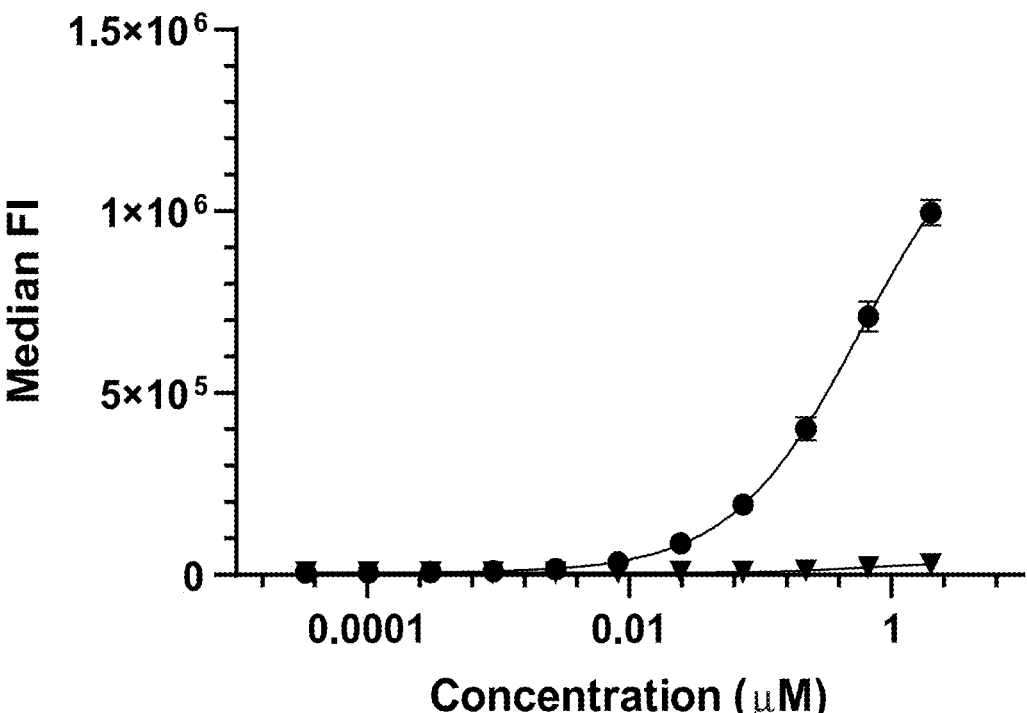
*FIG. 4C*
Human Pan T D326589

D329335

D327645

D326589

H929 WT, BGCB463.003 vs .004

MM1R WT, BGCB463.003 vs .004

Pan T donor D329335

Concentration (μM)

H929 WT

H929 GPRC5D-KO

H929 BCMA-KO

H929 GPRC5D/BCMA-KO

MM1R WT

MM1R GPRC5D-KO

MM1R BCMA-KO

MM1R GPRC5D/BCMA-KO

K562-Hum GPRC5D

K562-Hum BCMA

K562-Cyno GPRC5D

K562-Cyno BCMA

*FIG. 9E*

|  | BGCB463 EC50 (nM) Run 1 | BGCB463 EC50 (nM) Run 2 | EC50 AVE | BGCB463 EC90 (nM) Run 1 | BGCB463 EC90 (nM) Run 2 | EC90 AVE |
|---|---|---|---|---|---|---|
| Human GPRC5D | 12.5 | 49.7 | 31.1 | 142.6 | 208.7 | 175.7 |
| Cyno GPRC5D | 435.1 | 309.7 | 372.4 | 2989.8 | 2058.6 | 2524.2 |
| Human BCMA | 248.0 | 45.8 | 146.9 | 2333.8 | 192.5 | 1263.2 |
| Cyno BCMA | No fit | No fit | No fit | No fit | No fit | No fit |

H929 1hr binding with and without serum

5:1-%Cytolysis - BGCB463

5:1-CD25-Total Integrated Intensity - BGCB463

5:1-%Cytolysis - Isotype (B23B251)

5:1-CD25-Total Integrated Intensity - Isotype (B23B251)

*FIG. 16*

| Anti-CD3 Fab | | Anti-BCMA |
| Hole, RF, AAS | | Knob, AAS |
| Anti-GPRC5d | | |

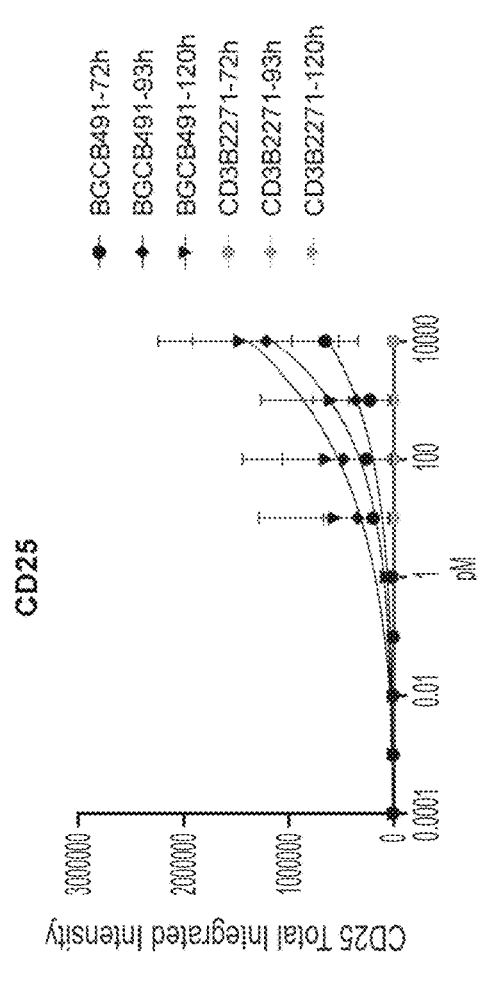
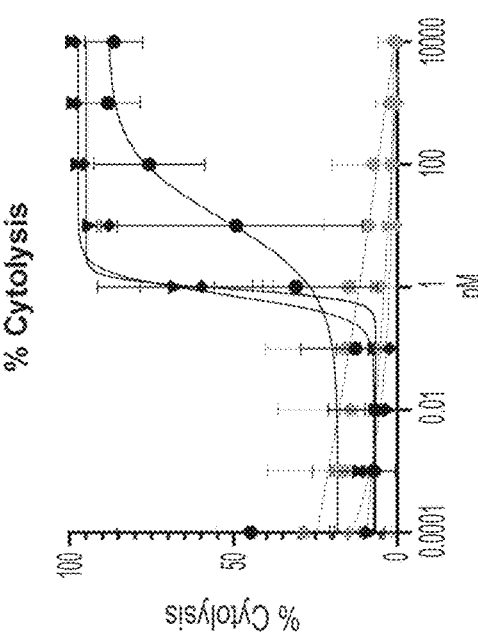
*FIG. 43*

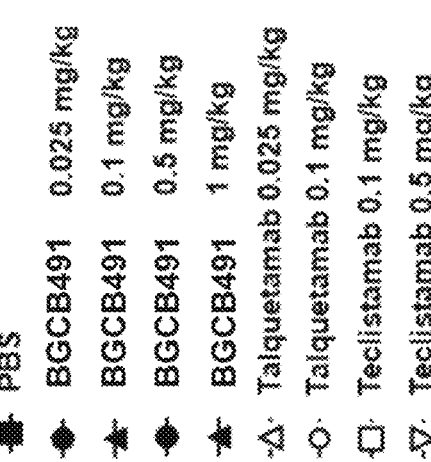
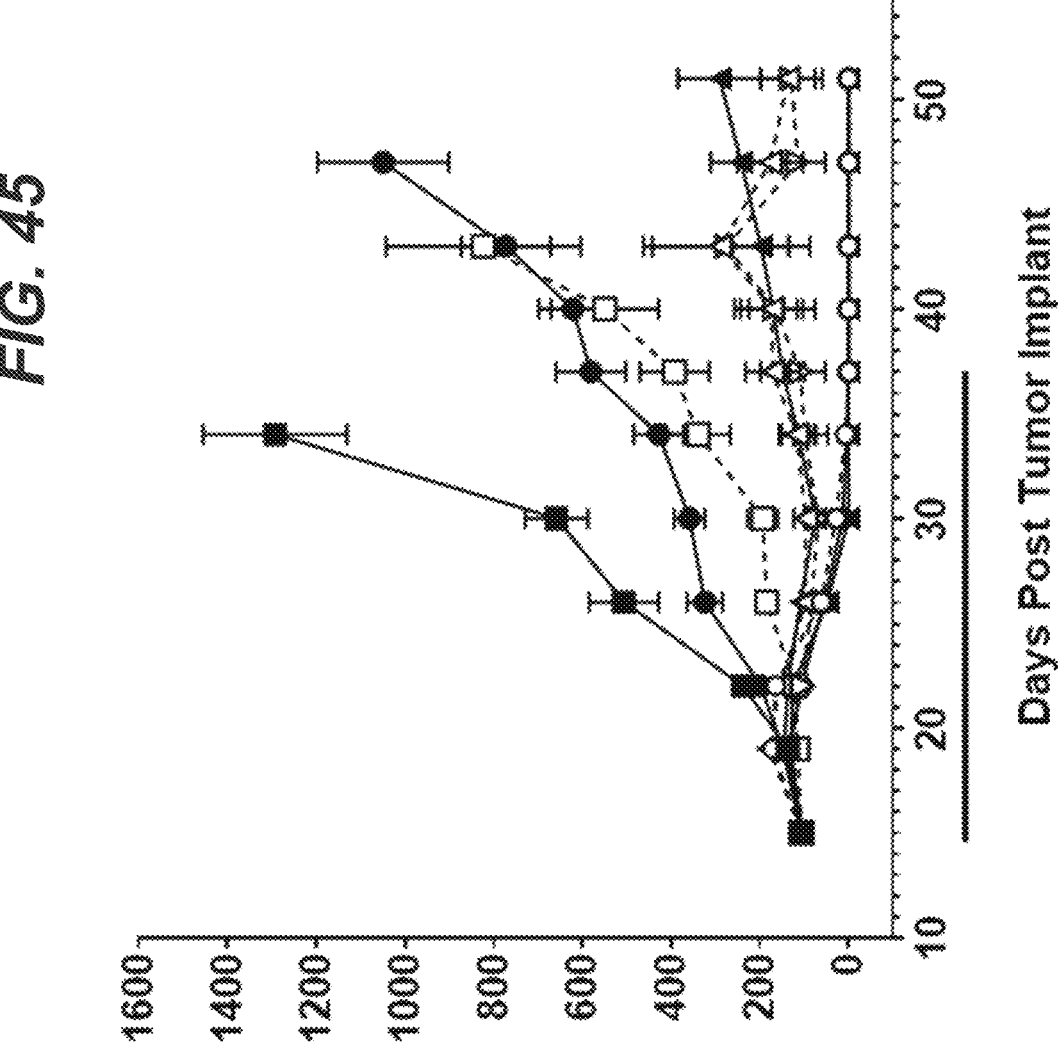
FIG. 45

FIG. 46A

| ID | Description | ScFv fitness % binding at 65C | Human BCMA KD (M) | Cyno BCMA KD (M) | H929, 1hr 37C EC50 (nM) | H929, 1hr 37C EC90 (nM) | MM.1R, 1 hr 37C EC50 (nM) | scFv Tm EC90 (nM) | scFv Tm °C | NSB |
|---|---|---|---|---|---|---|---|---|---|---|
| BCMB601 | BCMB519_L-H scFv | 116% | 2.80E-10 | N.B | 3.2 | 19 | 2.3 | 19 | 69 | Multiple surfaces None |

FIG. 46B

| Compound ID | Description | CD3 arm Description | BCMA arm Clone | BCMA arm Source | BCMA arm EC50 (nM) | % Tumor cell death pM EC50 | % Tumor cell death Max Kill % | % Tumor cell death pM EC90 |
|---|---|---|---|---|---|---|---|---|
| GCDB147 | BCMB519 scFv x CDB376 Fab | CD3B376 | BCMB519 | Ablexis | 3.4 | 115 | 92 | 214 |

FIG. 47

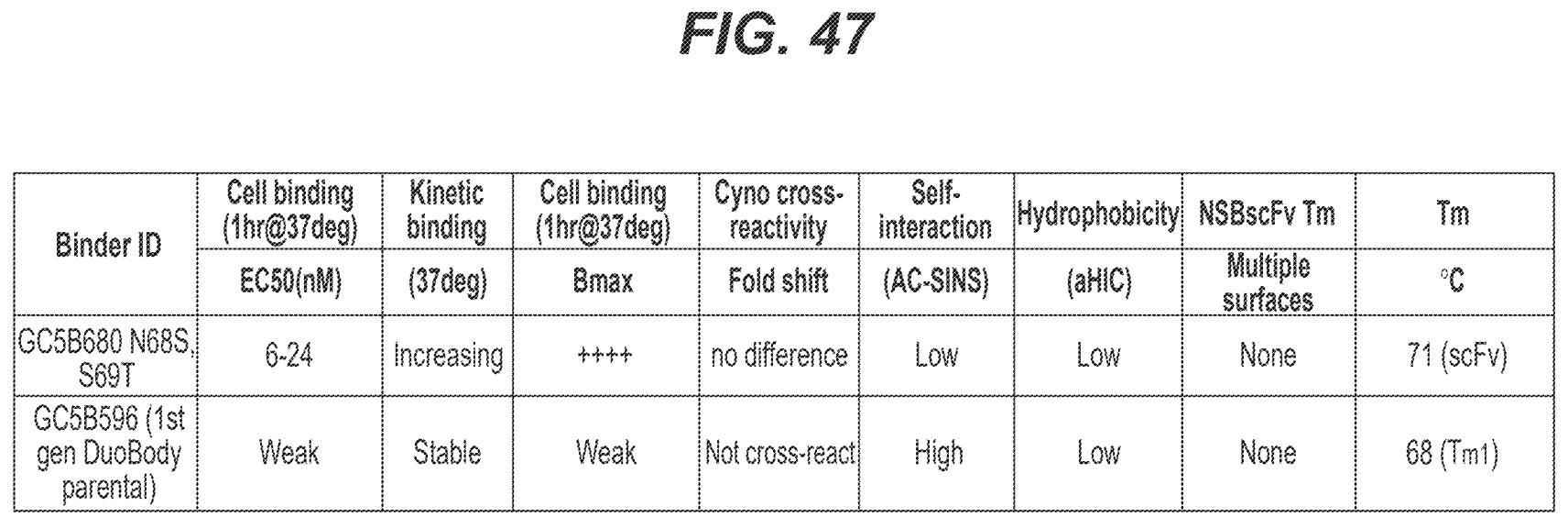

| Binder ID | Cell binding (1hr@37deg) | Kinetic binding | Cell binding (1hr@37deg) | Cyno cross-reactivity | Self-interaction | Hydrophobicity | NSBscFv | Tm |
|---|---|---|---|---|---|---|---|---|
| | EC50(nM) | (37deg) | Bmax | Fold shift | (AC-SINS) | (aHIC) | Multiple surfaces | °C |
| GC5B680 N68S, S69T | 6-24 | Increasing | ++++ | no difference | Low | Low | None | 71 (scFv) |
| GC5B596 (1st gen DuoBody parental) | Weak | Stable | Weak | Not cross-react | High | Low | None | 68 (Tm1) |

TRISPECIFIC ANTIBODY TARGETING BCMA, GPRC5D, AND CD3

CROSS-REFERENCE TO RELATED APPLICATIONS

This application claims the benefit of U.S. Provisional Application Ser. No. 63/149,921, filed 16 Feb. 2021. The entire content of the aforementioned application is incorporated herein by reference in its entirety.

TECHNICAL FIELD

The disclosure provided herein relates to multispecific antibodies that bind B-cell maturation antigen (BCMA), G-protein coupled receptor, class C, group 5, member D (GPRC5D), and cluster determinant 3 (CD3), monoclonal antibodies that bind BCMA, and methods of producing and using the described antibodies.

BACKGROUND

Multiple myeloma (MM) is the second most common hematological malignancy and constitutes 2% of all cancer deaths. MM is a heterogenous disease and caused mostly by chromosome translocations inter alia t(11; 14),t(4; 14),t(8; 14),del(13),del(17) (Drach et al., (1998) Blood 92(3):802-809; Gertz et al., (2005) Blood 106(8):2837-2840; Facon et al., (2001) Blood 97(6): 1566-1571). MM-affected patients may experience a variety of disease-related symptoms due to, bone marrow infiltration, bone destruction, renal failure, immunodeficiency, and the psychosocial burden of a cancer diagnosis. As of 2006, the 5-year relative survival rate for MM was approximately 34% highlighting that MM is a difficult-to-treat disease where there are currently no curative options.

B-cell maturation antigen, also known as BCMA, CD269, TNFRSF17 (UniProt Q02223), is a member of the tumor necrosis receptor superfamily that is preferentially expressed in differentiated plasma cells [Laabi et al. (1992) EMBO J 11(11):3897-3904; Madry et al. (1998) Int Immunol 10(11):1693-1702]. BCMA is a non-glycosylated type I transmembrane protein, which is involved in B cell maturation, growth and survival. BCMA is a receptor for two ligands of the TNF superfamily: APRIL (a proliferation-inducing ligand, CD256, TNFSF13), the high-affinity ligand to BCMA, and the B cell activation factor BAFF (THANK, BlyS, B lymphocyte stimulator, TALL-1 and zTNF4), the low-affinity ligand to BCMA. APRIL and BAFF show structural similarity and overlapping yet distinct receptor binding specificity. The negative regulator TACI also binds to both BAFF and APRIL. The coordinate binding of APRIL and BAFF to BCMA and/or TACI activates transcription factor NF-κB and increases the expression of pro-survival Bcl-2 family members (e.g. Bcl-2, Bcl-xL, Bcl-w, Mcl-1, A1) and down regulates expression of pro-apoptotic factors (e.g. Bid, Bad, Bik, Bim, etc.), thus inhibiting apoptosis and promoting survival. This combined action promotes B cell differentiation, proliferation, survival and antibody production (as reviewed in Rickert R C et al., Immunol Rev (2011) 244 (1): 115-133). In line with this finding, BCMA also supports growth and survival of malignant human B cells, including multiple myeloma (MM) cells. Novak et al. found that M M cell lines and freshly isolated MM cells express BCMA and TACI protein on their cell surfaces and have variable expression of BAFF-R protein on their cell surface (Novak et al., (2004) Blood 103(2):689-694).

The use of anti-BCMA antibodies for the treatment of lymphomas and multiple myeloma are mentioned in WO2002066516 and WO2010104949. Antibodies against BCMA are described e.g. in Gras M-P. et al. Int Immunol. 7 (1995) 1093-1106, WO200124811, and WO200124812. Nevertheless, despite the fact that BCMA, BAFF-R and TACI, i.e., B cell receptors belonging to the TNF receptor superfamily, and their ligands BAFF and APRIL are subject to therapies in fighting against cancer, further options for the treatment of such medical conditions are needed.

G-protein coupled receptor, class C, group 5, member D (GPRC5D) is an orphan, atypical, class C GPCR first identified in 2001 (Brauner-Osborne et al. Biochim Biophys Acta. 1518(3):237-248, 2001). GPRC5D and other group 5 GPCRs have unusually short amino-terminal domains for class C receptors, and are therefore, predicted to be conformationally similar to class A receptors. In this regard they are unique, with sequence homology to class C GPCRs and predicted structural topology comparable to class A receptors. Functional consequence of GPRC5D activation has not been described and the ligand remains unknown. The gene has three exons and is located on chromosome 12p13.3 in humans. GPRC5D receptor is highly conserved among various species and shares 92% identity with cynomolgus monkey GPRC5D.

The use of anti-GPRC5D antibodies for the treatment of multiple myeloma are mentioned in WO2016090329, WO2018017786, WO2018147245, and WO2019154890. Nevertheless, despite the fact that GPRC5D is subject to therapies in fighting against cancer, further options for the treatment of such medical conditions are needed.

GPRC5D mRNA is predominantly expressed in all malignant plasma cells from MM patients (Atamaniuk J A et al. Eur J Clin Invest 42(9) 953-960; 2012; Frigyesi-blood and Cohen, et al. Hematology 18(6): 348-35; 2013). GPRC5D expression is variable among the patients and correlate well with plasma cell burden and genetic aberrations such as Rb-1 deletion (Atamaniuk J A et al. Eur J Clin Invest 42(9) 953-960; 2012).

Clonal resistance is a common mechanism in relapse refractory myeloma. Targeting more than one myeloma tumor antigen and engaging T-cells could lead to efficient killing of malignant plasma cells and minimal residual disease (MRD) negativity. Dual BCMA and GPRC5D targeting enhances antibody avidity and potency, maximizes tumor eradication in presence of a heterogenous cell population, prevents tumor antigen escape (e.g., captures MM cells that do not express enough BCMA or GPRC5D alone), improves tumor efficacy and may mitigate potential for cytokine release syndrome (CRS). Accordingly, there is a need for therapeutic antibodies that target both BCMA and GPRC5D for the treatment of multiple myeloma and/or related medical conditions.

SUMMARY

In one aspect, provided herein are multispecific antibodies that bind to BCMA, GPRC5D and CD3 and multispecific antigen-binding fragments thereof. In some embodiments, provided herein are trispecific antibodies that bind to BCMA, GPRC5D and CD3 and trispecific antigen-binding fragments thereof. Also described are related polynucleotides capable of encoding the provided BCMA×GPRC5D× CD3-multispecific antibodies or multispecific antigen-binding fragments, cells expressing the provided antibodies or multispecific antigen-binding fragments, as well as associated vectors and detectably labeled multispecific antibodies or multispecific antigen-binding fragments. In addition, methods of using the provided multispecific antibodies are described. For example, the BCMA×GPRC5D×CD3-multispecific antibodies and multispecific antigen-binding fragments may be used to treat cancer (e.g., BCMA and/or GPRC5D-expressing cancer); the BCMA×GPRC5D×CD3-multispecific antibodies may be used to diagnose or monitor BCMA and/or GPRC5D-expressing cancer progression, regression, or stability; to determine whether or not a patient should be treated for cancer; or to determine whether or not a subject is afflicted with BCMA and/or GPRC5D-expressing cancer and thus may be amenable to treatment with a BCMA and/or GPRC5D-specific anti-cancer therapeutic, such as the BCMA×GPRC5D×CD3-multispecific antibodies described herein.

BCMA×GPRC5D×CD3-Multispecific Antibodies

Described herein are isolated multispecific antibodies that bind BCMA, GPRC5D and CD3 ("BCMA×GPRC5D×CD3 multispecific antibodies") and multispecific antigen-binding fragments thereof.

In preferred embodiments, the BCMA×GPRC5D×CD3 multispecific antibody or antigen-binding fragment is a trispecific antibody or antigen-binding fragment. In some embodiments, an isolated BCMA×GPRC5D×CD3 trispecific antibody, or a trispecific binding fragment thereof, comprises: (a) a first antigen-binding arm comprising a first heavy chain variable domain (VH1) and a first light chain variable domain (VL1); (b) a second antigen-binding arm comprising a second heavy chain variable domain (VH2) and a second light chain variable domain (VL2); and (c) a third antigen-binding arm comprising a third heavy chain variable domain (VH3) and a third light chain variable domain (VL3). In some embodiments, the first antigen-binding arm binds to an epitope on CD3, the second antigen-binding arm binds to an epitope on GPRC5D, and the third antigen-binding arm binds to an epitope on BCMA.

In some embodiments, the first antigen-binding arm of the trispecific antibody, or a trispecific binding fragment thereof comprises a first heavy chain portion (HC1) comprising the VH1 and a light chain portion comprising the VL1. The VH1 and the VL1 form a first antigen-binding domain that binds a first antigen. The second antigen-binding arm of the trispecific antibody or trispecific binding fragment thereof comprises a second heavy chain portion (HC2) comprising the VH2. The VH2 of the HC2 forms a second antigen-binding domain that binds a second antigen. The HC1 or the HC2 is further coupled to the third antigen-binding arm comprising the VH3 that forms a third antigen-binding domain that binds a third antigen. The HC1 and HC2 each optionally comprise a Fragment crystallizable (Fc) domain, where the Fc domain comprises a constant heavy chain region 2 (CH2) and CH3. In some embodiments, the first antigen is cluster of differentiation 3 (CD3), and the second antigen is B cell maturation antigen (BCMA), and the third antigen is G-protein coupled receptor family C group 5 member D (GPRC5D). In some embodiments, the first antigen is cluster of differentiation 3 (CD3), and the second antigen is G-protein coupled receptor family C group 5 member D (GPRC5D), and the third antigen is B cell maturation antigen (BCMA). Some aspects of the BCMA×GPRC5D×CD3 trispecific antibody, or a trispecific binding fragment thereof, are further described in the Detailed Description and Examples sections below.

In some embodiments, the BCMA-binding arm binds human BCMA but not to cynomolgus monkey BCMA. In some embodiments, the BCMA-binding arm binds bind to an epitope including one or more residues from the BCMA extracellular domain (ECD). In some embodiments, the BCMA-binding arm (or "BCMA-specific arm") of the BCMA×GPRC5D×CD3 multispecific antibody is derived from a BCMA antibody described herein (for example, from an antibody having the CDR sequences listed in Table 1).

In some embodiments, the GPRC5D-specific arm of the multispecific antibody binds human GPRC5D but not to cynomolgus monkey GPRC5D. In some embodiments, the GPRC5D-specific arm of the BCMA×GPRC5D×CD3-multispecific antibodies or antigen-binding fragments binds the extracellular domain of human GPRC5D. In some embodiments, the GPRC5D-binding arm (or "GPRC5D-specific arm") of the BCMA×GPRC5D×CD3 multispecific antibody is derived from a GPRC5D antibody described herein (for example, from an antibody having the CDR sequences listed in Table 2).

The redirection of T-lymphocytes to MM cells expressing BCMA and/or GPRC5D via the TCR/CD3 complex represents an attractive alternative approach. The TCR/CD3 complex of T-lymphocytes consists of either a TCR alpha (α)/beta (β) or TCR gamma (γ)/delta (δ) heterodimer coexpressed at the cell surface with the invariant subunits of CD3 labeled gamma (γ), delta (δ), epsilon (ε), zeta (ζ), and eta (η). In some embodiments, the multispecific antibodies or multispecific antigen-binding fragments described herein bind to CD3P. In some embodiments, the CD3-binding arm (or "CD3-specific arm") of the BCMA×GPRC5D×CD3 multispecific antibody is derived from the monoclonal antibody CD3B376. In some embodiments, the CD3-binding arm (or "CD3-specific arm") of the BCMA×GPRC5D×CD3 multispecific antibody is derived from the monoclonal antibody SP34, a mouse IgG3/lambda isotype. (K. R. Abhinandan and A. C. Martin, 2008. Mol. Immunol. 45, 3832-3839). In some embodiments, the CD3-binding arm of the BCMA× GPRC5D×CD3 multispecific antibody comprises the heavy chain CDRs and/or light chain CDRs described in Table 3, or any one VH domain and/or any one VL domain selected from Table 3.

In some embodiments, the BCMA-, GPRC5D- and/or CD3-specific arms of the BCMA×GPRC5D×CD3-multispecific antibodies or antigen-binding fragments are IgG, or derivatives thereof. The IgG class is divided in four isotypes: IgG1, IgG2, IgG3 and IgG4 in humans. They share more than 95% homology in the amino acid sequences of the Fc regions but show major differences in the amino acid composition and structure of the hinge region. The Fc region mediates effector functions, such as antibody-dependent cellular cytotoxicity (ADCC) and complement-dependent cytotoxicity (CDC). In ADCC, the Fc region of an antibody binds to Fc receptors (FcγRs) on the surface of immune effector cells such as natural killers and macrophages, leading to the phagocytosis or lysis of the targeted cells. In CDC, the antibodies kill the targeted cells by triggering the complement cascade at the cell surface.

For many applications of therapeutic antibodies, Fc-mediated effector functions are not part of the mechanism of action. These Fc-mediated effector functions can be detrimental and potentially pose a safety risk by causing off-mechanism toxicity. Modifying effector functions can be achieved by engineering the Fc regions to reduce their binding to FcγRs or the complement factors. The binding of IgG to the activating (FcγRI, FcγRIIa, FcγRIIIa and FcγRIIIb) and inhibitory (FcγRIIb) FcγRs or the first component of complement (C1q) depends on residues located in the hinge region and the CH2 domain. Mutations have been introduced in IgG1, IgG2 and IgG4 to reduce or silence Fc functionalities.

In one embodiment, the antibody comprises an Fc region with one or more of the following properties: (a) reduced effector function when compared to the parent Fc; (b) reduced affinity to FcγRI, FcγRIIa, FcγRIIb, FcγRIIIb and/or FcγRIIIa, (c) reduced affinity to FcγRI (d) reduced affinity to FcγRIIa (e) reduced affinity to FcγRIIb, (f) reduced affinity to FcγRIIIb or (g) reduced affinity to FcγRIIIa.

In some embodiments, the CD3-specific antibody or antigen-binding fragment from which the CD3-specific arm of the multispecific antibody is derived is IgG, or a derivative thereof. In some embodiments, the CD3-specific antibody or antigen-binding fragment from which the CD3-specific arm of the multispecific antibody is derived is IgG1, or a derivative thereof. In some embodiments, for example, the Fc region of the CD3-specific IgG1 antibody from which the CD3-binding arm is derived comprises L234A, L235A, and D265S substitutions in its Fc region. In some embodiments, the CD3-specific antibody or antigen-binding fragment from which the CD3-specific arm of the multispecific antibody is derived is IgG4, or a derivative thereof. In some embodiments, for example, the Fc region of the CD3-specific IgG4 antibody from which the CD3-binding arm is derived comprises S228P, L234A, L235A, F405L, and R409K substitutions in its Fc region. In some embodiments, the CD3-specific antibody or antigen-binding fragment from which the CD3-specific arm of the multispecific antibody is derived binds CD3ε on primary human T cells and/or primary cynomolgus T cells. In some embodiments, the CD3-specific antibody or antigen-binding fragment from which the CD3-specific arm of the multispecific antibody is derived activates primary human CD4+ T cells and/or primary cynomolgus CD4+ T cells.

In addition to the described BCMA×GPRC5D×CD3-multispecific antibodies, also provided are polynucleotide sequences capable of encoding the described BCMA×GPRC5D×CD3-multispecific antibodies. In some embodiments, an isolated synthetic polynucleotide encoding the one or more CDRs of the heavy chain variable domain and/or one or more CDRs of the light chain variable domain of each antigen-binding arm of the BCMA×GPRC5D×CD3 trispecific antibody or trispecific binding fragment is provided. In some embodiments, an isolated synthetic polynucleotide encoding one or more heavy chain variable domains and/or one or more light chain variable domains of the BCMA×GPRC5D×CD3 trispecific antibody or trispecific binding fragment is provided. In some embodiments, an isolated synthetic polynucleotide encoding one or more polypeptide chains of the first, second, and/or third antigen-binding arms of the BCMA×GPRC5D×CD3 trispecific antibody or trispecific binding fragment is provided. Vectors comprising the described polynucleotides are also provided, as are cells expressing the BCMA×GPRC5D×CD3-multispecific antibodies provided herein. In another embodiment, an isolated cell expressing the multispecific antibody or multispecific binding fragment is provided. Also described are cells capable of expressing the disclosed vectors. These cells may be mammalian cells (such as 293 cells, 293F cells, CHO cells), insect cells (such as Sf7 cells), yeast cells, plant cells, or bacteria cells (such as E. coli). The described antibodies may also be produced by hybridoma cells. In some embodiments, methods for generating the BCMA×GPRC5D×CD3 trispecific antibody or trispecific binding fragment by culturing cells is provided.

Further provided herein are pharmaceutical compositions comprising the BCMA×GPRC5D×CD3 multispecific antibodies or antigen-binding fragments and a pharmaceutically acceptable carrier.

Methods of Using BCMA×GPRC5D×CD3-Multispecific Antibodies

Methods of using the described BCMA×GPRC5D×CD3-multispecific antibodies and multispecific antigen-binding fragments thereof are also disclosed. For example, the BCMA×GPRC5D×CD3-multispecific antibodies and multispecific antigen-binding fragments thereof may be useful in the treatment of a GPRC5D and/or BCMA-expressing cancer in a subject in need thereof. In some embodiments, the GPRC5D and/or BCMA-expressing cancer is a lymphoma, such as multiple myeloma including smoldering multiple myeloma (SMM). In some embodiments, the GPRC5D and/or BCMA-expressing cancer is a relapsed or refractory form of a lymphoma, such as a relapsed or refractory form of multiple myeloma.

The described methods of treating GPRC5D and/or BCMA-expressing cancer in a subject in need thereof include administering to the subject a therapeutically effective amount of a described BCMA×GPRC5D×CD3-multispecific antibody or multispecific antigen-binding fragment thereof. In some embodiments, the subject is a mammal, preferably a human. In preferred embodiments are provided methods for treating a subject having cancer by administering a therapeutically effective amount of the BCMA×GPRC5D×CD3 trispecific antibody or trispecific antigen-binding fragment to a patient in need thereof for a time sufficient to treat the cancer.

Further provided herein are methods for inhibiting growth or proliferation of cancer cells by administering a therapeutically effective amount of the BCMA×GPRC5D×CD3 trispecific antibody or trispecific binding fragment to inhibit the growth or proliferation of cancer cells.

Also provided herein are methods of redirecting a T cell to a GPRC5D and/or BCMA-expressing cancer cell by administering a therapeutically effective amount of the BCMA×GPRC5D×CD3 trispecific antibody or trispecific binding fragment to redirect a T cell to a cancer.

BCMA×GPRC5D×CD3-Specific Antibody Kits

Described herein are kits including the disclosed BCMA×GPRC5D×CD3-multispecific antibodies. The described kits may be used to carry out the methods of using the BCMA×GPRC5D×CD3-multispecific antibodies provided herein, or other methods known to those skilled in the art. In some embodiments the described kits may include the antibodies described herein and reagents for use in treating a GPRC5D and/or BCMA-expressing cancer. Accordingly, the described kits may include one or more of the multispecific antibodies, or a multispecific antigen-binding fragment(s) thereof, described herein and a vessel for containing the antibody or fragment when not in use, and/or instructions for use of the antibody or fragment, the antibody or fragment affixed to a solid support, and/or detectably labeled forms of the antibody or fragment, as described herein.

BCMA-Specific Antibodies

Also provided herein are antibodies that bind to BCMA and antigen-binding fragments thereof. Also described are related polynucleotides capable of encoding the provided BCMA-specific antibodies and antigen-binding fragments, cells expressing the provided antibodies and antigen-binding fragments, as well as associated vectors and detectably labeled antibodies and antigen-binding fragments. In addition, methods of using the provided antibodies and antigen-binding fragments are described. For example, the BCMA-specific antibodies and antigen-binding fragments may be used to treat cancer (e.g., BCMA-expressing cancer); the BCMA-specific antibodies and antigen-binding fragments may be used to diagnose or monitor BCMA-expressing cancer progression, regression, or stability; to determine whether or not a patient should be treated for cancer; or to determine whether or not a subject is afflicted with BCMA-expressing cancer and thus may be amenable to treatment with a BCMA-specific anti-cancer therapeutic, such as the multispecific antibodies against BCMA and CD3 described herein. Some aspects of the BCMA-specific antibody, or an antigen-binding fragment, are further described in the Detailed Description and Examples sections below.

Methods of Using BCMA-Specific Antibodies

Methods of using the described BCMA-specific antibodies or antigen-binding fragments are also disclosed. Particular antibodies for use in the methods discussed in this section include those with the set of CDRs described for antibodies in Table 1 (e.g., BCMB519). For example, these antibodies or antigen-binding fragments may be useful in treating cancer, by interfering with BCMA-receptor interactions or where the antibody is conjugated to a toxin, so targeting the toxin to the BCMA-expressing cancer. Further, these antibodies or antigen-binding fragments may be useful for detecting the presence of BCMA in a biological sample, such as blood or serum; for quantifying the amount of BCMA in a biological sample, such as blood or serum; for diagnosing BCMA-expressing cancer; determining a method of treating a subject afflicted with cancer; or monitoring the progression of BCMA-expressing cancer in a subject. In some embodiments, BCMA-expressing cancer may be a lymphoma, such as multiple myeloma (MM) including smoldering multiple myeloma (SMM). In some embodiments, the BCMA-expressing cancer is a relapsed or refractory form of a lymphoma, such as a relapsed or refractory form of multiple myeloma. The described methods may be carried out before the subject receives treatment for BCMA-expressing cancer, such as treatment with a multispecific antibody against BCMA and CD3. Furthermore, the described methods may be carried out after the subject receives treatment for BCMA-expressing cancer, such as treatment with a multispecific antibody against BCMA and CD3 described herein.

The described methods of detecting BCMA in a biological sample include exposing the biological sample to one or more of the BCMA-specific antibodies or antigen-binding fragments described herein.

The described methods of diagnosing BCMA-expressing cancer in a subject also involve exposing the biological sample to one or more of the BCMA-specific antibodies or antigen-binding fragments described herein; however, the methods also include quantifying the amount of BCMA present in the sample; comparing the amount of BCMA present in the sample to a known standard or reference sample; and determining whether the subject's BCMA levels fall within the levels of BCMA associated with cancer.

Also described herein are methods of monitoring BCMA-expressing cancer in a subject. The described methods include exposing the biological sample to one or more of the BCMA-specific antibodies or antigen-binding fragments described herein; quantifying the amount of BCMA present in the sample that is bound by the antibody, or antigen-binding fragment thereof, comparing the amount of BCMA present in the sample to either a known standard or reference sample or the amount of BCMA in a similar sample previously obtained from the subject; and determining whether the subject's BCMA levels are indicative of cancer progression, regression or stable disease based on the difference in the amount of BCMA in the compared samples.

The samples obtained, or derived from, subjects are biological samples such as urine, blood, serum, plasma, saliva, ascites, circulating cells, circulating tumor cells, cells that are not tissue associated, tissues, surgically resected tumor tissue, biopsies, fine needle aspiration samples, or histological preparations.

The described BCMA-specific antibodies or antigen-binding fragments may be labeled for use with the described methods, or other methods known to those skilled in the art. For example, the antibodies described herein, or antigen-binding fragments thereof, may be labeled with a radiolabel, a fluorescent label, an epitope tag, biotin, a chromophore label, an ECL label, an enzyme, ruthenium, $^{111}$In-DOTA, $^{111}$In-diethylenetriaminepentaacetic acid (DTPA), horseradish peroxidase, alkaline phosphatase and beta-galactosidase, or poly-histidine or similar such labels known in the art.

BCMA-Specific Antibody Kits

Described herein are kits including the disclosed BCMA-specific antibodies or antigen-binding fragments thereof. The described kits may be used to carry out the methods of using the BCMA-specific antibodies or antigen-binding fragments provided herein, or other methods known to those skilled in the art. In some embodiments the described kits may include the antibodies or antigen-binding fragments described herein and reagents for use in detecting the presence of BCMA in a biological sample. Accordingly, the described kits may include one or more of the antibodies, or an antigen-binding fragment(s) thereof, described herein and a vessel for containing the antibody or fragment when not in use, instructions for use of the antibody or fragment, the antibody or fragment affixed to a solid support, and/or detectably labeled forms of the antibody or fragment, as described herein.

BRIEF DESCRIPTION OF THE DRAWINGS

FIGS. 4A-4C. BGCB463 (circles) or negative control B23B251 (triangles) were all incubated with Pan T cells (3 random donors, FIG. 4A-4C) for 1 hr at 37° C. at a starting concentration of 2 µM. After secondary detection with AF647-labeled material, the MFI signal was analyzed to generate an $EC_{50}$ and $EC_{90}$. Data are representative of two individual runs, both with three donors.

FIGS. 9A-E. BGCB463 (circles) or negative control B23B251 (triangles) were all incubated with K562 cells expressing human GPRC5D (FIG. 9A), human BCMA (FIG. 9B), cynomolgus GPRC5D (FIG. 9C) or cynomolgus BCMA (FIG. 9D) for 1 hr at 37° C. at a starting concentration of 2 μM. After secondary detection with AF647-anti-human IgG, the MFI signal was analyzed to generate an $EC_{50}$ and $EC_{90}$ (FIG. 9E). Data are representative of two independent experiments.

FIG. 16. Depiction of BGCB491 trispecific antibody.

In FIG. 28A, target cell death was measured and expressed as percent cytotoxicity on Y axis. In FIG. 28B, T cell activation was measured as percent CD25+ CD3+ T cells.

(FIG. 33A) BGCB491, BCMA×GPRC5D×Null, and CD3×Null× Null were tested in presence of pan T cells from 1 healthy donor (donor ID: 20063323) at 4 different E:T ratios (5:1, 3:1, 1:1, and 0.5:1) for 72 hours. (FIG. 33B) BGCB491 was tested at an E:T ratio of 3:1 and 1:1 for various time points (24 hours—Circle, 48 hours—Upward triangle, 72 hours— Downward triangle, 96 hours—Hexagonal, 120 hours— Diamond, 144 hours—Star, and 168 hours—Square) using 4 different T cell donors (donor ID: 20062105, 20063309, 20061963, and 20063310). Target cell death and T cell activation were measured and expressed as percent cytotoxicity and percent CD25+CD3+ T cells. The plots were generated using Prism 8 by fitting separate 4PL models to the observed data. The data points aligned tightly along the generated fit curve and little variability was observed between T cell donors: (FIG. 33A) 1 and (FIG. 33B) 4 donor averages plotted.

FIGS. 34A-34C. BGCB491 effect on T cell activation in absence of target cells. A T cell activation assay was performed using (FIG. 34A) 6 normal healthy donor T cells (donor ID: 20063323, 20063309, 20062062, 20063310, 20062105, and 20061963) or (FIG. 34B) 6 normal donor whole-blood samples (donor ID:10274, 10402, 10427, 10470, 10500, and 10509). (FIG. 34C) Non-specific cytotoxicity was measured for various subsets. BGCB491, BCMA×GPRC5D×Null, and CD3×Null×Null were added at various concentrations (0.00005 to 533.33 nM, X axis) for (FIG. 34A) 72 hours and (FIG. 34B, 34C) 48 hours.

FIG. 43. Percent cytolysis and T-cell activation of BGCB491 and CD3B2271(null control) at 72-, 93-, and 120-hour timepoints at 1:1 effector-to-target (E:T) ratio.

FIG. 45. Antitumor efficacy of JNJ-79635322, teclistamab, and talquetamab in subcutaneous MM.1 S xenografts in T cell-humanized NSG mice (Study C). NSG, non-obese diabetic (NOD) severe combined immunodeficiency (scid) gamma or NOD.Cg-Prkdc$^{scid}$ Il2rg$^{tm1 Wjl}$/SzJ; PBS, phosphate-buffered saline; SEM, standard error of the mean. T-cell-humanized NSG mice bearing established SC MM.1S tumors were IP dosed with BGCB491 at 0.025, 0.1, 0.5, and 1 mg/kg. Talquetamab was IP dosed at 0.025 and 0.1 mg/kg. Teclistamab was IP dosed at 0.1 and 0.5 mg/kg treatments were administered on Days 15, 19, 22, 26, 30, 34, and 37 (indicated by black line beneath X-axis). Tumor volume was measured twice weekly, and the results presented as the mean tumor volume±SEM for each group. Data graphically represented for each group with at least 70% of animals remaining in the study. Animals were monitored post treatment until signs of graft-versus-host disease (GvHD)-related morbidity manifested at which time the animals were euthanized and the study was concluded on Day 51.

FIGS. 46A-46B. BCMA lead (BCMB519) demonstrates comparable binding and cytotoxicity as Teclistamab with ideal scFv biophysical properties.

FIG. 47. GPRC5d lead (GC5B680) demonstrates specific and improved binding compared to Talquetamab with ideal scFv biophysical properties.

DETAILED DESCRIPTION OF ILLUSTRATIVE EMBODIMENTS

Definitions

Figure 1A:
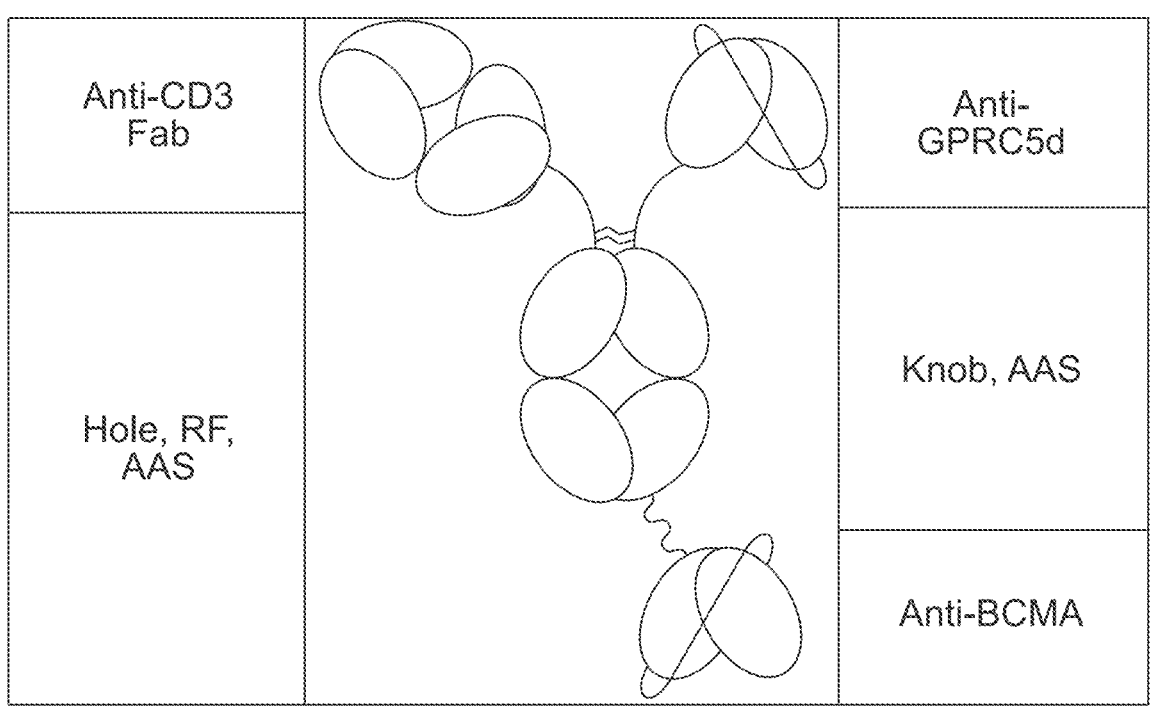
FIG. 1A-1B. Depiction of BGCB463 trispecific antibody (FIG. 1A) and proposed mode of action (FIG. 1).

Various terms relating to aspects of the description are used throughout the specification and claims. Such terms are to be given their ordinary meaning in the art unless otherwise indicated. Other specifically defined terms are to be construed in a manner consistent with the definitions provided herein.

As used in this specification and the appended claims, the singular forms "a," "an," and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of up to ±10% from the specified value, as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

"Isolated" means a biological component (such as a nucleic acid, peptide or protein) has been substantially separated, produced apart from, or purified away from other biological components of the organism in which the component naturally occurs, i.e., other chromosomal and extra-chromosomal DNA and RNA, and proteins. Nucleic acids, peptides and proteins that have been "isolated" thus include nucleic acids and proteins purified by standard purification methods. "Isolated" nucleic acids, peptides and proteins can be part of a composition and still be isolated if such composition is not part of the native environment of the nucleic acid, peptide, or protein. The term also embraces nucleic acids, peptides and proteins prepared by recombi-nant expression in a host cell as well as chemically synthe-sized nucleic acids. An "isolated" antibody or antigen-binding fragment, as used herein, is intended to refer to an antibody or antigen-binding fragment which is substantially free of other antibodies or antigen-binding fragments having different antigenic specificities (for instance, an isolated antibody that specifically binds to BCMA is substantially free of antibodies that specifically bind antigens other than BCMA). An isolated antibody that specifically binds to an epitope, isoform or variant of BCMA or GPRC5D may, however, have cross-reactivity to other related antigens, for instance from other species (such as BCMA or GPRC5D species homologs).

"Polynucleotide," synonymously referred to as "nucleic acid molecule," "nucleotides" or "nucleic acids," refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of poly-nucleotides as typically found in nature, as well as the chemical forms of DNA and RNA characteristic of viruses and cells. "Polynucleotide" also embraces relatively short nucleic acid chains, often referred to as oligonucleotides.

The meaning of "substantially the same" can differ depending on the context in which the term is used. Because of the natural sequence variation likely to exist among heavy and light chains and the genes encoding them, one would expect to find some level of variation within the amino acid sequences or the genes encoding the antibodies or antigen-binding fragments described herein, with little or no impact on their unique binding properties (e.g., specificity and affinity). Such an expectation is due in part to the degeneracy of the genetic code, as well as to the evolutionary success of conservative amino acid sequence variations, which do not appreciably alter the nature of the encoded protein. Accord-ingly, in the context of nucleic acid sequences, "substantially the same" means at least 65% identity between two or more sequences. Preferably, the term refers to at least 70% identity between two or more sequences, more preferably at least 75% identity, more preferably at least 80% identity, more preferably at least 85% identity, more preferably at least 90% identity, more preferably at least 91% identity, more preferably at least 92% identity, more preferably at least 93% identity, more preferably at least 94% identity, more preferably at least 95% identity, more preferably at least 96% identity, more preferably at least 97% identity, more preferably at least 98% identity, and more preferably at least 99% or greater identity. The percent identity between two sequences is a function of the number of identical positions shared by the sequences (i.e., % homology=#of identical positions/total #of positions×100), taking into account the number of gaps, and the length of each gap, which need to be introduced for optimal alignment of the two sequences. The percent identity between two nucleotide or amino acid sequences may e.g. be determined using the algorithm of E. Meyers and W. Miller, Comput. Appl. Biosci 4, 11-17 (1988) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, J. Mol. Biol. 48, 444-453 (1970) algorithm.

The degree of variation that may occur within the amino acid sequence of a protein without having a substantial effect on protein function is much lower than that of a nucleic acid sequence, since the same degeneracy principles do not apply to amino acid sequences. Accordingly, in the context of an antibody or antigen-binding fragment, "substantially the same" means antibodies or antigen-binding fragments hav-ing 90%, 91%, 92%, 93%, 94%, 95%, 96%, 97%, 98%, or 99% identity to the antibodies or antigen-binding fragments described. Other embodiments include antibodies, or anti-gen-binding fragments, that have framework, scaffold, or other non-binding regions that do not share significant identity with the antibodies and antigen-binding fragments described herein, but do incorporate one or more CDRs or other sequences needed to confer binding that are 90%, 91%, 92%, 93%, 94%, 95%, 96%, 97%, 98%, or 99% identical to such sequences described herein.

A "clone" is a population of cells derived from a single cell or common ancestor by mitosis. A "cell line" is a clone of a primary cell that is capable of stable growth in vitro for many generations. In some examples provided herein, cells are transformed by transfecting the cells with DNA.

The terms "express" and "produce" are used synony-mously herein, and refer to the biosynthesis of a gene product. These terms encompass the transcription of a gene into RNA. These terms also encompass translation of RNA into one or more polypeptides, and further encompass all naturally occurring post-transcriptional and post-transla-tional modifications. The expression or production of an antibody or antigen-binding fragment thereof may be within the cytoplasm of the cell, or into the extracellular milieu such as the growth medium of a cell culture.

The terms "treating" or "treatment" refer to any success or indicia of success in the attenuation or amelioration of an injury, pathology or condition, including any objective or subjective parameter such as abatement, remission, dimin-ishing of symptoms or making the condition more tolerable to the patient, slowing in the rate of degeneration or decline, making the final point of degeneration less debilitating, improving a subject's physical or mental well-being, or prolonging the length of survival. The treatment may be assessed by objective or subjective parameters; including the results of a physical examination, neurological examination, or psychiatric evaluations.

An "effective amount" or "therapeutically effective amount" refers to an amount effective, at dosages and for periods of time necessary, to achieve a desired therapeutic result. A therapeutically effective amount of a BCMA× GPRC5D×CD3 antibody may vary according to factors such as the disease state, age, sex, and weight of the individual, and the ability of the antibody to elicit a desired response in the individual. A therapeutically effective amount is also one in which any toxic or detrimental effects of the antibody or antibody portion are outweighed by the therapeutically beneficial effects.

"Antibody" refers to all isotypes of immunoglobulins (IgG, IgA, IgE, IgM, IgD, and IgY) including various monomeric, polymeric and chimeric forms, unless otherwise specified. Specifically encompassed by the term "antibody" are polyclonal antibodies, monoclonal antibodies (mAbs), and antibody-like polypeptides, such as chimeric antibodies and humanized antibodies.

The term "antigen-binding arm" refers to a portion of an antibody that includes an antigen-binding domain that binds to an antigen (e.g., BCMA, GPRC5D, or CD3), and optionally includes one or more other antibody regions (e.g., Fc domain).

The term "antigen-binding fragment" refers to a fragment of the antigen-binding arm containing an antigen-binding domain. Antigen-binding fragments include those provided by any known technique, such as enzymatic cleavage, peptide synthesis, and recombinant techniques. Some antigen-binding fragments are composed of portions of intact antibodies that retain antigen-binding specificity of the parent antibody molecule. For example, antigen-binding fragments may comprise at least one variable region (either a heavy chain or light chain variable region) or one or more CDRs of an antibody known to bind a particular antigen. Examples of suitable antigen-binding fragments include, without limitation diabodies and single-chain molecules as well as Fab, F(ab')2, Fc, Fabc, and Fv molecules, single chain (Sc) antibodies, individual antibody light chains, individual antibody heavy chains, chimeric fusions between antibody chains or CDRs and other proteins, protein scaffolds, heavy chain monomers or dimers, light chain monomers or dimers, dimers consisting of one heavy and one light chain, a monovalent fragment consisting of the VL, VH, CL and CH1 domains, or a monovalent antibody as described in WO2007059782, bivalent fragments comprising two Fab fragments linked by a disulfide bridge at the hinge region, a Fd fragment consisting essentially of the VH and CH1 domains; a Fv fragment consisting essentially of the VL and VH domains of a single arm of an antibody, a dAb fragment (Ward et al., Nature 341, 544-546 (1989)), which consists essentially of a VH domain and also called domain antibodies (Holt et al; Trends Biotechnol. 2003 November; 21(11): 484-90); camelid or nanobodies (Revets et al; Expert Opin Biol Ther. 2005 January; 5(1):111-24); an isolated complementarity determining region (CDR), and the like. All antibody isotypes may be used to produce antigen-binding fragments. Additionally, antigen-binding fragments may include non-antibody proteinaceous frameworks that may successfully incorporate polypeptide segments in an orientation that confers affinity for a given antigen of interest, such as protein scaffolds. Antigen-binding fragments may be recombinantly produced or produced by enzymatic or chemical cleavage of intact antibodies. The phrase "an antibody or antigen-binding fragment thereof" may be used to denote that a given antigen-binding fragment incorporates one or more amino acid segments of the antibody referred to in the phrase.

The term "antigen-binding domain" refers to the proteinaceous structure of an antigen-binding arm that exhibits binding affinity for a particular antigen. This proteinaceous structure is mediated by the complementarity determining regions (CDRs) of the antigen-binding domain.

The terms "CDR", and its plural "CDRs", refer to a complementarity determining region (CDR) of which three make up the binding character of a light chain variable region (CDRL1, CDRL2 and CDRL3) and three make up the binding character of a heavy chain variable region (CDRH1, CDRH2 and CDRH3). CDRs contribute to the functional activity of an antibody molecule and are separated by amino acid sequences that comprise scaffolding or framework regions. The exact definitional CDR boundaries and lengths are subject to different classification and numbering systems. CDRs may therefore be referred to by Kabat, Chothia, contact or any other boundary definitions. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat et al., *Sequences of Proteins of Immunological Interest,* 5th ed. NIH Publication No. 91-3242 (1991); Chothia et al., "Canonical Structures For the Hypervariable Regions of Immunoglobulins," *J. Mol. Biol.* 196:901 (1987); and MacCallum et al., "Antibody-Antigen Interactions: Contact Analysis and Binding Site Topography," J. Mol. Biol. 262:732 (1996)), each of which is hereby incorporated by reference in its entirety.

Typically, CDRs form a loop structure that can be classified as a canonical structure. The term "canonical structure" refers to the main chain conformation that is adopted by the antigen binding (CDR) loops. From comparative structural studies, it has been found that five of the six antigen binding loops have only a limited repertoire of available conformations. Each canonical structure can be characterized by the torsion angles of the polypeptide backbone. Correspondent loops between antibodies may, therefore, have very similar three dimensional structures, despite high amino acid sequence variability in most parts of the loops (Chothia et al., "Canonical Structures For the Hypervariable Regions of Immunoglobulins," *J. Mol. Biol.* 196: 901 (1987); Chothia et al., "Conformations of Immunoglobulin Hypervariable Regions," I 342:877 (1989); Martin and Thornton, "Structural Families in Loops of Homologous Proteins: Automatic Classification, Modelling and Application to Antibodies," *J Mol. Biol.* 263:800 (1996), each of which is incorporated by reference in its entirety). Furthermore, there is a relationship between the adopted loop structure and the amino acid sequences surrounding it. The conformation of a particular canonical class is determined by the length of the loop and the amino acid residues residing at key positions within the loop, as well as within the conserved framework (i.e., outside of the loop). Assignment to a particular canonical class can therefore be made based on the presence of these key amino acid residues.

The term "polypeptide" is used interchangeably with the term "protein" and in its broadest sense refers to a compound of two or more subunit amino acids, amino acid analogs or peptidomimetics. The subunits may be linked by peptide bonds. In another embodiment, the subunit may be linked by other bonds, e.g., ester, ether, etc. As used herein the term "amino acid" refers to either natural and/or unnatural or synthetic amino acids, including glycine and both the D and L optical isomers, amino acid analogs and peptidomimetics. A peptide of three or more amino acids is commonly called an oligopeptide if the peptide chain is short. If the peptide chain is long, the peptide is commonly called a polypeptide or a protein.

"Specifically binds" or "binds specifically" or derivatives thereof when used in the context of antibodies, or antibody fragments, represents binding via domains encoded by immunoglobulin genes or fragments of immunoglobulin genes to one or more epitopes of a protein of interest, without preferentially binding other molecules in a sample containing a mixed population of molecules. Typically, an antibody binds to a cognate antigen with a $K_d$ of less than about $1 \times 10^{-8}$ M, as measured by a surface plasmon resonance assay or a cell-binding assay. Phrases such as "[antigen]-specific" antibody (e.g., BCMA-specific antibody) are meant to convey that the recited antibody specifically binds the recited antigen.

As used herein, the term "chimeric" refers to an antibody, or antigen-binding fragment thereof, having at least some portion of at least one variable domain derived from the antibody amino acid sequence of a non-human mammal, a rodent, or a reptile, while the remaining portions of the antibody, or antigen-binding fragment thereof, are derived from a human.

A "vector" is a replicon, such as plasmid, phage, cosmid, or virus in which another nucleic acid segment may be operably inserted so as to bring about the replication or expression of the segment.

As used herein, the term "host cell" can be any type of cell, e.g., a primary cell, a cell in culture, or a cell from a cell line. In specific embodiments, the term "host cell" refers to a cell transfected with a nucleic acid molecule and the progeny or potential progeny of such a cell. Progeny of such a cell may not be identical to the parent cell transfected with the nucleic acid molecule, e.g., due to mutations or environmental influences that may occur in succeeding generations or integration of the nucleic acid molecule into the host cell genome. The terms "expression" and "production" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications.

The term "subject" refers to human and non-human animals, including all vertebrates, e.g., mammals and non-mammals, such as non-human primates, mice, rabbits, sheep, dogs, cats, horses, cows, chickens, amphibians, and reptiles. In many embodiments of the described methods, the subject is a human.

The term "redirect" or "redirecting" as used herein refers to the ability of the BCMA×GPRC5D×CD3 antibody to traffic the activity of T cells effectively, from its inherent cognate specificity toward reactivity against GPRC5D and/or BCMA-expressing cells.

The term "sample" as used herein refers to a collection of similar fluids, cells, or tissues (e.g., surgically resected tumor tissue, biopsies, including fine needle aspiration), isolated from a subject, as well as fluids, cells, or tissues present within a subject. In some embodiments the sample is a biological fluid. Biological fluids are typically liquids at physiological temperatures and may include naturally occurring fluids present in, withdrawn from, expressed or otherwise extracted from a subject or biological source. Certain biological fluids derive from particular tissues, organs or localized regions and certain other biological fluids may be more globally or systemically situated in a subject or biological source. Examples of biological fluids include blood, serum and serosal fluids, plasma, lymph, urine, saliva, cystic fluid, tear drops, feces, sputum, mucosal secretions of the secretory tissues and organs, vaginal secretions, ascites fluids such as those associated with non-solid tumors, fluids of the pleural, pericardial, peritoneal, abdominal and other body cavities, fluids collected by bronchial lavage and the like. Biological fluids may also include liquid solutions contacted with a subject or biological source, for example, cell and organ culture medium including cell or organ conditioned medium, lavage fluids and the like. The term "sample," as used herein, encompasses materials removed from a subject or materials present in a subject.

A "known standard" may be a solution having a known amount or concentration of GPRC5D and/or BCMA, where the solution may be a naturally occurring solution, such as a sample from a patient known to have early, moderate, late, progressive, or static cancer, or the solution may be a synthetic solution such as buffered water having a known amount of GPRC5D and/or BCMA diluted therein. The known standards, described herein may include GPRC5D and/or BCMA isolated from a subject, recombinant or purified GPRC5D and/or BCMA protein, or a value of GPRC5D and/or BCMA concentration associated with a disease condition.

The terms "B-cell maturation antigen" and "BCMA" as used herein include human B cell maturation antigen, also known as BCMA, CD269, and TNFRSF17 (UniProt Q02223), which is a member of the tumor necrosis receptor superfamily that is preferentially expressed in differentiated plasma cells. The extracellular domain of human BCMA consists, according to UniProt of amino acids 1-54 (or 5-51). The term "antibody against BCMA, anti-BCMA antibody" as used herein relates to an antibody specifically binding to BCMA.

The terms "G-protein coupled receptor family C group 5 member D" and "GPRC5D" specifically include the human GPRC5D protein, for example as described in GenBank Accession No. BC069341, NCBI Reference Sequence: NP_061124.1 and UniProtKB/Swiss-Prot Accession No. Q9NZD1 (see also Brauner-Osborne, H. et al. 2001, Biochim. Biophys. Acta 1518, 237-248).

The terms "cluster determinant 3" and "CD3" include the human CD3 protein multi-subunit complex. The CD3 protein multi-subunit complex is composed to 6 distinctive polypeptide chains. These include a CD3γ chain (SwissProt P09693), a CD36 chain (SwissProt P04234), two CD3ε chains (SwissProt P07766), and one CD3 ζ chain homodimer (SwissProt 20963), and which is associated with the T cell receptor a and R chain. The term "CD3" includes any CD3 variant, isoform and species homolog which is naturally expressed by cells (including T cells) or can be expressed on cells transfected with genes or cDNA encoding those polypeptides, unless noted.

A "BCMA×GPRC5D×CD3 antibody" is a multispecific antibody, optionally a trispecific antibody, which comprises three different antigen-binding arms, one of which binds to the antigen BCMA, one of which binds to the antigen GPRC5D, and one of which binds to CD3. A "BCMA×CD3 antibody" is a multispecific antibody, optionally a bispecific antibody, which comprises two different antigen-binding arms, one of which binds to the antigen BCMA and one of which binds to CD3. A "GPRC5D×CD3 antibody" is a multispecific antibody, optionally a bispecific antibody, which comprises two different antigen-binding arms, one of which binds to the antigen GPRC5D and one of which binds to CD3. The term "multispecific antibody" is used herein in the broadest sense and specifically covers an antibody that has polyepitopic specificity. Multispecific antibodies include, but are not limited to, an antibody comprising a heavy chain variable domain (VH) and a light chain variable domain (V$_L$), where the V$_H$V$_L$ unit has polyepitopic specificity, antibodies having two or more V$_L$ and V$_H$ domains where each V$_H$V$_L$ unit binds to a different epitope, antibodies having two or more single variable domains with each single variable domain binding to a different epitope, full length antibodies, and antibodies comprising one or more antibody fragments as well as antibodies comprising antibody fragments that have been linked covalently or non-covalently.

A multispecific antibody can be a bispecific antibody, a trispecific antibody, diabody, or similar molecule (see for instance *PNAS USA* 90(14), 6444-8 (1993) for a description of diabodies). The bispecific antibodies, trispecific antibodies, diabodies, and the like, provided herein may bind any suitable target in addition to a portion of BCMA or GPRC5D. The term "bispecific antibody" is to be understood as an antibody having two different antigen-binding arms defined by different antibody sequences. The term "trispecific antibody" is to be understood as an antibody having three different antigen-binding arms defined by different antibody sequences. This can be understood as different target binding but includes as well binding to different epitopes in one target.

A "reference sample" is a sample that may be compared against another sample, such as a test sample, to allow for characterization of the compared sample. The reference sample will have some characterized property that serves as the basis for comparison with the test sample. For instance, a reference sample may be used as a benchmark for GPRC5D or BCMA levels that are indicative of a subject having cancer. The reference sample does not necessarily have to be analyzed in parallel with the test sample, thus in some instances the reference sample may be a numerical value or range previously determined to characterize a given condition, such as GPRC5D or BCMA levels that are indicative of cancer in a subject. The term also includes samples used for comparative purposes that are known to be associated with a physiologic state or disease condition, such as GPRC5D- or BCMA-expressing cancer, but that have an unknown amount of GPRC5D or BCMA.

"Relapsed" refers to the return of a disease or the signs and symptoms of a disease after a period of improvement after prior treatment with a therapeutic.

"Refractory" refers to a disease that does not respond to a treatment. A refractory disease can be resistant to a treatment before or at the beginning of the treatment, or a refractory disease can become resistant during a treatment.

The term "progression," as used in the context of progression of GPRC5D and/or BCMA—expressing cancer, includes the change of a cancer from a less severe to a more severe state. This may include an increase in the number or severity of tumors, the degree of metastasis, the speed with which the cancer is growing or spreading, and the like. For example, "the progression of colon cancer" includes the progression of such a cancer from a less severe to a more severe state, such as the progression from stage I to stage II, from stage II to stage III, etc.

The term "regression," as used in the context of regression of GPRC5D and/or BCMA-expressing cancer, includes the change of a cancer from a more severe to a less severe state. This could include a decrease in the number or severity of tumors, the degree of metastasis, the speed with which the cancer is growing or spreading, and the like. For example, "the regression of colon cancer" includes the regression of such a cancer from a more severe to a less severe state, such as the progression from stage III to stage II, from stage II to stage I, etc.

The term "stable" as used in the context of stable GPRC5D and/or BCMA-expressing cancer, is intended to describe a disease condition that is not, or has not, changed significantly enough over a clinically relevant period of time to be considered a progressing cancer or a regressing cancer.

The embodiments described herein are not limited to particular methods, reagents, compounds, compositions or biological systems, which can, of course, vary.

Multispecific Antibodies

Multispecific antibodies that bind to BCMA, GPRC5D, and CD3, and trispecific binding fragments thereof are provided herein. Such antibodies or antibody fragments may allow for more specific targeting to particular subsets of cells as compared to antibodies targeting only one or two of these targets.

This can be achieved by, for example, making a molecule which comprises a first antigen-binding arm binding to CD3, a second antigen-binding arm binding to GPRC5D and a third antigen-binding arm binding to the BCMA. The antigen-binding arms can take any form that allows specific recognition of the target, for example the binding arm may be or may include a heavy chain variable domain, an Fv (combination of a heavy chain variable domain and a light chain variable domain), an single-chain Fv (scFv), an Fab, a binding domain based on a fibronectin type III domain (such as from fibronectin, or based on a consensus of the type III domains from fibronectin, or from tenascin or based on a consensus of the type III domains from tenascin, such as the Centyrin molecules from Janssen Biotech, Inc., see e.g. WO2010/051274 and WO2010/093627). In certain embodiments, the trispecific antibody comprises three antigen-binding arms. In some embodiments, the trispecific antibody is comprised of an antibody (e.g. in IgG format) to which an additional antigen-binding arm, e.g. in the form of a single chain variable fragment, is fused, e.g. to the N or C-terminus of one of the heavy or one of the light chains of the antibody.

Accordingly, trispecific molecules comprising three different antigen-binding arms which bind BCMA, GPRC5D, and CD3, respectively, are provided.

In some embodiments, the BCMA×GPRC5D×CD3-multispecific antibody comprises (a) a first antigen-binding arm comprising a first heavy chain variable domain (VH1) and a first light chain variable domain (VL1);

(b) a second antigen-binding arm comprising a second heavy chain variable domain (VH2) and a second light chain variable domain (VL2); and (c) a third antigen-binding arm comprising a third heavy chain variable domain (VH3) and a third light chain variable domain (VL3).

In some embodiments, the first antigen-binding arm binds to an epitope on CD3, the second antigen-binding arm binds to an epitope on GPRC5D, and the third antigen-binding arm binds to an epitope on BCMA.

In some embodiments, the first antigen-binding arm that binds CD3 comprises a HCDR 1, a HCDR2 and a HCDR3 of the VH1 of SEQ ID NO: 8. In some embodiments, the first antigen-binding arm that binds CD3 comprises a LCDR1, a LCDR2 and a LCDR3 of the VL1 of SEQ ID NO: 7. In some embodiments, the first antigen-binding arm that binds CD3 comprises a HCDR1 comprising the amino acid sequence of GDSVFNNNAAWS (SEQ ID NO: 4), a HCDR2 comprising the amino acid sequence of RTYYRSKWLYD (SEQ ID NO: 5), and a HCDR3 comprising the amino acid sequence of GYSSSFDY (SEQ ID NO: 6). In some embodiments, the first antigen-binding arm that binds CD3 comprises a LCDR1 comprising the amino acid sequence of TGTSSNIGTYKFVS (SEQ ID NO: 1), a LCDR2 comprising the amino acid sequence of EVSKRPS (SEQ ID NO: 2), and a LCDR3 comprising the amino acid sequence of VSYAGSGTLL (SEQ ID NO: 3). In some embodiments, the first antigen-binding arm that binds CD3 comprises the VH1 of SEQ ID NO: 8. In some embodiments, the first antigen-binding arm that binds CD3 comprises the VL1 of SEQ ID NO: 7.

In some embodiments, the second antigen-binding arm that binds GPRC5D comprises a HCDR1, a HCDR2 and a HCDR3 of the VH2 of SEQ ID NO: 16. In some embodiments, the second antigen-binding arm that binds GPRC5D comprises a LCDR1, a LCDR2 and a LCDR3 of the VL2 of SEQ ID NO: 15. In some embodiments, the second antigen-binding arm that binds GPRC5D comprises a HCDR1 comprising the amino acid sequence of GFSLTNIRMSVS (SEQ ID NO: 12), HCDR2 comprising the amino acid sequence of HIFSNDEKS (SEQ ID NO: 13), and a HCDR3 comprising the amino acid sequence of MRLPYGMDV (SEQ ID NO: 14). In some embodiments, the second anti-gen-binding arm that binds GPRC5D comprises a LCDR1 comprising the amino acid sequence of RSSQSLVHSDGN-TYLS (SEQ ID NO: 9), a LCDR2 comprising the amino acid sequence of KISNRFF (SEQ ID NO: 10), and a LCDR3 comprising the amino acid sequence of MQATQFPHT (SEQ ID NO: 11). In some embodiments, the second antigen-binding arm that binds GPRC5D comprises the VH1 of SEQ ID NO: 16. In some embodiments, the second antigen-binding arm that binds GPRC5D comprises the VL1 of SEQ ID NO: 15.

In some embodiments, the third antigen-binding arm that binds BCMA comprises a HCDR1, a HCDR2 and a HCDR3 of the VH3 of SEQ ID NO: 24. In some embodiments, the third antigen-binding arm that binds BCMA comprises a LCDR1, a LCDR2 and a LCDR3 of the VL3 of SEQ ID NO: 23. In some embodiments, the third antigen-binding arm that binds BCMA comprises a HCDR1 comprising the amino acid sequence of GFTFSSYAMS (SEQ ID NO: 20), a HCDR2 comprising the amino acid sequence of AISGSGG-STY (SEQ ID NO: 21), and a HCDR3 comprising the amino acid sequence of DEGYSSGHYYGMDV (SEQ ID NO: 22); and a LCDR1 comprising the amino acid sequence of RASQSISSSFLT (SEQ ID NO: 17). In some embodiments, the third antigen-binding arm that binds BCMA comprises a LCDR2 comprising the amino acid sequence of GASSRAT (SEQ ID NO: 18), and a LCDR3 comprising the amino acid sequence of QHYGSSPMYT (SEQ ID NO: 19). In some embodiments, the third antigen-binding arm that binds BCMA comprises the VH1 of SEQ ID NO: 24. In some embodiments, the third antigen-binding arm that binds BCMA comprises the VL1 of SEQ ID NO: 23.

In some embodiments, the VH1 and VL1 of the antigen-binding arm that binds to CD3 epitope are present in a diabody, a Fab, Fab', a F(ab')2, a Fv, a scFv, a Fd, a disulfide stabilized Fv fragment (dsFv), or a disulfide stabilized diabody (ds diabody).

In some embodiments, the VH2 and VL2 of the antigen-binding arm that binds to GPRC5D epitope are present in a diabody, a Fab, Fab', a F(ab')2, a Fv, a scFv, a Fd, a disulfide stabilized Fv fragment (dsFv), or a disulfide stabilized diabody (ds diabody).

In some embodiments, the VH3 and VL3 of the antigen-binding arm that binds to BCMA epitope are present in a diabody, a Fab, Fab', a F(ab')2, a Fv, a scFv, a Fd, a disulfide stabilized Fv fragment (dsFv), or a disulfide stabilized diabody (ds diabody).

In some embodiments, the first antigen-binding arm of the BCMA×GPRC5D×CD3 multispecific antibody comprises a first heavy chain portion (HC1) comprising the VH1 and a light chain portion (LC) comprising the VL1, wherein the VH1 and VL1 pair to form a first antigen-binding domain that binds a first antigen. In some embodiments, the HC1 comprises, from N to C-terminus, the VH1, a first heavy chain constant domain (CH1), and a first Fc domain. In some embodiments, the VH1 and CH1 of the HC1 together with the LC form a fragment antigen binding (Fab) domain.

In some embodiments, the VH1 of the first antigen-binding arm is coupled to the VH3 of the third antigen-binding arm via the first Fc domain. In some embodiments, the first Fc domain of the first antigen-binding arm is coupled, via a first linker (L1), to the third antigen-binding arm, thereby forming a coupled first and third antigen-binding arm. The coupled first and third antigen-binding arms may comprise, from N to C-terminus, the VH1, the CH1 domain, and the Fc domain of the first antigen-binding arm, the first linker, and the third antigen-binding arm. In some embodiments, the third antigen-binding arm is a single-chain variable fragment (scFv) formed from the VH3 and VL3 of the third-antigen-binding arm.

In some embodiments, the second antigen-binding arm of the BCMA×GPRC5D×CD3 multispecific antibody com-prises a second heavy chain portion (HC2) comprising the second heavy chain variable domain (VH2) which forms a second antigen-binding domain that binds a second antigen. In some embodiments, the second binding arm comprises from N to C-terminus, a single-chain variable fragment (scFv) formed from the VH2 and VL2, and a second Fc domain.

In some embodiments, the VH2 of the second antigen-binding arm is coupled to the VH3 of the third antigen-binding arm via the second Fc domain. In some embodi-ments, the second Fc domain of the second antigen-binding arm is coupled, via a linker, to the third antigen-binding arm, thereby forming a coupled second and third antigen-binding arm. The coupled second and third antigen-binding arms may comprise, from N to C-terminus, the second antigen-binding domain, the second Fc domain, the first linker, and the third antigen-binding arm. In some embodiments, the third antigen-binding arm is a single-chain variable fragment (scFv) formed from the VH3 and VL3 of the third-antigen-binding arm.

In preferred embodiments, the BCMA×GPRC5D×CD3-multispecific antibody is a trispecific antibody comprising a CD3-specific arm comprising a first heavy chain portion (HC1) comprising the VH1 and a light chain portion (LC) comprising the VL1. The VH1 and VL1 domains pair to form a first antigen-binding domain that binds CD3. The second antigen-binding arm of the trispecific antibody com-prises a second heavy chain portion (HC2) with the VH2 which forms the second antigen-binding domain that binds the second antigen. The HC1 of the CD3-specific binding arm or the HC2 of the second antigen-binding arm is coupled to the third antigen-binding arm comprising the VH3 domain, which forms the third antigen-binding domain that binds the third antigen. In some embodiments, the second antigen is BCMA, and the third antigen is GPRC5D. In some embodiments, the second antigen is GPRC5D, and the third antigen is BCMA.

In one embodiment, the BCMA×GPRC5D×CD3-multi-specific antibody is a trispecific antibody comprising a CD3-specific binding arm comprising the HC1 with the VH1 and the LC with the VL1. The VH1 and VL1 pair to form the first CD3-specific antigen-binding domain that binds CD3. The second antigen-binding arm comprises the VH2 and VL2 that form the second antigen-binding domain that binds GPRC5D. The third antigen-binding arm is coupled to the second antigen-binding arm and comprises the VH3 and VL3 that form the third antigen-binding domain that binds BCMA.

In one embodiment, the BCMA×GPRC5D×CD3-multi-specific antibody is a trispecific antibody comprising a CD3-specific binding arm comprising the HC1 with the VH1 and the LC with the VL1. The VH1 and VL1 pair to form the first CD3-specific antigen-binding domain that binds CD3. The second antigen-binding arm comprises the VH2 and VL2 that form the second antigen-binding domain that binds BCMA. The third antigen-binding arm is coupled to the second antigen-binding arm and comprises the VH3 and VL3 that form the third antigen-binding domain that binds GPRC5D.

In one embodiment, the BCMA×GPRC5D×CD3-multi-specific antibody is a trispecific antibody comprising a CD3-specific binding arm comprising the HC1 with the VH1 and the LC with the VL1. The VH1 and VL1 pair to form the first CD3-specific antigen-binding domain that binds CD3. The second antigen-binding arm comprises the VH2 and VL2 that form the second antigen-binding domain that binds GPRC5D. The third antigen-binding arm is coupled to the first CD3-specific antigen-binding arm and comprises the VH3 and VL3 that form the third antigen-binding domain that binds BCMA.

In one embodiment, the BCMA×GPRC5D×CD3-multi-specific antibody is a trispecific antibody comprising a CD3-specific binding arm comprising the HC1 with the VH1 and the LC with the VL1. The VH1 and VL1 pair to form the first CD3-specific antigen-binding domain that binds CD3. The second antigen-binding arm comprises the VH2 and VL2 that form the second antigen-binding domain that binds BCMA. The third antigen-binding arm is coupled to the first CD3-specific antigen-binding arm and comprises the VH3 and VL3 that form the third antigen-binding domain that binds GPRC5D.

In some embodiments, the HC1 with the VH1 and LC with the VL1 domains of the first antigen-binding arm form an antigen-binding fragment (Fab) comprising the first antigen-binding domain. In some embodiments, the VH2 and VL2 of the second antigen-binding arm form a single-chain variable fragment (scFv) comprising the second antigen-binding domain. In some embodiments, the VH3 and VL3 of the third antigen-binding arm form a single-chain variable fragment (scFv) comprising the third antigen-binding domain.

In one embodiment, the CD3-binding arm comprises an antigen-binding fragment (Fab), the BCMA-binding arm comprises a single-chain variable fragment (scFv), and the GPRC5D-binding arm comprises a single-chain variable fragment (scFv).

In one embodiment, the CD3-binding arm comprises a single-chain variable fragment (scFv), the BCMA-binding arm comprises an antigen-binding fragment (Fab), and the GPRC5D-binding arm comprises a single-chain variable fragment (scFv).

In one embodiment, the CD3-binding arm comprises a single-chain variable fragment (scFv), the BCMA-binding arm comprises a single-chain variable fragment (scFv), and the GPRC5D-binding arm comprises an antigen-binding fragment (Fab).

In some embodiments, the CD3-binding arm of the trispecific antibody comprises the HC1 and the LC. The HC1 may comprise constant heavy chain regions (CH1, CH2, and CH3) and the VH1. The LC may comprise the VL1. The VH1 and VL1 combine to form the CD3 antigen binding domain.

In some embodiments, GPRC5D-binding arm of the trispecific antibody comprises the HC2. The HC2 may comprise constant heavy chain regions (CH2 and CH3), and a single-chain variable fragment (scFv) attached at the N-terminus of the CH2 region, wherein the scFv comprises the GPRC5D antigen binding domain.

In some embodiments, the trispecific antibody further comprises BCMA antigen-binding arm attached to the C-terminus of the CH3 region of the GPRC5D-binding arm to form a GPRC5D/BCMA binding arm. In some embodiments, the BCMA antigen-binding arm comprises a second single-chain variable fragment (scFv). In some embodiments, the GPRC5D/BCMA arm may have the structure: scFv containing the GPRC5D binding domain, CH2 and CH3 regions, scFv containing the BCMA binding domain.

In some embodiments, the CD3-binding arm of the trispecific antibody comprises the HC1 and the LC. The HC1 may comprise constant heavy chain regions (CH1, CH2, and CH3) and the VH1. The LC may comprise the VL1. The VH1 and VL1 combine to form the CD3 antigen binding domain.

In some embodiments, BCMA-binding arm of the trispecific antibody comprises the HC2. The HC2 may comprise constant heavy chain regions (CH2 and CH3), and a single-chain variable fragment (scFv) attached at the N-terminus of the CH2 region, wherein the scFv comprises the BCMA antigen binding domain.

In some embodiments, the trispecific antibody further comprises GPRC5D antigen-binding arm attached to the C-terminus of the CH3 region of the CD3-binding arm to form a CD3/GPRC5D binding arm. In some embodiments, the BCMA antigen-binding arm comprises a second single-chain variable fragment (scFv). In some embodiments, the CD3/GPRC5D arm may have the structure: Fab containing the CD3 binding domain, CH2 and CH3 regions, scFv containing the GPRC5D binding domain.

In some embodiments, the multispecific antibodies of the invention include antibodies having a full length antibody structure. "Full length antibody" as used herein refers to an antibody having two full length antibody heavy chains and two full length antibody light chains. A full length antibody heavy chain (HC) includes heavy chain variable and constant domains VH, CH1, CH2, and CH3. A full length antibody light chain (LC) includes light chain variable and constant domains VL and CL. The full length antibody may be lacking the C-terminal lysine (K) in either one or both heavy chains. The term "Fab-arm" or "half molecule" refers to one heavy chain-light chain pair that binds an antigen. In some embodiments, one of the antigen-binding domains is a non-antibody based binding domain, e.g. a binding domain of based on a fibronectin type 3 domain, e.g. Centyrin.

BCMA-Binding Arm

The BCMA×GPRC5D×CD3-multispecific antibody described herein comprises an antigen-binding arm specific for BCMA. In some embodiments, the BCMA-binding arm binds human BCMA. In some embodiments, the BCMA-binding arm binds human BCMA and cynomolgus monkey BCMA. In some embodiments, the BCMA-binding arm binds human BCMA but not to cynomolgus monkey BCMA. In some embodiments, the BCMA-binding arm binds bind to an epitope including one or more residues from the BCMA extracellular domain (ECD). In some embodiments, the BCMA-binding arm binds to residues 17-26 (LLHACIPCQL (SEQ ID NO: 161)) of BCMA BCMW37 chain.

The BCMA-binding arms may bind to BCMA with an affinity of $5 \times 10^{-7}$M or less, such as $1 \times 10^{-7}$M or less, $5 \times 10^{-8}$M or less, $1 \times 10^{-8}$M or less, $5 \times 10^{-9}$M or less, $1 \times 10^{-9}$M, or $5 \times 10^{-0}$ M or less. In one embodiment, the BCMA-binding arm binds to the BCMA with an affinity of about $1 \times 10^{-10}$ M to $1 \times 10^{-7}$M. In one embodiment, the BCMA-binding arm binds to the BCMA with an affinity of about $1 \times 10^{-10}$M, about $2 \times 10^{-10}$M, about $3 \times 10^{-10}$M, about $4 \times 10^{-10}$M, about $5 \times 10^{-10}$M, about $6 \times 10^{-10}$M, about $7 \times 10^{-10}$M, about $8 \times 10^{-10}$M, about $9 \times 10^{-10}$M, about $1 \times 10^{-9}$M, about $2 \times 10^{-9}$M, about $3 \times 10^{-9}$M, about $4 \times 10^{-9}$M, about $5 \times 10^{-9}$M, about $6 \times 10^{-9}$M, about $7 \times 10^{-9}$M, about $8 \times 10^{-9}$M, or about $9 \times 10^{-9}$M. In one embodiment, the BCMA-binding arm binds to the BCMA with an affinity of about $1 \times 10^{-10}$ to $5 \times 10^{-10}$M, about $1 \times 10^{-10}$ to $8 \times 10^{-10}$M, about $2 \times 10^{-10}$ to $9 \times 10^{-10}$M, about $3 \times 10^{-10}$ to $10 \times 10^{-10}$M, about $4 \times 10^{-10}$ to $10 \times 10^{-10}$M, or about $5 \times 10^{-10}$ to $10 \times 10^{-10}$M. In one embodiment, the BCMA-binding arm binds to the BCMA with an affinity of about $8.4 \times 10^{-10}$M as determined by a surface plasmon resonance (SPR) assay. In one embodiment, the BCMA-binding arm binds to the BCMA with an affinity of about $2.1 \times 10^{-10}$M as determined by a surface plasmon resonance (SPR) assay.

Table 1 provides a summary of examples of some BCMA-specific antibodies described herein:

TABLE 1

CDR sequences of exemplary mAbs generated against human BCMA

| ID | HC-CDRI | HC-CDR2 | HC-CDR3 | LC-CDR1 | LC-CDR2 | LC-CDR3 |
|---|---|---|---|---|---|---|
| BCMB519 | GFTFSSYAMS (SEQ ID NO 20) | AISGSGGSTY (SEQ ID NO 21) | DEGYSSGHYYG MDV (SEQ ID NO 22) | RASQSISSSFLT (SEQ ID NO 17) | GASSRAT (SEQ ID NO 18) | QHYGSSPMY T (SEQ ID NO 19) |
| BCMB69 | SGSYFWG (SEQ ID NO 32) | SIYYSGITYYNPSLKS (SEQ ID NO 33) | HDGAVAGLFDY (SEQ ID NO 34) | GGNNIGSKSVH (SEQ ID NO 39) | DDSDRPS (SEQ ID NO 40) | QVWDSSSDH VV (SEQ ID NO 41) |
| BCMB117 | SGSYFWG (SEQ ID NO 32) | SIYYSGITYYNPSLKS (SEQ ID NO 33) | HDGAVAGLFDY (SEQ ID NO 34) | GGNNIGSKSVH (SEQ ID NO 39) | DDSDRPS (SEQ ID NO 40) | QVWDSSSDH VV (SEQ ID NO 41) |
| BCMB123 | SSSYFWG (SEQ ID NO 38) | SIYYSGITYYNPSLKS (SEQ ID NO 33) | HDGAVAGLFDY (SEQ ID NO 34) | GGNNIGSKSVH (SEQ ID NO 39) | DDSDRPS (SEQ ID NO 40) | QVWDSSSDH VV (SEQ ID NO 41) |
| BCMB128 | SGSYFWG (SEQ ID NO 32) | SIYYSGITYYNPSLKS (SEQ ID NO 33) | HDGATAGLFDY (SEQ ID NO 37) | GGNNIGSKSVH (SEQ ID NO 39) | DDSDRPS (SEQ ID NO 40) | QVWDSSSDH VV (SEQ ID NO 41) |
| BCMB129 | SGSYFWG (SEQ ID NO 32) | SIYYSGSTYYNPSLKS (SEQ ID NO 36) | HDGAVAGLFDY (SEQ ID NO 34) | GGNNIGSKSVH (SEQ ID NO 39) | DDSDRPS (SEQ ID NO 40) | QVWDSSSDH VV (SEQ ID NO 41) |
| BCMB176 | SSSYFWG (SEQ ID NO 38) | SIYYSGITYYNPSLKS (SEQ ID NO 33) | HDGATAGLFDY (SEQ ID NO 37) | GGNNIGSKSVH (SEQ ID NO 39) | DDSDRPS (SEQ ID NO 40) | QVWDSSSDH VV (SEQ ID NO 41) |
| BCMB177 | SSSYFWG (SEQ ID NO 38) | SIYYSGRTYYNPSLK S (SEQ ID NO 164) | HDGATAGLFDY (SEQ ID NO 37) | GGNNIGSKSVH (SEQ ID NO 39) | DDSDRPS (SEQ ID NO 40) | QVWDSSSDH VV (SEQ ID NO 41) |

Characteristics of some BCMA-specific antibodies or antigen-binding fragments may be found in e.g., U.S. Pat. No. 10,072,088, the content of which is herein incorporated by reference in its entirety.

In some embodiments, the BCMA-binding arm comprises a heavy chain variable domain comprising a heavy chain CDR1, CDR2, and CDR3 of any one of the antibodies described in Table 1. In some embodiments, the BCMA-binding arm comprises a light chain variable region comprising a light chain CDR1, CDR2, and CDR3 of any one of the antibodies described in Table 1. In some embodiments, the BCMA-binding arm comprises a heavy chain variable domain comprising a heavy chain CDR1, CDR2, and CDR3 of any one of the antibodies described in Table 1 and a light chain variable region comprising a light chain CDR1, CDR2, and CDR3 of any one of the antibodies described in Table 1. In some embodiments, the BCMA-binding arm competes for binding to BCMA with an antibody or antigen-binding comprising a heavy chain comprising a heavy chain CDR1, CDR2, and CDR3 of any one of the antibodies described in Table 1 and a light chain comprising a light chain CDR1, CDR2, and CDR3 of any one of the antibodies described in Table 1.

In some embodiments, the BCMA-binding arm comprises a heavy chain comprising a heavy chain CDR1, CDR2, and CDR3 of any one of the antibodies described in Table 1. In some embodiments, the BCMA-binding arm comprises a light chain comprising a light chain CDR1, CDR2, and CDR3 of any one of the antibodies described in Table 1. In some embodiments, the BCMA-binding arm comprises a heavy chain comprising a heavy chain CDR1, CDR2, and CDR3 of any one of the antibodies described in Table 1 and a light chain comprising a light chain CDR1, CDR2, and CDR3 of any one of the antibodies described in Table 1.

In some embodiments, the BCMA-binding arm comprises heavy chain CDR1, CDR2, and CDR3 of clone BCMB519, BCMB69, BCMB117, BCMB123, BCMB128, BCMB129, BCMB176, or BCMB177. In some embodiments, the BCMA-binding arm comprises heavy chain CDR1, CDR2, and CDR3 and light chain CDR1, CDR2, and CDR3 of clone BCMB519, BCMB69, BCMB117, BCMB123, BCMB128, BCMB129, BCMB176, or BCMB177. In one embodiment, the BCMA-binding arm comprises heavy chain CDR1, CDR2, and CDR3 and light chain CDR1, CDR2, and CDR3 of clone BCMB519.

In some embodiments, the BCMA-binding arm comprises a heavy chain variable domain derived from an antibody clone as described in Table 1. In some exemplary embodiments, the BCMA-binding arm comprises heavy chain variable domain and light chain variable domain derived from an antibody clone as described in Table 1. In some exemplary embodiments, the BCMA-binding arm comprises heavy chain variable domain and light chain variable domain of clone BCMB519, BCMB69, BCMB117, BCMB123, BCMB128, BCMB129, BCMB176, or BCMB177. In one embodiment, the BCMA-binding arm comprises heavy chain variable domain and light chain variable domain of clone BCMB519.

In some embodiments, the BCMA-binding arm comprises a heavy chain CDR1 comprising SEQ ID NO: 20, a heavy chain CDR2 comprising SEQ ID NO: 21, and a heavy chain CDR3 comprising SEQ ID NO: 22. In some embodiments, the BCMA-binding arm comprises a heavy chain CDR1 comprising SEQ ID NO: 20, a heavy chain CDR2 comprising SEQ ID NO: 21, a heavy chain CDR3 comprising SEQ ID NO: 22, a light chain CDR1 comprising SEQ ID NO: 17, a light chain CDR2 comprising SEQ ID NO: 18, and a light chain CDR3 comprising SEQ ID NO: 19. The BCMA-binding arm may comprise human framework sequences. In some embodiments, the BCMA-binding arm comprises a heavy chain variable domain substantially the same as, or identical to, SEQ ID NO: 24. In some embodiments, the BCMA-binding arm comprises a heavy chain variable domain substantially the same as, or identical to, SEQ ID NO: 24 and a light chain variable domain substantially the same as, or identical to, SEQ ID NO: 23.

In some embodiments, the BCMA-binding arm comprises a heavy chain CDR1 comprising SEQ ID NO: 32, a heavy chain CDR2 comprising SEQ ID NO: 33, and a heavy chain CDR3 comprising SEQ ID NO: 34. In some embodiments, the BCMA-binding arm comprises a heavy chain CDR1 comprising SEQ ID NO: 32, a heavy chain CDR2 comprising SEQ ID NO: 33, a heavy chain CDR3 comprising SEQ ID NO: 34, a light chain CDR1 comprising SEQ ID NO: 39, a light chain CDR2 comprising SEQ ID NO: 40, and a light chain CDR3 comprising SEQ ID NO: 41. The BCMA-binding arm may comprise human framework sequences. In some embodiments, the BCMA-binding arm comprises a heavy chain variable domain substantially the same as, or identical to, SEQ ID NO: 42. In some embodiments, the BCMA-binding arm comprises a heavy chain variable domain substantially the same as, or identical to, SEQ ID NO: 42 and a light chain variable domain substantially the same as, or identical to, SEQ ID NO: 48.

In some embodiments, the BCMA-binding arm comprises a heavy chain CDR1 comprising SEQ ID NO: 38, a heavy chain CDR2 comprising SEQ ID NO: 33, and a heavy chain CDR3 comprising SEQ ID NO: 34. In some embodiments, the BCMA-binding arm comprises a heavy chain CDR1 comprising SEQ ID NO: 38, a heavy chain CDR2 comprising SEQ ID NO: 33, a heavy chain CDR3 comprising SEQ ID NO: 34, a light chain CDR1 comprising SEQ ID NO: 39, a light chain CDR2 comprising SEQ ID NO: 40, and a light chain CDR3 comprising SEQ ID NO: 41. The BCMA-binding arm may comprise human framework sequences. In some embodiments, the BCMA-binding arm comprises a heavy chain variable domain substantially the same as, or identical to, SEQ ID NO: 43. In some embodiments, the BCMA-binding arm comprises a heavy chain variable domain substantially the same as, or identical to, SEQ ID NO: 43 and a light chain variable domain substantially the same as, or identical to, SEQ ID NO: 48.

In some embodiments, the BCMA-binding arm comprises comprise a heavy chain CDR1 comprising SEQ ID NO: 32, a heavy chain CDR2 comprising SEQ ID NO: 33, and a heavy chain CDR3 comprising SEQ ID NO: 37. In some embodiments, the BCMA-binding arm comprises a heavy chain CDR1 comprising SEQ ID NO: 32, a heavy chain CDR2 comprising SEQ ID NO: 33, a heavy chain CDR3 comprising SEQ ID NO: 37, a light chain CDR1 comprising SEQ ID NO: 39, a light chain CDR2 comprising SEQ ID NO: 40, and a light chain CDR3 comprising SEQ ID NO: 41. The BCMA-binding arm may comprise human framework sequences. In some embodiments, the BCMA-binding arm comprises a heavy chain variable domain substantially the same as, or identical to, SEQ ID NO: 44. In some embodiments, the BCMA-binding arm comprises a heavy chain variable domain substantially the same as, or identical to, SEQ ID NO: 44 and a light chain variable domain substantially the same as, or identical to, SEQ ID NO: 48.

In some embodiments, the BCMA-binding arm comprises a heavy chain CDR1 comprising SEQ ID NO: 32, a heavy chain CDR2 comprising SEQ ID NO: 36, and a heavy chain CDR3 comprising SEQ ID NO: 34. In some embodiments, the BCMA-binding arm comprises a heavy chain CDR1 comprising SEQ ID NO: 32, a heavy chain CDR2 comprising SEQ ID NO: 36, a heavy chain CDR3 comprising SEQ ID NO: 34, a light chain CDR1 comprising SEQ ID NO: 39, a light chain CDR2 comprising SEQ ID NO: 40, and a light chain CDR3 comprising SEQ ID NO: 41. The BCMA-binding arm comprise human framework sequences. In some embodiments, the BCMA-binding arm comprises a heavy chain variable domain substantially the same as, or identical to, SEQ ID NO: 45. In some embodiments, the BCMA-binding arm comprises a heavy chain variable domain substantially the same as, or identical to, SEQ ID NO: 45 and a light chain variable domain substantially the same as, or identical to, SEQ ID NO: 48.

In some embodiments, the BCMA-binding arm comprises a heavy chain CDR1 comprising SEQ ID NO: 38, a heavy chain CDR2 comprising SEQ ID NO: 33, and a heavy chain CDR3 comprising SEQ ID NO: 37. In some embodiments, the BCMA-binding arm comprises a heavy chain CDR1 comprising SEQ ID NO: 38, a heavy chain CDR2 comprising SEQ ID NO: 33, a heavy chain CDR3 comprising SEQ ID NO: 37, a light chain CDR1 comprising SEQ ID NO: 39, a light chain CDR2 comprising SEQ ID NO: 40, and a light chain CDR3 comprising SEQ ID NO: 41. The BCMA-binding arm may comprise human framework sequences. In some embodiments, the BCMA-binding arm comprises a heavy chain variable domain substantially the same as, or identical to, SEQ ID NO: 46. In some embodiments, the BCMA-binding arm comprises a heavy chain variable domain substantially the same as, or identical to, SEQ ID NO: 46 and a light chain variable domain substantially the same as, or identical to, SEQ ID NO: 48.

In some embodiments, the BCMA-binding arm comprises a heavy chain CDR1 comprising SEQ ID NO: 38, a heavy chain CDR2 comprising SEQ ID NO: 164, and a heavy chain CDR3 comprising SEQ ID NO: 37. In some embodiments, the BCMA-binding arm comprises a heavy chain CDR1 comprising SEQ ID NO: 38, a heavy chain CDR2 comprising SEQ ID NO: 164, a heavy chain CDR3 comprising SEQ ID NO: 37, a light chain CDR1 comprising SEQ ID NO: 39, a light chain CDR2 comprising SEQ ID NO: 40, and a light chain CDR3 comprising SEQ ID NO: 41. The BCMA-binding arm may comprise human framework sequences. In some embodiments, the BCMA-binding arm comprises a heavy chain variable domain substantially the same as, or identical to, SEQ ID NO: 47. In some embodiments, the BCMA-binding arm comprises a heavy chain variable domain substantially the same as, or identical to, SEQ ID NO: 47 and a light chain variable domain substantially the same as, or identical to, SEQ ID NO: 48.

The BCMA-binding arm may be derived from any species by recombinant means. For example, the BCMA antigen-binding arm may be derived from mouse, rat, goat, horse, swine, bovine, chicken, rabbit, camelid, donkey, human, or chimeric versions thereof. For use in administration to humans, non-human derived antigen-binding fragments may be genetically or structurally altered to be less antigenic upon administration to a human patient. In some embodiments, the BCMA-binding arm comprises antigen-binding fragments which is chimeric.

In some embodiments, the BCMA-binding arm comprises humanized antigen-binding fragments. Humanized antigen-binding fragments may be derived from chimeric immuno-globulins, immunoglobulin chains or fragments thereof (such as Fv, Fab, Fab', F(ab')2 or other antigen-binding subsequences of antibodies) that contain minimal sequence derived from non-human immunoglobulin. For the most part, humanized antibodies or antigen-binding fragments are human immunoglobulins (recipient antibody) or antigen-binding fragments in which residues from a complementary-determining region (CDR) of the recipient are replaced by residues from a CDR of a non-human species (donor antibody) such as mouse, rat or rabbit having the desired specificity, affinity, and capacity. In general, the humanized antibody antigen-binding fragments will comprise substantially all of at least one, and typically two, variable domains, in which all or substantially all of the CDR regions correspond to those of a non-human immunoglobulin and all or substantially all of the framework regions are those of a human immunoglobulin sequence. The humanized antibody antigen-binding fragments may include at least a portion of an immunoglobulin constant region (Fc), typically that of a human immunoglobulin.

GPRC5D-Binding Arm

The BCMAxGPRC5DxCD3-multispecific antibody described herein comprises an antigen-binding arm specific for GPRC5D. In some embodiments, the GPRC5D-binding arm binds human GPRC5D. In some embodiments, GPRC5D-binding arm binds human GPRC5D and cyno-molgus monkey GPRC5D, preferably the extracellular domain thereof. In some embodiments, GPRC5D-binding arm binds human GPRC5D but not to cynomolgus monkey GPRC5D. In some embodiments, the GPRC5D-binding arm binds to one or more residues of a polypeptide having the amino acid sequence of SEQ ID NO: 116.

Table 2 provides a summary of examples of some GPRC5D-specific antibodies described herein:

TABLE 2

CDR sequences of exemplary mAbs generated against human GPRC5D

| ID | HC-CDR1 | HC-CDR2 | HC-CDR3 | LC-CDR1 | LC-CDR2 | LC-CDR3 |
|---|---|---|---|---|---|---|
| GC5B680 | GFSLTNIRMSV S (SEQ ID NO: 12) | HIFSNDEKS (SEQ ID NO: 13) | MRLPYGMDV (SEQ ID NO: 14) | RSSQSLVHSDG NTYLS (SEQ ID NO: 9) | KISNRFF (SEQ ID NO: 10) | MQATQFPHT (SEQ ID NO: 11) |
| GC5B81 | SYAIS (SEQ ID NO 49) | GIIPIFGTANYA QKFQG (SEQ ID NO 53) | ESRWRGYKLD (SEQ ID NO 57) | RASQSISSYLN (SEQ ID NO 61) | AASSLQS (SEQ ID NO 64) | QQSYSTPLT (SEQ ID NO 67) |
| GC5B465 GC5B597 GC5B598 | NYWMS (SEQ ID NO 50) | GISYSGGSKYY ASSVKG (SEQ ID NO 54) | AAFDFGRRAV RLD (SEQ ID NO 58) | RASQSISSYLN (SEQ ID NO 61) | AASSLQS (SEQ ID NO 64) | QQSYSTPLT (SEQ ID NO 67) |

TABLE 2-continued

CDR sequences of exemplary mAbs generated against human GPRC5D

| ID | HC-CDR1 | HC-CDR2 | HC-CDR3 | LC-CDR1 | LC-CDR2 | LC-CDR3 |
|---|---|---|---|---|---|---|
| GC5B483 GC5B599 | SYFIG (SEQ ID NO 51) | IIYPGKSDTRYS PSFQG (SEQ ID NO 55) | VYSFGGRHKA LFDY (SEQ ID NO 59) | RASQSVSSYLA (SEQ ID NO 62) | DASNRAT (SEQ ID NO 65) | QQRSNWPLT (SEQ ID NO 68) |
| GC5B596 | GYTMN (SEQ ID NO 52) | LINPYNSDTNY AQKLQG (SEQ ID NO 56) | VALRVALDY (SEQ ID NO 60) | KASQNVATHV G (SEQ ID NO 63) | SASYRYS (SEQ ID NO 66) | QQYNRYPYT (SEQ ID NO 69) |
| GC5B382 | DYGMH (SEQ ID NO 70) | AIKYSGGSTYY ADSVKG (SEQ ID NO 77) | RAESGPGLDY (SEQ ID NO 84) | KSSQSVLYSSN NKNYLA (SEQ ID NO 91) | WASTRES (SEQ ID NO 93) | QQYYSTPLT (SEQ ID NO 95) |
| GC5B379 | NYWMS (SEQ ID NO 50) | GISYSGGSKYY ADSVKG (SEQ ID NO 78) | AAWDFGRRAV RLDY (SEQ ID NO 85) | RASQSISSYLN (SEQ ID NO 61) | AASSLQS (SEQ ID NO 64) | QQSYSTPLT (SEQ ID NO 67) |
| GC5B373 | SYWIG (SEQ ID NO 71) | IIYPGDSDTRYS PSFQG (SEQ ID NO 79) | IGFYGRSFRIFD Y (SEQ ID NO 86) | RASQSVSSYLA (SEQ ID NO 62) | DASNRAT (SEQ ID NO 65) | QQRSNWPLT (SEQ ID NO 68) |
| GC5B376 | SYWIG (SEQ ID NO 71) | IIYPGDSDTRYS PSFQG (SEQ ID NO 79) | VYSFGGRHKA LFDY (SEQ ID NO 59) | RASQSVSSYLA (SEQ ID NO 62) | DASNRAT (SEQ ID NO 65) | QQRSNWPLT (SEQ ID NO 68) |
| GC5B385 | GYAMS (SEQ ID NO 72) | AISGSGGSTYY ADSVKG (SEQ ID NO 80) | VDRSFGRSRYT LDY (SEQ ID NO 87) | RASQSVSSYLA (SEQ ID NO 62) | DASNRAT (SEQ ID NO 65) | QQRSNWPLT (SEQ ID NO 68) |
| GC5B370 | SYGIS (SEQ ID NO 73) | GIIPIFGNINYA QKFQG (SEQ ID NO 81) | VSRRFKRFAYY FDY (SEQ ID NO 88) | KSSQSVLYSSN NKNYLA (SEQ ID NO 91) | WASTRES (SEQ ID NO 93) | QQYYSTPLT (SEQ ID NO 95) |
| GC5B602 | GYSFTGYTMN (SEQ ID NO 74) | LINPYNGDTN (SEQ ID NO 82) | VALRVALDY (SEQ ID NO 60) | KASQNVATHV G (SEQ ID NO 63) | SASYRYS (SEQ ID NO 66) | QQYNRYPYT (SEQ ID NO 69) |
| GC5B603 | SYAMS (SEQ ID NO 75) | AISGSGGSTYY ADSVKG (SEQ ID NO 80) | SNFLPVVFDY (SEQ ID NO 89) | RASQSVRKSLA (SEQ ID NO 92) | TASNRAT (SEQ ID NO 94) | QQYFRAPIT (SEQ ID NO 96) |
| GC5B601 | GFSLTSYNVH (SEQ ID NO 76) | VIWAGGSTNY NSALMS (SEQ ID NO 83) | DGIRLRFAY (SEQ ID NO 90) | KASQNVATHV G (SEQ ID NO 63) | SASYRYS (SEQ ID NO 66) | QQYNRYPYT (SEQ ID NO 69) |

Characteristics of some GPRC5D-specific antibodies or antigen-binding fragments may be found in e.g., U.S. Pat. No. 10,562,968, United States Published Application US2020/0231686, the content of each of which is herein incorporated by reference in its entirety.

In some embodiments, the GPRC5D-binding arm comprises a heavy chain variable domain comprising a heavy chain CDR1, CDR2, and CDR3 of any one of the antibodies described in Table 2. In some embodiments, the GPRC5D-binding arm comprises a light chain variable domain comprising a light chain CDR1, a CDR2, and a CDR3 of any one of the antibodies described in Table 2. In some embodiments, the GPRC5D-binding arm comprises a heavy chain variable domain comprising a heavy chain CDR1, CDR2, and CDR3 of any one of the antibodies described in Table 2 and a light chain variable domain comprising a light chain CDR1, CDR2, and CDR3 of any one of the antibodies described in Table 2. In some embodiments, the GPRC5D-binding arm competes for binding to GPRC5D with an antibody or antigen-binding comprising a heavy chain comprising a heavy chain CDR1, a CDR2, and a CDR3 of any one of the antibodies described in Table 2 and a light chain comprising a light chain CDR1, a CDR2, and a CDR3 of any one of the antibodies described in Table 2.

In some embodiments, the GPRC5D-binding arm comprises a heavy chain comprising a heavy chain CDR1, CDR2, and CDR3 of any one of the antibodies described in Table 2. In some embodiments, the GPRC5D-binding arm comprises a light chain comprising a light chain CDR1, CDR2, and CDR3 of any one of the antibodies described in Table 2. In some embodiments, the GPRC5D-binding arm comprises a heavy chain comprising a heavy chain CDR1, CDR2, and CDR3 of any one of the antibodies described in Table 2 and a light chain comprising a light chain CDR1, CDR2, and CDR3 of any one of the antibodies described in Table 2.

In some embodiments, the GPRC5D-binding arm comprises a heavy chain CDR1, CDR2, and CDR3 derived from an antibody clone as described in Table 2. In some embodiments, the GPRC5D-binding arm comprises a light chain CDR1, CDR2, and CDR3 derived from an antibody clone as described in Table 2. In some embodiments, the GPRC5D-binding arm comprises heavy chain CDR1, CDR2, and CDR3 and light chain CDR1, CDR2, and CDR3 derived from an antibody clone as described in Table 2. In some embodiments, the GPRC5D-binding arm comprises heavy chain CDR1, CDR2, and CDR3 of clone GC5B680, GC5B81, GC5B465, GS5B483, GC5B596, GC5B382, GC5B379, GC5B373, GC5B376, GC5B385, GC5B370, GC5B602, GC5B603, GC5B599, GC5B601, GC5B598, or GC5B597. In some embodiments, the GPRC5D-binding arm comprises heavy chain CDR1, CDR2, and CDR3 and light chain CDR1, CDR2, and CDR3 of clone GC5B680, GC5B81, GC5B465, GS5B483, GC5B596, GC5B382, GC5B379, GC5B373, GC5B376, GC5B385, GC5B370, GC5B602, GC5B603, GC5B599, GC5B601, GC5B598, or GC5B597. In one embodiment, the GPRC5D-binding arm comprises heavy chain CDR1, CDR2, and CDR3 and light chain CDR1, CDR2, and CDR3 of clone GC5B680.

In some exemplary embodiments, the GPRC5D-binding arm comprises a heavy chain variable domain derived from an antibody clone as described in Table 2. In some exemplary embodiments, the GPRC5D-binding arm comprises heavy chain variable domain and light chain variable domain derived from an antibody clone as described in Table 2. In some exemplary embodiments, the GPRC5D-binding arm comprises heavy chain variable domain and light chain variable domain of clone GC5B680, GC5B81, GC5B465, GS5B483, GC5B596, GC5B382, GC5B379, GC5B373, GC5B376, GC5B385, GC5B370, GC5B602, GC5B603, GC5B599, GC5B601, GC5B598, or GC5B597. In one embodiment, the GPRC5D-binding arm comprises heavy chain variable domain and light chain variable domain of clone GC5B680. In some embodiments, the GPRC5D-specific antibody clone may induce ADCC in vitro with an $EC_{50}$ of 28 nM or less.

In some embodiments, the GPRC5D-binding arm comprises a heavy chain CDR1 comprising SEQ ID NO: 12, a heavy chain CDR2 comprising SEQ ID NO: 13, and a heavy chain CDR3 comprising SEQ ID NO: 14. In some embodiments, the GPRC5D-binding arm comprises a heavy chain CDR1 comprising SEQ ID NO: 12, a heavy chain CDR2 comprising SEQ ID NO: 13, a heavy chain CDR3 comprising SEQ ID NO: 14, a light chain CDR1 comprising SEQ ID NO: 9, a light chain CDR2 comprising SEQ ID NO: 10, and a light chain CDR3 comprising SEQ ID NO: 11. The GPRC5D-binding arm may comprise human framework sequences. In some embodiments, the GPRC5D-binding arm comprises a heavy chain variable domain substantially the same as, or identical to, SEQ ID NO: 16. In some embodiments, the GPRC5D-binding arm comprises a heavy chain variable domain substantially the same as, or identical to, SEQ ID NO: 16 and a light chain variable domain substantially the same as, or identical to, SEQ ID NO: 15.

In some embodiments, the GPRC5D-binding arm comprises a heavy chain CDR1 comprising SEQ ID NO: 49, a heavy chain CDR2 comprising SEQ ID NO: 53, and a heavy chain CDR3 comprising SEQ ID NO: 57. In some embodiments, the GPRC5D-binding arm comprises a heavy chain CDR1 comprising SEQ ID NO: 49, a heavy chain CDR2 comprising SEQ ID NO: 53, a heavy chain CDR3 comprising SEQ ID NO: 57, a light chain CDR1 comprising SEQ ID NO: 61, a light chain CDR2 comprising SEQ ID NO: 64, and a light chain CDR3 comprising SEQ ID NO: 67. The GPRC5D-binding arm may comprise human framework sequences. In some embodiments, the GPRC5D-binding arm comprises a heavy chain variable domain substantially the same as, or identical to, SEQ ID NO: 97. In some embodiments, the GPRC5D-binding arm comprises a heavy chain variable domain substantially the same as, or identical to, SEQ ID NO: 97 and a light chain variable domain substantially the same as, or identical to, SEQ ID NO: 101.

In some embodiments, the GPRC5D-binding arm comprises a heavy chain CDR1 comprising SEQ ID NO: 50, a heavy chain CDR2 comprising SEQ ID NO: 54, and a heavy chain CDR3 comprising SEQ ID NO: 58. In some embodiments, the GPRC5D-binding arm comprises a heavy chain CDR1 comprising SEQ ID NO: 50, a heavy chain CDR2 comprising SEQ ID NO: 54, a heavy chain CDR3 comprising SEQ ID NO: 58, a light chain CDR1 comprising SEQ ID NO: 61, a light chain CDR2 comprising SEQ ID NO: 64, and a light chain CDR3 comprising SEQ ID NO: 67. The GPRC5D-binding arm may comprise human framework sequences. In some embodiments, the GPRC5D-binding arm comprises a heavy chain variable domain substantially the same as, or identical to, SEQ ID NO: 98. In some embodiments, the GPRC5D-binding arm comprises a heavy chain variable domain substantially the same as, or identical to, SEQ ID NO: 98 and a light chain variable domain substantially the same as, or identical to, SEQ ID NO: 101.

In some embodiments, the GPRC5D-binding arm comprises a heavy chain CDR1 comprising SEQ ID NO: 51, a heavy chain CDR2 comprising SEQ ID NO: 55, and a heavy chain CDR3 comprising SEQ ID NO: 59. In some embodiments, the GPRC5D-binding arm comprises a heavy chain CDR1 comprising SEQ ID NO: 51, a heavy chain CDR2 comprising SEQ ID NO: 55, a heavy chain CDR3 comprising SEQ ID NO: 59, a light chain CDR1 comprising SEQ ID NO: 62, a light chain CDR2 comprising SEQ ID NO: 65, and a light chain CDR3 comprising SEQ ID NO: 68. The GPRC5D-binding arm may comprise human framework sequences. In some embodiments, the GPRC5D-binding arm comprises a heavy chain variable domain substantially the same as, or identical to, SEQ ID NO: 99. In some embodiments, the GPRC5D-binding arm comprises a heavy chain variable domain substantially the same as, or identical to, SEQ ID NO: 99 and a light chain variable domain substantially the same as, or identical to, SEQ ID NO: 102.

In some embodiments, the GPRC5D-binding arm comprises a heavy chain CDR1 comprising SEQ ID NO: 52, a heavy chain CDR2 comprising SEQ ID NO: 56, and a heavy chain CDR3 comprising SEQ ID NO: 60. In some embodiments, the GPRC5D-binding arm comprises a heavy chain CDR1 comprising SEQ ID NO: 52, a heavy chain CDR2 comprising SEQ ID NO: 56, a heavy chain CDR3 comprising SEQ ID NO: 60, a light chain CDR1 comprising SEQ ID NO: 63, a light chain CDR2 comprising SEQ ID NO: 66, and a light chain CDR3 comprising SEQ ID NO: 69. The GPRC5D-binding arm may comprise human framework sequences. In some embodiments, the GPRC5D-binding arm comprises a heavy chain variable domain substantially the same as, or identical to, SEQ ID NO: 100. In some embodiments, the GPRC5D-binding arm comprises a heavy chain variable domain substantially the same as, or identical to, SEQ ID NO: 100 and a light chain variable domain substantially the same as, or identical to, SEQ ID NO: 103.

In some embodiments, the GPRC5D-binding arm comprises a heavy chain CDR1 comprising SEQ ID NO: 70, a heavy chain CDR2 comprising SEQ ID NO: 77, and a heavy chain CDR3 comprising SEQ ID NO: 84. In some embodiments, the GPRC5D-binding arm comprises a heavy chain CDR1 comprising SEQ ID NO: 70, a heavy chain CDR2 comprising SEQ ID NO: 77, a heavy chain CDR3 comprising SEQ ID NO: 84, a light chain CDR1 comprising SEQ ID NO: 91, a light chain CDR2 comprising SEQ ID NO: 93, and a light chain CDR3 comprising SEQ ID NO: 95. The GPRC5D-binding arm may comprise human framework sequences. In some embodiments, the GPRC5D-binding arm comprises a heavy chain variable domain substantially the same as, or identical to, SEQ ID NO: 104. In some embodiments, the GPRC5D-binding arm comprises a heavy chain variable domain substantially the same as, or identical to, SEQ ID NO: 104 and a light chain variable domain substantially the same as, or identical to, SEQ ID NO: 113.

In some embodiments, the GPRC5D-binding arm comprises a heavy chain CDR1 comprising SEQ ID NO: 50, a heavy chain CDR2 comprising SEQ ID NO: 78, and a heavy chain CDR3 comprising SEQ ID NO: 85. In some embodiments, the GPRC5D-binding arm comprises a heavy chain CDR1 comprising SEQ ID NO: 50, a heavy chain CDR2 comprising SEQ ID NO: 78, a heavy chain CDR3 comprising SEQ ID NO: 85, a light chain CDR1 comprising SEQ ID NO: 61, a light chain CDR2 comprising SEQ ID NO: 64, and a light chain CDR3 comprising SEQ ID NO: 67. The GPRC5D-binding arm may comprise human framework sequences. In some embodiments, the GPRC5D-binding arm comprises a heavy chain variable domain substantially the same as, or identical to, SEQ ID NO: 105. In some embodiments, the GPRC5D-binding arm comprises a heavy chain variable domain substantially the same as, or identical to, SEQ ID NO: 105 and a light chain variable domain substantially the same as, or identical to, SEQ ID NO: 101.

In some embodiments, the GPRC5D-binding arm comprises a heavy chain CDR1 comprising SEQ ID NO: 71, a heavy chain CDR2 comprising SEQ ID NO: 79, and a heavy chain CDR3 comprising SEQ ID NO: 86. In some embodiments, the GPRC5D-binding arm comprises a heavy chain CDR1 comprising SEQ ID NO: 71, a heavy chain CDR2 comprising SEQ ID NO: 79, a heavy chain CDR3 comprising SEQ ID NO: 86, a light chain CDR1 comprising SEQ ID NO: 62, a light chain CDR2 comprising SEQ ID NO: 65, and a light chain CDR3 comprising SEQ ID NO: 68. The GPRC5D-binding arm may comprise human framework sequences. In some embodiments, the GPRC5D-binding arm comprises a heavy chain variable domain substantially the same as, or identical to, SEQ ID NO: 106. In some embodiments, the GPRC5D-binding arm comprises a heavy chain variable domain substantially the same as, or identical to, SEQ ID NO: 106 and a light chain variable domain substantially the same as, or identical to, SEQ ID NO: 102.

In some embodiments, the GPRC5D-binding arm comprises a heavy chain CDR1 comprising SEQ ID NO: 71, a heavy chain CDR2 comprising SEQ ID NO: 79, and a heavy chain CDR3 comprising SEQ ID NO: 59. In some embodiments, the GPRC5D-binding arm comprises a heavy chain CDR1 comprising SEQ ID NO: 71, a heavy chain CDR2 comprising SEQ ID NO: 79, a heavy chain CDR3 comprising SEQ ID NO: 59, a light chain CDR1 comprising SEQ ID NO: 62, a light chain CDR2 comprising SEQ ID NO: 65, and a light chain CDR3 comprising SEQ ID NO: 68. The GPRC5D-binding arm may comprise human framework sequences. In some embodiments, the GPRC5D-binding arm comprises a heavy chain variable domain substantially the same as, or identical to, SEQ ID NO: 107. In some embodiments, the GPRC5D-binding arm comprises a heavy chain variable domain substantially the same as, or identical to, SEQ ID NO: 107 and a light chain variable domain substantially the same as, or identical to, SEQ ID NO: 102.

In some embodiments, the GPRC5D-binding arm comprises a heavy chain CDR1 comprising SEQ ID NO: 72, a heavy chain CDR2 comprising SEQ ID NO: 80, and a heavy chain CDR3 comprising SEQ ID NO: 87. In some embodiments, the GPRC5D-binding arm comprises a heavy chain CDR1 comprising SEQ ID NO: 72, a heavy chain CDR2 comprising SEQ ID NO: 80, a heavy chain CDR3 comprising SEQ ID NO: 87, a light chain CDR1 comprising SEQ ID NO: 62, a light chain CDR2 comprising SEQ ID NO: 65, and a light chain CDR3 comprising SEQ ID NO: 68. The GPRC5D-binding arm may comprise human framework sequences. In some embodiments, the GPRC5D-binding arm comprises a heavy chain variable domain substantially the same as, or identical to, SEQ ID NO: 108. In some embodiments, the GPRC5D-binding arm comprises a heavy chain variable domain substantially the same as, or identical to, SEQ ID NO: 108 and a light chain variable domain substantially the same as, or identical to, SEQ ID NO: 102.

In some embodiments, the GPRC5D-binding arm comprises a heavy chain CDR1 comprising SEQ ID NO: 73, a heavy chain CDR2 comprising SEQ ID NO: 81, and a heavy chain CDR3 comprising SEQ ID NO: 88. In some embodiments, the GPRC5D-binding arm comprises a heavy chain CDR1 comprising SEQ ID NO: 73, a heavy chain CDR2 comprising SEQ ID NO: 81, a heavy chain CDR3 comprising SEQ ID NO: 88, a light chain CDR1 comprising SEQ ID NO: 91, a light chain CDR2 comprising SEQ ID NO: 93, and a light chain CDR3 comprising SEQ ID NO: 95. The GPRC5D-binding arm may comprise human framework sequences. In some embodiments, the GPRC5D-binding arm comprises a heavy chain variable domain substantially the same as, or identical to, SEQ ID NO: 109. In some embodiments, the GPRC5D-binding arm comprises a heavy chain variable domain substantially the same as, or identical to, SEQ ID NO: 109 and a light chain variable domain substantially the same as, or identical to, SEQ ID NO: 113.

In some embodiments, the GPRC5D-binding arm comprises a heavy chain CDR1 comprising SEQ ID NO: 74, a heavy chain CDR2 comprising SEQ ID NO: 82, and a heavy chain CDR3 comprising SEQ ID NO: 60. In some embodiments, the GPRC5D-binding arm comprises a heavy chain CDR1 comprising SEQ ID NO: 74, a heavy chain CDR2 comprising SEQ ID NO: 82, a heavy chain CDR3 comprising SEQ ID NO: 60, a light chain CDR1 comprising SEQ ID NO: 63, a light chain CDR2 comprising SEQ ID NO: 66, and a light chain CDR3 comprising SEQ ID NO: 69. The GPRC5D-binding arm may comprise human framework sequences. In some embodiments, the GPRC5D-binding arm comprises a heavy chain variable domain substantially the same as, or identical to, SEQ ID NO: 110. In some embodiments, the GPRC5D-binding arm comprises a heavy chain variable domain substantially the same as, or identical to, SEQ ID NO: 110 and a light chain variable domain substantially the same as, or identical to, SEQ ID NO: 103.

In some embodiments, the GPRC5D-binding arm comprises a heavy chain CDR1 comprising SEQ ID NO: 75, a heavy chain CDR2 comprising SEQ ID NO: 80, and a heavy chain CDR3 comprising SEQ ID NO: 89. In some embodiments, the GPRC5D-binding arm comprises a heavy chain CDR1 comprising SEQ ID NO: 75, a heavy chain CDR2 comprising SEQ ID NO: 80, a heavy chain CDR3 comprising SEQ ID NO: 89, a light chain CDR1 comprising SEQ ID NO: 92, a light chain CDR2 comprising SEQ ID NO: 94, and a light chain CDR3 comprising SEQ ID NO: 96. The GPRC5D-binding arm may comprise human framework sequences. In some embodiments, the GPRC5D-binding arm comprises a heavy chain variable domain substantially the same as, or identical to, SEQ ID NO: 111. In some embodiments, the GPRC5D-binding arm comprises a heavy chain variable domain substantially the same as, or identical to, SEQ ID NO: 111 and a light chain variable domain substantially the same as, or identical to, SEQ ID NO: 114.

In some embodiments, the GPRC5D-binding arm comprises a heavy chain CDR1 comprising SEQ ID NO: 76, a heavy chain CDR2 comprising SEQ ID NO: 83, and a heavy chain CDR3 comprising SEQ ID NO: 90. In some embodiments, the GPRC5D-binding arm comprises a heavy chain CDR1 comprising SEQ ID NO: 76, a heavy chain CDR2 comprising SEQ ID NO: 83, a heavy chain CDR3 comprising SEQ ID NO: 90, a light chain CDR1 comprising SEQ ID NO: 63, a light chain CDR2 comprising SEQ ID NO: 66, and a light chain CDR3 comprising SEQ ID NO: 69. The GPRC5D-binding arm may comprise human framework sequences. In some embodiments, the GPRC5D-binding arm comprises a heavy chain variable domain substantially the same as, or identical to, SEQ ID NO: 112. In some embodiments, the GPRC5D-binding arm comprises a heavy chain variable domain substantially the same as, or identical to, SEQ ID NO: 112 and a light chain variable domain substantially the same as, or identical to, SEQ ID NO: 115.

The GPRC5D-binding arm may be derived from any species by recombinant means. For example, the GPRC5D antigen-binding arm may be derived from mouse, rat, goat, horse, swine, bovine, chicken, rabbit, camelid, donkey, human, or chimeric versions thereof. For use in administration to humans, non-human derived antigen-binding fragments may be genetically or structurally altered to be less antigenic upon administration to a human patient. In some embodiments, the GPRC5D-binding arm comprises antigen-binding fragments which is chimeric.

In some embodiments, the GPRC5D-binding arm comprises humanized antigen-binding fragments. Humanized antigen-binding fragments may be derived from chimeric immunoglobulins, immunoglobulin chains or fragments thereof (such as Fv, Fab, Fab', F(ab')2 or other antigen-binding subsequences of antibodies) that contain minimal sequence derived from non-human immunoglobulin. For the most part, humanized antibodies or antigen-binding fragments are human immunoglobulins (recipient antibody) or antigen-binding fragments in which residues from a complementary-determining region (CDR) of the recipient are replaced by residues from a CDR of a non-human species (donor antibody) such as mouse, rat or rabbit having the desired specificity, affinity, and capacity. In general, the humanized antibody antigen-binding fragments will comprise substantially all of at least one, and typically two, variable domains, in which all or substantially all of the CDR regions correspond to those of a non-human immunoglobulin and all or substantially all of the framework regions are those of a human immunoglobulin sequence. The humanized antibody antigen-binding fragments may include at least a portion of an immunoglobulin constant region (Fc), typically that of a human immunoglobulin.

CD3-Binding Arm

The BCMA×GPRC5D×CD3-multispecific antibodies described herein comprise an antigen-binding arm that binds CD3. In some embodiments, the CD3-binding arm binds human CD3. In some preferred embodiments, the CD3-specific arm of the BCMA×GPRC5D×CD3 multispecific antibody is derived from a CD3-specific antibody that binds and activates human primary T cells and/or cynomolgus monkey primary T cells. In some embodiments, the CD3-binding arm binds to an epitope at the N-terminus of CD3ε.

In some embodiments, the CD3-binding arm binds to residues 22-35 (QDGNEEMGGITQTP (SEQ ID NO: 160)) of the CD3ε chain.

The CD3-binding arm may bind to CD3 with an affinity of $5 \times 10^{-7}$M or less, such as $1 \times 10^{-7}$M or less, $5 \times 10^{-8}$M or less, $1 \times 10^{-8}$M or less, $5 \times 10^{-9}$M or less, or $1 \times 10^{-9}$M or less. In some embodiments, the CD3-binding arm binds to the CD3 with an affinity of about $1 \times 10^{-8}$M, about $2 \times 10^{-8}$M, about $3 \times 10^{-8}$M, about $4 \times 10^{-8}$M, about $5 \times 10^{-8}$M, about $6 \times 10^{-8}$M, about $7 \times 10^{-8}$M, about $8 \times 10^{-8}$M, about $9 \times 10^{-8}$M, or about $1 \times 10^{-8}$M. In some embodiments, the CD3-binding arm binds to the CD3 with an affinity of about $1 \times 10^{-8}$M to about $3 \times 10^{-8}$M, about $2 \times 10^{-8}$M to about $4 \times 10^{-8}$M, about $1 \times 10^{-8}$M to about $5 \times 10^{-8}$M, about $2 \times 10^{-8}$M to about $6 \times 10^{-8}$M, or about $3 \times 10^{-8}$M to about $8 \times 10^{-8}$M. In one embodiment, the CD3-binding arm binds to the CD3 with an affinity of about $2.5 \times 10^{-8}$M. In one embodiment, the CD3-binding arm binds to the CD3 with an affinity of about $3.1 \times 10^{-8}$M.

Human CD3ε is described under UniProt P07766 (CD3E_HUMAN). An anti CD3ε antibody described in the state of the art is SP34 (Yang S J, The Journal of Immunology (1986) 137; 1097-1100). SP34 reacts with both primate and human CD3. SP34 is available from Pharmingen. A further anti CD3 antibody described in the state of the art is UCHT-1 (see WO2000041474). A further anti-CD3 antibody described in the state of the art is BC-3 (Fred Hutchinson Cancer Research Institute; used in Phase I/II trials of GvHD, Anasetti et al., Transplantation 54: 844 (1992)). SP34 differs from UCHT-1 and BC-3 in that SP-34 recognizes an epitope present on solely the F chain of CD3 (see Salmeron et al., (1991) J. Immunol. 147: 3047) whereas UCHT-1 and BC-3 recognize an epitope contributed by both the ε and γ chains. The sequence of an antibody with the same sequence as of antibody SP34 is mentioned in WO2008119565, WO2008119566, WO2008119567, WO2010037836, WO2010037837 and WO2010037838. A sequence which is 96% identical to VH of antibody SP34 is mentioned in U.S. Pat. No. 8,236,308 (WO2007042261).

In some embodiments, the CD3-binding arm contacts an epitope including the six N-terminal amino acids of CD3ε. In some embodiments, the CD3-specific binding arm of the multispecific antibody is derived from the mouse monoclonal antibody SP34, a mouse IgG3/lambda isotype. In some embodiments, the CD3-binding arm comprises the CDRs of antibody SP34. Such CD3-binding arms may bind to CD3 with an affinity of $5 \times 10^{-7}$M or less, such as $1 \times 10^{-7}$M or less, $5 \times 10^{-8}$M or less, $1 \times 10^{-8}$M or less, $5 \times 10^{-9}$M or less, or $1 \times 10^{-9}$M or less. The CD3-specific binding arm may be a humanized version of an arm of mouse monoclonal antibody SP34. Human framework adaptation (HFA) may be used to humanize the anti-CD3 antibody from which the CD3-specific arm is derived.

Table 3 provides a summary of examples of some CD3-specific antibodies described herein:

TABLE 3

Heavy chains and light chains of exemplary CD3-specific antibodies and antigen-binding fragments

| | Heavy Chain | Light Chain |
|---|---|---|
| CD3B376 | CDR 1: GDSVFNNNAAWS (SEQ ID NO: 4)<br>CDR 2: RTYYRSKWLYD (SEQ ID NO: 5)<br>CDR 3: GYSSSFDY (SEQ ID NO: 6)<br>VH:<br>QVQLQQSGPRLVRPSQTLSLTCAISGDSVFNNNA<br>AWSWIRQSPSRGLEWLGRTYYRSKWLYDYAVS<br>VKSRITVNPDTSRNQFTLQLNSVTPEDTALYYCA | CDR 1: TGTSSNIGTYKFVS (SEQ ID NO: 1)<br>CDR 2: EVSKRPS (SEQ ID NO: 2)<br>CDR 3: VSYAGSGTLL (SEQ ID NO: 3)<br>VL:<br>QSALTQPASVSGSPGQSITISCTGTSSNIGTYK<br>FVSWYQQHPDKAPKVLLYEVSKRPSGVSSR<br>FSGSKSGNTASLTISGLQAEDQADYHCVSYA |

TABLE 3-continued

Heavy chains and light chains of exemplary CD3-specific antibodies and
antigen-binding fragments

| Heavy Chain | Light Chain |
|---|---|
| RGYSSSFDYWGQGTLVTVSS (SEQ ID NO: 8)<br>Heavy chain:<br>QVQLQQSGPRLVRPSQTLSLTCAISGDSVFNNNA<br>AWSWIRQSPSRGLEWLGRTYYRSKWLYDYAVS<br>VKSRITVNPDTSRNQFTLQLNSVTPEDTALYYCA<br>RGYSSSFDYWGQGTLVTVSSASTKGPSVFPLAPS<br>SKSTSGGTAALGCLVKDYFPEPVTVSWNSGALT<br>SGVHTFPAVLQSSGLYSLSSVVTVPSSSLGTQTYI<br>CNVNHKPSNTKVDKKVEPKSCDKTHTCPPCPAP<br>EAAGGPSVFLFPPKPKDTLMISRTPEVTCVVVSV<br>SHEDPEVKFNWYVDGVEVHNAKTKPREEQYNS<br>TYRVVSVLTVLHQDWLNGKEYKCKVSNKALPA<br>PIEKTISKAKGQPREPQVYTLPPSREEMTKNQVSL<br>SCAVKGFYPSDIAVEWESNGQPENNYKTTPPVL<br>DSDGSFFLVSKLTVDKSRWQQGNVFSCSVMHEA<br>LHNRFTQKSLSLSPGK (SEQ ID NO: 26) | GSGTLLFGGGTKLTVL (SEQ ID NO: 7)<br>Light chain:<br>QSALTQPASVSGSPGQSITISCTGTSSNIGTYK<br>FVSWYQQHPDKAPKVLLYEVSKRPSGVSSR<br>FSGSKSGNTASLTISGLQAEDQADYHCVSYA<br>GSGTLLFGGGTKLTVLGQPKAAPSVTLFPPS<br>SEELQANKATLVCLISDFYPGAVTVAWKAD<br>SSPVKAGVETTTPSKQSNNKYAASSYLSLTP<br>EQWKSHRSYSCQVTHEGSTVEKTVAPTECS<br>(SEQ ID NO: 27) |
| CD3B219 CDR 1: TYAMN (SEQ ID NO: 117)<br><br>CDR 2: RIRSKYNNYATYYAASVKG (SEQ ID NO: 118)<br>CDR 3: HGNFGNSYVSWFAY (SEQ ID NO: 119)<br>VH:<br>EVQLVESGGGLVQPGGSLRLSCAASGFTFNTYA<br>MNWVRQAPGKGLEWVARIRSKYNNYATYYAA<br>SVKGRFTISRDDSKNSLYLQMNSLKTEDTAVYY<br>CARHGNFGNSYVSWFAYWGQGTLVTVSS (SEQ ID NO: 120)<br>Heavy chain:<br>EVQLVESGGGLVQPGGSLRLSCAASGFTFNTYA<br>MNWVRQAPGKGLEWVARIRSKYNNYATYYAA<br>SVKGRFTISRDDSKNSLYLQMNSLKTEDTAVYY<br>CARHGNFGNSYVSWFAYWGQGTLVTVSSASTK<br>GPSVFPLAPCSRSTSESTAALGCLVKDYFPEPVTV<br>SWNSGALTSGVHTFPAVLQSSGLYSLSSVVTVPS<br>SSLGTKTYTCNVDHKPSNTKVDKRVESKYGPPC<br>PPCPAPEAAGGPSVFLFPPKPKDTLMISRTPEVTC<br>VVVDVSQEDPEVQFNWYVDGVEVHNAKTKPRE<br>EQFNSTYRVVSVLTVLHQDWLNGKEYKCKVSN<br>KGLPSSIEKTISKAKGQPREPQVYTLPPSQEEMTK<br>NQVSLTCLVKGFYPSDIAVEWESNGQPENNYKT<br>TPPVLDSDGSFLLYSKLTVDKSRWQEGNVFSCSV<br>MHEALHNHYTQKSLSLSLGK (SEQ ID NO: 121) | CDR 1: RSSTGAVTTSNYAN (SEQ ID NO: 122)<br>CDR 2: GTNKRAP (SEQ ID NO: 123)<br><br>CDR 3: ALWYSNLWV (SEQ ID NO: 124)<br>VL:<br>QTVVTQEPSLTVSPGGTVTLTCRSSTGAVTT<br>SNYANWVQQKPGQAPRGLIGGTNKRAPGTP<br>ARFSGSLLGGKAALTLSGVQPEDEAEYYCA<br>LWYSNLWVFGGGTKLTVL (SEQ ID NO: 125)<br><br>Light chain:<br>QTVVTQEPSLTVSPGGTVTLTCRSSTGAVTT<br>SNYANWVQQKPGQAPRGLIGGINKRAPGTP<br>ARFSGSLLGGKAALTLSGVQPEDEAEYYCA<br>LWYSNLWVFGGGTKLTVLGQPKAAPSVTLF<br>PPSSEELQANKATLVCLISDFYPGAVTVAWK<br>ADSSPVKAGVETTTPSKQSNNKYAASSYLSL<br>TPEQWKSHRSYSCQVTHEGSTVEKTVAPTE<br>CS (SEQ ID NO: 126) |

Characteristics of some CD3-specific antibodies or antigen-binding fragments may be found in e.g., U.S. Pat. Nos. 10,562,968 and 10,072,088, United States Published Application US2019/0382481, the content of each of which is herein incorporated by reference in its entirety.

In some embodiments, the CD3-binding arm comprises a heavy chain variable domain comprising a heavy chain CDR1, CDR2, and CDR3 of any one of the antibodies described in Table 3. In some embodiments, the CD3-binding arm comprises a light chain variable domain comprising a light chain CDR1, CDR2, and CDR3 of any one of the antibodies described in Table 3. In some embodiments, the CD3-binding arm comprises a heavy chain variable domain comprising a heavy chain CDR1, CDR2, and CDR3 of any one of the antibodies described in Table 3 and a light chain variable domain comprising a light chain CDR1, CDR2, and CDR3 of any one of the antibodies described in Table 3. In some embodiments, the CD3-binding arm competes for binding to CD3 with an antibody or antigen-binding comprising a heavy chain comprising a heavy chain CDR1, CDR2, and CDR3 of any one of the antibodies described in Table 3 and a light chain comprising a light chain CDR1, CDR2, and CDR3 of any one of the antibodies described in Table 3.

In some embodiments, the CD3-binding arm comprises a heavy chain comprising a heavy chain CDR1, CDR2, and CDR3 of any one of the antibodies described in Table 3. In some embodiments, the CD3-binding arm comprises a light chain comprising a light chain CDR1, CDR2, and CDR3 of any one of the antibodies described in Table 3. In some embodiments, the CD3-binding arm comprises a heavy chain comprising a heavy chain CDR1, CDR2, and CDR3 of any one of the antibodies described in Table 3 and a light chain comprising a light chain CDR1, CDR2, and CDR3 of any one of the antibodies described in Table 3.

In some embodiments, the CD3-binding arm comprises a heavy chain CDR1, CDR2, and CDR3 of any one of the antibodies described in Table 3. In some embodiments, the CD3-binding arm comprises a light chain CDR1, CDR2, and CDR3 of any one of the antibodies described in Table 3. In some embodiments, the CD3-binding arm comprises a heavy chain comprising a CDR1, a CDR2, and a CDR3 of any one of the antibodies described in Table 3 and a light chain comprising a CDR1, a CDR2, and a CDR3 of any one of the antibodies described in Table 3. In some embodiments of the multispecific antibodies, the CD3-binding arm comprises a heavy chain and light chain pair selected from Table 3. In some embodiments, the GPRC5D-binding arm comprises heavy chain CDR1, CDR2, and CDR3 and light chain CDR1, CDR2, and CDR3 of clone CD3B376. In some embodiments, the GPRC5D-binding arm comprises heavy chain CDR1, CDR2, and CDR3 and light chain CDR1, CDR2, and CDR3 of clone CD3B219.

In some embodiments, the CD3-binding arm comprises a heavy chain CDR1 comprising SEQ ID NO: 4, a heavy chain CDR2 comprising SEQ ID NO: 5, and a heavy chain CDR3 comprising SEQ ID NO: 6. In some embodiments, the CD3-binding arm comprises a heavy chain CDR1 comprising SEQ ID NO: 4, a heavy chain CDR2 comprising SEQ ID NO: 5, a heavy chain CDR3 comprising SEQ ID NO: 6, a light chain CDR1 comprising SEQ ID NO: 1, a light chain CDR2 comprising SEQ ID NO: 2, and a light chain CDR3 comprising SEQ ID NO: 3. The CD3-binding arm may comprise human framework sequences. In some embodiments, the CD3-binding arm comprises a heavy chain variable domain substantially the same as, or identical to, SEQ ID NO: 8. In some embodiments, the CD3-binding arm comprises a heavy chain variable domain substantially the same as, or identical to, SEQ ID NO: 8 and a light chain variable domain substantially the same as, or identical to, SEQ ID NO: 7. In some embodiments, the CD3-binding arm comprises a heavy chain substantially the same as, or identical to, SEQ ID NO: 26. In some embodiments, the CD3-binding arm comprises a heavy chain substantially the same as, or identical to, SEQ ID NO: 26 and a light chain substantially the same as, or identical to, SEQ ID NO: 27.

In some embodiments, the CD3-binding arm comprises a heavy chain CDR1 comprising SEQ ID NO: 117, a heavy chain CDR2 comprising SEQ ID NO: 118, and a heavy chain CDR3 comprising SEQ ID NO: 119. In some embodiments, the CD3-binding arm comprises a heavy chain CDR1 comprising SEQ ID NO: 117, a heavy chain CDR2 comprising SEQ ID NO: 118, a heavy chain CDR3 comprising SEQ ID NO: 119, a light chain CDR1 comprising SEQ ID NO: 123, a light chain CDR2 comprising SEQ ID NO: 124, and a light chain CDR3 comprising SEQ ID NO: 125. The CD3-binding arm may comprise human framework sequences. In some embodiments, the CD3-binding arm comprises a heavy chain variable domain substantially the same as, or identical to, SEQ ID NO: 120. In some embodiments, the CD3-binding arm comprises a heavy chain variable domain substantially the same as, or identical to, SEQ ID NO: 120 and a light chain variable domain substantially the same as, or identical to, SEQ ID NO: 125. In some embodiments, the CD3-binding arm comprises a heavy chain substantially the same as, or identical to, SEQ ID NO: 121. In some embodiments, the CD3-binding arm comprises a heavy chain substantially the same as, or identical to, SEQ ID NO: 121 and a light chain substantially the same as, or identical to, SEQ ID NO: 126.

In some embodiments, the CDRs of the heavy chain and/or the light chain are derived from known anti-CD3 antibodies, such as, for example, muromonab-CD3 (OKT3), otelixizumab (TRX4), teplizumab (MGA031), visilizumab (Nuvion), TR-66 or X35-3, VIT3, BMA030 (BW264/56), CLB-T3/3, CRIS7, YTH12.5, Fl 11-409, CLB-T3.4.2, TR-66, WT32, SPv-T3b, 11D8, XIII-141, XIII-46, XIII-87, 12F6, T3/RW2-8C8, T3/RW2-4B6, OKT3D, M-T301, SMC2, F101.01, UCHT-1 and WT-31.

In some embodiments, the CD3-binding arm is IgG, or a derivative thereof. In some embodiments, the CD3-binding arm is IgG1, IgG2, IgG3, or IgG4. In some embodiments where in the CD3-binding arm has an IgG4 isotype, it contains S228P, L234A, L235A, F405L, and R409K substitution(s) in its Fc region. In some embodiments, the antibodies or antigen-binding fragments bind CD3ε on primary human T cells. In some embodiments, the antibodies or antigen-binding fragments bind CD3ε on primary cynomolgus T cells. In some embodiments, the antibodies or antigen-binding fragments bind CD3ε on primary human and cynomolgus T cells. In some embodiments, the antibodies or antigen-binding fragments activate primary human CD3+ T cells. In some embodiments, the antibodies or antigen-binding fragments activate primary cynomolgus CD4+ T cells.

In some embodiments, the trispecific antibodies described herein may adopt any format which has been described in the art for trispecific antibodies. In some embodiments, the trispecific antibodies described herein is constructed based on a bispecific antibody format. This can be achieved by adding a third antigen-binding arm to a bispecific antibody. Different formats of bispecific antibodies have been described and were recently reviewed by Chames and Baty (2009) Curr Opin Drug Disc Dev 12: 276. In some embodiments, the trispecific antibody comprises a bispecific antibody which is a diabody, a cross-body, or a bispecific antibody obtained via a controlled Fab arm exchange as those described in the present disclosure.

In some embodiments, the trispecific antibodies include IgG-like molecules with complementary CH3 domains to force heterodimerization; recombinant IgG-like dual targeting molecules, wherein the two sides of the molecule each contain the Fab fragment or part of the Fab fragment of at least two different antibodies; IgG fusion molecules, wherein full length IgG antibodies are fused to an extra Fab fragment or parts of Fab fragment; Fc fusion molecules, wherein single chain Fv molecules or stabilized diabodies are fused to heavy-chain constant-domains, Fc-regions or parts thereof, Fab fusion molecules, wherein different Fab-fragments are fused together; ScFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule.

In some embodiments, IgG-like molecules with complementary CH3 domains molecules include the Triomab/Quadroma (Trion Pharma/Fresenius Biotech), the Knobs-into-Holes (Genentech), CrossMAbs (Roche) and the electrostatically-matched (Amgen), the LUZ-Y (Genentech), the Strand Exchange Engineered Domain body (SEEDbody) (EMD Serono), the Biclonic (Merus), the DuoBody (Genmab A/S), and other asymmetric mutations (e.g., Zymeworks).

In some embodiments, recombinant IgG-like dual targeting molecules include Dual Targeting (DT)-Ig (GSK/Domantis), Two-in-one Antibody (Genentech), Cross-linked Mabs (Karmanos Cancer Center), mAb2 (F-Star) and CovX-body (CovX/Pfizer).

In some embodiments, IgG fusion molecules include Dual Variable Domain (DVD)-Ig (Abbott), IgG-like Bispecific (InnClone/Eli Lilly), Ts2Ab (MedImmune/AZ) and BsAb (Zymogenetics), HERCULES (Biogen Idec) and TvAb (Roche).

In some embodiments, Fc fusion molecules include to ScFv/Fc Fusions (Academic Institution), SCORPION (Emergent BioSolutions/Trubion, Zymogenetics/BMS), Dual Affinity Retargeting Technology (Fc-DART) (Macro-Genics) and Dual(ScFv).sub.2-Fab (National Research Center for Antibody Medicine—China).

In some embodiments, Fab fusion bispecific antibodies include F(ab)2 (Medarex/AMGEN), Dual-Action or Bis- Fab (Genentech), Dock-and-Lock (DNL) (ImmunoMedics), Bivalent Bispecific (Biotecnol) and Fab-Fv (UCB-Celltech). ScFv-, diabody-based and domain antibodies include but are not limited to Bispecific T Cell Engager (BiTE) (Micromet), Tandem Diabody (Tandab) (Affimed), Dual Affinity Retargeting Technology (DART) (MacroGenics), Single-chain Diabody (Academic), TCR-like Antibodies (AIT, Receptor-Logics), Human Serum Albumin ScFv Fusion (Merrimack) and COMBODY (Epigen Biotech), dual targeting nanobodies (Ablynx), dual targeting heavy chain only domain antibodies.

Full length trispecific antibodies of the present disclosure may be generated for example using Fab arm exchange (or half molecule exchange) between two mono specific bivalent antibodies by introducing substitutions at the heavy chain CH3 interface in each half molecule to favor heterodimer formation of two antibody half molecules having distinct specificity either in vitro in cell-free environment or using co-expression. The Fab arm exchange reaction is the result of a disulfide-bond isomerization reaction and dissociation-association of CH3 domains. The heavy-chain disulfide bonds in the hinge regions of the parent mono specific antibodies are reduced. The resulting free cysteines of one of the parent monospecific antibodies form an inter heavy-chain disulfide bond with cysteine residues of a second parent mono specific antibody molecule and simultaneously CH3 domains of the parent antibodies release and reform by dissociation-association. The CH3 domains of the Fab arms may be engineered to favor heterodimerization over homodimerization. The resulting product is a bispecific antibody having two Fab arms or half molecules which each bind a distinct epitope, e.g., an epitope on BCMA (or GPRC5D) and an epitope on CD3. A third antigen-binding arm can be then introduced to the bispecific antibody, for example, to the C-terminus of the first heavy chain or second heavy chain, which can bind to a third epitope, e.g., GPRC5D (or BCMA).

"Homodimerization" as used herein refers to an interaction of two heavy chains having identical CH3 amino acid sequences. "Homodimer" as used herein refers to an antibody having two heavy chains with identical CH3 amino acid sequences.

"Heterodimerization" as used herein refers to an interaction of two heavy chains having non-identical CH3 amino acid sequences. "Heterodimer" as used herein refers to an antibody having two heavy chains with non-identical CH3 amino acid sequences.

The "knob-in-hole" strategy (see, e.g., PCT Inti. Publ. No. WO 2006/028936) may be used to generate full length trispecific antibodies. Briefly, selected amino acids forming the interface of the CH3 domains in human IgG can be mutated at positions affecting CH3 domain interactions to promote heterodimer formation. An amino acid with a small side chain (hole) is introduced into a heavy chain of an antibody binding a first antigen and an amino acid with a large side chain (knob) is introduced into a heavy chain of an antibody binding a second antigen. After co-expression of the two antibodies, a heterodimer is formed as a result of the preferential interaction of the heavy chain with a "hole" with the heavy chain with a "knob". Exemplary CH3 substitution pairs forming a knob and a hole are (expressed as modified position in the first CH3 domain of the first heavy chain/modified position in the second CH3 domain of the second heavy chain): T366Y/F405A, T366W/F405W, F405W/Y407A, T394W/Y407T, T394S/Y407A, T366W/T394S, F405W/T394S and T366W/T366S_L368A_Y407V.

In some embodiments of the trispecific antibody or trispecific binding fragment described herein, one of the Fc domains comprise mutations T366S, L368A and Y407V and the other Fc domain comprises mutation T366W. In some embodiments, the Fc domain of the first heavy chain portion (HC1) of the first antigen binding arm (e.g., CD3 binding arm) comprises mutations T366S, L368A and Y407V, and the Fc domain of the second heavy chain portion (HC2) of the second antigen binding arm and/or third antigen-binding arm (e.g., the GPRC5D/BCMA binding arm, or BCMA binding arm) comprises mutation T366W. In some embodiments, the Fc domain of the HC2 of the second antigen-binding arm and/or third antigen-binding arm (e.g., the GPRC5D/BCMA binding arm, or BCMA binding arm) comprises mutations T366S, L368A and Y407V, and the Fc domain of the HC1 of the first antigen-binding arm (e.g., CD3 binding arm) comprises mutation T366W.

Other strategies such as promoting heavy chain heterodimerization using electrostatic interactions by substituting positively charged residues at one CH3 surface and negatively charged residues at a second CH3 surface may be used, as described in US Pat. Publ. No. US2010/0015133; US Pat. Publ. No. US2009/0182127; US Pat. Publ. No. US2010/028637 or US Pat. Publ. No. US2011/0123532. In other strategies, heterodimerization may be promoted by following substitutions (expressed as modified position in the first CH3 domain of the first heavy chain/modified position in the second CH3 domain of the second heavy chain): L351Y_F405AY407V/T394W, T3661_K392M_T394W/F405A_Y407V, T366L_K392M_T394W/F405A_Y407V, L351Y_Y407A/ T366A_K409F, L351Y_Y407A/T366V K409F Y407A/ T366A_K409F, or T350V_L351Y_F405A Y407V/ T350V_T366L_K392L_T394W as described in U.S. Pat. Publ. No. US2012/0149876 or U.S. Pat. Publ. No. US2013/0195849 (Zymeworks).

In addition to methods described above, trispecific antibodies of the invention may be generated in vitro in a cell-free environment by introducing asymmetrical mutations in the CH3 regions of two mono specific homodimeric antibodies and forming the trispecific heterodimeric antibody from two parent monospecific homodimeric antibodies in reducing conditions to allow disulfide bond isomerization according to methods described in Inti. Pat. Publ. No. WO2011/131746. In the methods, the first monospecific bivalent antibody (e.g., anti-GPRC5D antibody) and the second monospecific bivalent antibody (e.g., anti-CD3 antibody) are engineered to have certain substitutions at the CH3 domain that promotes heterodimer stability; the antibodies are incubated together under reducing conditions sufficient to allow the cysteines in the hinge region to undergo disulfide bond isomerization; thereby generating the trispecific antibody by Fab arm exchange. The incubation conditions may optimally be restored to non-reducing conditions. Exemplary reducing agents that may be used are 2-mercaptoethylamine (2-MEA), dithiothreitol (DTT), dithioerythritol (DTE), glutathione, tris (2-carboxyethyl) phosphine (TCEP), L-cysteine and beta-mercaptoethanol, preferably a reducing agent selected from the group consisting of: 2-mercaptoethylamine, dithiothreitol and tris (2-carboxyethyl) phosphine. For example, incubation for at least 90 min at a temperature of at least 20° C. in the presence of at least 25 mM 2-MEA or in the presence of at least 0.5 mM dithiothreitol at a pH from 5-8, for example at pH of 7.0 or at pH of 7.4 may be used.

In some embodiments, the trispecific antibodies or antigen-binding fragments are IgG, or derivatives thereof. The IgG class is divided in four isotypes: IgG1, IgG2, IgG3 and IgG4 in humans. They share more than 95% homology in the amino acid sequences of the Fc regions but show major differences in the amino acid composition and structure of the hinge region. The Fc region mediates effector functions, such as antibody-dependent cellular cytotoxicity (ADCC) and complement-dependent cytotoxicity (CDC). In ADCC, the Fc region of an antibody binds to Fc receptors (FcγRs) on the surface of immune effector cells such as natural killers and macrophages, leading to the phagocytosis or lysis of the targeted cells. In CDC, the antibodies kill the targeted cells by triggering the complement cascade at the cell surface. The antibodies described herein include antibodies with the described features of the variable domains in combination with any of the IgG isotypes, including modified versions in which the Fc sequence has been modified to effect different effector functions.

For many applications of therapeutic antibodies, Fc-mediated effector functions are not part of the mechanism of action. These Fc-mediated effector functions can be detrimental and potentially pose a safety risk by causing off-mechanism toxicity. Modifying effector functions can be achieved by engineering the Fc regions to reduce their binding to FcγRs or the complement factors. The binding of IgG to the activating (FcγRI, FcγRIIa, FcγRIIIa and FcγRIIIb) and inhibitory (FcγRIIb) FcγRs or the first component of complement (C1q) depends on residues located in the hinge region and the CH2 domain. Mutations have been introduced in IgG1, IgG2 and IgG4 to reduce or silence Fc functionalities. The antibodies described herein may include these modifications.

In one embodiment, the antibody comprises an Fc region with one or more of the following properties: (a) reduced effector function when compared to the parent Fc; (b) reduced affinity to FcγRI, FcγRIIa, FcγRIIb, FcγRIIIb and/or FcγRIIIa, (c) reduced affinity to FcγRI (d) reduced affinity to FcγRIIa (e) reduced affinity to FcγRIIb, (f) reduced affinity to FcγRIIIb or (g) reduced affinity to FcγRIIIa.

In some embodiments, the antibodies or antigen-binding fragments are IgG, or derivatives thereof, e.g., IgG1, IgG2, IgG3, and IgG4 isotypes. In some embodiments wherein the antibody has an IgG1 isotype, the antibody contains L234A, L235A, D265S and/or K409R substitution(s) in its Fc region. In some embodiments wherein the antibody has an IgG4 isotype, the antibody contains S228P, L234A, and L235A substitutions in its Fc region. The antibodies described herein may include these modifications.

In some embodiments, the Fc domains of a multispecific antibody described herein each comprise one or more mutations selected from L234A, L235A, and D265S. In some embodiments, the Fc domains of HC1 and HC2 each comprise mutations L234A, L235A, and D265S.

In some embodiments, the Fc domain of one of the heavy chain portions of a multispecific antibody described herein further comprise one or more mutations which reduce Fc binding to protein A. In some embodiments, the Fc domains of one of the heavy chain portions comprises mutations H435R and/or Y436F. In some embodiments, the Fc domain of the HC2 of the second antigen-binding arm and/or third antigen-binding arm (e.g., GPRC5D/BCMA binding arm, or BCMA binding arm) comprises mutations H435R and/or Y436F.

In various embodiments, the third antigen-binding arm is operatively linked to Fc domains of the first antigen-binding arm or second antigen-binding arm via a linker. In some embodiments, the linker is a peptide linker and may include any naturally occurring amino acid. Exemplary amino acids that may be included into the linker are Gly, Ser Pro, Thr, Glu, Lys, Arg, Ile, Leu, His and The. The linker should have a length that is adequate to link the third antigen-binding arm and the first antigen-binding arm or the second antigen-binding arm in such a way that they form the correct conformation relative to one another so that they retain the desired activity, such as binding to a third antigen (e.g., BCMA or GPRC5D).

In some embodiments of a trispecific antibody described herein, the HC1 comprises, from the N- to C-terminus, the VH1 of the first antigen-binding arm, a CH1 domain, the Fc domain, a linker, and the third antigen-binding arm.

In some embodiments of a trispecific antibody described herein, the HC2 comprises, from the N-to C-terminus, the second antigen-binding arm, the Fc domain, a linker, and the third antigen-binding arm.

In various embodiments, the scFvs used in multispecific antibodies described herein comprise, from the N- to C-terminus, a VH, a linker and a VL (VH-L-VL) or the VL, the linker and the VH (VL-L-VH). In some embodiments, the scFv comprises, from the N- to C-terminus, the VL, the linker and the VH (VL-L-VH). In some embodiments, the scFv comprises, from the N- to C-terminus, the VH, the linker, and the VL (VH-L-VL).

The linker may be about 5-50 amino acids long. In some embodiments, the linker is about 10-40 amino acids long. In some embodiments, the linker is about 10-35 amino acids long. In some embodiments, the linker is about 10-30 amino acids long. In some embodiments, the linker is about 10-25 amino acids long. In some embodiments, the linker is about 10-20 amino acids long. In some embodiments, the linker is about 15-20 amino acids long. In some embodiments, the linker is 6 amino acids long. In some embodiments, the linker is 7 amino acids long. In some embodiments, the linker is 8 amino acids long. In some embodiments, the linker is 9 amino acids long. In some embodiments, the linker is amino acids long. In some embodiments, the linker is 11 amino acids long. In some embodiments, the linker is 12 amino acids long. In some embodiments, the linker is 13 amino acids long. In some embodiments, the linker is 14 amino acids long. In some embodiments, the linker is 15 amino acids long. In some embodiments, the linker is 16 amino acids long. In some embodiments, the linker is 17 amino acids long. In some embodiments, the linker is 18 amino acids long. In some embodiments, the linker is 19 amino acids long. In some embodiments, the linker is 20 amino acids long. In some embodiments, the linker is 21 amino acids long. In some embodiments, the linker is 22 amino acids long. In some embodiments, the linker is 23 amino acids long. In some embodiments, the linker is 24 amino acids long. In some embodiments, the linker is 25 amino acids long. In some embodiments, the linker is 26 amino acids long. In some embodiments, the linker is 27 amino acids long. In some embodiments, the linker is 28 amino acids long. In some embodiments, the linker is 29 amino acids long. In some embodiments, the linker is 30 amino acids long. In some embodiments, the linker is 31 amino acids long. In some embodiments, the linker is 32 amino acids long. In some embodiments, the linker is 33 amino acids long. In some embodiments, the linker is 34 amino acids long. In some embodiments, the linker is 35 amino acids long. In some embodiments, the linker is 36 amino acids long. In some embodiments, the linker is 37 amino acids long. In some embodiments, the linker is 38 amino acids long. In some embodiments, the linker is 39 amino acids long. In some embodiments, the linker is 40 amino acids long. Exemplary linkers that may be used are Gly rich linkers, Gly and Ser containing linkers, Gly and Ala containing linkers, Ala and Ser containing linkers, and other flexible linkers.

Other linker sequences may include portions of immunoglobulin hinge area, CL or CH1 derived from any immunoglobulin heavy or light chain isotype. Exemplary linkers that may be used are shown in Table 4. Additional linkers are described for example in Int. Pat. Publ. No. WO2019/060695.

In some embodiments, the linker comprises the amino acid sequence of SEQ ID NO: 25.

In some embodiments, the linker comprises the amino acid sequence of SEQ ID NO: 163.

In some embodiments, the linker comprises the amino acid sequence of SEQ ID NO: 127.

In some embodiments, the linker comprises the amino acid sequence of SEQ ID NO: 128.

In some embodiments, the linker comprises the amino acid sequence of SEQ ID NO: 129.

In some embodiments, the linker comprises the amino acid sequence of SEQ ID NO: 130.

In some embodiments, the linker comprises the amino acid sequence of SEQ ID NO: 131.

In some embodiments, the linker comprises the amino acid sequence of SEQ ID NO: 132.

In some embodiments, the linker comprises the amino acid sequence of SEQ ID NO: 133.

In some embodiments, the linker comprises the amino acid sequence of SEQ ID NO: 134.

In some embodiments, the linker comprises the amino acid sequence of SEQ ID NO: 135.

In some embodiments, the linker comprises the amino acid sequence of SEQ ID NO: 136.

In some embodiments, the linker comprises the amino acid sequence of SEQ ID NO: 137.

In some embodiments, the linker comprises the amino acid sequence of SEQ ID NO: 138.

In some embodiments, the linker comprises the amino acid sequence of SEQ ID NO: 139.

In some embodiments, the linker comprises the amino acid sequence of SEQ ID NO: 140.

In some embodiments, the linker comprises the amino acid sequence of SEQ ID NO: 141.

In some embodiments, the linker comprises the amino acid sequence of SEQ ID NO: 142.

In some embodiments, the linker comprises the amino acid sequence of SEQ ID NO: 143.

In some embodiments, the linker comprises the amino acid sequence of SEQ ID NO: 144.

In some embodiments, the linker comprises the amino acid sequence of SEQ ID NO: 145.

In some embodiments, the linker comprises the amino acid sequence of SEQ ID NO: 146.

In some embodiments, the linker comprises the amino acid sequence of SEQ ID NO: 147.

In some embodiments, the linker comprises the amino acid sequence of SEQ ID NO: 148.

In some embodiments, the linker comprises the amino acid sequence of SEQ ID NO: 149.

In some embodiments, the linker comprises the amino acid sequence of SEQ ID NO: 150.

In some embodiments, the linker comprises the amino acid sequence of SEQ ID NO: 151.

In some embodiments, the linker comprises the amino acid sequence of SEQ ID NO: 152.

In some embodiments, the linker comprises the amino acid sequence of SEQ ID NO: 153.

In some embodiments, the linker comprises the amino acid sequence of SEQ ID NO 154.

In some embodiments, the linker comprises the amino acid sequence of SEQ ID NO: 155.

In some embodiments, the linker comprises the amino acid sequence of SEQ ID NO 156.

In some embodiments, the linker comprises the amino acid sequence of SEQ TD NO: 157.

TABLE 4

| Exemplary linker sequences | | |
|---|---|---|
| Linker name | Amino acid sequence | SEQ ID NO: |
| Linker 1 | GGSEGKSSGSGSESKSTGGS | 25 |
| Linker 2 | GGGSGGGS | 127 |
| Linker 3 | GGGSGGGSGGGS | 128 |
| Linker 4 | GGGSGGGSGGGSGGGS | 129 |
| Linker 5 | GGGSGGGSGGGSGGGSGGGS | 130 |
| Linker 6 | GGGGSGGGGSGGGGS | 131 |
| Linker 7 | GGGGSGGGGSGGGGSGGGGS | 163 |
| Linker 8 | GGGGSGGGGSGGGGSGGGGSGGGGS | 132 |
| Linker 9 | GSTSGSGKPGSGEGSTKG | 133 |
| Linker 10 | IRPRAIGGSKPRVA | 134 |
| Linker 11 | GKGGSGKGGSGKGGS | 135 |
| Linker 12 | GGKGSGGKGSGGKGS | 136 |
| Linker 13 | GGGKSGGGKSGGGKS | 137 |
| Linker 14 | GKGKSGKGKSGKGKS | 138 |
| Linker 15 | GGGKSGGKGSGKGGS | 139 |
| Linker 16 | GKPGSGKPGSGKPGS | 140 |
| Linker 17 | GKPGSGKPGSGKPGSGKPGS | 141 |
| Linker 18 | GKGKSGKGKSGKGKSGKGKS | 142 |
| Linker 19 | STAGDTHLGGEDFD | 143 |
| Linker 20 | GEGGSGEGGSGEGGS | 144 |
| Linker 21 | GGEGSGGEGSGGEGS | 145 |
| Linker 22 | GEGESGEGESGEGES | 146 |
| Linker 23 | GGGESGGEGSGEGGS | 147 |
| Linker 24 | GEGESGEGESGEGESGEGES | 148 |
| Linker 25 | GSTSGSGKPGSGEGSTKG | 149 |
| Linker 26 | PRGASKSGSASQTGSAPGS | 150 |
| Linker 27 | GTAAAGAGAAGGAAAGAAG | 151 |
| Linker 28 | GTSGSSGSGSGGSGSGGGG | 152 |
| Linker 29 | GKPGSGKPGSGKPGSGKPGS | 153 |

TABLE 4-continued

Exemplary linker sequences

| Linker name | Amino acid sequence | SEQ ID NO: |
|---|---|---|
| Linker 30 | GSGS | 154 |
| Linker 31 | APAPAPAPAP | 155 |
| Linker 32 | APAPAPAPAPAPAPAPAP | 156 |
| Linker 33 | AEAAAKEAAAKEAAAAKEAAAAKEAAAAKAAA | 157 |

In one embodiment, the HC1 of a BCMA×GPRC5D×CD3 trispecific antibody comprises an amino acid sequence substantially the same as, or identical to, SEQ ID NO: 26.

In one embodiment, the LC of a BCMA×GPRC5D×CD3 trispecific antibody comprises an amino acid sequence substantially the same as, or identical to, SEQ ID NO: 27.

In one embodiment, the GPRC5D/BCMA binding arm of a BCMA×GPRC5D×CD3 trispecific antibody comprises an amino acid sequence substantially the same as, or identical to, SEQ ID NO: 28.

In one embodiment, a CD3/GPRC5D coupled HC1 of a BCMA×GPRC5D×CD3 trispecific antibody comprises an amino acid sequence substantially the same as, or identical to, SEQ ID NO: 29.

In one embodiment, the LC of a BCMA×GPRC5D×CD3 trispecific antibody comprises an amino acid sequence substantially the same as, or identical to, SEQ ID NO: 30.

In one embodiment, the BCMA binding arm comprises an amino acid sequence substantially the same as, or identical to, SEQ ID NO: 31.

In one embodiment, provided herein is an isolated trispecific antibody, or a trispecific binding fragment thereof, comprising:

a) a CD3 binding arm comprising a heavy chain (HC1) and a light chain (LC); and b) a GPRC5D/BCMA binding arm, wherein HC1 comprises an amino acid sequence substantially the same as, or identical to, SEQ ID NO: 26, LC comprises an amino acid sequence substantially the same as, or identical to, SEQ ID NO: 27, and the GPRC5D/BCMA binding arm comprises an amino acid sequence substantially the same as, or identical to, SEQ ID NO: 28.

In one embodiment, provided herein is an isolated trispecific antibody, or a trispecific binding fragment thereof, comprising:

a) a CD3 binding arm comprising a heavy chain (HC1) and a light chain (LC); and b) a GPRC5D/BCMA binding arm, wherein HC1 comprises the amino acid sequence of SEQ ID NO: 26, LC comprises the amino acid sequence of SEQ ID NO: 27, and the GPRC5D/BCMA binding arm comprises the amino acid sequence of SEQ ID NO: 28.

In one embodiment, provided herein is an isolated trispecific antibody, or a trispecific binding fragment thereof, comprising:

a) a CD3 binding arm comprising a heavy chain (HC1) and a light chain (LC), wherein the HC1 further comprises the GPRC5D binding arm; and b) a BCMA binding arm, wherein HC1 comprises an amino acid sequence substantially the same as, or identical to, SEQ ID NO: 29, LC comprises an amino acid sequence substantially the same as, or identical to, SEQ ID NO: 30, and the BCMA binding arm comprises an amino acid sequence substantially the same as, or identical to, SEQ ID NO: 31.

In one embodiment, provided herein is an isolated trispecific antibody, or a trispecific binding fragment thereof, comprising:

a) a CD3 binding arm comprising a heavy chain (HC1) and a light chain (LC), wherein the HC1 further comprises the GPRC5D binding arm; and b) a BCMA binding arm, wherein HC1 comprises the amino acid sequence of SEQ ID NO: 29, LC comprises the amino acid sequence of SEQ ID NO: 30, and the BCMA binding arm comprises the amino acid sequence of SEQ ID NO: 31.

In one embodiment, the BCMA×GPRC5D×CD3 trispecific antibody is BGCB463.

In one embodiment, the BCMA×GPRC5D×CD3 trispecific antibody is BGCB491.

In addition to the described BCMA×GPRC5D×CD3-multispecific antibodies or antigen-binding fragments, also provided are polynucleotide sequences capable of encoding the described BCMA×GPRC5D×CD3-multispecific antibodies or antigen-binding fragments. Vectors comprising the described polynucleotides are also provided, as are cells expressing the BCMA×GPRC5D×CD3-multispecific antibodies or antigen-binding fragments provided herein. Also described are cells capable of expressing the disclosed vectors. These cells may be mammalian cells (such as 293F cells, CHO cells), insect cells (such as Sf7 cells), yeast cells, plant cells, or bacteria cells (such as *E. coli*). The described antibodies may also be produced by hybridoma cells. The described antibodies may also be recombinantly produced.

Polynucleotides encoding recombinant antigen-binding proteins also are within the scope of the disclosure. In some embodiments, the polynucleotides described (and the peptides they encode) include a leader sequence. Any leader sequence known in the art may be employed. The leader sequence may include, but is not limited to, a restriction site or a translation start site.

The BCMA×GPRC5D×CD3-multispecific antibodies or antigen-binding fragments described herein include variants having single or multiple amino acid substitutions, deletions, or additions that retain the biological properties (e.g., binding affinity or immune effector activity) of the described BCMA×GPRC5D×CD3-multispecific antibodies or antigen-binding fragments. In the context of the present invention the following notations are, unless otherwise indicated, used to describe a mutation; i) substitution of an amino acid in a given position is written as e.g. K409R which means a substitution of a Lysine in position 409 with an Arginine; and ii) for specific variants the specific three or one letter codes are used, including the codes Xaa and X to indicate any amino acid residue. Thus, the substitution of Arginine for Lysine in position 409 is designated as: K409R, or the substitution of any amino acid residue for Lysine in position 409 is designated as K409X. In case of deletion of Lysine in position 409 it is indicated by K409*. The skilled person may produce variants having single or multiple amino acid substitutions, deletions, or additions.

These variants may include: (a) variants in which one or more amino acid residues are substituted with conservative or nonconservative amino acids, (b) variants in which one or more amino acids are added to or deleted from the polypeptide, (c) variants in which one or more amino acids include a substituent group, and (d) variants in which the polypeptide is fused with another peptide or polypeptide such as a fusion partner, a protein tag or other chemical moiety, that may confer useful properties to the polypeptide, such as, for example, an epitope for an antibody, a polyhistidine sequence, a biotin moiety and the like. Antibodies or antigen-binding fragments described herein may include variants in which amino acid residues from one species are substituted for the corresponding residue in another species, either at the conserved or nonconserved positions. In other embodiments, amino acid residues at nonconserved positions are substituted with conservative or nonconservative residues. The techniques for obtaining these variants, including genetic (deletions, mutations, etc.), chemical, and enzymatic techniques, are known to persons having ordinary skill in the art.

The BCMA×GPRC5D×CD3-multispecific antibodies or antigen-binding fragments described herein may embody several antibody isotypes, such as IgM, IgD, IgG, IgA and IgE. In some embodiments the antibody isotype is IgG1, IgG2, IgG3, or IgG4 isotype, preferably IgG1 or IgG4 isotype. Antibody or antigen-binding fragment thereof specificity is largely determined by the amino acid sequence, and arrangement, of the CDRs. Therefore, the CDRs of one isotype may be transferred to another isotype without altering antigen specificity. Alternatively, techniques have been established to cause hybridomas to switch from producing one antibody isotype to another (isotype switching) without altering antigen specificity. Accordingly, such antibody isotypes are within the scope of the described antibodies or antigen-binding fragments.

The BCMA×GPRC5D×CD3-multispecific antibodies or antigen-binding fragments described herein may have $IC_{50}$ values of at least 5.9 nM for APRIL binding. The $IC_{50}$ of the described BCMA×GPRC5D×CD3-multispecific antibodies, or antigen-binding fragments, may be determined by a variety of methods known in the art, such as ELISA-based methods or flow cytometry (FACS). Assays for measuring $IC_{50}$ by ELISA have plate-bound BCMA in the presence and absence of a BCMA×GPRC5D×CD3-multispecific antibody, or antigen-binding fragment, and varying concentrations of the APRIL are used. A BCMA×GPRC5D×CD3-multispecific antibody, or antigen-binding fragment, that blocks the binding of APRIL to BCMA is to "block APRIL as measured by ELISA."

Also provided are vectors comprising the polynucleotides described herein. The vectors can be expression vectors. Recombinant expression vectors containing a sequence encoding a polypeptide of interest are thus contemplated as within the scope of this disclosure. The expression vector may contain one or more additional sequences such as but not limited to regulatory sequences (e.g., promoter, enhancer), a selection marker, and a polyadenylation signal. Vectors for transforming a wide variety of host cells are well known and include, but are not limited to, plasmids, phagemids, cosmids, baculoviruses, bacmids, bacterial artificial chromosomes (BACs), yeast artificial chromosomes (YACs), as well as other bacterial, yeast and viral vectors.

Recombinant expression vectors within the scope of the description include synthetic, genomic, or cDNA-derived nucleic acid fragments that encode at least one recombinant protein which may be operably linked to suitable regulatory elements. Such regulatory elements may include a transcriptional promoter, sequences encoding suitable mRNA ribosomal binding sites, and sequences that control the termination of transcription and translation. Expression vectors, especially mammalian expression vectors, may also include one or more nontranscribed elements such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a host may also be incorporated.

The transcriptional and translational control sequences in expression vectors to be used in transforming vertebrate cells may be provided by viral sources. Exemplary vectors may be constructed as described by Okayama and Berg, 3 *Mol. Cell. Biol.* 280 (1983).

In some embodiments, the multispecific antibody- or antigen-binding fragment-coding sequence is placed under control of a powerful constitutive promoter, such as the promoters for the following genes: hypoxanthine phosphoribosyl transferase (HPRT), adenosine deaminase, pyruvate kinase, beta-actin, human myosin, human hemoglobin, human muscle creatine, and others. In addition, many viral promoters function constitutively in eukaryotic cells and are suitable for use with the described embodiments. Such viral promoters include without limitation, Cytomegalovirus (CMV) immediate early promoter, the early and late promoters of SV40, the Mouse Mammary Tumor Virus (MMTV) promoter, the long terminal repeats (LTRs) of Maloney leukemia virus, Human Immunodeficiency Virus (HIV), Epstein Barr Virus (EBV), Rous Sarcoma Virus (RSV), and other retroviruses, and the thymidine kinase promoter of Herpes Simplex Virus. In one embodiment, the BCMA×GPRC5D×CD3-multispecific antibody or antigen-binding fragment thereof coding sequence is placed under control of an inducible promoter such as the metallothionein promoter, tetracycline-inducible promoter, doxycycline-inducible promoter, promoters that contain one or more interferon-stimulated response elements (ISRE) such as protein kinase R 2',5'-oligoadenylate synthetases, Mx genes, ADAR1, and the like.

Vectors described herein may contain one or more Internal Ribosome Entry Site(s) (IRES). Inclusion of an IRES sequence into fusion vectors may be beneficial for enhancing expression of some proteins. In some embodiments the vector system will include one or more polyadenylation sites (e.g., SV40), which may be upstream or downstream of any of the aforementioned nucleic acid sequences. Vector components may be contiguously linked, or arranged in a manner that provides optimal spacing for expressing the gene products (i.e., by the introduction of "spacer" nucleotides between the ORFs), or positioned in another way. Regulatory elements, such as the IRES motif, may also be arranged to provide optimal spacing for expression.

The vectors may comprise selection markers, which are well known in the art. Selection markers include positive and negative selection markers, for example, antibiotic resistance genes (e.g., neomycin resistance gene, a hygromycin resistance gene, a kanamycin resistance gene, a tetracycline resistance gene, a penicillin resistance gene, a puromycin resistance gene, a blasticidin resistance gene), glutamate synthase genes, HSV-TK, HSV-TK derivatives for ganciclovir selection, or bacterial purine nucleoside phosphorylase gene for 6-methylpurine selection (Gadi et al., 7 *Gene Ther.* 1738-1743 (2000)). A nucleic acid sequence encoding a selection marker or the cloning site may be upstream or downstream of a nucleic acid sequence encoding a polypeptide of interest or cloning site.

The vectors described herein may be used to transform various cells with the genes encoding the described antibodies or antigen-binding fragments. For example, the vectors may be used to generate BCMA×GPRC5D×CD3-multispecific antibody or antigen-binding fragment-producing cells. Thus, another aspect features host cells transformed with vectors comprising a nucleic acid sequence encoding an antibody or antigen-binding fragment thereof that binds BCMA, GPRC5D, and CD3, such as the antibodies or antigen-binding fragments described and exemplified herein.

Numerous techniques are known in the art for the introduction of foreign genes into cells and may be used to construct the recombinant cells for purposes of carrying out the described methods, in accordance with the various embodiments described and exemplified herein. The technique used should provide for the stable transfer of the heterologous gene sequence to the host cell, such that the heterologous gene sequence is heritable and expressible by the cell progeny, and so that the necessary development and physiological functions of the recipient cells are not disrupted. Techniques which may be used include but are not limited to chromosome transfer (e.g., cell fusion, chromosome mediated gene transfer, micro cell mediated gene transfer), physical methods (e.g., transfection, spheroplast fusion, microinjection, electroporation, liposome carrier), viral vector transfer (e.g., recombinant DNA viruses, recombinant RNA viruses) and the like (described in Cline, 29 *Pharmac. Ther.* 69-92 (1985)). Calcium phosphate precipitation and polyethylene glycol (PEG)-induced fusion of bacterial protoplasts with mammalian cells may also be used to transform cells.

Cells suitable for use in the expression of the BCMA× GPRC5D×CD3-multispecific antibodies or antigen-binding fragments described herein are preferably eukaryotic cells, more preferably cells of plant, rodent, or human origin, for example but not limited to NSO, CHO, CHOK1, perC.6, Tk-ts13, BHK, HEK293 cells, COS-7, T98G, CV-1/EBNA, L cells, C127, 3T3, HeLa, NS1, Sp2/0 myeloma cells, and BHK cell lines, among others. In addition, expression of antibodies may be accomplished using hybridoma cells. Methods for producing hybridomas are well established in the art.

Cells transformed with expression vectors described herein may be selected or screened for recombinant expression of the antibodies or antigen-binding fragments described herein. Recombinant-positive cells are expanded and screened for subclones exhibiting a desired phenotype, such as high level expression, enhanced growth properties, or the ability to yield proteins with desired biochemical characteristics, for example, due to protein modification or altered post-translational modifications. These phenotypes may be due to inherent properties of a given subclone or to mutation. Mutations may be effected through the use of chemicals, UV-wavelength light, radiation, viruses, insertional mutagens, inhibition of DNA mismatch repair, or a combination of such methods.

Therapeutic Composition and Methods of Treatment Using Multispecific Antibodies and Multispecific Antigen-Binding Fragments Thereof The multispecific antibodies discussed above, for example the BCMA×GPRC5D×CD3 trispecific antibodies discussed above, are useful in therapy. In particular, the multispecific antibodies are useful in treating cancer. Also provided herein are therapeutic compositions for the treatment of a hyperproliferative disorder in a mammal which comprises a therapeutically effective amount of a multispecific antibody or multispecific antigen-binding fragment described herein and a pharmaceutically acceptable carrier. In preferred embodiments, the multispecific antibody is a BCMA×GPRC5D×CD3-multispecific antibody as described herein, or a multispecific antigen-binding fragment thereof, and more preferably a BCMA×GPRC5D× CD3-trispecific antibody as described herein, or a BCMA× GPRC5D×CD3-trispecific antigen-binding fragment thereof. In one embodiment said pharmaceutical composition is for the treatment of a GPRC5D and/or BCMA-expressing cancer, including (but not limited to) the following: GPRC5D and/or BCMA-expressing B cell cancers, such as multiple myeloma (MM) including smoldering multiple myeloma (SMM); and other cancers yet to be determined in which GPRC5D and/or BCMA is expressed. In some embodiments, the GPRC5D and/or BCMA-expressing cancer is a relapsed or refractory form of a lymphoma, such as a relapsed or refractory form of multiple myeloma. Particular trispecific antibodies that may be used to treat cancer, such as hematological cancer, including the specific cancers discussed above, include antibodies BGCB463, and BGCB491.

In some embodiments, the BCMA×GPRC5D×CD3 trispecific antibody or binding fragment thereof is utilized for the treatment of R/R multiple myeloma.

In some embodiments, the subject receiving the BCMA× GPRC5D×CD3 trispecific antibody or binding fragment thereof has received a prior treatment. For example, the subject may have received one or more therapeutics, such as proteasome inhibitors (PIs) (e.g., Marizomib (salinosporamide A), Carfilzomib, Ixazomib), immunomodulatory drugs (IMiDs), bispecific agents, CAR-T therapies, and/or anti-CD38 antibodies, for treating multiple myeloma.

The pharmaceutical compositions provided herein comprise: a) an effective amount of a multispecific antibody or antibody fragment of the present invention, and b) a pharmaceutically acceptable carrier, which may be inert or physiologically active. In preferred embodiments, the multispecific antibody is a BCMA×GPRC5D×CD3-multispecific antibody as described herein, or a multispecific antigen-binding fragment thereof, and more preferably a BCMA× GPRC5D×CD3-trispecific antibody as described herein, or a BCMA×GPRC5D×CD3-trispecific antigen-binding fragment thereof. As used herein, the term "pharmaceutically acceptable carriers" includes any and all solvents, dispersion media, coatings, antibacterial and antifungal agents, and the like that are physiologically compatible. Examples of suitable carriers, diluents and/or excipients include one or more of water, saline, phosphate buffered saline, dextrose, glycerol, ethanol, and the like, as well as any combination thereof. In many cases, it will be preferable to include isotonic agents, such as sugars, polyalcohols, or sodium chloride in the composition. In particular, relevant examples of suitable carrier include: (1) Dulbecco's phosphate buffered saline, pH.about.7.4, containing or not containing about 1 mg/mL to 25 mg/mL human serum albumin, (2) 0.9% saline (0.9% w/v sodium chloride (NaCl)), and (3) 5% (w/v) dextrose; and may also contain an antioxidant such as tryptamine and a stabilizing agent such as Tween 20®.

The compositions herein may also contain a further therapeutic agent, as necessary for the particular disorder being treated. Preferably, the multispecific antibody or antibody fragment and the supplementary active compound will have complementary activities that do not adversely affect each other. In some embodiments, the further therapeutic agent is cytarabine, an anthracycline, histamine dihydrochloride, or interleukin 2. In some embodiments, the further therapeutic agent is a chemotherapeutic agent, an anti-CD38 agent, an immunomodulatory imide drug (IMiD), an immune checkpoint inhibitor, an immune co-stimulating agent, a gamma secretase inhibitor, a T-cell enhancer, or any combination thereof. In some embodiments, the further therapeutic agent is an anti-CD38 agent, such as an anti-CD38 antibody (e.g., daratumumab). In some embodiments, the further therapeutic agent is an immunomodulatory imide drug (IMiD), such as lenalidomide, and pomalidomide. In some embodiments, the further therapeutic agent is an immune checkpoint inhibitor such as anti-PD-1 and anti T cell immunoreceptor with Ig and ITIM domains (TIGIT). In some embodiments, the further therapeutic agent is an immune co-stimulating agent, such as agents targeting CD137 (e.g., CD137 costimulatory bispecific antibody). In some embodiments, the further therapeutic agent is a T-cell enhancer, such as IL-2 addition.

The compositions of the invention may be in a variety of forms. These include for example liquid, semi-solid, and solid dosage forms, but the preferred form depends on the intended mode of administration and therapeutic application. Typical preferred compositions are in the form of injectable or infusible solutions. The preferred mode of administration is parenteral (e.g. intravenous, intramuscular, intraperitoneal, subcutaneous). In a preferred embodiment, the compositions of the invention are administered intravenously as a bolus or by continuous infusion over a period of time. In another preferred embodiment, they are injected by intramuscular, subcutaneous, intra-articular, intrasynovial, intratumoral, peritumoral, intralesional, or perilesional routes, to exert local as well as systemic therapeutic effects.

Sterile compositions for parenteral administration can be prepared by incorporating the antibody, antibody fragment or antibody conjugate of the present invention in the required amount in the appropriate solvent, followed by sterilization by microfiltration. As solvent or vehicle, there may be used water, saline, phosphate buffered saline, dextrose, glycerol, ethanol, and the like, as well as combination thereof. In many cases, it will be preferable to include isotonic agents, such as sugars, polyalcohol's, or sodium chloride in the composition. These compositions may also contain adjuvants, in particular wetting, isotonizing, emulsifying, dispersing and stabilizing agents. Sterile compositions for parenteral administration may also be prepared in the form of sterile solid compositions which may be dissolved at the time of use in sterile water or any other injectable sterile medium.

The multispecific antibody or antibody fragment may also be orally administered. As solid compositions for oral administration, tablets, pills, powders (gelatin capsules, sachets) or granules may be used. In these compositions, the active ingredient according to the invention is mixed with one or more inert diluents, such as starch, cellulose, sucrose, lactose or silica, under an argon stream. These compositions may also comprise substances other than diluents, for example one or more lubricants such as magnesium stearate or talc, a coloring, a coating (sugar-coated tablet) or a glaze.

As liquid compositions for oral administration, there may be used pharmaceutically acceptable solutions, suspensions, emulsions, syrups and elixirs containing inert diluents such as water, ethanol, glycerol, vegetable oils or paraffin oil. These compositions may comprise substances other than diluents, for example wetting, sweetening, thickening, flavoring or stabilizing products.

The doses depend on the desired effect, the duration of the treatment and the route of administration used; they are generally between 5 mg and 1000 mg per day orally for an adult with unit doses ranging from 1 mg to 250 mg of active substance. In general, the doctor will determine the appropriate dosage depending on the age, weight and any other factors specific to the subject to be treated.

Also provided herein are methods for killing a GPRC5D and/or BCMA+ cell by administering to a patient in need thereof a multispecific antibody which binds said GPRC5D and/or BCMA and is able to recruit T cells to kill said GPRC5D and/or BCMA+ cell (i.e., T cell redirection). Any of the multispecific antibodies or antibody fragments of the invention may be used therapeutically. For example, in one embodiment the BCMA×GPRC5D×CD3-multispecific antibody may be used therapeutically to treat cancer in a subject.

In a preferred embodiment, multispecific antibodies or antibody fragments of the invention are used for the treatment of a hyperproliferative disorder in a mammal. In a more preferred embodiment, one of the pharmaceutical compositions disclosed above, and which contains a multispecific antibody or antibody fragment of the invention, is used for the treatment of a hyperproliferative disorder in a mammal. In one embodiment, the disorder is a cancer. In particular, the cancer is a GPRC5D and/or BCMA-expressing cancer, including (but not limited to) the following: GPRC5D and/or BCMA-expressing B-cell cancers, such as multiple myeloma (MM) including smoldering multiple myeloma (SMM); and other cancers yet to be determined in which GPRC5D and/or BCMA is expressed. In some embodiments, the GPRC5D and/or BCMA-expressing cancer is a relapsed or refractory form of a lymphoma, such as a relapsed or refractory form of multiple myeloma. In preferred embodiments, the multispecific antibody is a BCMA×GPRC5D×CD3-multispecific antibody as described herein, or a multispecific antigen-binding fragment thereof, and more preferably a BCMA×GPRC5D×CD3-trispecific antibody as described herein, or a BCMA×GPRC5D×CD3-triispecific antigen-binding fragment thereof.

Accordingly, the pharmaceutical compositions of the invention are useful in the treatment or prevention of a variety of cancers or disorders, including (but not limited to) the following: a GPRC5D and/or BCMA-expressing cancer, including (but not limited to) the following: GPRC5D and/or BCMA-expressing B/Plasma cell cancers, such as acute multiple myeloma (MM) or premalignant myelomas such as MGUS (Monoclonal Gammopathy of Undetermined Significance) and SMM (Smoldering Multiple myeloma) and plasmacytoma; and other cancers yet to be determined in which GPRC5D and/or BCMA is expressed, or other plasma cell disorders such as amyloidosis and lupus. In some embodiments, the GPRC5D and/or BCMA-expressing cancer is a relapsed or refractory form of a lymphoma, such as a relapsed or refractory form of multiple myeloma.

Similarly, further provided herein is a method for inhibiting the growth of selected cell populations comprising contacting GPRC5D and/or BCMA-expressing target cells, or tissue containing such target cells, with an effective amount of a multispecific antibody or antibody fragment of the present invention, either alone or in combination with other cytotoxic or therapeutic agents, in the presence of a peripheral blood mononuclear cell (PBMC). A BCMA×GPRC5D×CD3 antibody that blocks the binding of ligands (APIL, BAFF and others) to BCMA and GPRC5D may block BCMA– and GPRC5D– mediated signaling and lead to inhibition or cell death of the target cells. In preferred embodiments, the multispecific antibody is a BCMA×GPRC5D×CD3-multispecific antibody as described herein, or a multispecific antigen-binding fragment thereof, and more preferably a BCMA×GPRC5D×CD3-trispecific antibody as described herein, or a BCMA×GPRC5D×CD3-trispecific antigen-binding fragment thereof.

In some embodiments, the methods described herein involving the administration of a multispecific antibody or pharmaceutical composition comprising the same, further involve administering another therapeutic agent. Suitable other therapeutic agents include, without limitation, an anti-CD38 agent, an immunomodulatory imide drug (IMiD), an immune checkpoint inhibitor, an immune co-stimulating agent, a gamma secretase inhibitor, a T-cell enhancer (e.g., IL-2 addition), tocilizumab, or any combination thereof. In some embodiments, the further therapeutic agent is an anti-CD38 agent, such as an anti-CD38 antibody (e.g., daratumumab). In some embodiments, the further therapeutic agent is an immunomodulatory imide drug (IMiD), such as lenalidomide, and pomalidomide. In some embodiments, the further therapeutic agent is an immune checkpoint inhibitor such as anti-PD-1 and anti-T cell immunoreceptor with Ig and ITIM domains (TIGIT). In some embodiments, the further therapeutic agent is an immune co-stimulating agent, such as agents targeting CD137 (e.g., CD137 costimulatory bispecific antibody). The use of a low-affinity CD137 binder with conditional agonism in the presence of a T cell-redirecting antibody like the BCMA×GPRC5D× CD3 trispecific antibody described herein could enhance antitumor activity and potentially improve T cell persistence. In some embodiments, the further therapeutic agent is cytarabine, an anthracycline, histamine dihydrochloride, or interleukin 2. In some embodiments, the further therapeutic agent is a chemotherapeutic agent. The method for inhibiting the growth of selected cell populations can be practiced in vitro, in vivo, or ex vivo.

Examples of in vitro uses include treatments of autologous bone marrow prior to their transplant into the same patient in order to kill diseased or malignant cells; and prevent graft-versus-host-disease (GVHD); treatments of cell cultures in order to kill all cells except for desired variants that do not express the target antigen; or to kill variants that express undesired antigen. The conditions of non-clinical in vitro use are readily determined by one of ordinary skill in the art.

Examples of clinical ex vivo use are to remove tumor cells from bone marrow prior to autologous transplantation in cancer treatment. Treatment can be carried out as follows. Bone marrow is harvested from the patient or other individual and then incubated in medium containing serum to which is added the cytotoxic agent of the invention. Concentrations range from about 10 μM to 1 μM, for about 30 min to about 48 hr at about 37° C. The exact conditions of concentration and time of incubation, i.e., the dose, are readily determined by one of ordinary skill in the art. After incubation the bone marrow cells are washed with medium containing serum and returned to the patient by i.v. infusion according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, a therapeutically effective amount of the multispecific antibody or antigen-binding fragment is administered to a subject in need thereof. For example, the BCMA×GPRC5D×CD3-multispecific antibodies and multispecific antigen-binding fragments thereof may be useful in the treatment of a GPRC5D and/or BCMA-expressing cancer in a subject in need thereof. In some embodiments, the GPRC5D and/or BCMA-expressing cancer is a B-cell cancer, such as multiple myeloma (MM) including smoldering multiple myeloma (SMM). In some embodiments, the GPRC5D and/or BCMA-expressing cancer is a relapsed or refractory form of a lymphoma, such as a relapsed or refractory form of multiple myeloma. In preferred embodiments, the multispecific antibody is a BCMA×GPRC5D× CD3-multispecific antibody as described herein, or a multispecific antigen-binding fragment thereof, and more preferably a BCMA×GPRC5D×CD3-trispecific antibody as described herein, or a BCMA×GPRC5D×CD3-trispecific antigen-binding fragment thereof. In some embodiments, the subject is a mammal, preferably a human. In some embodiments, the multispecific antibody or antigen-binding fragment will be administered as a solution that has been tested for sterility.

Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage.

The efficient dosages and the dosage regimens for the multispecific antibodies and fragments depend on the disease or condition to be treated and may be determined by one skilled in the art. An exemplary, non-limiting range for a therapeutically effective amount of a compound of the present invention is about 0.001-10 mg/kg, such as about 0.001-5 mg/kg, for example about 0.001-2 mg/kg, such as about 0.001-1 mg/kg, for instance about 0.001, about 0.01, about 0.1, about 1 or about 10 mg/kg.

A physician, pharmacist or veterinarian having ordinary skill in the art may readily determine and prescribe the effective amount of the pharmaceutical composition required. For example, the physician or veterinarian could start doses of the multispecific antibody or fragment employed in the pharmaceutical composition at levels lower than that required in order to achieve the desired therapeutic effect and gradually increase the dosage until the desired effect is achieved. In general, a suitable daily dose of a multispecific antibody of the present invention will be that amount of the compound which is the lowest dose effective to produce a therapeutic effect. Administration may e.g. be parenteral, such as intravenous, intramuscular, intratumoral (e.g., bone marrow) or subcutaneous. In one embodiment, the multispecific antibody or fragment may be administered by infusion in a weekly dosage of calculated by mg/m². Such dosages can, for example, be based on the mg/kg dosages provided above according to the following: dose (mg/kg)×body weight (e.g., 50-100 kg). Such administration may be repeated, e.g., 1 to 8 times, such as 3 to 5 times. The administration may be performed by continuous infusion over a period of from 2 to 24 hr, such as of from 2 to 12 hr. In one embodiment, the multispecific antibody or fragment may be administered by slow continuous infusion over a long period, such as more than 24 hours, in order to reduce toxic side effects.

In one embodiment, the multispecific antibody or fragment may be administered in a weekly dosage of calculated as a fixed dose for up to eight times, such as from four to six times when given once a week. Such regimen may be repeated one or more times as necessary, for example, after six months or twelve months. Such fixed dosages can, for example, be based on the mg/kg dosages provided above, with a body weight estimate of 50-100 kg. The dosage may be determined or adjusted by measuring the amount of multispecific antibody of the present invention in the blood upon administration by for instance taking out a biological sample and using anti-idiotypic antibodies which target the GPRC5D and/or BCMA antigen binding arms of the multispecific antibodies of the present invention.

In one embodiment, the multispecific antibody or fragment may be administered by maintenance therapy, such as, e.g., once a week for a period of six months or more.

A multispecific antibody or fragment may also be administered prophylactically in order to reduce the risk of developing cancer, delay the onset of the occurrence of an event in cancer progression, and/or reduce the risk of recurrence when a cancer is in remission.

The multispecific antibodies and fragments thereof as described herein may also be administered in combination therapy, i.e., combined with other therapeutic agents relevant for the disease or condition to be treated. Accordingly, in one embodiment, the antibody-containing medicament is for combination with one or more further therapeutic agent, such as a chemotherapeutic agent an anti-CD38 agent, an immunomodulatory imide drug (IMiD), an immune checkpoint inhibitor, an immune co-stimulating agent, a gamma secretase inhibitor, a T-cell enhancer (e.g., IL-2 addition), or any combination thereof. In some embodiments, the further therapeutic agent is an anti-CD38 agent, such as an anti-CD38 antibody (e.g., daratumumab). In some embodiments, the further therapeutic agent is an immunomodulatory imide drug (IMiD), such as lenalidomide, and pomalidomide. In some embodiments, the further therapeutic agent is an immune checkpoint inhibitor such as anti-PD-1 and anti-T cell immunoreceptor with Ig and ITIM domains (TIGIT). In some embodiments, the further therapeutic agent is an immune co-stimulating agent, such as agents targeting CD137 (e.g., CD137 costimulatory bispecific antibody). In some embodiments, the other therapeutic agent is cytarabine, an anthracycline, histamine dihydrochloride, or interleukin 2. Such combined administration may be simultaneous, separate or sequential, in any order. For simultaneous administration the agents may be administered as one composition or as separate compositions, as appropriate.

In one embodiment, a method for treating a disorder involving cells expressing GPRC5D and/or BCMA in a subject, which method comprises administration of a therapeutically effective amount of a multispecific antibody or fragment, such as a BCMA×GPRC5D×CD3 multispecific antibody described herein, and radiotherapy to a subject in need thereof is provided. In one embodiment is provided a method for treating or preventing cancer, which method comprises administration of a therapeutically effective amount of a multispecific antibody or fragment, such as a BCMA×GPRC5D×CD3 antibody described herein, and radiotherapy to a subject in need thereof. Radiotherapy may comprise radiation or associated administration of radiopharmaceuticals to a patient is provided. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, actinium-225, and indium-111.

Kits

Also provided herein are includes kits, e.g., comprising a described multispecific antibody or antigen-binding fragment thereof and instructions for the use of the antibody or fragments for killing of particular cell types. In preferred embodiments, the multispecific antibody is a BCMA×

GPRC5D×CD3-multispecific antibody as described herein, or a multispecific antigen-binding fragment thereof, and more preferably a BCMA×GPRC5D×CD3-trispecific antibody as described herein, or a BCMA×GPRC5D×CD3-trispecific antigen-binding fragment thereof. The instructions may include directions for using the multispecific antibody or antigen-binding fragment thereof in vitro, in vivo or ex vivo.

Typically, the kit will have a compartment containing the multispecific antibody or antigen-binding fragment thereof. The multispecific antibody or antigen-binding fragment thereof may be in a lyophilized form, liquid form, or other form amendable to being included in a kit. The kit may also contain additional elements needed to practice the method described on the instructions in the kit, such a sterilized solution for reconstituting a lyophilized powder, additional agents for combining with the multispecific antibody or antigen-binding fragment thereof prior to administering to a patient, and tools that aid in administering the multispecific antibody or antigen-binding fragment thereof to a patient.

Diagnostic Uses

The multispecific antibodies and fragments described herein may also be used for diagnostic purposes. Thus, also provided are diagnostic compositions comprising a multispecific antibody or fragments as defined herein, and to its use. In preferred embodiments, the multispecific antibody is a BCMA×GPRC5D×CD3-multispecific antibody as described herein, or a multispecific antigen-binding fragment thereof, and more preferably a BCMA×GPRC5D×CD3-trispecific antibody as described herein, or a BCMA×GPRC5D×CD3-trispecific antigen-binding fragment thereof. In one embodiment, the present invention provides a kit for diagnosis of cancer comprising a container comprising a BCMA×GPRC5D×CD3 trispecific antibody, and one or more reagents for detecting binding of the antibody to GPRC5D and/or BCMA. Reagents may include, for example, fluorescent tags, enzymatic tags, or other detectable tags. The reagents may also include secondary or tertiary antibodies or reagents for enzymatic reactions, wherein the enzymatic reactions produce a product that may be visualized. For example, the multispecific antibodies described herein, or antigen-binding fragments thereof, may be labeled with a radiolabel, a fluorescent label, an epitope tag, biotin, a chromophore label, an ECL label, an enzyme, ruthenium, $^{111}$In-DOTA, $^{111}$In-diethylenetriaminepentaacetic acid (DTPA), horseradish peroxidase, alkaline phosphatase and beta-galactosidase, or poly-histidine or similar such labels known in the art.

BCMA-Specific Antibodies

Described herein are isolated antibodies and antigen-binding fragments specific for BCMA. In some embodiments, the BCMA-specific antibodies and antigen-binding fragments bind human BCMA. The general structure of an BCMA-specific antibody molecule may comprise an antigen binding domain, which includes heavy and light chains, and the Fc domain, which serves a variety of functions, including complement fixation and binding antibody receptors.

In some embodiments are provided a BCMA-specific antibody, or an antigen-binding fragment thereof, comprising a heavy chain comprising a CDR1, a CDR2, and a CDR3 of any one of the antibodies described in Table 1 (e.g., BCMB519). In some embodiments are provided a BCMA-specific antibody, or an antigen-binding fragment thereof, comprising a heavy chain comprising a CDR1, a CDR2, and a CDR3 of any one of the antibodies described in Table 1

(e.g., BCMB519) and a light chain comprising a CDR1, a CDR2, and a CDR3 of any one of the antibodies described in Table 1 (e.g., BCMB519).

In some embodiments, the BCMA-specific antibody, or an antigen-binding fragment thereof, comprises a heavy chain CDR1 comprising SEQ ID NO: 20, a heavy chain CDR2 comprising SEQ ID NO: 21, and a heavy chain CDR3 comprising SEQ ID NO: 22. In some embodiments, the BCMA-binding arm comprises a heavy chain CDR1 comprising SEQ ID NO: 20, a heavy chain CDR2 comprising SEQ ID NO: 21, a heavy chain CDR3 comprising SEQ ID NO: 22, a light chain CDR1 comprising SEQ ID NO: 17, a light chain CDR2 comprising SEQ ID NO: 18, and a light chain CDR3 comprising SEQ ID NO: 19. The BCMA-binding arm may comprise human framework sequences. In some embodiments, the BCMA-binding arm comprises a heavy chain variable domain substantially the same as, or identical to, SEQ ID NO: 24. In some embodiments, the BCMA-binding arm comprises a heavy chain variable domain substantially the same as, or identical to, SEQ ID NO: 24 and a light chain variable domain substantially the same as, or identical to, SEQ ID NO: 23. The heavy chain variable domain and light chain variable domain of antibodies discussed in this paragraph are suitable for inclusion in multispecific (e.g., bispecific or trispecific) constructs in which one arm is an anti-BCMA arm. Exemplary trispecific constructs comprising the BCMA-specific antibody, or an antigen-binding fragment thereof, discussed in this paragraph are provided herein.

In some embodiments, the BCMA-specific antibodies and antigen-binding fragments bind human BCMA and cynomolgus monkey BCMA. In some embodiments, the BCMA-specific antibodies and antigen-binding fragments bind human BCMA but not to cynomolgus monkey BCMA. In some embodiments, the BCMA-specific antibodies and antigen-binding fragments bind to an epitope including one or more residues from the BCMA extracellular domain (ECD). In some embodiments, the BCMA-specific antibody or antigen-binding fragment binds to residues 17-26 (LL-HACIPCQL (SEQ ID NO: 161)) of BCMA BCMW37 chain. Such BCMA-specific antibody or antigen-binding fragment may bind to BCMA with an affinity of $5\times10^{-7}$M or less, such as $1\times10^{-7}$M or less, $5\times10^{-8}$M or less, $1\times10^{-8}$M or less, $5\times10^{-9}$M or less, $1\times10^{-9}$M, or $5\times10^{-10}$ M or less. In one embodiment, the BCMA-specific antibody or antigen-binding fragment binds to BCMA with an affinity of about $1\times10^{10}$M to $1\times10^{-9}$M. In one embodiment, the BCMA-binding arm binds to the BCMA with an affinity of about $1\times10^{-10}$ M, about $2\times10^{-10}$ M, about $3\times10^{-10}$M, about $4\times10^{-10}$ M, about $5\times10^{-10}$ M, about $6\times10^{-10}$ M, about $7\times10^{-10}$ M, about $8\times10^{-10}$M, about $9\times10^{-1\circ}$ M or about $1\times10^{-9}$M. In one embodiment, the BCMA-specific antibody or antigen-binding fragment binds to BCMA with an affinity of about $8.4\times10^{-1\circ}$ M as determined by a surface plasmon resonance (SPR) assay. In one embodiment, the BCMA-specific antibody pr antigen-binding fragment binds to BCMA with an affinity of about $2.1\times10^{-10}$ M as determined by a surface plasmon resonance (SPR) assay.

The IgG class is divided in four isotypes: IgG1, IgG2, IgG3 and IgG4 in humans. They share more than 95% homology in the amino acid sequences of the Fc regions but show major differences in the amino acid composition and structure of the hinge region. The Fc region mediates effector functions, such as antibody-dependent cellular cytotoxicity (ADCC) and complement-dependent cytotoxicity (CDC). In ADCC, the Fc region of an antibody binds to Fc receptors (FcγRs) on the surface of immune effector cells such as natural killers and macrophages, leading to the phagocytosis or lysis of the targeted cells. In CDC, the antibodies kill the targeted cells by triggering the complement cascade at the cell surface. The antibodies described herein include antibodies with the described features of the variable domains in combination with any of the IgG isotypes, including modified versions in which the Fc sequence has been modified to effect different effector functions.

For many applications of therapeutic antibodies, Fc-mediated effector functions are not part of the mechanism of action. These Fc-mediated effector functions can be detrimental and potentially pose a safety risk by causing off-mechanism toxicity. Modifying effector functions can be achieved by engineering the Fc regions to reduce their binding to FcγRs or the complement factors. The binding of IgG to the activating (FcγRI, FcγRIIa, FcγRIIIa and FcγRIIIb) and inhibitory (FcγRIIb) FcγRs or the first component of complement (C1q) depends on residues located in the hinge region and the CH2 domain. Mutations have been introduced in IgG1, IgG2 and IgG4 to reduce or silence Fc functionalities. The antibodies described herein may include these modifications.

In one embodiment, the antibody comprises an Fc region with one or more of the following properties: (a) reduced effector function when compared to the parent Fc; (b) reduced affinity to FcγRI, FcγRIIa, FcγRIIb, FcγRIIIb and/or FcγRIIIa, (c) reduced affinity to FcγRI (d) reduced affinity to FcγRIIa (e) reduced affinity to FcγRIIb, (f) reduced affinity to FcγRIIIb or (g) reduced affinity to FcγRIIIa.

In some embodiments, the antibodies or antigen-binding fragments are IgG, or derivatives thereof, e.g., IgG1, IgG2, IgG3, and IgG4 isotypes. In some embodiments wherein the antibody has an IgG1 isotype, the antibody contains L234A, L235A, D265S and/or K409R substitutions in its Fc region. In some embodiments wherein the antibody has an IgG4 isotype, the antibody contains K409R, S228P, L234A, and L235A substitutions in its Fc region. The antibodies described herein may include these modifications.

In some embodiments the described antibodies may be capable of inhibiting APRIL binding with a $IC_{50}$ of low nanomolar as measured by ELISA. In some embodiments the described antibodies may be capable of inhibiting BAFF binding with a $IC_{50}$ of low micromolar as measured by ELISA.

In some embodiments the described antibodies bind to BCMA-positive multiple myeloma cell lines.

In addition to the described BCMA-specific antibodies and antigen-binding fragments, also provided are polynucleotide sequences capable of encoding the described antibodies and antigen-binding fragments. Vectors comprising the described polynucleotides are also provided, as are cells expressing the BCMA-specific antibodies or antigen-binding fragments provided herein. Also described are cells capable of expressing the disclosed vectors. These cells may be mammalian cells (such as 293 cells, 293F cells, CHO cells), insect cells (such as Sf7 cells), yeast cells, plant cells, or bacteria cells (such as E. coli). The described antibodies may also be produced by hybridoma cells.

The described BCMA-specific antibodies or antigen-binding fragments include all isotypes, IgA, IgD, IgE, IgG and IgM, and synthetic multimers of the four-chain immunoglobulin structure. The described antibodies or antigen-binding fragments also include the IgY isotype generally found in hen or turkey serum and hen or turkey egg yolk.

The BCMA-specific antibodies and antigen-binding fragments may be derived from any species by recombinant means. For example, the antibodies or antigen-binding fragments may be mouse, rat, goat, horse, swine, bovine, chicken, rabbit, camelid, donkey, llama, human, or chimeric versions thereof. For use in administration to humans, non-human derived antibodies or antigen-binding fragments may be genetically or structurally altered to be less antigenic upon administration to a human patient.

In some embodiments, the antibodies or antigen-binding fragments are chimeric. As used herein, the term "chimeric" refers to an antibody, or antigen-binding fragment thereof, having at least some portion of at least one variable domain derived from the antibody amino acid sequence of a non-human mammal, a rodent, or a reptile, while the remaining portions of the antibody, or antigen-binding fragment thereof, are derived from a human.

In some embodiments, the antibodies are humanized antibodies. Humanized antibodies may be chimeric immunoglobulins, immunoglobulin chains or fragments thereof (such as Fv, Fab, Fab', F(ab')2 or other antigen-binding subsequences of antibodies) that contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin sequence. The humanized antibody may include at least a portion of an immunoglobulin constant region (Fc), typically that of a human immunoglobulin.

The antibodies or antigen-binding fragments described herein can occur in a variety of forms, but will include one or more of the antibody CDRs shown in Table 1 (e.g., BCMB519).

Described herein are recombinant antibodies and antigen-binding fragments that bind to BCMA. In some embodiments, the BCMA-specific antibodies or antigen-binding fragments are human IgG, or derivatives thereof. While the BCMA-specific antibodies or antigen-binding fragments exemplified herein are human, the antibodies or antigen-binding fragments exemplified may be chimerized.

In some embodiments, the antibodies or antigen-binding fragments are IgG, or derivatives thereof, e.g., IgG1, IgG2, IgG3, and IgG4 isotypes. In some embodiments wherein the antibody is of IgG1 isotype, the antibody comprises an IgG1 Fc region (SEQ ID NO: 158).

```
                                  SEQ ID NO: 158
ASTKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEPKS

CDKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYKC

KVSNKALPAPIEKTISKAKGQPREPQVYTLPPSREEMTKNQVSLTCLVKGF

YPSDIAVEWESNGQPENNYKTTPPVLDSDGSFFLYSKLTVDKSRWQQGNVF

SCSVMHEALHNHYTQKSLSLSPGK
```

66

In some embodiments wherein the antibody is of IgG1 isotype, the antibody comprises L234A, L235A, and D265S substitutions (underlined) in its Fc region (SEQ ID NO: 159).

```
                                  SEQ ID NO: 159
ASTKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEPKS

CDKTHTCPPCPAPEAAGGPSVFLFPPKPKDTLMISRTPEVTCVVVSVSHED

PEVKFNWYVDGVEVHNAKTKPREEQYNSTYRVVSVLTVLHQDWLNGKEYKC

KVSNKALPAPIEKTISKAKGQPREPQVYTLPPSREEMTKNQVSLTCLVKGF

YPSDIAVEWESNGQPENNYKTTPPVLDSDGSFFLYSKLTVDKSRWQQGNVF

SCSVMHEALHNHYTQKSLSLSPGK
```

In some embodiments wherein the antibody is of IgG4 isotype, the antibody comprises S228P, L234A, and L235A substitutions (underlined) in its Fc region (SEQ ID NO: 160).

```
                                  SEQ ID NO: 160
ASTKGPSVFPLAPCSRSTSESTAALGCLVKDYFPEPVTVSWNSGALTSGVH

TFPAVLQSSGLYSLSSVVTVPSSSLGTKTYTCNVDHKPSNTKVDKRVESKY

GPPCPPCPAPEAAGGPSVFLFPPKPKDTLMISRTPEVTCVVVDVSQEDPEV

QFNWYVDGVEVHNAKTKPREEQFNSTYRVVSVLTVLHQDWLNGKEYKCKVS

NKGLPSSIEKTISKAKGQPREPQVYTLPPSQEEMTKNQVSLTCLVKGFYPS

DIAVEWESNGQPENNYKTTPPVLDSDGSFFLYSRLTVDKSRWQEGNVFSCS

VMHEALHNHYTQKSLSLSLGK
```

The BCMA specific antibodies defined by CDR and/or variable domain sequence discussed in the above paragraphs may include these IgG Fc regions.

Also disclosed are isolated synthetic polynucleotides that encode the antibodies or antigen-binding fragments that bind to BCMA. The isolated polynucleotides capable of encoding the variable domain segments provided herein may be included on the same, or different, vectors to produce antibodies or antigen-binding fragments. Polynucleotides encoding recombinant antigen-binding proteins also are within the scope of the disclosure. In some embodiments, the polynucleotides described (and the peptides they encode) include a leader sequence. Any leader sequence known in the art may be employed. The leader sequence may include, but is not limited to, a restriction site or a translation start site.

The BCMA-specific antibodies or antigen-binding fragments described herein include variants having single or multiple amino acid substitutions, deletions, or additions that retain the biological properties (e.g., binding affinity or immune effector activity) of the described BCMA-specific antibodies or antigen-binding fragments. In the context of the present invention the following notations are, unless otherwise indicated, used to describe a mutation; i) substitution of an amino acid in a given position is written as e.g. K409R which means a substitution of a Lysine in position 409 with an Arginine; and ii) for specific variants the specific three or one letter codes are used, including the codes Xaa and X to indicate any amino acid residue. Thus, the substitution of Arginine for Lysine in position 409 is designated as: K409R, or the substitution of any amino acid residue for Lysine in position 409 is designated as K409X. In case of deletion of Lysine in position 409 it is indicated by K409*. The skilled person may produce variants having single or multiple amino acid substitutions, deletions, or additions.

These variants may include: (a) variants in which one or more amino acid residues are substituted with conservative or nonconservative amino acids, (b) variants in which one or more amino acids are added to or deleted from the polypeptide, (c) variants in which one or more amino acids include a substituent group, and (d) variants in which the polypeptide is fused with another peptide or polypeptide such as a fusion partner, a protein tag or other chemical moiety, that may confer useful properties to the polypeptide, such as, for example, an epitope for an antibody, a polyhistidine sequence, a biotin moiety and the like. Antibodies or antigen-binding fragments described herein may include variants in which amino acid residues from one species are substituted for the corresponding residue in another species, either at the conserved or nonconserved positions. In other embodiments, amino acid residues at nonconserved positions are substituted with conservative or nonconservative residues. The techniques for obtaining these variants, including genetic (deletions, mutations, etc.), chemical, and enzymatic techniques, are known to persons having ordinary skill in the art.

The BCMA-specific antibodies or antigen-binding fragments described herein may embody several antibody isotypes, such as IgM, IgD, IgG, IgA and IgE. In some embodiments the antibody isotype is IgG1, IgG2, IgG3, or IgG4 isotype, preferably IgG1 or IgG4 isotype. Antibody or antigen-binding fragment thereof specificity is largely determined by the amino acid sequence, and arrangement, of the CDRs. Therefore, the CDRs of one isotype may be transferred to another isotype without altering antigen specificity. Alternatively, techniques have been established to cause hybridomas to switch from producing one antibody isotype to another (isotype switching) without altering antigen specificity. Accordingly, such antibody isotypes are within the scope of the described antibodies or antigen-binding fragments.

The BCMA-specific antibodies or antigen-binding fragments described herein may have $IC_{50}$ values of low nanomolar for APRIL binding. The $IC_{50}$ of the described BCMA-specific antibodies, or antigen-binding fragments, may be determined by a variety of methods known in the art, such as ELISA-based methods or flow cytometry (FACS). Assays for measuring $IC_{50}$ by ELISA have plate-bound BCMA in the presence and absence of a BCMA specific antibody and varying concentrations of the APRIL are used. A BCMA antibody that blocks the binding of APRIL to BCMA is to "block APRIL as measured by ELISA."

Also provided are vectors comprising the polynucleotides described herein. The vectors can be expression vectors. Recombinant expression vectors containing a sequence encoding a polypeptide of interest are thus contemplated as within the scope of this disclosure. The expression vector may contain one or more additional sequences such as but not limited to regulatory sequences (e.g., promoter, enhancer), a selection marker, and a polyadenylation signal. Vectors for transforming a wide variety of host cells are well known and include, but are not limited to, plasmids, phagemids, cosmids, baculoviruses, bacmids, bacterial artificial chromosomes (BACs), yeast artificial chromosomes (YACs), as well as other bacterial, yeast and viral vectors. Recombinant expression vectors within the scope of the description include synthetic, genomic, or cDNA-derived nucleic acid fragments that encode at least one recombinant protein which may be operably linked to suitable regulatory elements. Such regulatory elements may include a transcriptional promoter, sequences encoding suitable mRNA ribosomal binding sites, and sequences that control the termination of transcription and translation. Expression vectors, especially mammalian expression vectors, may also include one or more nontranscribed elements such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a host may also be incorporated.

The transcriptional and translational control sequences in expression vectors to be used in transforming vertebrate cells may be provided by viral sources. Exemplary vectors may be constructed as described by Okayama and Berg, 3 *Mol. Cell. Biol.* 280 (1983).

In some embodiments, the antibody- or antigen-binding fragment-coding sequence is placed under control of a powerful constitutive promoter, such as the promoters for the following genes: hypoxanthine phosphoribosyl transferase (HPRT), adenosine deaminase, pyruvate kinase, beta-actin, human myosin, human hemoglobin, human muscle creatine, and others. In addition, many viral promoters function constitutively in eukaryotic cells and are suitable for use with the described embodiments. Such viral promoters include without limitation, Cytomegalovirus (CMV) immediate early promoter, the early and late promoters of SV40, the Mouse Mammary Tumor Virus (MMTV) promoter, the long terminal repeats (LTRs) of Maloney leukemia virus, Human Immunodeficiency Virus (HIV), Epstein Barr Virus (EBV), Rous Sarcoma Virus (RSV), and other retroviruses, and the thymidine kinase promoter of Herpes Simplex Virus. In one embodiment, the BCMA-specific antibody or antigen-binding fragment thereof coding sequence is placed under control of an inducible promoter such as the metallothionein promoter, tetracycline-inducible promoter, doxycycline-inducible promoter, promoters that contain one or more interferon-stimulated response elements (ISRE) such as protein kinase R 2',5'-oligoadenylate synthetases, Mx genes, ADAR1, and the like.

Vectors described herein may contain one or more Internal Ribosome Entry Site(s) (IRES). Inclusion of an IRES sequence into fusion vectors may be beneficial for enhancing expression of some proteins. In some embodiments the vector system will include one or more polyadenylation sites (e.g., SV40), which may be upstream or downstream of any of the aforementioned nucleic acid sequences. Vector components may be contiguously linked, or arranged in a manner that provides optimal spacing for expressing the gene products (i.e., by the introduction of "spacer" nucleotides between the ORFs), or positioned in another way. Regulatory elements, such as the IRES motif, may also be arranged to provide optimal spacing for expression.

The vectors may comprise selection markers, which are well known in the art. Selection markers include positive and negative selection markers, for example, antibiotic resistance genes (e.g., neomycin resistance gene, a hygromycin resistance gene, a kanamycin resistance gene, a tetracycline resistance gene, a penicillin resistance gene, a puromycin resistance gene, a blasticidin resistance gene), glutamate synthase genes, HSV-TK, HSV-TK derivatives for ganciclovir selection, or bacterial purine nucleoside phosphorylase gene for 6-methylpurine selection (*Gadi* et al., 7 Gene Ther. 1738-1743 (2000)). A nucleic acid sequence encoding a selection marker or the cloning site may be upstream or downstream of a nucleic acid sequence encoding a polypeptide of interest or cloning site.

The vectors described herein may be used to transform various cells with the genes encoding the described antibodies or antigen-binding fragments. For example, the vectors may be used to generate BCMA-specific antibody or antigen-binding fragment-producing cells. Thus, another aspect features host cells transformed with vectors comprising a nucleic acid sequence encoding an antibody or antigen-binding fragment thereof that binds BCMA, such as the antibodies or antigen-binding fragments described and exemplified herein.

Numerous techniques are known in the art for the introduction of foreign genes into cells and may be used to construct the recombinant cells for purposes of carrying out the described methods, in accordance with the various embodiments described and exemplified herein. The technique used should provide for the stable transfer of the heterologous gene sequence to the host cell, such that the heterologous gene sequence is heritable and expressible by the cell progeny, and so that the necessary development and physiological functions of the recipient cells are not disrupted. Techniques which may be used include but are not limited to chromosome transfer (e.g., cell fusion, chromosome mediated gene transfer, micro cell mediated gene transfer), physical methods (e.g., transfection, spheroplast fusion, microinjection, electroporation, liposome carrier), viral vector transfer (e.g., recombinant DNA viruses, recombinant RNA viruses) and the like (described in Cline, 29 Pharmac. Ther. 69-92 (1985)). Calcium phosphate precipitation and polyethylene glycol (PEG)-induced fusion of bacterial protoplasts with mammalian cells may also be used to transform cells.

Cells suitable for use in the expression of the BCMA-specific antibodies or antigen-binding fragments described herein are preferably eukaryotic cells, more preferably cells of plant, rodent, or human origin, for example but not limited to NSO, CHO, CHOK1, perC.6, Tk-ts13, BHK, HEK293 cells, COS-7, T98G, CV-1/EBNA, L cells, C127, 3T3, HeLa, NS1, Sp2/0 myeloma cells, and BHK cell lines, among others. In addition, expression of antibodies may be accomplished using hybridoma cells. Methods for producing hybridomas are well established in the art.

Cells transformed with expression vectors described herein may be selected or screened for recombinant expression of the antibodies or antigen-binding fragments described herein. Recombinant-positive cells are expanded and screened for subclones exhibiting a desired phenotype, such as high level expression, enhanced growth properties, or the ability to yield proteins with desired biochemical characteristics, for example, due to protein modification or altered post-translational modifications. These phenotypes may be due to inherent properties of a given subclone or to mutation. Mutations may be effected through the use of chemicals, UV-wavelength light, radiation, viruses, insertional mutagens, inhibition of DNA mismatch repair, or a combination of such methods.

Methods of Using BCMA-Specific Antibodies for Treatment

Provided herein are BCMA-specific antibodies or antigen-binding fragments thereof for use in therapy. In particular, these antibodies or antigen-binding fragments may be useful in treating cancer, such as BCMA-expressing cancer, or other BCMA-expressing disorders. Accordingly, the invention provides a method of treating cancer comprising administering an antibody as described herein, such as BCMA-specific antibodies or antigen-binding fragments.

For example, the use may be by interfering with BCMA-receptor interactions or where the antibody is conjugated to a toxin, so targeting the toxin to the BCMA-expressing cancer. In some embodiments BCMA-expressing cancer or disorder includes lymphoma, such as multiple myeloma (MM) including smoldering multiple myeloma (SMM), or amyloidosis, plasma cell leukemia and lupus. In some embodiments, the BCMA-expressing cancer is a relapsed or refractory form of a lymphoma, such as a relapsed or refractory form of multiple myeloma. The antibodies for use in these methods include those described herein above, for example a BCMA-specific antibody or antigen-binding fragment with the features set out in Table 1 (e.g., BCMB519), for example the CDRs or variable domain sequences, and in the further discussion of these antibodies.

In some embodiments described herein, immune effector properties of the BCMA-specific antibodies may be enhanced or silenced through Fc modifications by techniques known to those skilled in the art and described herein. For example, Fc effector functions such as C1q binding, complement dependent cytotoxicity (CDC), antibody-dependent cell-mediated cytotoxicity (ADCC), antibody-dependent cell-mediated phagocytosis (ADCP), down regulation of cell surface receptors (e.g., B cell receptor; BCR), etc. may be provided and/or controlled by modifying residues in the Fc responsible for these activities.

"Antibody-dependent cell-mediated cytotoxicity" or "ADCC" refers to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell.

The ability of monoclonal antibodies to induce ADCC can be enhanced by engineering their oligosaccharide component. Human IgG1 or IgG3 are N-glycosylated at Asn297 with the majority of the glycans in the well-known biantennary G0, G0F, G1, G1F, G2 or G2F forms. Antibodies produced by non-engineered CHO cells typically have a glycan fucose content of about at least 85%. The removal of the core fucose from the biantennary complex-type oligosaccharides attached to the Fc regions enhances the ADCC of antibodies via improved FcγRIIIa binding without altering antigen binding or CDC activity. Such mAbs can be achieved using different methods reported to lead to the successful expression of relatively high defucosylated antibodies bearing the biantennary complex-type of Fc oligosaccharides such as control of culture osmolality (Konno et al., Cytotechnology 64:249-65, 2012), application of a variant CHO line Lec13 as the host cell line (Shields et al., J Biol Chem 277:26733-26740, 2002), application of a variant CHO line EB66 as the host cell line (Olivier et al., MAbs; 2(4), 2010; Epub ahead of print; PMID:20562582), application of a rat hybridoma cell line YB2/0 as the host cell line (Shinkawa et al., J Biol Chem 278:3466-3473, 2003), introduction of small interfering RNA specifically against the .alpha. 1,6-fucosyltrasferase (FUT8) gene (Mori et al., Biotechnol Bioeng 88:901-908, 2004), or coexpression of β-1, 4-N-acetylglucosaminyltransferase III and golgi α-mannosidase II or a potent alpha-mannosidase I inhibitor, kifunensine (Ferrara et al., J Biol Chem 281:5032-5036, 2006, Ferrara et al., Biotechnol Bioeng 93:851-861, 2006; Xhou et al., Biotechnol Bioeng 99:652-65, 2008).

In some embodiments described herein, ADCC elicited by the BCMA antibodies may also be enhanced by certain substitutions in the antibody Fc. Exemplary substitutions are for example substitutions at amino acid positions 256, 290, 298, 312, 356, 330, 333, 334, 360, 378 or 430 (residue numbering according to the EU index) as described in U.S. Pat. No. 6,737,056.

Methods of Detecting BCMA

Provided herein are methods for detecting BCMA in a biological sample by contacting the sample with an antibody, or antigen-binding fragment thereof, described herein. As described herein, the sample may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like. In some embodiments the described methods include detecting BCMA in a biological sample by contacting the sample with any of the BCMA-specific antibodies or antigen-binding fragments thereof described herein.

In some embodiments the sample may be contacted with more than one of the BCMA-specific antibodies or antigen-binding fragments described herein. For example, a sample may be contacted with a first BCMA-specific antibody, or antigen-binding fragment thereof, and then contacted with a second BCMA-specific antibody, or antigen-binding fragment thereof, wherein the first antibody or antigen-binding fragment and the second antibody or antigen-binding fragment are not the same antibody or antigen-binding fragment. In some embodiments, the first antibody, or antigen-binding fragment thereof, may be affixed to a surface, such as a multiwell plate, chip, or similar substrate prior to contacting the sample. In other embodiments the first antibody, or antigen-binding fragment thereof, may not be affixed, or attached, to anything at all prior to contacting the sample.

The described BCMA-specific antibodies and antigen-binding fragments may be detectably labeled. In some embodiments labeled antibodies and antigen-binding fragments may facilitate the detection BCMA via the methods described herein. Many such labels are readily known to those skilled in the art. For example, suitable labels include, but should not be considered limited to, radiolabels, fluorescent labels, epitope tags, biotin, chromophore labels, ECL labels, or enzymes. More specifically, the described labels include ruthenium, $^{111}$In-DOTA, $^{111}$In-diethylenetriamine-pentaacetic acid (DTPA), horseradish peroxidase, alkaline phosphatase and beta-galactosidase, poly-histidine (HIS tag), acridine dyes, cyanine dyes, fluorone dyes, oxazin dyes, phenanthridine dyes, rhodamine dyes, Alexafluor® dyes, and the like.

The described BCMA-specific antibodies and antigen-binding fragments may be used in a variety of assays to detect BCMA in a biological sample. Some suitable assays include, but should not be considered limited to, western blot analysis, radioimmunoassay, surface plasmon resonance, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

In some embodiments described herein detection of BCMA-expressing cancer cells in a subject may be used to determine that the subject may be treated with a therapeutic agent directed against BCMA.

BCMA is present at detectable levels in blood and serum samples. Thus, provided herein are methods for detecting BCMA in a sample derived from blood, such as a serum sample, by contacting the sample with an antibody, or antigen-binding fragment thereof, that binds BCMA. The blood sample, or a derivative thereof, may be diluted, fractionated, or otherwise processed to yield a sample upon which the described method may be performed. In some embodiments, BCMA may be detected in a blood sample, or a derivative thereof, by any number of assays known in the art, such as, but not limited to, western blot analysis, radioimmunoassay, surface plasmon resonance, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

Methods for Diagnosing Cancer or Disorder

Provided herein are methods for diagnosing BCMA-expressing cancer or disorder in a subject. In some embodiments BCMA-expressing cancer or disorder include lymphomas, such as multiple myeloma (MM) including smoldering multiple myeloma (SMM), or amyloidosis, plasma cell leukemia, and lupus. In some embodiments, as described above, detecting BCMA in a biological sample, such as a blood sample or a serum sample, provides the ability to diagnose cancer in the subject from whom the sample was obtained. Alternatively, in some embodiments other samples such as a histological sample, a fine needle aspirate sample, resected tumor tissue, circulating cells, circulating tumor cells, and the like, may also be used to assess whether the subject from whom the sample was obtained has cancer. In some embodiments, it may already be known that the subject from whom the sample was obtained has cancer, but the type of cancer afflicting the subject may not yet have been diagnosed or a preliminary diagnosis may be unclear, thus detecting BCMA in a biological sample obtained from the subject can allow for, or clarify, diagnosis of the cancer. For example, a subject may be known to have cancer, but it may not be known, or may be unclear, whether the subject's cancer is BCMA-expressing.

In some embodiments the described methods involve assessing whether a subject is afflicted with BCMA-expressing cancer or disorder by determining the amount of BCMA that is present in a biological sample derived from the subject; and comparing the observed amount of BCMA with the amount of BCMA in a control, or reference, sample, wherein a difference between the amount of BCMA in the sample derived from the subject and the amount of BCMA in the control, or reference, sample is an indication that the subject is afflicted with a BCMA-expressing cancer or disorder. In another embodiment the amount of BCMA observed in a biological sample obtained from a subject may be compared to levels of BCMA known to be associated with certain forms or stages of cancer, to determine the form or stage of the subject's cancer. In some embodiments the amount of BCMA in the sample derived from the subject is assessed by contacting the sample with an antibody, or an antigen-binding fragment thereof, that binds BCMA, such as the BCMA-specific antibodies described herein. The sample assessed for the presence of BCMA may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like. In some embodiments BCMA-expressing cancer or disorder includes hematological cancer, such as multiple myeloma (MM) including smoldering multiple myeloma (SMM), or amyloidosis, plasma cell leukemia and lupus. In some embodiments, the BCMA-expressing cancer is a relapsed or refractory form of a lymphoma, such as a relapsed or refractory form of multiple myeloma. In some embodiments the subject is a human.

In some embodiments the method of diagnosing a BCMA-expressing cancer or disorder will involve: contacting a biological sample of a subject with a BCMA-specific antibody, or an antigen-binding fragment thereof (such as those derivable from the antibodies and fragments provided in Table 1 (e.g., BCMB519)), quantifying the amount of BCMA present in the sample that is bound by the antibody or antigen-binding fragment thereof, comparing the amount of BCMA present in the sample to a known standard or reference sample; and determining whether the subject's BCMA levels fall within the levels of BCMA associated with cancer or disorder. In an additional embodiment, the diagnostic method can be followed with an additional step of administering or prescribing a BCMA specific treatment. In another embodiment, the diagnostic method can be followed with an additional step of transmitting the results of the determination to facilitate treatment of the cancer or disorder. In some embodiments the BCMA specific treatment may be directed against BCMA-expressing cancers or disorders, such as the BCMA×CD3 multispecific antibodies described herein.

In some embodiments the described methods involve assessing whether a subject is afflicted with BCMA-expressing cancer or disorder by determining the amount of BCMA present in a blood or serum sample obtained from the subject; and comparing the observed amount of BCMA with the amount of BCMA in a control, or reference, sample, wherein a difference between the amount of BCMA in the sample derived from the subject and the amount of BCMA in the control, or reference, sample is an indication that the subject is afflicted with a BCMA-expressing cancer or disorder.

In some embodiments the control, or reference, sample may be derived from a subject that is not afflicted with BCMA-expressing cancer or disorder. In some embodiments the control, or reference, sample may be derived from a subject that is afflicted with BCMA-expressing cancer or disorder. In some embodiments where the control, or reference, sample is derived from a subject that is not afflicted with BCMA-expressing cancer or disorder, an observed increase in the amount of BCMA present in the test sample, relative to that observed for the control or reference sample, is an indication that the subject being assessed is afflicted with BCMA-expressing cancer or disorder. In some embodiments where the control sample is derived from a subject that is not afflicted with BCMA-expressing cancer or disorder, an observed decrease or similarity in the amount of BCMA present in the test sample, relative to that observed for the control or reference sample, is an indication that the subject being assessed is not afflicted with BCMA-expressing cancer or disorder. In some embodiments where the control or reference sample is derived from a subject that is afflicted with BCMA-expressing cancer or disorder, an observed similarity in the amount of BCMA present in the test sample, relative to that observed for the control or reference sample, is an indication that the subject being assessed is afflicted with BCMA-expressing cancer or disorder. In some embodiments where the control or reference sample is derived from a subject that is afflicted with BCMA-expressing cancer or disorder, an observed decrease in the amount of BCMA present in the test sample, relative to that observed for the control or reference sample, is an indication that the subject being assessed is not afflicted with BCMA-expressing cancer or disorder.

In some embodiments the amount of BCMA in the sample derived from the subject is assessed by contacting the sample with an antibody, or an antigen-binding fragment thereof, that binds BCMA, such as the antibodies described herein. The sample assessed for the presence of BCMA may be derived from a blood sample, a serum sample, circulating cells, circulating tumor cells, cells that are not tissue associated (i.e., free cells), tissues (e.g., surgically resected tumor tissue, biopsies, including fine needle aspiration), histological preparations, and the like.

In various aspects, the amount of BCMA is determined by contacting the sample with an antibody, or antigen-binding fragment thereof, that binds BCMA. In some embodiments, the sample may be contacted by more than one type of antibody, or antigen-binding fragment thereof, that binds BCMA. In some embodiments, the sample may be contacted by a first antibody, or antigen-binding fragment thereof, that binds BCMA and then contacted by a second antibody, or antigen-binding fragment thereof, that binds BCMA. BCMA-specific antibodies or antigen-binding fragments such as those described herein may be used in this capacity.

Various combinations of the BCMA-specific antibodies and antigen-binding fragments can be used to provide a "first" and "second" antibody or antigen-binding fragment to carry out the described diagnostic methods. In some embodiments BCMA-expressing cancer or disorder includes lymphomas, such as multiple myeloma (MM) including smoldering multiple myeloma (SMM). In some embodiments, the BCMA-expressing cancer is a relapsed or refractory form of a lymphoma, such as a relapsed or refractory form of multiple myeloma.

In certain embodiments, the amount of BCMA is determined by western blot analysis, radioimmunoassay, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

In various embodiments of the described diagnostic methods a control or reference sample is used. This sample may be a positive or negative assay control that ensures the assay used is working properly; for example, an assay control of this nature might be commonly used for immunohistochemistry assays. Alternatively, the sample may be a standardized reference for the amount of BCMA in a biological sample from a healthy subject. In some embodiments, the observed BCMA levels of the tested subject may be compared with BCMA levels observed in samples from subjects known to have BCMA-expressing cancer or disorder. In some embodiments, the control subject may be afflicted with a particular cancer or disorder of interest. In some embodiments, the control subject is known to have early stage cancer, which may or may not be BCMA-expressing cancer. In some embodiments, the control subject is known to have intermediate stage cancer, which may or may not be BCMA-expressing cancer. In some embodiments, the control subject is known to have late stage, which may or may not be BCMA-expressing cancer.

Methods for Monitoring Cancer or Disorder

Provided herein are methods for monitoring BCMA-expressing cancer or disorder in a subject. In some embodiments BCMA-expressing cancer or disorder includes lymphomas, such as multiple myeloma (MM) including smoldering multiple myeloma (SMM), or amyloidosis, plasma cell leukemia and lupus. In some embodiments, the BCMA-expressing cancer is a relapsed or refractory form of a lymphoma, such as a relapsed or refractory form of multiple myeloma. In some embodiments the described methods involve assessing whether BCMA-expressing cancer or disorder is progressing, regressing, or remaining stable by determining the amount of BCMA that is present in a test sample derived from the subject; and comparing the observed amount of BCMA with the amount of BCMA in a biological sample obtained, in a similar manner, from the subject at an earlier point in time, wherein a difference between the amount of BCMA in the test sample and the earlier sample provides an indication of whether the cancer is progressing, regressing, or remaining stable. In this regard, a test sample with an increased amount of BCMA, relative to the amount observed for the earlier sample, may indicate progression of a BCMA-expressing cancer or disorder. Conversely, a test sample with a decreased amount of BCMA, relative to the amount observed for the earlier sample, may indicate regression of a BCMA-expressing cancer or disorder.

Accordingly, a test sample with an insignificant difference in the amount of BCMA, relative to the amount observed for the earlier sample, may indicate a state of stable disease for a BCMA-expressing cancer or disorder. In some embodiments the amount of BCMA in a biological sample derived from the subject is assessed by contacting the sample with an antibody, or an antibody fragment thereof, that binds BCMA, such as the antibodies described herein. The sample assessed for the presence of BCMA may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like. In some embodiments the subject is a human.

In some embodiments the methods of monitoring a BCMA-expressing cancer or disorder will involve: contacting a biological sample of a subject with a BCMA-specific antibody, or antigen-binding fragment thereof (such as those derivable from the antibodies and fragments provided in Table 1 (e.g., BCMB519)), quantifying the amount of BCMA present in the sample, comparing the amount of BCMA present in the sample to the amount of BCMA determined to be in a biological sample obtained, in a similar manner, from the same subject at an earlier point in time; and determining whether the subject's BCMA level has changed over time. A test sample with an increased amount of BCMA, relative to the amount observed for the earlier sample, may indicate progression of cancer. Conversely, a test sample with a decreased amount of BCMA, relative to the amount observed for the earlier sample, may indicate regression of a BCMA-expressing cancer or disorder. Accordingly, a test sample with an insignificant difference in the amount of BCMA, relative to the amount observed for the earlier sample, may indicate a state of stable disease for a BCMA-expressing cancer or disorder. In some embodiments, the BCMA levels of the sample may be compared to a known standard or a reference sample, alone or in addition to the BCMA levels observed for a sample assessed at an earlier point in time. In an additional embodiment, the diagnostic method can be followed with an additional step of administering a BCMA-specific treatment. In some embodiments the BCMA-specific treatment may be directed against BCMA-expressing cancers or disorders, such as the BCMA×CD3 multispecific antibodies described herein.

In various aspects, the amount of BCMA is determined by contacting the sample with an antibody, or antigen-binding fragment thereof, that binds BCMA. In some embodiments, the sample may be contacted by more than one type of antibody, or antigen-binding fragment thereof, that binds BCMA. In some embodiments, the sample may be contacted by a first antibody, or antigen-binding fragment thereof, that binds BCMA and then contacted by a second antibody, or antigen-binding fragment thereof, that binds BCMA. Antibodies such as those described herein may be used in this capacity.

Various combinations of the antibodies and antigen-binding fragments described in Table 1 can be used to provide a "first" and "second" antibody or antigen-binding fragment to carry out the described monitoring methods. In some embodiments BCMA-expressing cancer or disorder includes a hematological cancer, such as acute myeloid leukemia (AML) or lymphomas (e.g., multiple myeloma (MM), smoldering multiple myeloma (SMM)), or amyloidosis, plasma cell leukemia, and lupus.

In certain embodiments, the amount of BCMA is determined by western blot analysis, radioimmunoassay, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

Kits for Detecting BCMA

Provided herein are kits for detecting BCMA in a biological sample. These kits include one or more of the BCMA-specific antibodies described herein, or an antigen-binding fragment thereof, and instructions for use of the kit.

The provided BCMA-specific antibody, or antigen-binding fragment, may be in solution; lyophilized; affixed to a substrate, carrier, or plate; or detectably labeled.

The described kits may also include additional components useful for performing the methods described herein. By way of example, the kits may comprise means for obtaining a sample from a subject, a control or reference sample, e.g., a sample from a subject having slowly progressing cancer and/or a subject not having cancer, one or more sample compartments, and/or instructional material which describes performance of a method of the invention and tissue specific controls or standards.

The means for determining the level of BCMA can further include, for example, buffers or other reagents for use in an assay for determining the level of BCMA. The instructions can be, for example, printed instructions for performing the assay and/or instructions for evaluating the level of expression of BCMA.

The described kits may also include means for isolating a sample from a subject. These means can comprise one or more items of equipment or reagents that can be used to obtain a fluid or tissue from a subject. The means for obtaining a sample from a subject may also comprise means for isolating blood components, such as serum, from a blood sample. Preferably, the kit is designed for use with a human subject.

EMBODIMENTS

The disclosure provided herein also provides the following non-limiting embodiments.

Embodiment 1. A trispecific antibody, or a trispecific binding fragment thereof, comprising:

(a) a first antigen-binding arm comprising a first heavy chain variable domain (VH1) and a first light chain variable domain (VL1);

(b) a second antigen-binding arm comprising a second heavy chain variable domain (VH2) and a second light chain variable domain (VL2);

(c) a third antigen-binding arm comprising a third heavy chain variable domain (VH3) and a third light chain variable domain (VL3), wherein the first antigen-binding arm binds to an epitope on cluster of differentiation 3 (CD3), the second antigen-binding arm binds to an epitope on G-protein coupled receptor family C group 5 member D (GPRC5D), and the third antigen-binding arm binds to an epitope on B cell maturation antigen (BCMA).

Embodiment 2. The trispecific antibody or trispecific binding fragment of embodiment 1, wherein the VH1 and VL1 of first antigen-binding arm are present in a diabody, a Fab, Fab', a F(ab')2, a Fv, a scFv, a Fd, a disulfide stabilized Fv fragment (dsFv), or a disulfide stabilized diabody (ds diabody).

Embodiment 3. The trispecific antibody or trispecific binding fragment of embodiment 1 or 2, wherein the VH2 and VL2 of the second antigen-binding arm are present in a diabody, a Fab, Fab', a F(ab')2, a Fv, a scFv, a Fv, a Fd, a disulfide stabilized Fv fragment (dsFv), or a disulfide stabilized diabody (ds diabody).

Embodiment 4. The trispecific antibody or trispecific binding fragment of any one of embodiments 1-3, wherein the VH3 and VL3 of the third antigen-binding arm are present in an antibody fragment, a diabody, a Fab, Fab', a F(ab')2, a Fv, a scFv, a Fd, a disulfide stabilized Fv fragment (dsFv), or a disulfide stabilized diabody (ds diabody).

Embodiment 5. The trispecific antibody or trispecific binding fragment of any one of embodiments 1-4, wherein the first antigen-binding arm that binds CD3 comprises a heavy chain complementarity determining region (HCDR) 1, a HCDR2 and a HCDR3 of the heavy chain variable domain (VH1) of SEQ ID NO: 8 and a light chain complementarity determining region (LCDR) 1, a LCDR2 and a LCDR3 of the light chain variable domain (VL1) of SEQ ID NO: 7.

Embodiment 6. The trispecific antibody or trispecific binding fragment of any one of embodiments 1-5, wherein the first antigen-binding arm that binds CD3 comprises a HCDR1 comprising the amino acid sequence of GDSVFNNNAAWS (SEQ ID NO: 4), a HCDR2 comprising the amino acid sequence of RTYYRSKWLYD (SEQ ID NO: 5), and a HCDR3 comprising the amino acid sequence of GYSSSFDY (SEQ ID NO: 6); and a LCDR1 comprising the amino acid sequence of TGTSSNIGTYKFVS (SEQ ID NO: 1), a LCDR2 comprising the amino acid sequence of EVSKRPS (SEQ ID NO: 2), and a LCDR3 comprising the amino acid sequence of VSYAGSGTLL (SEQ ID NO: 3).

Embodiment 7. The trispecific antibody or trispecific binding fragment of any one of embodiments 1-6, wherein the first antigen-binding arm that binds CD3 comprises the VH1 of SEQ ID NO: 8 and the VL1 of SEQ ID NO: 7.

Embodiment 8. The trispecific antibody or trispecific binding fragment of any one of embodiments 1-7, wherein the second antigen-binding arm that binds GPRC5D comprises a heavy chain complementarity determining region (HCDR) 1, a HCDR2 and a HCDR3 of the heavy chain variable domain (VH2) of SEQ ID NO: 16 and a light chain complementarity determining region (LCDR) 1, a LCDR2 and a LCDR3 of the light chain variable domain (VL2) of SEQ ID NO: 15.

Embodiment 9. The trispecific antibody or trispecific binding fragment of any one of embodiments 1-8, wherein the second antigen-binding arm that binds GPRC5D comprises a HCDR1 comprising the amino acid sequence of GFSLTNIRMSVS (SEQ ID NO: 12), HCDR2 comprising the amino acid sequence of HIFSNDEKS (SEQ ID NO: 13), and a HCDR3 comprising the amino acid sequence of MRLPYGMDV (SEQ ID NO: 14); and a LCDR1 comprising the amino acid sequence of RSSQSLVHSDGNTYLS (SEQ ID NO: 9), a LCDR2 comprising the amino acid sequence of KISNRFF (SEQ ID NO: 10), and a LCDR3 comprising the amino acid sequence of MQATQFPHT (SEQ ID NO: 11).

Embodiment 10. The trispecific antibody or trispecific binding fragment of any one of embodiments 1-9, wherein the second antigen-binding arm that binds GPRC5D comprises the VH2 of SEQ ID NO: 16 and the VL2 of SEQ ID NO: 15.

Embodiment 11. The trispecific antibody or trispecific binding fragment of any one of embodiments 1-10, wherein the third antigen-binding arm that binds BCMA comprises a heavy chain complementarity determining region (HCDR) 1, a HCDR2 and a HCDR3 of the heavy chain variable domain (VH3) of SEQ ID NO: 24 and a light chain complementarity determining region (LCDR) 1, a LCDR2 and a LCDR3 of the light chain variable domain (VL3) of SEQ ID NO: 23.

Embodiment 12. The trispecific antibody or trispecific binding fragment of any one of embodiments 1-11, wherein the third antigen-binding arm that binds BCMA comprises a HCDR1 comprising the amino acid sequence of GFTFSSYAMS (SEQ ID NO: 20), a HCDR2 comprising the amino acid sequence of AISGSGGSTY (SEQ ID NO: 21), and a HCDR3 comprising the amino acid sequence of DEGYSSGHYYGMDV (SEQ ID NO: 22); and a LCDR1 comprising the amino acid sequence of RASQSISSSFLT (SEQ ID NO: 17), a LCDR2 comprising the amino acid sequence of GASSRAT (SEQ ID NO: 18), and a LCDR3 comprising the amino acid sequence of QHYGSSPMYT (SEQ ID NO: 19).

Embodiment 13. The trispecific antibody or trispecific binding fragment of any one of embodiments 1-12, wherein the third antigen-binding arm that binds BCMA comprises the VH3 of SEQ ID NO: 24 and the VL3 of SEQ ID NO: 23.

Embodiment 14. The trispecific antibody or trispecific binding fragment of any one of embodiments 1-4, wherein the first antigen-binding arm that binds CD3 comprises the HCDR1, the HCDR2 and the HCDR3 of the VH1 of SEQ ID NO: 8 and the LCDR1, the LCDR2 and the LCDR3 of the VL1 of SEQ ID NO: 7;

the second antigen-binding arm that binds GPRC5D comprises the HCDR1, the HCDR2 and the HCDR3 of the VH2 of SEQ ID NO: 16 and the LCDR1, the LCDR2 and the LCDR3 of the VL2 of SEQ ID NO: 15; and the third antigen-binding arm that binds BCMA comprises the HCDR1, the HCDR2 and the HCDR3 of the VH3 of SEQ ID NO: 24 and the LCDR1, the LCDR2 and the LCDR3 of the VL3 of SEQ ID NO: 23.

Embodiment 15. The trispecific antibody or trispecific binding fragment of any one of embodiments 1-4 and 14, wherein the first antigen-binding arm that binds CD3 comprises the HCDR1, the HCDR2, the HCDR3, the LCDR1, the LCDR2 and the LCDR3 of SEQ ID NOs: 4, 5, 6, 1, 2, 3, respectively;

the second antigen-binding arm that binds GPRC5D comprises the HCDR1, the HCDR2, the HCDR3, the LCDR1, the LCDR2 and the LCDR3 of SEQ ID NOs: 12, 13, 14, 9, 10 and 11, respectively; and the third antigen-binding arm that binds BCMA comprises the HCDR1, the HCDR2, the HCDR3, the LCDR1, the LCDR2 and the LCDR3 of SEQ ID NOs: 20, 21, 22, 17, 18 and 19, respectively.

Embodiment 16. The trispecific antibody or trispecific binding fragment of any one of embodiments 1-4, 14 and 15, wherein the first antigen-binding arm that binds CD3 comprises the VH1 of SEQ ID NO: 8 and the VL1 of SEQ ID NO: 7;

the second antigen-binding arm that binds GPRC5D comprises the VH2 of SEQ ID NO: 16 and the VL2 of SEQ ID NO: 15; and the third antigen-binding arm that binds BCMA comprises the VH3 of SEQ ID NO: 24 and the VL3 of SEQ ID NO: 23.

Embodiment 17. The trispecific antibody or trispecific binding fragment thereof of embodiments 1-16, the first antigen-binding arm comprises a Fragment crystallizable (Fc) domain, and the second antigen-binding arm or the third antigen-binding arm comprises a Fc domain.

Embodiment 18. The trispecific antibody or trispecific binding fragment thereof of embodiment 17, wherein the Fe domains comprise one or more mutations which promote heterodimerization of the Fc domains.

Embodiment 19. The trispecific antibody or trispecific binding fragment of embodiment 18, wherein the mutations are selected from T366S, L368A, T366W and Y407V (EU numbering).

Embodiment 20. The trispecific antibody or trispecific binding fragment of any one of embodiments 17-19, wherein the Fc domains further comprise one or more mutations which reduce Fc binding to a Fcγ receptor.

Embodiment 21. The trispecific antibody or trispecific binding fragment of embodiment 20, wherein the Fcγ receptor is FcγRI, FcγRIIA, FcγRIIB, FcγRIIIA, and/or FcγRIIIB.

Embodiment 22. The trispecific antibody or trispecific binding fragment of embodiment 20 or 21, wherein the Fc domains comprise one or more mutations selected from L234A, L235A, and D265S (EU numbering).

Embodiment 23. The trispecific antibody or trispecific binding fragment of any one of embodiments 17-22, wherein the Fc domains further comprise one or more mutations which reduce Fc binding to protein A.

Embodiment 24. The trispecific antibody or trispecific binding fragment of embodiment 23, wherein the Fc domain comprises mutations H435R and/or Y436F (EU numbering).

Embodiment 25. The trispecific antibody or trispecific binding fragment of any one of embodiments 1 to 24, wherein the first antigen-binding arm that specifically binds to residues 22-35 (QDGNEEMGGITQTP (SEQ ID NO: 160)) of the CD38 chain.

Embodiment 26. The trispecific antibody or trispecific binding fragment of any one of embodiments 1-25, wherein the first antigen-binding arm that specifically binds to CD3 with an affinity of about $1\times10^{-8}$ to $1\times10^{-7}$ M.

Embodiment 27. The trispecific antibody or trispecific binding fragment of embodiment 26, wherein the first antigen-binding arm that specifically binds to CD3 with an affinity of about $2\times10^{-8}$ to $4\times10^{-8}$ M.

Embodiment 28. The trispecific antibody or trispecific binding fragment of any one of embodiments 1 to 27, wherein the third antigen-binding arm specifically binds residues 17-26 (LLHACIPCQL (SEQ ID NO: 161)) of BCMA BCMW37 chain.

Embodiment 29. The trispecific antibody or trispecific binding fragment of any one of embodiments 1-28, wherein the third antigen-binding arm specifically binds to BCMA with an affinity of about $1\times10^{-10}$ to $1\times10^{-7}$ M.

Embodiment 30. The trispecific antibody or trispecific binding fragment of embodiment 29, wherein the third antigen-binding arm specifically binds to BCMA with an affinity of about $2\times10^{-10}$ to $9\times10^{-10}$ M.

Embodiment 31. A trispecific antibody, or a trispecific binding fragment, comprising a first antigen-binding arm that binds to an epitope on cluster of differentiation 3 (CD3), a second antigen-binding arm that binds to an epitope on G-protein coupled receptor family C group 5 member D (GPRC5D), and the third antigen-binding arm that binds to an epitope on B cell maturation antigen (BCMA), wherein the first antigen-binding arm comprises a heavy chain (HC1) polypeptide and a light chain (LC) polypeptide; and wherein the trispecific antibody, or a trispecific binding fragment thereof, comprises a single polypeptide comprising the second antigen-binding arm and the third antigen-binding arm.

Embodiment 32. The trispecific antibody or trispecific binding fragment of embodiment 31, wherein the HC1 of the first antigen-binding arm comprises the amino acid sequence of SEQ ID NO: 26.

Embodiment 33. The trispecific antibody or trispecific binding fragment of embodiment 32, wherein the LC of the first antigen-binding arm comprises the amino acid sequence of SEQ ID NO: 27.

Embodiment 34. The trispecific antibody or trispecific binding fragment of embodiment 32 or 33, wherein the polypeptide comprising the second antigen-binding arm and the third antigen-binding arm comprises an amino acid sequence of SEQ ID NO: 28.

Embodiment 35. The trispecific antibody or trispecific binding fragment of embodiment 31, wherein the first antigen-binding arm comprises an HC1 comprising the amino acid sequence of SEQ ID NO: 26, and a LC comprising the amino acid sequence of SEQ ID NO: 27, and the polypeptide comprising the second antigen-binding arm and the third antigen-binding arm comprises the amino acid sequence of SEQ ID NO: 28.

Embodiment 36. A trispecific antibody, or a trispecific binding fragment, comprising a first antigen-binding arm that binds to an epitope on cluster of differentiation 3 (CD3), a second antigen-binding arm that binds to an epitope on G-protein coupled receptor family C group 5 member D (GPRC5D), and the third antigen-binding arm that binds to an epitope on B cell maturation antigen (BCMA), wherein the first antigen-binding arm comprises a heavy chain (HC1) polypeptide and a light chain (LC) polypeptide, wherein the heavy chain (HC1) polypeptide further comprises the second antigen-binding arm, wherein the trispecific antibody, or a trispecific binding fragment thereof, further comprises a single polypeptide comprising the third antigen-binding arm.

Embodiment 37. The trispecific antibody or trispecific binding fragment of embodiment 36, wherein the HC1 of the first antigen-binding arm comprises the amino acid sequence of SEQ ID NO: 29.

Embodiment 38. The trispecific antibody or trispecific binding fragment of embodiment 37, wherein the LC of the first antigen-binding arm comprises the amino acid sequence of SEQ ID NO: 30.

Embodiment 39. The trispecific antibody or trispecific binding fragment of embodiment 37 or 38, wherein the single polypeptide comprising the third antigen-binding arm comprises an amino acid sequence of SEQ ID NO: 31.

Embodiment 40. The trispecific antibody or trispecific binding fragment of embodiment 36, wherein the first antigen-binding arm comprises an HC1 comprising the amino acid sequence of SEQ ID NO: 29, and a LC comprising the amino acid sequence of SEQ ID NO: 30, and the single polypeptide comprising the third antigen-binding arm comprises the amino acid sequence of SEQ ID NO: 31.

Embodiment 41. The trispecific antibody or trispecific binding fragment of any one of embodiments 1-40, wherein the antibody or antigen-binding fragment thereof is an IgG1, IgG2, IgG3, or IgG4 isotype.

Embodiment 42. The trispecific antibody or trispecific binding fragment of any of embodiments 1-41, wherein the antibody or antigen-binding fragment thereof is an IgG1 isotype.

Embodiment 43. A synthetic polynucleotide encoding the trispecific antibody or trispecific binding fragment of any one of embodiments 1 to 42.

Embodiment 44. A pharmaceutical composition comprising the trispecific antibody or trispecific binding fragment of any one of embodiments 1 to 42 and a pharmaceutically acceptable carrier.

Embodiment 45. The pharmaceutical composition of embodiment 44, wherein the pharmaceutical composition further comprises a second therapeutic agent.

Embodiment 46. The pharmaceutical composition of embodiment 45, wherein the second therapeutic agent comprises an anti-CD38 agent, an immunomodulatory imide drug (IMiD), an immune checkpoint inhibitor, an immune co-stimulating agent, a gamma secretase inhibitor, a T-cell enhancer, or any combination thereof.

Embodiment 47. A cell expressing the trispecific antibody or trispecific binding fragment of any one of embodiments 1 to 42.

Embodiment 48. The cell of embodiment 47 wherein the cell is a hybridoma.

Embodiment 49. The cell of embodiment 47 wherein the trispecific antibody is recombinantly produced.

Embodiment 50. A method for treating cancer in a subject in need thereof, said method comprising administering to the subject a therapeutically effective amount of the trispecific antibody or trispecific binding fragment of any one of embodiments 1 to 42 or the pharmaceutical composition of any one of embodiments 43-46.

Embodiment 51. The method of embodiment 50, wherein the trispecific antibody or trispecific binding fragment or the pharmaceutical composition is administered for a time sufficient to treat the cancer.

Embodiment 52. A method for inhibiting growth or proliferation of a cancer cell, said method comprising administering to said cell an effective amount of the trispecific antibody or trispecific binding fragment of any one of embodiments 1 to 42 or the pharmaceutical composition of any one of embodiments 43-46, wherein said effective amount is sufficient to inhibit the growth or proliferation of said cancer cell.

Embodiment 53. The method of embodiment 52, wherein said cancer cell is in a subject and the trispecific antibody or trispecific binding fragment or the pharmaceutical composition is administered to the subject.

Embodiment 54. The method of embodiment 52, wherein said administration is conducted ex vivo.

Embodiment 55. A method of redirecting a T cell to BCMA and/or GPRC5D-expressing cancer cells in a subject in need thereof, said method comprising administering to said subject a therapeutically effective amount of the trispecific antibody or trispecific binding fragment of any one of embodiments 1 to 42 or the pharmaceutical composition of any one of embodiments 43-46.

Embodiment 56. The method of embodiment 55, wherein the said therapeutically effective amount is sufficient to direct said T cell response to said cancer cells.

Embodiment 57. The method of any one of embodiments 50-56, wherein the cancer is a hematological cancer.

Embodiment 58. The method of embodiment 57 wherein the hematological cancer is a BCMA and/or GPRC5D-expressing B cell cancer.

Embodiment 59. The method of embodiment 58 wherein the BCMA and/or GPRC5D-expressing B cell cancer is multiple myeloma.

Embodiment 60. The method of embodiment 59 wherein the BCMA and/or GPRC5D-expressing B cell cancer is smoldering multiple myeloma (SMM).

Embodiment 61. The method of any one of embodiments 50-60, wherein the cancer is relapsed, refractory, or malignant cancer, or any combination thereof.

Embodiment 62. The method of any one of embodiments 50-51, 53, and 55-61, wherein the subject has received a prior treatment.

Embodiment 63. The method of embodiment 62, the prior treatment comprises a proteasome inhibitor, an immuno-modulatory drug, a CD38 antibody, a bispecific agent, a CAR-T therapy, or a combination thereof.

Embodiment 64. The method of any one of embodiments 50-63 further comprising administering a second therapeutic agent.

Embodiment 65. The method of embodiment 64 wherein the second therapeutic agent is a chemotherapeutic agent or a targeted anti-cancer therapy.

Embodiment 66. The method of embodiment 65 wherein the chemotherapeutic agent is cytarabine, an anthracycline, histamine dihydrochloride, or interleukin 2 (IL-2).

Embodiment 67. The method of embodiment 64 wherein the second therapeutic agent is an anti-CD38 agent, an immunomodulatory imide drug (IMiD), an immune check-point inhibitor, an immune co-stimulating agent, a gamma secretase inhibitor, a T-cell enhancer, or any combination thereof.

Embodiment 68. The method of any one of embodiments 50-51, 53, and 55-67, wherein the trispecific antibody or trispecific binding fragment, or the pharmaceutical composition is administered intravenously, intramuscularly, intra-peritoneally, and/or subcutaneously to the subject.

Embodiment 69. The method of any one of embodiments 50-51, 53, and 55-68, wherein the trispecific antibody or trispecific binding fragment, or the pharmaceutical composition is administered subcutaneously to the subject.

Embodiment 70. A method for generating the trispecific antibody or trispecific binding fragment of any one of embodiments 1 to 42, wherein said method comprises culturing the cell of any one of embodiments 47 to 49 and isolating said trispecific antibody or trispecific binding fragment.

Embodiment 71. A kit comprising (i) the trispecific antibody or trispecific binding fragment of any one of embodiments 1 to 42 and/or a polynucleotide of embodiment 43 and (ii) packaging for the same.

Embodiment 72. An antibody, or an antigen-binding fragment thereof, that binds to BCMA, comprising: a heavy chain complementarity determining region 1 (CDR1) having the amino acid sequence of GFTFSSYAMS (SEQ ID NO: 20), a heavy chain CDR2 having the amino acid sequence of AISGSGGSTY (SEQ ID NO: 21), and a heavy chain CDR3 having the amino acid sequence of DEGYSSGHYYGMDV (SEQ ID NO: 22).

Embodiment 73. The antibody or antigen-binding fragment of embodiment 72, further comprising: a light chain complementarity determining region 1 (CDR1) having the amino acid sequence of RASQSISSSFLT (SEQ ID NO: 17), a light chain CDR2 having the amino acid sequence of GASSRAT (SEQ ID NO: 18), and a light chain CDR3 having the amino acid sequence of QHYGSSPMYT (SEQ ID NO: 19).

Embodiment 74. The antibody or antigen-binding fragment of embodiment 72 or 73, comprising a heavy chain variable domain (VH) having the amino acid sequence of SEQ ID NO: 24.

Embodiment 75. The antibody or antigen-binding fragment of any one of embodiments 72-74, comprising a light chain variable domain (VL) having the amino acid sequence of SEQ ID NO: 23.

Embodiment 76. The antibody or antigen-binding fragment of any one of embodiments 72-75, wherein the antibody or antigen-binding fragment specifically binds residues 17-26 (LLHACIPCQL (SEQ ID NO: 161)) of BCMA BCMW37 chain.

Embodiment 77. The antibody or antigen-binding fragment of any one of embodiments 72-76, wherein the antibody or antigen-binding fragment specifically binds to BCMA with an affinity of about $1 \times 10^{-10}$ to $1 \times 10^{-7}$ M.

Embodiment 78. The antibody or antigen-binding fragment of embodiment 77, wherein the antibody or antigen-binding fragment specifically binds to BCMA with an affinity of about $2 \times 10^{-10}$ to $9 \times 10^{-10}$ M.

Embodiment 79. The antibody or antigen-binding fragment of any one of embodiments 72-78 wherein the antibody or antigen-binding fragment is a human antibody or antigen-binding fragment.

Embodiment 80. The antibody or antigen-binding fragment of any one of embodiments 72-79 wherein the antibody or antigen-binding fragment is recombinant.

Embodiment 81. The antigen binding fragment of any one of embodiments 72 to 80 wherein the antigen binding fragment is a Fab fragment, a Fab2 fragment, or a single chain antibody.

Embodiment 82. The antibody or antigen-binding fragment of any one of embodiments 72-81 wherein the antibody or antigen-binding fragment thereof is an IgG1, IgG2, IgG3, or IgG4 isotype.

Embodiment 83. The antibody or antigen-binding fragment of any of embodiments 72-82, wherein the antibody or antigen-binding fragment thereof is an IgG1 or an IgG4 isotype.

Embodiment 84. A pharmaceutical composition comprising the antibody or antigen-binding fragment of any one of embodiments 72-83 and a pharmaceutically acceptable carrier.

Embodiment 85. The pharmaceutical composition of embodiment 84, wherein the pharmaceutical composition further comprises a second therapeutic agent.

Embodiment 86. The pharmaceutical composition of embodiment 85, wherein the second therapeutic agent comprises an anti-CD38 agent, an immunomodulatory imide drug (IMiD), an immune checkpoint inhibitor, an immune co-stimulating agent, a gamma secretase inhibitor, a T-cell enhancer, or any combination thereof.

Embodiment 87. A cell expressing the antibody or antigen-binding fragment of any one of embodiments 72-83.

Embodiment 88. The cell of embodiment 87 wherein the cell is a hybridoma.

Embodiment 89. The cell of embodiment 87 wherein the antibody is recombinantly produced.

Embodiment 90. A method for treating cancer in a subject in need thereof, said method comprising administering to the subject a therapeutically effective amount of the antibody or antigen-binding fragment of any one of embodiments 72-83 or the pharmaceutical composition of any one of embodiments 84-86.

Embodiment 91. The method of embodiment 90, wherein the antibody or antigen-binding fragment or the pharmaceutical composition is administered for a time sufficient to treat the cancer.

Embodiment 92. A method for inhibiting growth or proliferation of a cancer cell, said method comprising administering to said cell an effective amount of the antibody or antigen-binding fragment of any one of embodiments 72-83 or the pharmaceutical composition of any one of embodiments 84-86, wherein said effective amount is sufficient to inhibit the growth or proliferation of said cancer cell.

Embodiment 93. The method of embodiment 92, wherein said cancer cell is in a subject and the antibody or antigen-binding fragment or the pharmaceutical composition is administered to the subject.

Embodiment 94. The method of embodiment 92, wherein said administration is conducted ex vivo.

Embodiment 95. The method of any one of embodiments 90-94 wherein the cancer is a hematological cancer.

Embodiment 96. The method of embodiment 95 wherein the hematological cancer is a BCMA-expressing B cell cancer.

Embodiment 97. The method of embodiment 96 wherein the BCMA-expressing B cell cancer is multiple myeloma.

Embodiment 98. The method of embodiment 97 wherein the BCMA-expressing B cell cancer is smoldering multiple myeloma (SMM).

Embodiment 99. The method of any one of embodiments 90-98, wherein the cancer is relapsed, refractory, or malignant cancer, or any combination thereof.

Embodiment 100. The method of any one of embodiments 90-91, 93, and 95-99, wherein the subject has received a prior treatment.

Embodiment 101. The method of embodiment 100, the prior treatment comprises a proteasome inhibitor, an immunomodulatory drug, a CD38 antibody, a bispecific agent, a CAR-T therapy, or a combination thereof.

Embodiment 102. The method of any one of embodiments 90-101 further comprising administering a second therapeutic agent.

Embodiment 103. The method of embodiment 102 wherein the second therapeutic agent is a chemotherapeutic agent or a targeted anti-cancer therapy.

Embodiment 104. The method of embodiment 103 wherein the chemotherapeutic agent is cytarabine, an anthracycline, histamine dihydrochloride, or interleukin 2 (IL-2).

Embodiment 105. The method of embodiment 104 wherein the second therapeutic agent is an anti-CD38 agent, an immunomodulatory imide drug (IMiD), an immune checkpoint inhibitor, an immune co-stimulating agent, a gamma secretase inhibitor, a T-cell enhancer, or any combination thereof.

Embodiment 106. The method of any one of embodiments 90-91, 93, and 95-105, wherein the antibody or antigen-binding fragment or the pharmaceutical composition is administered intravenously, intramuscularly, intraperitoneally, and/or subcutaneously to the subject.

Embodiment 107. The method of any one of embodiments 90-91, 93, and 95-106, wherein the antibody or antigen-binding fragment, or the pharmaceutical composition is administered subcutaneously to the subject.

Embodiment 108. A method for generating the antibody or antigen-binding fragment of any one of embodiments 72-83, wherein said method comprises culturing the cell of any one of embodiments 87 to 89 and isolating said antibody or antigen-binding fragment.

Embodiment 109. A synthetic polynucleotide encoding the antibody or antigen-binding fragment of any one of embodiments 72-83.

Embodiment 110. A kit comprising (i) the antibody or antigen-binding fragment of any one of embodiments 72-83 and/or a polynucleotide of embodiment 109 and (ii) packaging for the same.

Embodiment 111. A trispecific antibody, or a trispecific binding fragment thereof, comprising:
- a) a first heavy chain portion (HC1) comprising a first heavy chain variable domain (VH);
- b) a light chain portion (LC) comprising a light chain variable domain (VL); and c) a second heavy chain portion (HC2) comprising a second VH domain, wherein
- (i) the HC1 VH and the LC VL domains form a first antigen-binding site that binds a first antigen,
- (ii) the HC2 VH domain forms a second antigen-binding site that binds a second antigen, (iii) the HC1 or the HC2 further comprise a third VH domain forming a third antigen-binding site that binds a third antigen,
- (iv) the HC1 and HC2 each optionally comprise a Fragment crystallizable (Fc) domain comprising a CH2-CH3 domain; and wherein the first antigen is cluster of differentiation 3 (CD3), and
- (v) the second antigen is B cell maturation antigen (BCMA), and the third antigen is G-protein coupled receptor family C group 5 member D (GPRC5D); or
- (vi) the second antigen is G-protein coupled receptor family C group 5 member D (GPRC5D), and the third antigen is B cell maturation antigen (BCMA).

Embodiment 112. The trispecific antibody or trispecific binding fragment of embodiment 111, wherein the HC2 comprises the third VH domain forming the third antigen-binding site that binds the third antigen.

Embodiment 113. The trispecific antibody or trispecific binding fragment of embodiment 112, wherein the HC2 comprises, from N to C-terminus, the second VH domain forming the second antigen-binding site, the Fc domain, a first linker (L1), and the third VH domain forming the third antigen-binding site.

Embodiment 114. The trispecific antibody or trispecific binding fragment of any one of embodiments 111-113, wherein the HC2 comprises the second VH domain forming the second antigen-binding site that binds GPRC5D, and the HC2 further comprises the third VH domain forming the third antigen-binding site that binds BCMA.

Embodiment 115. The trispecific antibody or trispecific binding fragment of embodiment 111, wherein the HC1 comprises the third VH domain forming the third antigen-binding site that binds the third antigen.

Embodiment 116. The trispecific antibody or trispecific binding fragment of embodiment 115, wherein the HC1 comprises, from N to C-terminus, a the first VH forming the first antigen-binding site, a CH1 domain, the Fc domain, a first linker (L1), and the third VH domain forming the third antigen-binding site.

Embodiment 117. The trispecific antibody or trispecific binding fragment of any one of embodiments 111, 115, and 116, wherein the HC2 comprises the second VH domain forming the second antigen-binding site that binds BCMA, and the HC1 further comprises the third VH domain forming the third antigen-binding site that binds GPRC5D.

Embodiment 118. The trispecific antibody or trispecific binding fragment of any one of embodiments 111-117, wherein the HC1 VH and LC VL form the first antigen-binding site comprises an antigen-binding fragment (Fab) comprising the first antigen-binding site.

Embodiment 119. The trispecific antibody or trispecific binding fragment of any one of embodiments 111-118, wherein the HC2 VH forms a single-chain variable fragment (scFv) comprising the second antigen-binding site.

Embodiment 120. The trispecific antibody or trispecific binding fragment of any one of embodiments 111-119, wherein the third VH forms a single-chain variable fragment (scFv) comprising the third antigen-binding site.

Embodiment 121. The trispecific antibody or trispecific binding fragment of any one of embodiments 111-120, wherein the Fc domains of HC1 and HC2 comprise one or more different mutations which promote heterodimerization.

Embodiment 122. The trispecific antibody or trispecific binding fragment of embodiment 121, wherein the Fc domain of the HC1 comprise mutations T366S, L368A and Y407V (EU numbering) and the Fc domain of the HC2 comprises mutation T366W (EU numbering).

Embodiment 123. The trispecific antibody or trispecific binding fragment of embodiment 121, wherein the Fc domain of the HC2 comprise mutations T366S, L368A and Y407V (EU numbering) and the Fc domain of the HC1 comprises mutation T366W (EU numbering).

Embodiment 124. The trispecific antibody or trispecific binding fragment of any one of embodiments 111-123, wherein the Fc domains of HC1 and/or HC2 further comprise one or more mutations which reduce Fc binding to a Fcγ receptor.

Embodiment 125. The trispecific antibody or trispecific binding fragment of embodiment 124, wherein the Fcγ receptor is FcγRI, FcγRIIA, FcγRIIB, FcγRIIIA, and/or FcγRIIIB.

Embodiment 126. The trispecific antibody or trispecific binding fragment of embodiment 124 or 125, wherein the Fc domains of HC1 and/or HC2 each comprise one or more mutations selected from L234A, L235A, and D265S (EU numbering).

Embodiment 127. The trispecific antibody or trispecific binding fragment of embodiment 126, wherein the Fc domains of HC1 and HC2 each comprise mutations L234A, L235A, and D265S (EU numbering).

Embodiment 128. The trispecific antibody or trispecific binding fragment of any one of embodiments 111-127, wherein the Fc domains of HC1 or HC2 further comprise one or more mutations which reduce Fc binding to protein A.

Embodiment 129. The trispecific antibody or trispecific binding fragment of embodiment 128, wherein the Fc domains of HC1 or HC2 comprises mutations H435R and/or Y436F (EU numbering).

Embodiment 130. The trispecific antibody or trispecific binding fragment of embodiment 129, wherein the Fc domain of HC1 comprises mutations H435R and Y436F (EU numbering).

Embodiment 131. The trispecific antibody or trispecific binding fragment of any one of embodiments 113-114 and 116-130, wherein the first linker (L1) comprises any one of the amino acid sequences of SEQ ID NOs: 25, 127-157, and 163.

Embodiment 132. The trispecific antibody or trispecific binding fragment of any one of embodiments 131, wherein the first linker (L1) comprises the amino acid sequence of GGSEGKSSGSGSESKSTGGS (SEQ ID NO: 25) or GGGGSGGGGSGGGGSGGGGS ((G4S)4, SEQ ID NO: 163).

Embodiment 133. The trispecific antibody or trispecific binding fragment of any one of embodiments 111-132, wherein the first antigen-binding site that binds CD3 comprises: a heavy chain complementarity determining region 1 (CDR1) comprising the amino acid sequence of GDSVFNNNAAWS (SEQ ID NO: 4), a heavy chain CDR2 comprising the amino acid sequence of RTYYRSKWLYD (SEQ ID NO: 5), and a heavy chain CDR3 comprising the amino acid sequence of GYSSSFDY (SEQ ID NO: 6).

Embodiment 134. The trispecific antibody or trispecific binding fragment of any one of embodiments 111-133, wherein the first antigen-binding site that binds CD3 comprises: a light chain complementarity determining region 1 (CDR1) comprising the amino acid sequence of TGTSSNIGTYKFVS (SEQ ID NO: 1), a light chain CDR2 comprising the amino acid sequence of EVSKRPS (SEQ ID NO: 2), and a light chain CDR3 comprising the amino acid sequence of VSYAGSGTLL (SEQ ID NO: 3).

Embodiment 135. The trispecific antibody or trispecific binding fragment of any one of embodiments 111-134, wherein the first antigen-binding site that binds CD3 comprises a heavy chain variable domain (VH) comprising the amino acid sequence of SEQ ID NO: 8.

Embodiment 136. The trispecific antibody or trispecific binding fragment of any one of embodiments 111-135, wherein the first antigen-binding site that binds CD3 comprises a light chain variable domain (VL) comprising the amino acid sequence of SEQ ID NO: 7.

Embodiment 137. The trispecific antibody or trispecific binding fragment of any one of embodiments 111-136, wherein the second or third antigen-binding site that binds GPRC5D comprises: a heavy chain complementarity determining region 1 (CDR1) comprising the amino acid sequence of GFSLTNIRMSVS (SEQ ID NO: 12), a heavy chain CDR2 comprising the amino acid sequence of HIFSNDEKS (SEQ ID NO: 13), and a heavy chain CDR3 comprising the amino acid sequence of MRLPYGMDV (SEQ ID NO: 14).

Embodiment 138. The trispecific antibody or trispecific binding fragment of any one of embodiments 111-137, wherein the second or third antigen-binding site that binds GPRC5D comprises: a light chain complementarity determining region 1 (CDR1) comprising the amino acid sequence of RSSQSLVHSDGNTYLS (SEQ ID NO: 9), a light chain CDR2 comprising the amino acid sequence of KISNRFF (SEQ ID NO: 10), and a light chain CDR3 comprising the amino acid sequence of MQATQFPHT (SEQ ID NO: 11).

Embodiment 139. The trispecific antibody or trispecific binding fragment of any one of embodiments 111-138, wherein the second or third antigen-binding site that binds GPRC5D comprises a heavy chain variable domain (VH) comprising the amino acid sequence of SEQ ID NO: 16.

Embodiment 140. The trispecific antibody or trispecific binding fragment of any one of embodiments 111-139, wherein the second or third antigen-binding site that binds GPRC5D comprises a light chain variable domain (VL) comprising the amino acid sequence of SEQ ID NO: 15.

Embodiment 141. The trispecific antibody or trispecific binding fragment of any one of embodiments 111-140, wherein the second or third antigen-binding site that binds BCMA comprises: a heavy chain complementarity determining region 1 (CDR1) comprising the amino acid sequence of GFTFSSYAMS (SEQ ID NO: 20), a heavy chain CDR2 comprising the amino acid sequence of AIS-GSGGSTY (SEQ ID NO: 21), and a heavy chain CDR3 comprising the amino acid sequence of DEGYSSGHYYGMDV (SEQ ID NO: 22).

Embodiment 142. The trispecific antibody or trispecific binding fragment of any one of embodiments 111-141, wherein the second or third antigen-binding site that binds BCMA comprises: a light chain complementarity determining region 1 (CDR1) comprising the amino acid sequence of RASQSISSSFLT (SEQ ID NO: 17), a light chain CDR2 comprising the amino acid sequence of GASSRAT (SEQ ID NO: 18), and a light chain CDR3 comprising the amino acid sequence of QHYGSSPMYT (SEQ ID NO: 19).

Embodiment 143. The trispecific antibody or trispecific binding fragment of any one of embodiments 111-142, wherein the second or third antigen-binding site that binds BCMA comprises a heavy chain variable domain (VH) comprising the amino acid sequence of SEQ ID NO: 24.

Embodiment 144. The trispecific antibody or trispecific binding fragment of any one of embodiments 111-143, wherein the second or third antigen-binding site that binds BCMA comprises a light chain variable domain (VL) comprising the amino acid sequence of SEQ ID NO: 23.

Embodiment 145. The trispecific antibody or trispecific binding fragment of any one of embodiments 119-144, wherein the scFv comprises, from the N- to C-terminus, a VH, a second linker (L2) and a VL (VH-L2-VL); or the VL, the L2 and the VH (VL-L2-VH).

Embodiment 146. The trispecific antibody or trispecific binding fragment of any one of embodiments 119-145, wherein the scFv comprises, from the N- to C-terminus, the VL, the L2 and the VH (VL-L2-VH).

Embodiment 147. The trispecific antibody or trispecific binding fragment of embodiment 145 or 146, wherein the second linker (L2) comprises any one of the amino acid sequences of SEQ ID NOs: 25, 127-157, and 163.

Embodiment 148. The trispecific antibody or trispecific binding fragment of any one of embodiments 145-147, wherein the L2 comprises an amino acid sequence of GGSEGKSSGSGSESKSTGGS (SEQ ID NO: 25).

Embodiment 149. The antibody or antigen-binding fragment of any one of embodiments 111 to 148, wherein the first antigen-binding site that specifically binds to residues 22-35 (QDGNEEMGGITQTP (SEQ ID NO: 160)) of the CD3ε chain.

Embodiment 150. The antibody or antigen-binding fragment of any one of embodiments 111-149, wherein the first antigen-binding site that specifically binds to CD3 with an affinity of about $1\times10^{-8}$ to $1\times10^{-7}$ M.

Embodiment 151. The antibody or antigen-binding fragment of embodiment 150, wherein the first antigen-binding site that specifically binds to CD3 with an affinity of about $2\times10^{-8}$ to $4\times10^{-8}$ M.

Embodiment 152. The antibody or antigen-binding fragment of any one of embodiments 111 to 151, wherein the second or third antigen-binding site specifically binds residues 17-26 (LLHACIPCQL (SEQ ID NO: 161)) of BCMA BCMW37 chain.

Embodiment 153. The antibody or antigen-binding fragment of embodiment 152, wherein the second or third antigen-binding site specifically binds to BCMA with an affinity of about $1\times10^{-10}$ to $1\times10^{-7}$ M.

Embodiment 154. The antibody or antigen-binding fragment of embodiment 153, wherein the second or third antigen-binding site specifically binds to BCMA with an affinity of about $2\times10^{-10}$ to $9\times10^{-10}$ M.

Embodiment 155. The antibody or antigen-binding fragment of any one of embodiments 111 to 154, wherein the antibody or antigen-binding fragment thereof is an IgG1, IgG2, IgG3, or IgG4 isotype.

Embodiment 156. The antibody or antigen-binding fragment of any of embodiments 111 to 155 wherein the antibody or antigen-binding fragment thereof is an IgG1 isotype.

Embodiment 157. The trispecific antibody or trispecific binding fragment of embodiment 111, wherein the HC1 comprises the amino acid sequence of SEQ ID NO: 26.

Embodiment 158. The trispecific antibody or trispecific binding fragment of embodiment 111 or 157, wherein the LC comprises the amino acid sequence of SEQ ID NO: 27.

Embodiment 159. The trispecific antibody or trispecific binding fragment of embodiment 111, 157 or 158, wherein the HC2 comprises the amino acid sequence of SEQ ID NO: 28.

Embodiment 160. The trispecific antibody or trispecific binding fragment of embodiment 111, wherein the HC1 comprises the amino acid sequence of SEQ ID NO: 29.

Embodiment 161. The trispecific antibody or trispecific binding fragment of embodiment 111 or 160, wherein the LC comprises the amino acid sequence of SEQ ID NO: 30.

Embodiment 162. The trispecific antibody or trispecific binding fragment of embodiment 111, 160 or 161, wherein the HC2 comprises the amino acid sequence of SEQ ID NO: 31.

EXAMPLES

The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within, and can be made without departing from, the true scope of the invention.

Example 1: Target Validation

Figure 1B:
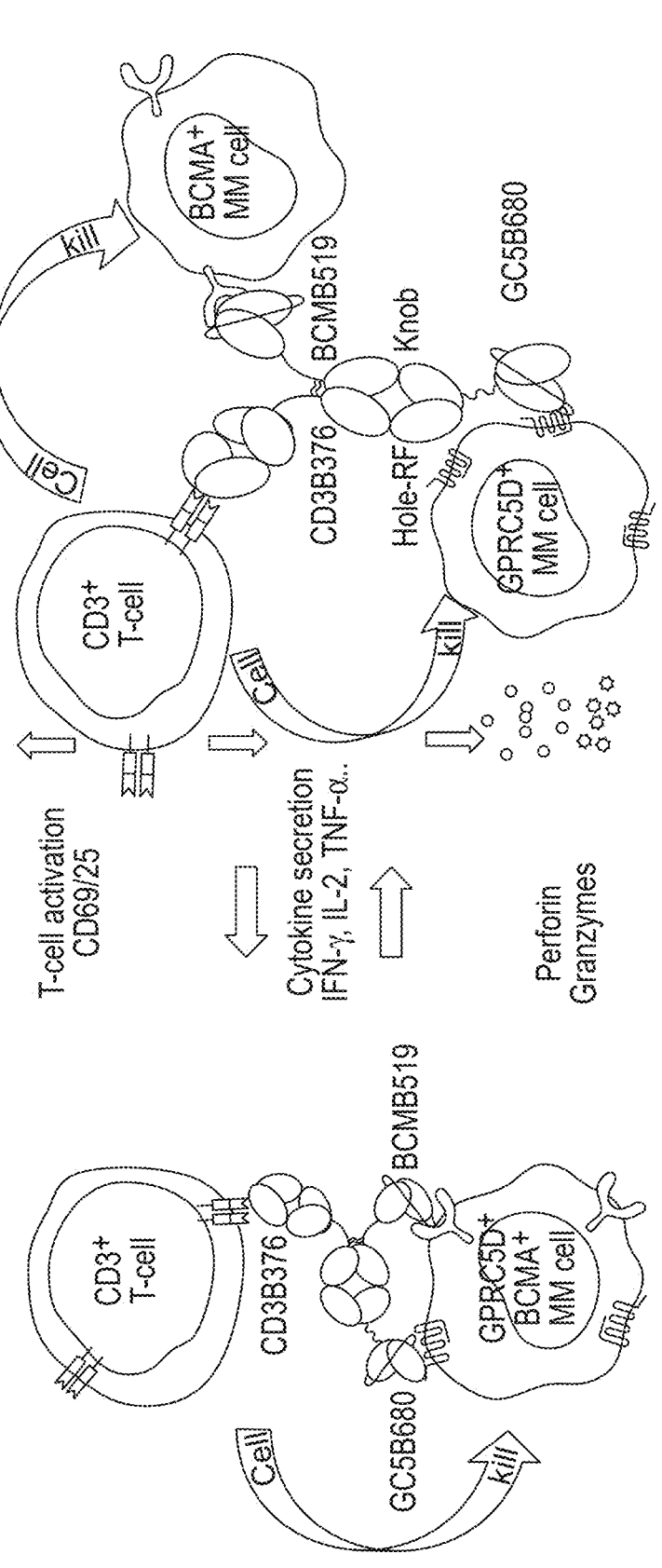
Figure 2A:
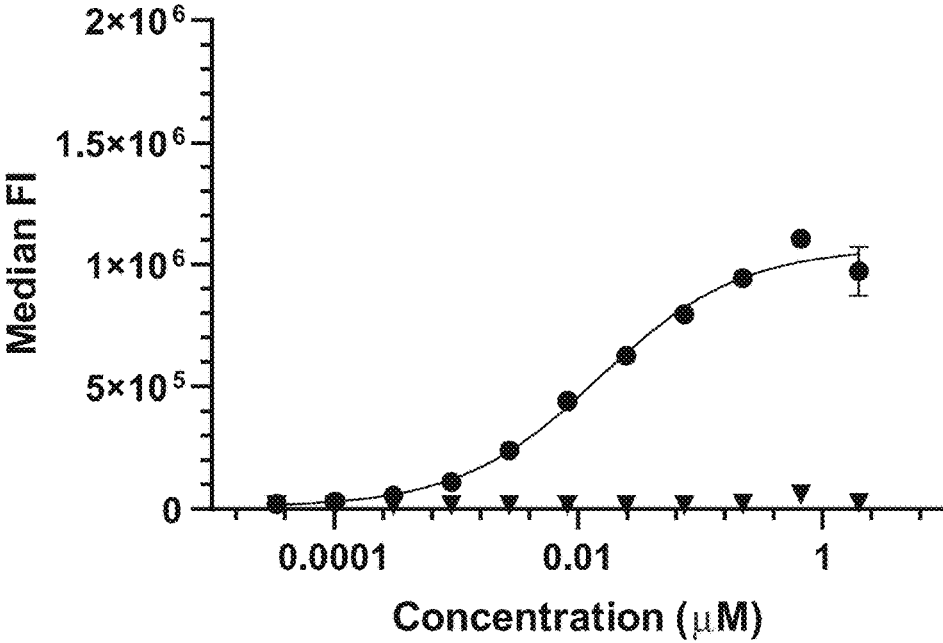
FIGS. 2A-2D. BGCB463 (circles) or negative control B23B251 (triangles) were all incubated with H929 wild type (WT) (FIG. 2A), H929-GPRC5D knock out (KO) (FIG. 2B), H929-BCMA KO (FIG. 2C), and H929-GPRC5D/BCMA KO (FIG. 2D) cells for 1 hr at 37° C. at a starting concentration of 2 µM. After secondary detection with AF647-labeled material, the MFI signal was analyzed to generate an $EC_{50}$ and $EC_{90}$. Curves are representative of five independent experiments. $EC_{50}$ or $EC_{90}$ values are averages of these.
Figure 2B:
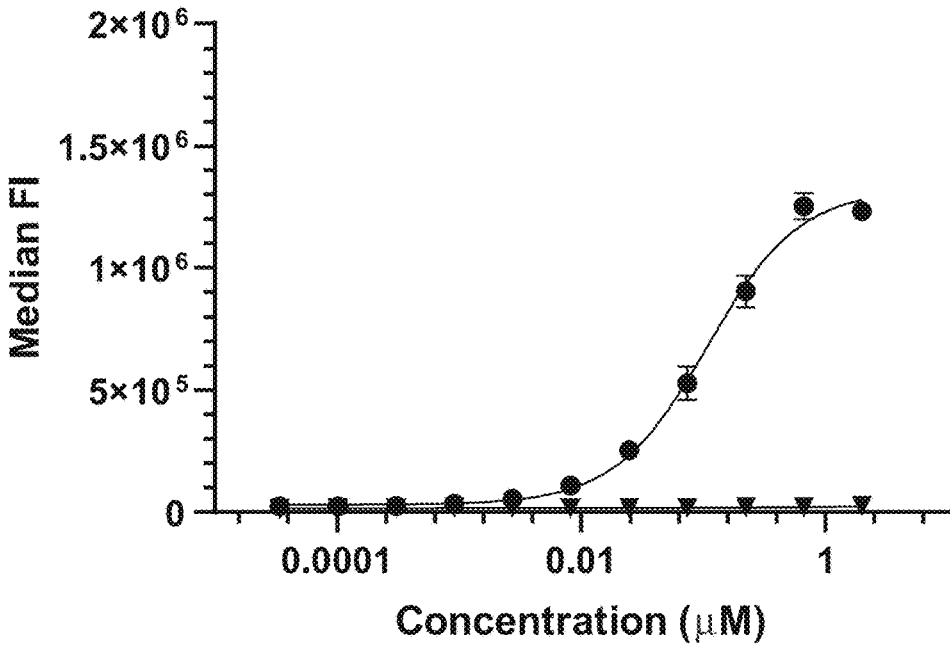
Figure 2C:
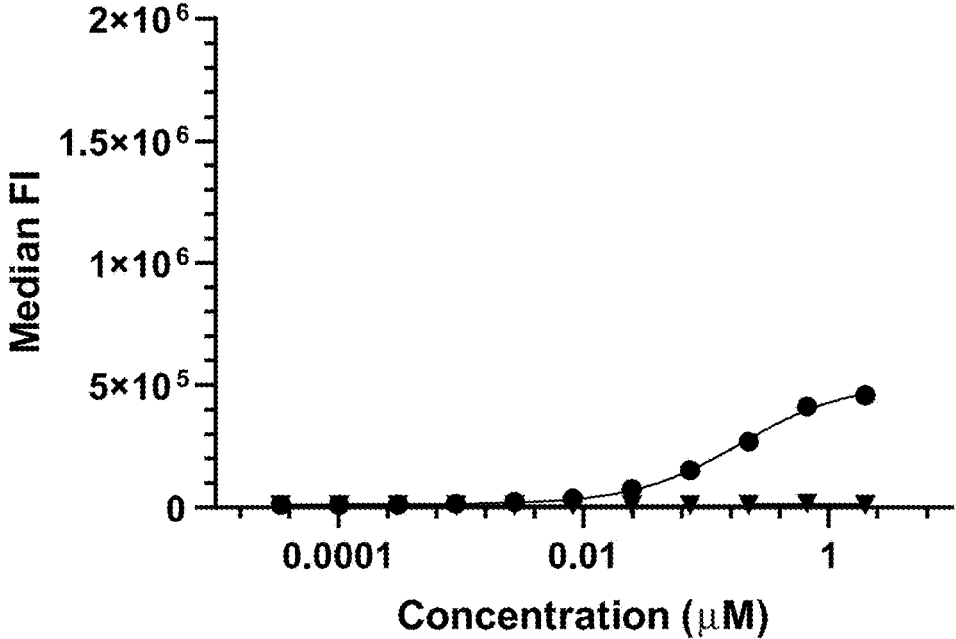
Figure 2D:
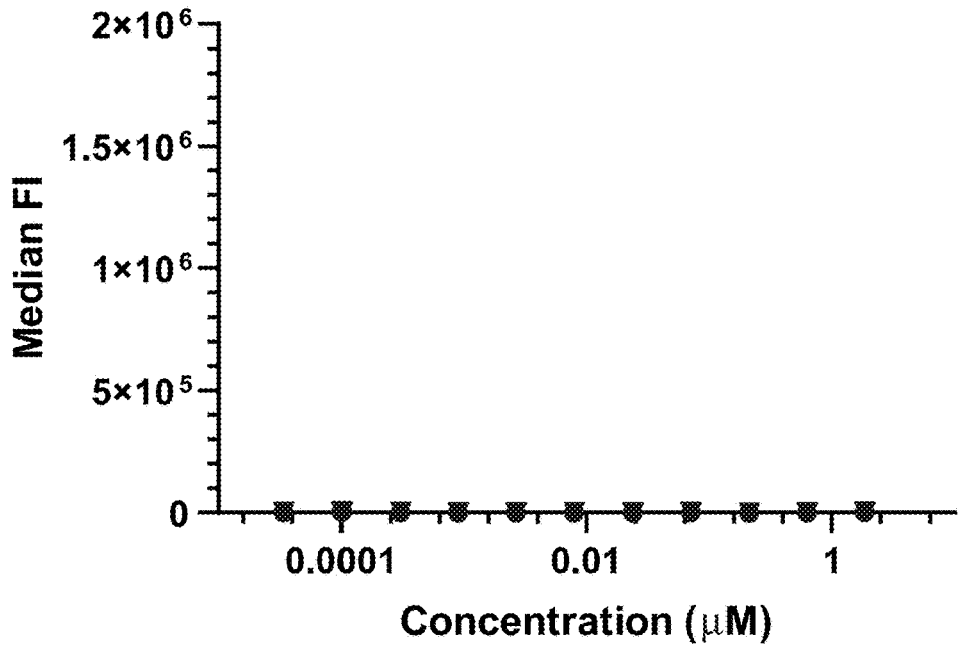
Figures 3A, 3B:
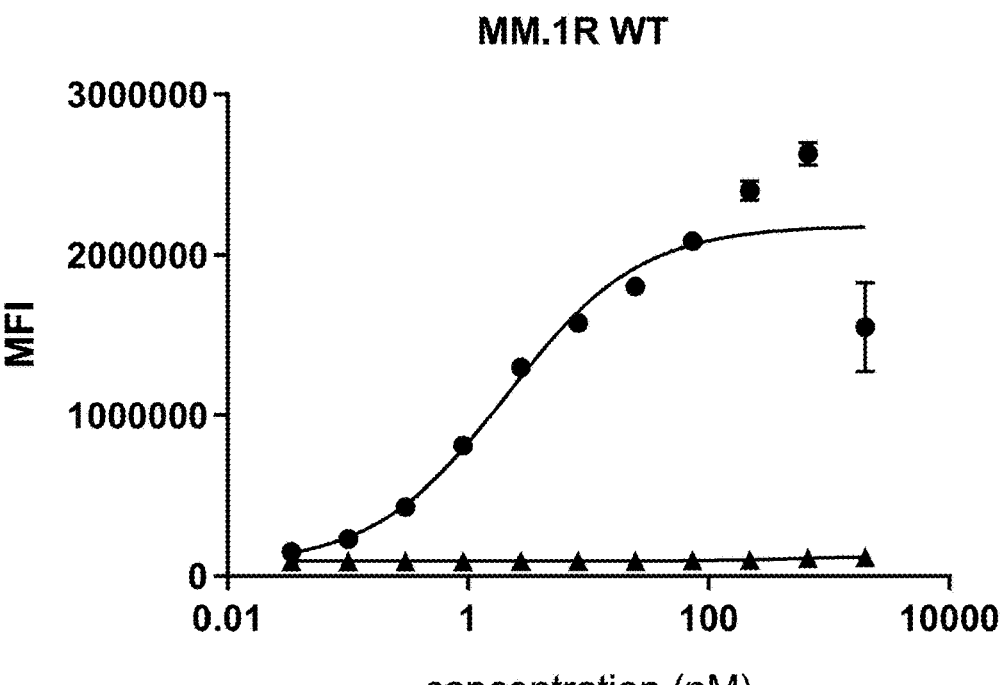
FIGS. 3A-3D. BGCB463 (circles) or negative control B23B251 (triangles) were all incubated with MM.1R WT (FIG. 3A), MM.1R-GPRC5D KO (FIG. 3B), MM.1R-BCMA KO (FIG. 3C), and MM.1R-GPRC5D/BCMA KO (FIG. 3D) cells for 1 hr at 37° C. at a starting concentration of 2 µM. After secondary detection with AF647-labeled material, the MFI signal was analyzed to generate an $EC_{50}$ and $EC_{90}$. Curves are representative of five independent experiments.
Figure 3C:
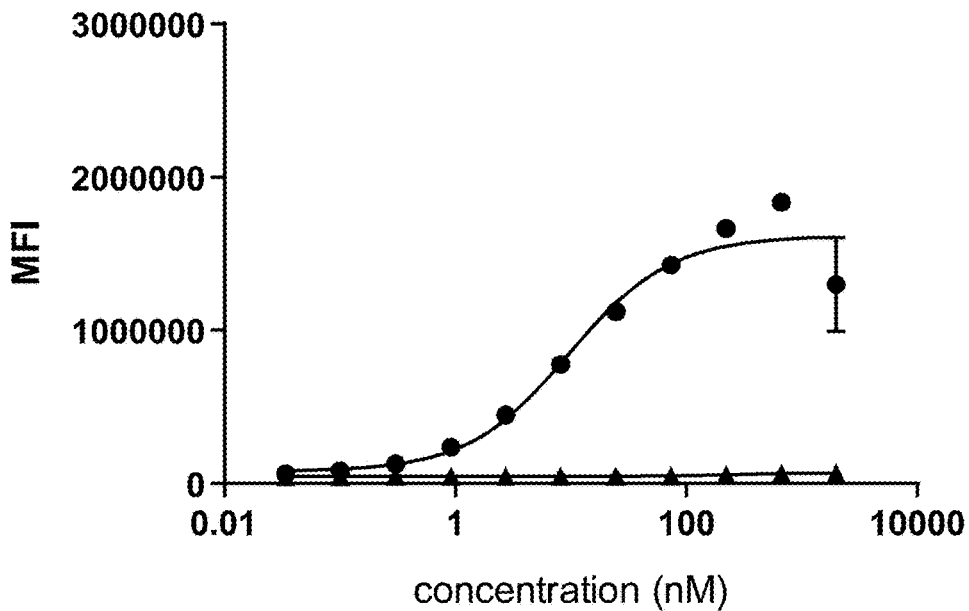
Figure 3D:
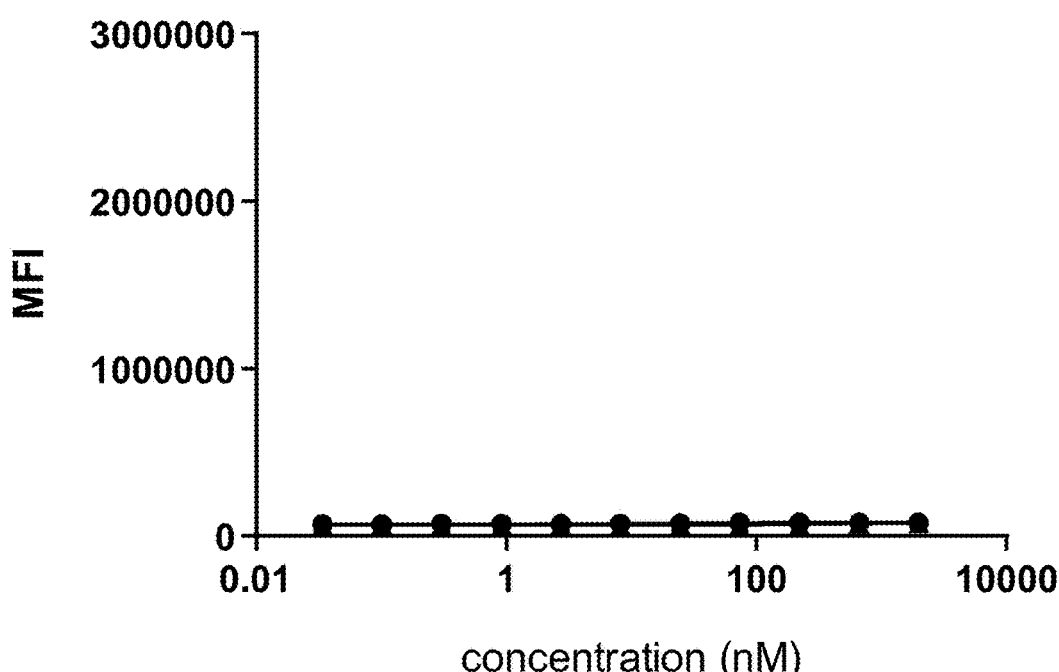

The scientific rationale for the development of BCMA× GPRC5D×CD3 trispecific antibodies is to efficiently eradicate malignant clonal plasma cells from bone marrow and other organs of MM patients. This is to be achieved through the administration of a trispecific antibody that can simultaneously bind to the TCR co-receptor CD3ε that is expressed on the effector T cells and to target proteins, GPRC5D and BCMA, that are expressed on B-cell lineage cells, mostly plasma blasts and mature plasma cells (8). By bringing the T cells and cancer cells in proximity, BCMA× GPRC5D×CD3 trispecific antibodies promote the activation of T cells with the subsequent cancer cell lysis mediated by secreted perforin and various granzymes stored in the secretory vesicles of CTLs (FIG. 1B).

The mechanistic advantage of these approaches includes their ability to draw CD3+ T cells in close proximity to plasma cells without regard to TCR specificity or reliance on major histocompatibility complex (MHC) Class I molecules on the surface of antigen-presenting cells for activation, circumventing the known MoR to T cell-based therapies through down-regulation of MHC class molecules.

Target Selection Validation

The potential success of T-cell-mediated therapeutic approaches relies on the presence of antigens specifically found on the surface of tumor cells. Out of the most common plasma cell markers, BCMA and GPRC5D exhibited selective expression patterns and clinical proof of concept (PoC) has been established for both targets.

BCMA (also known as CD269; gene name TNFRSF17) is a 20 kDa, Type I membrane protein that is exclusively expressed on B-cell lineage cells, plays a critical role in B-cell maturation, and is selectively induced during plasma cell differentiation (9,10). BCMA binds 2 ligands: APRIL (CD256) and BAFF (CD257; 11). The BCMA receptor is a 184 amino acid protein with a 54 amino acid extracellular domain. In addition to expression on the cell surface, BCMA is cleaved by gamma secretase activity at the transmembrane domain, generating a~6 kDa soluble BCMA protein fragment (12). High levels of soluble BCMA were measured in MM patient serum samples (13) and correlated with plasma cell counts (14). Inhibition of gamma secretase results in significant increase of BCMA surface protein expression in human primary B cells (12) and MM cell lines and bone marrow mononuclear cells (13). BCMA has been established as a validated target in MM with several approved therapeutics (15-17).

GPRC5D is a 7-transmembrane receptor protein that is classified as a Type C G-protein-coupled receptor (GPCR) based on the sequence homology score. GPRC5D is an orphan receptor whose ligand and signaling mechanisms are yet to be identified. GPRC5D receptor is a 354 amino acid protein that has a typical 7-transmembrane structure with a short 27 amino acid N-terminus unlike other family members (18). GPRC5D mRNA is predominantly expressed in cells with a plasma cell phenotype and is also expressed in all malignant plasma cells from subjects with MM (19-23). Levels of GPRC5D expression in subjects with MM correlated well with plasma cell burden and genetic aberrations such as Rb-1 deletion (19).

Target Expression

BCMA and GPRC5D mRNA and protein expression is restricted to limited cell types. BCMA is expressed on mature B cells and plasma cells whereas GPRC5D expression is further limited to only the plasma cell phenotype on immune cells. In addition to immune cell expression, GPRC5D mRNA is expressed in hard keratinized tissues. GPRC5D mRNA levels on bone marrow CD138+ cells from myeloma patients were elevated compared to the normal healthy subject CD138+ cells and high mRNA levels of BCMA were mostly restricted to matured B cells including plasma cells (10,13,19,21-26). BCMA (13,25) and GPRC5D (19,21,22) protein expression in normal tissues was mainly found in plasma cells by immunohistochemistry (IHC) staining. In addition, GPRC5D expression was also detected in hard keratinized tissues such as hair follicles (27). MM patient bone marrow mononuclear cells exhibited clonal heterogeneity in terms of BCMA and GPRC5D expression (21,22). Detailed target expression profiles are described in Example 2.

Importantly, the selective expression of BCMA and GPRC5D on CD138+ bone marrow cells of MM origin and their low risks for on-target/off-tumor toxicity designates them as potential targets for T-cell-mediated therapeutics (10,13,20-22).

Example 2: Molecule Design, Sequence, and Structure of BGCB463 Trispecific Antibody BGCB463 is an immunoglobulin (Ig) G1 trispecific antibody that can bind simultaneously or individually to the epsilon subunit of the cluster of differentiation 3 receptor complex (CD3ε) on T lymphocytes (T cells), and to GPRC5D (G-protein coupled receptor family C group 5 member D) and to BCMA (B cell maturation antigen, TNFRSF17) on tumor cells. The antibody has mutations of L234A, L235A, and D265S in the constant region (Fc) to abolish interaction with Fc receptors and heterodimerization has been enhanced using the knobs-into-holes platform mutations. The anti-CD3ε "hole" chain also comprises "RF" mutations (H435R, Y436F) to disrupt protein A binding of monomeric and homodimerized hole chains. The molecule comprises an anti-CD3ε Fab region on the "hole, RF" chain and an anti-GPRC5D scFv v-region on the "knob" chain. The trispecific antibody was developed to evaluate the therapeutic potential of dual tumor targeting GPRC5D and BCMA and CD3 for T cell redirection. An illustration of BGCB463 is depicted in FIG. 1A.

The trispecific BGCB463 antibody was generated by co-expression of the anti-CD3 heavy chain (HC) A and light chain (LC) with the anti-GPRC5D, anti-BCMA heavy chain B. The anti-CD3 variable region was discovered by immunizing transgenic humanized rats [OmniRat (OMT™)] with recombinant CD3ε protein. The anti-GPRC5D variable region (VR000038761) featured in BGCB463 is derived from the mAb GC5B680, discovered by immunizing transgenic humanized mice [Ablexis] with DNA encoding GPRC5D. The parent v-region (VR000029832) contained an "NSS" motif in the HC framework 3 region which presented a risk for N-linked glycosylation and which represented a mutation from the IGHV2-26*01 germline. The site was mutated back to the germline sequence "STS" to eliminate the risk for N-linked glycosylation, and this change resulted in the final variable region VR000038761. The anti-BCMA variable region (VR000003260) featured in BGCB463 is derived from the mAb BCMB519, discovered by immunizing transgenic humanized mice [Ablexis] with recombinant BCMA protein. No further modifications were made to this v-region. Both the anti-GPRC5D and anti-BCMA v-regions were formatted as single-chain fragment variable (scFv) in the final molecule.

The amino acid sequence for the BGCB463 heavy chains and light chain, as deduced from the cDNA sequence of BGCB463, and confirmed by peptide mapping and mass spectrometry, is shown below (Table 5). The 3 complementarity-determining regions (CDRs), defined according to ABM numbering, in each chain are bolded and underlined. The Gln residue at position 1 of BGCB463 heavy chain 1, Gln residue at position 1 of BGCB463 light chain, and Asp at position 1 of BGCB463 heavy chain 2 constitute the N-termini of the mature chains. Both heavy chains comprising BGCB463 IgG1 AAS have the following point mutations: L234A, L235A, and D265S. Heavy chain 1 from BGCB463 features the "hole" mutations: T366S, L368A, Y407V and the RF mutations: H435R, Y436F, while heavy chain 2 features the "knob" mutation: T366W. The knobs-into-holes mutations promote heterodimerization of the Fc. The "RF" mutations disrupt binding to protein A. The mutations for FcγR receptor silencing (AAS) and the knobs-into-holes mutations are underlined in the sequences below.

TABLE 5

Amino Acid Sequence of BGCB463

| Area | AA Sequence | | SEQ ID NO. |
|------|-------------|---|------------|
| Light Chain 1 | QSALTQPASV SGSPGQSITI SCTGTSSNIG TYKFVSWYQQ HPDKAPKVLL YEVSKRPSGV SSRFSGSKSG NTASLTISGL QAEDQADYHC VSYAGSGTLL FGGGTKLTVL GQPKAAPSVT LFPPSSEELQ ANKATLVCLI SDFYPGAVTV AWKADSSPVK AGVETTTPSK QSNNKYAASS YLSLTPEQWK SHRSYSCQVT HEGSTVEKTV APTECS | | 27 |
| Heavy Chain 1 | QVQLQQSGPR LVRPSQTLSL TCAISGDSVF NNNAAWSWIR QSPSRGLEWL GRTYYRSKWL YDYAVSVKSR ITVNPDTSRN QFTLQLNSVT PEDTALYYCA RGYSSSFDYW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPEAAGG PSVFLFPPKP KDTLMISRTP EVTCVV̱S̱VS HEDPEVKFNW YVDGVEVHNA KTKPREEQ̱YN STYRVVSVLT VLHQDWLNGK EYKCKVSNKA LPAPIEKTIS KAKGQPREPQ VYTLPPSREE MTKNQVSLSC AVKGFYPSDI AVEWESNGQP ENNYKTTPP̱V ḺDSDGSFFLV SKLTVDKSRW QQGNVFSCSV MHEALHNRF̱Ṯ QKSLSLSPGK | | 26 |
| Heavy Chain 2 | DIVMTQTPLS SPVTLGQPAS ISCRSSQSLV HSDGNTYLSW LQQRPGQPPR LLIYKISNRF FGVPDRFSGS GAGTDFTLKI SRVEAEDVGV YYCMQATQFP HTFGQGTKLE IKGGSEGKSS GSGSESKSTG GSQVTLKESG PVLVKPTETL TLTCTVSGFS LTNIRMSVSW IRQPPGKALE WLAHIFSNDE KSYSTSLKSR LTISRDTSKS QVVLTLTNVD PVDTATYYCA RMRLPYGMDV WGQGTTVTVS SEPKSSDKTH TCPPCPAPEA AGGPSVFLFP PKPKDTLMIS RTPEVTCVV̱V̱ S̱VSHEDPEVK FNWYVDGVEV HNAKTKPREE Q̱YNSTYRVVS VLTVLHQDWL NGKEYKCKVS NKALPAPIEK TISKAKGQPR EPQVYTLPPS REEMTKNQVS LWCLVKGFYP SDIAVEWESN GQPENNYKTT P̱PVLDSDGSF FLYSKLTVDK SRWQQGNVFS CSVMHEALHN HYTQKSLSLS PGKGGSEGKS SGSGSESKST GGSEIVLTQS PGTLSLSPGE RATLSCRASQ SISSSFLTWY QQKPGQAPRL LIYGASSRAT GIPDRFSGGG SGTDFTLTIS RLEPEDFAVY YCQHYGSSPM YTFGQGTKLE IKGGSEGKSS GSGSESKSTG GSEVQLLESG GGLVQPGGSL RLSCAASGFT FSSYAMSWVR QAPGKGLEWV SAISGSGGST YYADSVKGRF TISRDNSKNT LYLQMNSLRA EDTAVYYCAK DEGYSSGHYY GMDVWGQGTT VTVSS | | 28 |

Example 3: Immunogenicity Risk Assessment of BGCB463 trispecific antibody

The trispecific antibody sequences were analyzed for potential immunogenicity using the T-regulatory ($T_{reg}$) adjusted scores from the EpiVax Epimatrix in silico immunogenicity prediction program (Table 6). EpiVax program computationally calculates the binding potential to the most common BILA molecules within each of the "supertypes". The report provides results that are representative of >90%0 of human populations worldwide without the necessity of testing each haplotype individually. The EpiVax score is calculated by aggregating the EpiMatrix scores of all predicted T-cell epitopes contained within a given protein sequence and adjusting for expected T-cell epitope content and protein length. The Epivax score interpretation is as follows: an EpiVax score of <−20 is "Ideal"; an EpiVax score from −20 to +20 is "Acceptable"; and an EpiVax score of >+20 is "Unacceptable."

TABLE 6

| Immunogenicity assessment for BGCB463 | | | | |
|---|---|---|---|---|
| BGCB463 Chain info | Amino acid sequence of variable region | SEQ ID NO. | EpiVax score | EpiVax score interpretation |
| Light chain 1 (CD3B376) VL | QSALTQPASVSGSPGQSITISCTGT SSNIGTYKFVSWYQQHPDKAPKVLL YEVSKRPSGVSSRFSGSKSGNTASL TISGLQAEDQADYHCVSYAGSGTLL FGGGTKLTVL | 7 | -44.88 | Ideal |
| Heavy Chain 1 (CD3B376) VH | QVQLQQSGPRLVRPSQTLSLTCAIS GDSVFNNNAAWSWIRQSPSRGLEWL GRTYYRSKWLYDYAVSVKSRITVNP DTSRNQFTLQLNSVTPEDTALYYCA RGYSSSFDYWGQGTLVTVSS | 8 | +65.28 | Unacceptable |
| Heavy chain 2 N-terminal scFv (GC5B680 N68S, S69T) VL | DIVMTQTPLSSPVTLGQPASISCRS SQSLVHSDGNTYLSWLQQRPGQPPR LLIYKISNRFFGVPDRFSGSGAGTD FTLKISRVEAEDVGVYYCMQATQFP HTFGQGTKLEIK | 15 | -3.12 | Acceptable |
| Heavy chain 2 N-terminal scFv (GC5B680 N68S, S69T) VH | QVTLKESGPVLVKPTETLTLTCTVS GFSLTNIRMSVSWIRQPPGKALEWL AHIFSNDEKSYSTSLKSRLTISRDT SKSQVVLTLTNVDPVDTATYYCARM RLPYGMDVWGQGTTVTVSS | 16 | -11.65 | Acceptable |
| Heavy chain 2 C-terminal scFv (BCMB519) VL | EIVLTQSPGTLSLSPGERATLSCRA SQSISSSFLTWYQQKPGQAPRLLIY GASSRATGIPDRFSGGGSGTDFTLT ISRLEPEDFAVYYCQHYGSSPMYTF GQGTKLEIK | 23 | -52.88 | Ideal |
| Heavy chain 2 C-terminal scFv (BCMB519) VH | EVQLLESGGGLVQPGGSLRLSCAAS GFTFSSYAMSWVRQAPGKGLEWVSA ISGSGGSTYYADSVKGRFTISRDNS KNTLYLQMNSLRAEDTAVYYCAKDE GYSSGHYYGMDVWGQGTTVTVSS | 24 | -54.35 | Ideal |

Example 4: Binding Characterization of BGCB463 Trispecific Antibody

Part 1. Materials and Methods

Cell Lines

Cell lines assessed for GPRC5D and BCMA binding characterization were multiple myeloma derived H929 and MM.1R. Additionally, an H929 suite of CRISPR knockouts (H929-GPRC5D-KO monoclonal line D11), H929-BCMA-KO and H929-GPRC5D/BCMA-KO were generated. Similar MM.1R knockouts were also developed for assessing GPRC5D and BCMA binding. All lines were sourced from within (ABS) and were cultured with Complete RPMI Medium, which was comprised of RPMI 1640 Medium, GlutaMAX™ Supplement, HEPES, Heat-Inactivated (HI) FBS, Non-essential amino acids (NEAA), Sodium Pyruvate, and 2-ME (all ThermoFisher).

K562 monoclonal cell lines overexpressing human GPRC5D (monoclone H1B5), and human BCMA (monoclone H1/B5) were utilized. Additionally, K562-Fluc-GFP cells expressing cynomolgus GPRC5D (monoclone M1C11) and cynomolgus BCMA were used. Both cell lines were maintained in IMDM, 10% FBS, 2 mM Glutamine, and 2 mg/mL G418 (all ThermoFisher).

Cell Binding by FACS

BGCB463.003 and BGCB463.004, or B23B251 (Isotype control for IgG1-AAS) was either used as an unlabeled molecule or was directly conjugated to Alexa Fluor 647. BGCB463.003 was expressed by transient transfection, while BGCB463.004 was expressed from a stable transfection pool.

For binding of BGCB463 to human and cynomolgus Pan T cells, three human donors (Hemacare) were selected, quickly thawed, resuspended, and aliquoted into a 96-well plate at $1 \times 10^6$ cells/mL. Cells were then washed, Fc blocked if necessary (Innovex), and stained with viability dye (Invitrogen). BGCB463 and its corresponding isotype (B23B251) were diluted in complete media to an initial concentration of 2 µM and 1:3 serial dilutions in duplicate were performed for a dose-response curve. The cells were incubated with molecules at 4° C. or 37° C. for 1 hour. When necessary, incubation with 90% human serum (Sigma) was also performed as described above.

To determine potential interference from soluble BCMA (sBCMA), patient serums with known concentrations were obtained from BDS (1 pool) and incubated with BGCB463 and H929 cells. For the incubation, patient serums were diluted with normal serums to assay sBCMA while maintaining 90% total human serum.

Utilizing the ForeCyt software, singlet-live populations were gated, and median fluorescent intensity (MFI) of the AlexaFluor 647 channel was calculated for each sample. Raw data was exported into Excel (Office 365, Microsoft) where duplicates were averaged and further analyzed in Prism software (v. 8.0, Graphpad). When required, isotype background was subtracted. Herein, dose-response curve graphs and $EC_{50}$ were calculated for each molecule for each donor. Lastly, the averages of all three donors of each respective species was calculated in order obtain an average $EC_{50}$ for the species.

Time Course Binding

Cell lines assessed for GPRC5D and BCMA time course kinetic binding were the H929 and MM.1R KO suites mentioned above. FACS analysis of BGCB463 binding to the above cell lines was done at varying final concentrations based on the dose-response curves of 1 hr 37° C. binding, so that at least one of the concentrations was close to the $EC_{50}$. Three final concentrations were chosen with 5-fold differences, all with 1 hr, 3 hr, 5 hr, and 24 hr incubations. BGCB463 binding was assessed in Complete RPMI at 37° C.

BGCB463 or accompanying B23B251 isotype control was first diluted in complete RPMI at 2× concentration and incubated at 37° C. Next, cells were harvested and counted using Vi-Cell XR (Beckman Coulter) and then added to the master deep well plate to yield ~1E5 cells per timepoint. At each time point, cells were removed and transferred to a round bottom 96-well plate that contained cold FACS buffer (Stain buffer containing 0.2% BSA (BD)+2 mM EDTA (ThermoFisher)). Plates were next washed three to four times by centrifugation (1200 RPM, 5 min) followed by buffer aspiration. After two more washes with FACS buffer, cells were stained on ice with Alexa Fluor 647 goat anti-human IgG1 (H+L) (Jackson Immuno) for 30 minutes. After incubation, cells were washed three more times with cold FACS buffer and then resuspended in FACS buffer containing Sytox Green to label all dead cells (ThermoFisher). Plates were then run on the Intellicyt iQue Screener Plus (Sartorius) within three hours following staining.

T Cell Activation and Killing Assay Using Incucyte Live Cell Imaging

In order to determine the effect of test molecules upon T cell activation and killing potential of tumor cells, the Incucyte live imaging system (Sartorious) was utilized. The in-house generated H929-Fluc-GFP cell line served as target cells for human donor Pan T cells (Hemacare). The assay was set up in a 96-well plate at a T cell to target ratio of 1:1, 3:1, and 5:1 over several experiments. Test molecules (BGCB463 and B23B251) were added at a starting concentration of 40 nM or 10 nM and serially diluted at 1:4 in complete media. All molecules were tested in duplicate at minimum. Detection of T cell activation status was monitored with Anti-human CD25-Alexa Fluor 647 (Biolegend). Cells in plates were normalized to temperature and then placed into an Incucyte (Model S3) live cell imaging system contained within a 37° C. incubator. Four images per well in the phase, green, and red channels were captured every 3 hours for approximately 5 days. Using sample images, an analysis definition was created in the Incucyte analysis software (Sartorious, v.2019B Rev2) to generate the counts of objects in the green (target cells) and counts or total integrated intensity of red (activated T cells) channels.

Using the raw counts from the green channel (target cells) generated from the Incucyte software analysis, percent cytolysis of targets at each concentration and time point was calculated against the average of all untreated wells on the corresponding plate using the following formula on raw data exported to Excel (Microsoft, Office 365): (100-(GPRC5D test concentration Untreated average)×100). To automate this, raw data was transformed and transferred using a Shiny Application developed by Data Sciences to rapidly calculate and transfer the data into Prism software, where graphical representation of the data is presented. Once transferred into Prism software (Graphpad Software, v.8.0.0), data were graphed and standard error of mean and cytolysis and T cell activation over time curves were calculated. For T cell activation, raw counts or total integrated intensity from the red channel (CD25-AF647) replicates were used and further graphed in the Prism software to generate dose-response and activation graphs.

Part 2. Results

T Cell and Cell Line Dose Responsive Binding

Figure 4A:
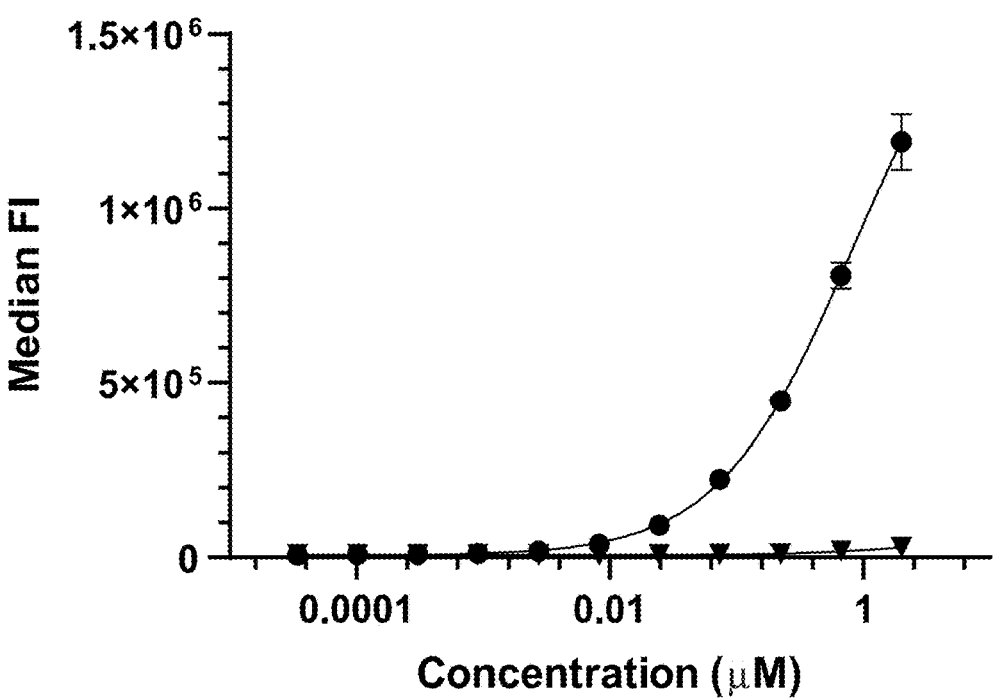
Figure 4B:
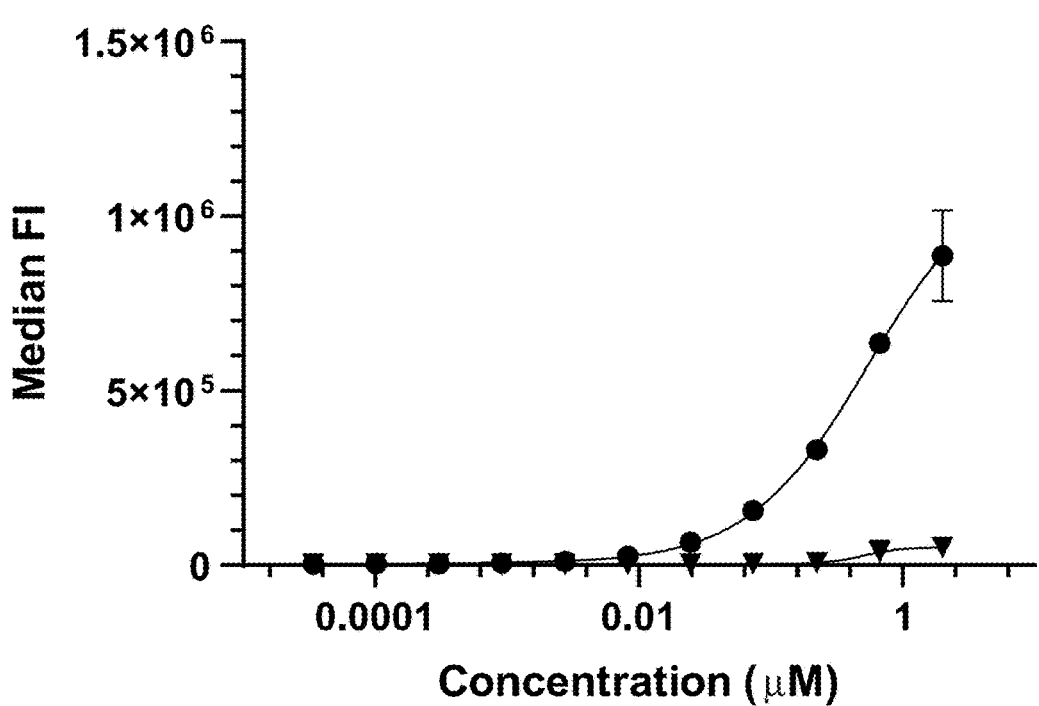
Figure 5A:
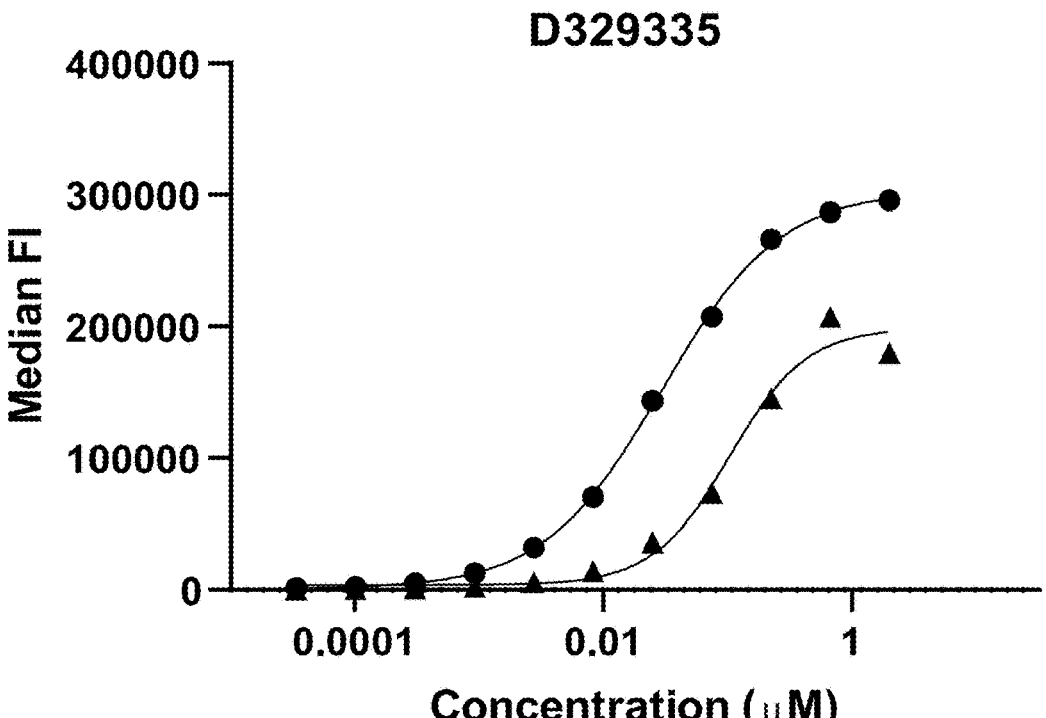
FIGS. 5A-5C. BGCB463 was incubated with Pan T cells (3 random donors, FIG. 5A, FIG. 5B, and FIG. 5C) for 1 hr at 4° C. (circles) or 37° C. (triangles) at a starting concentration of 2 µM. After secondary detection with AF647-labeled material, the MFI signal was analyzed to generate an $EC_{50}$.
Figure 5B:
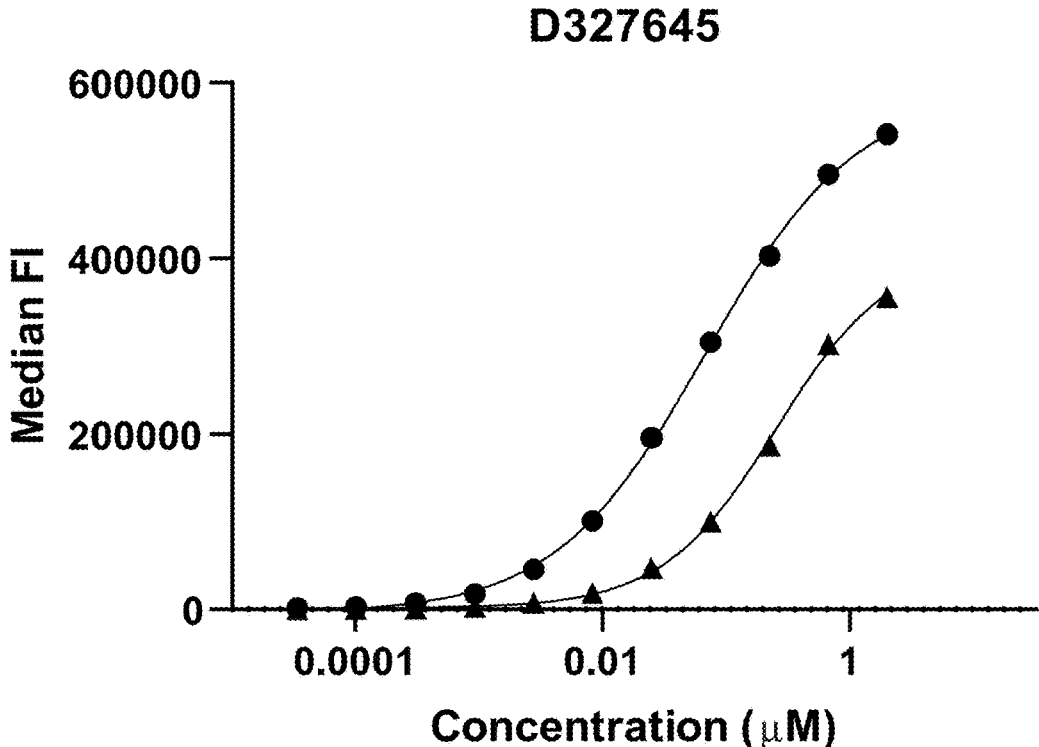
Figure 5C:
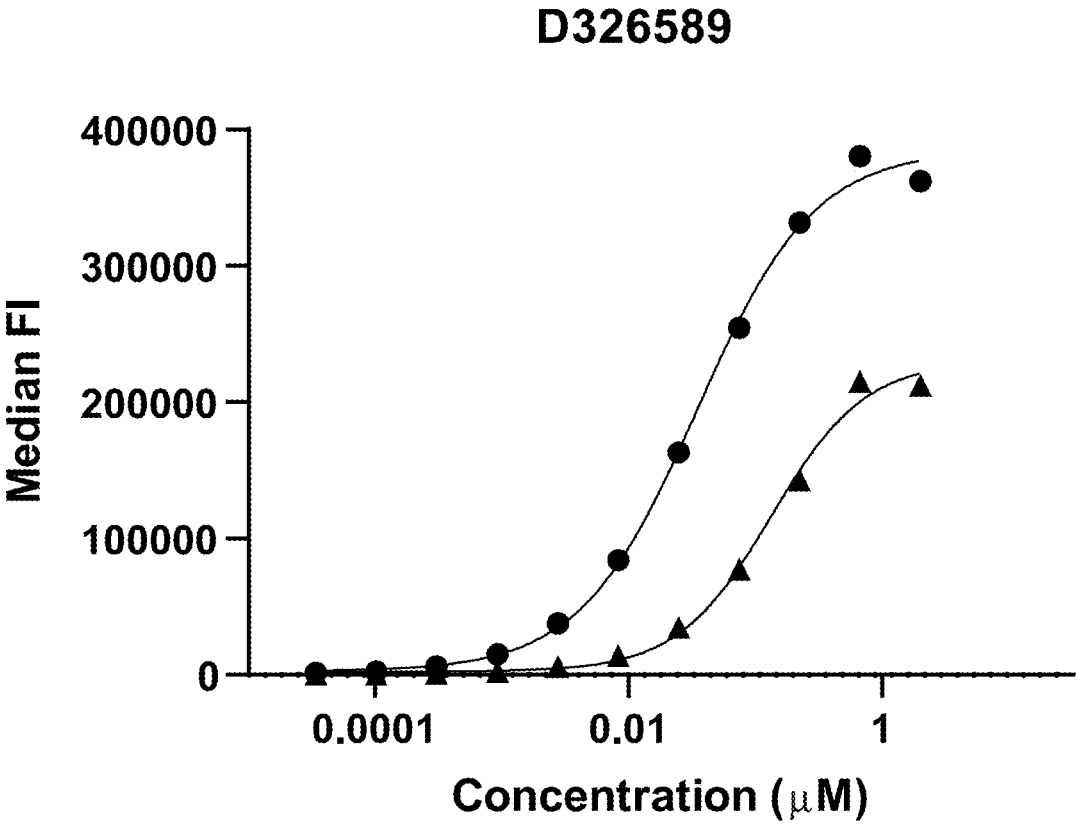
Figure 6A:
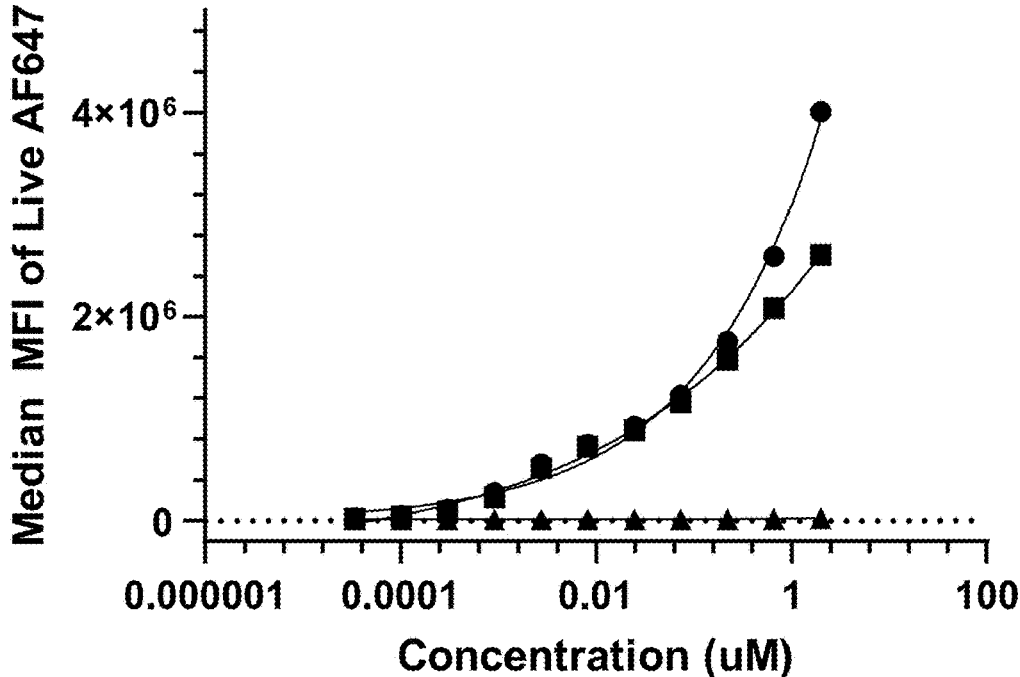
FIGS. 6A-6C. BGCB463.003 (circles), BGCB463.004 (squares), and negative control B23B251 (triangles) were tested with H929 (FIG. 6A), MM.1R (FIG. 6B), and Pan T (FIG. 6C) cells from 3 donors. Molecules were incubated for 1 hr at 37° C. at a starting concentration of 2 μM. After secondary detection with AF647-labeled material, the MFI signal was analyzed.
Figure 6B:
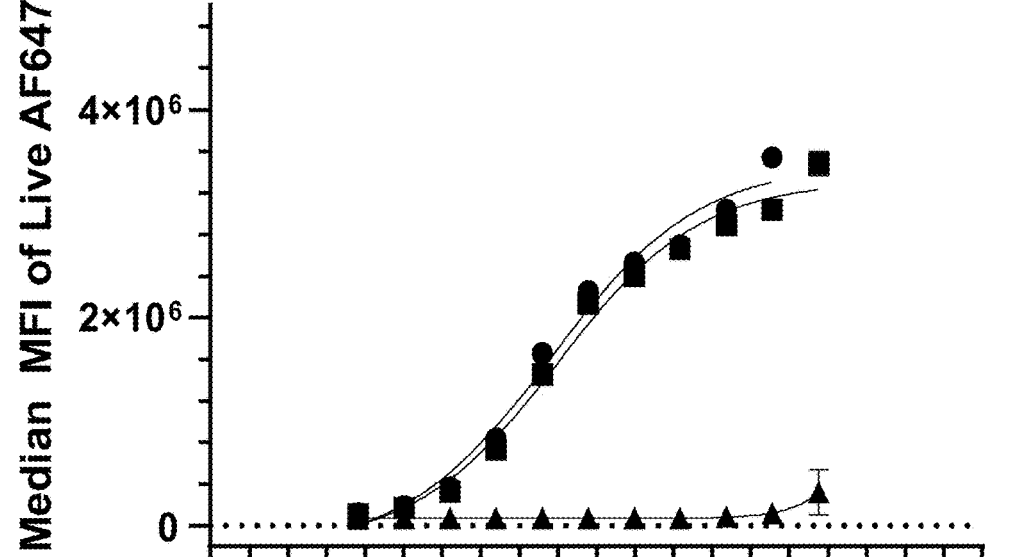
Figure 6C:
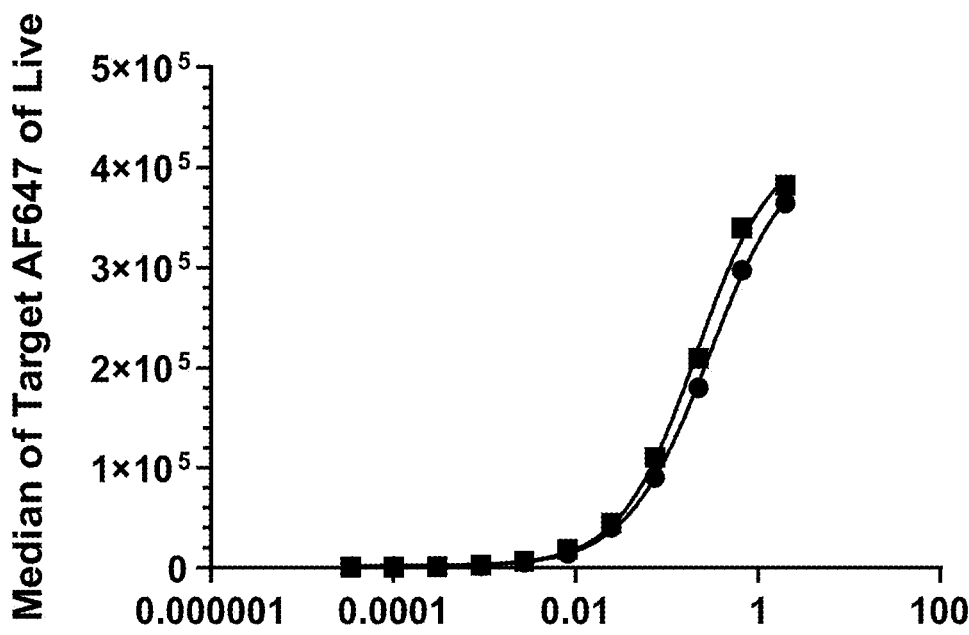
Figure 7A:
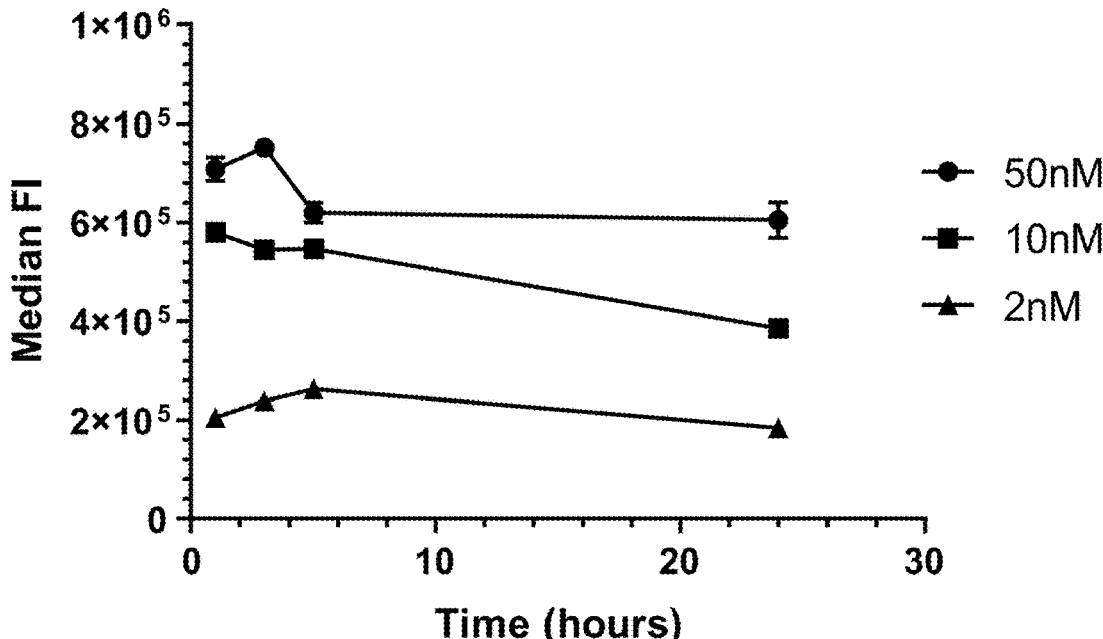
FIGS. 7A-7D. H929 (FIG. 7A), H929-GPRC5D KO (FIG. 7B), H929-BCMA KO (FIG. 7C), and H929-GPRC5D/BCMA KO (FIG. 7D) cells were all incubated for 1 hr, 3 hr, 5 hr, and 24 hr at three optimized concentrations of BGCB463 at 37° C. Cells were then washed and incubated for 30 min on ice with AF647-anti-human IgG. Read out is MFI of AF647 signal.
Figure 7B:
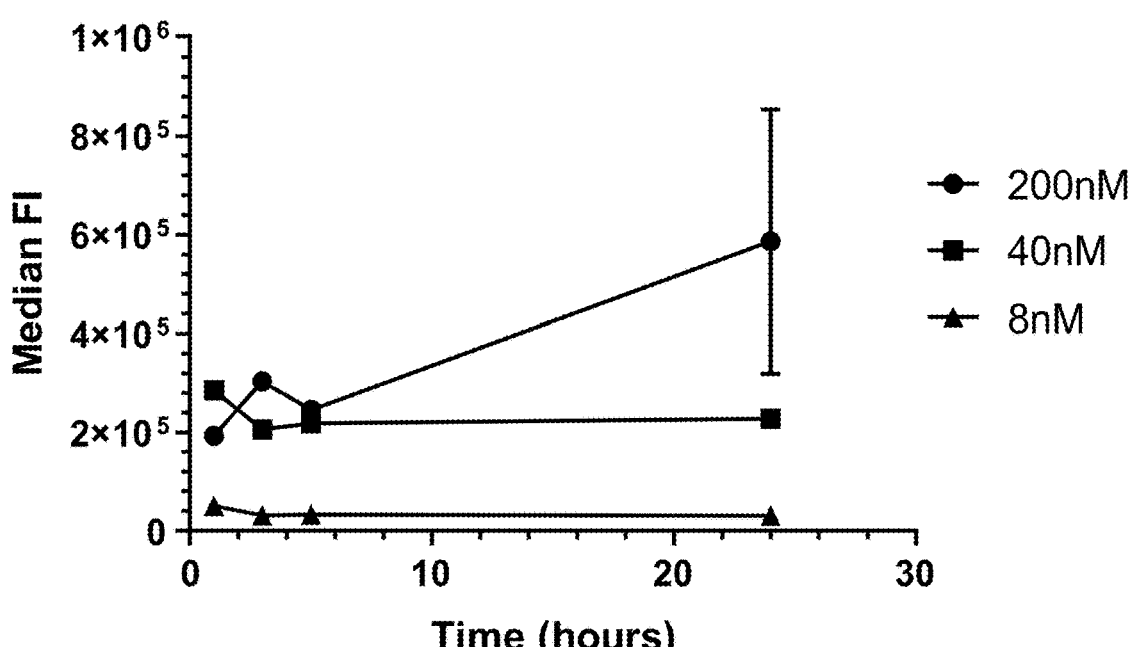
Figure 7C:
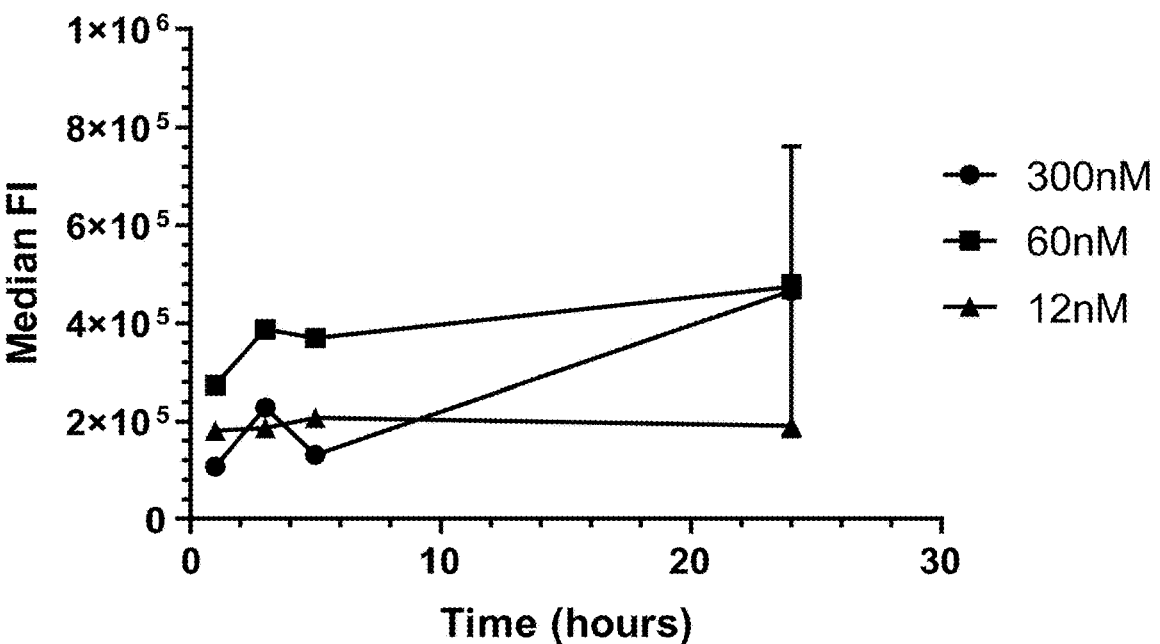
Figure 7D:
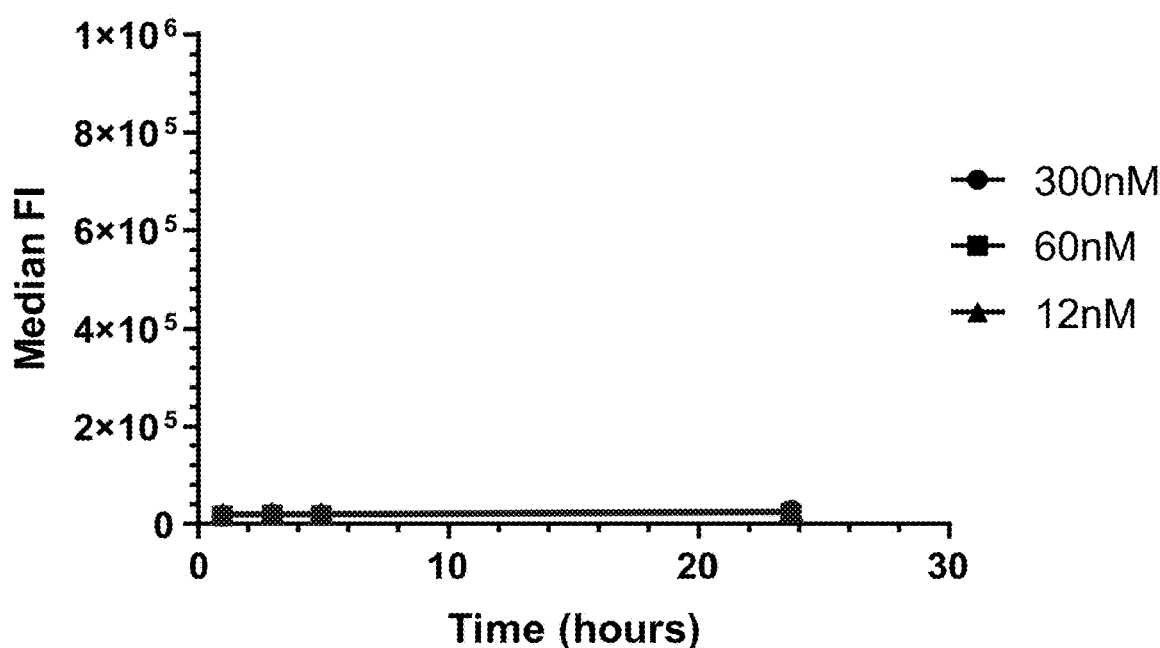
Figure 8A:
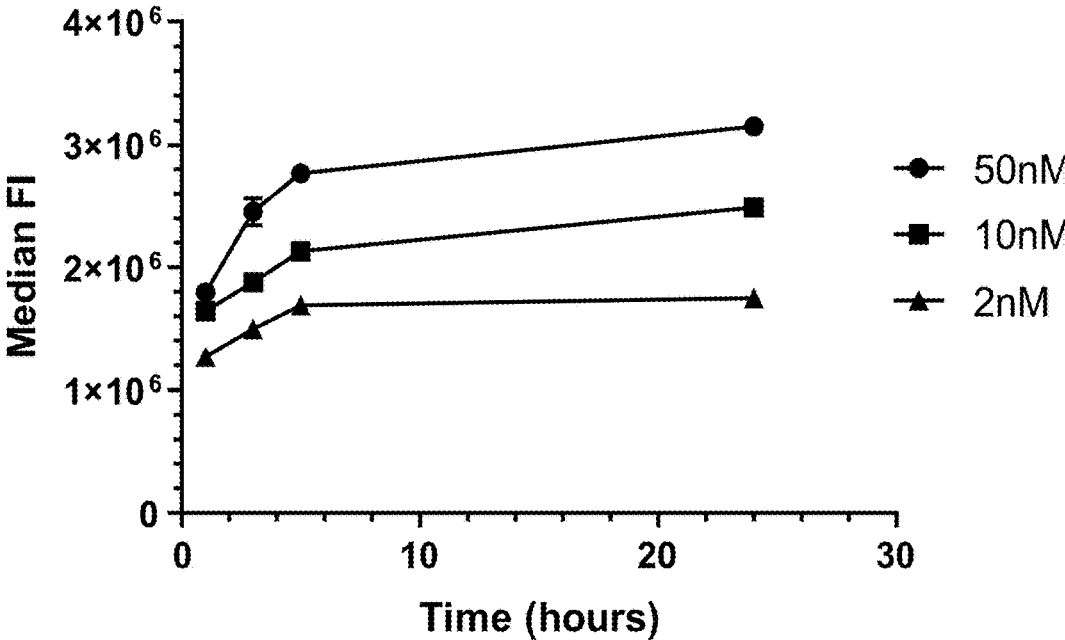
FIGS. 8A-8D. MM.1R WT (FIG. 8A), MM.1R-GPRC5D KO (FIG. 8B), MM.1R-BCMA KO (FIG. 8C), and MM.1R-GPRC5D/BCMA KO (FIG. 8D) cells were all incubated for 1 hr, 3 hr, 5 hr, and 24 hr at three optimized concentrations of BGCB463 at 37° C. Cells were then washed and incubated for 30 min on ice with AF647-anti-human IgG. Read out is MFI of AF647 signal.
Figure 8B:
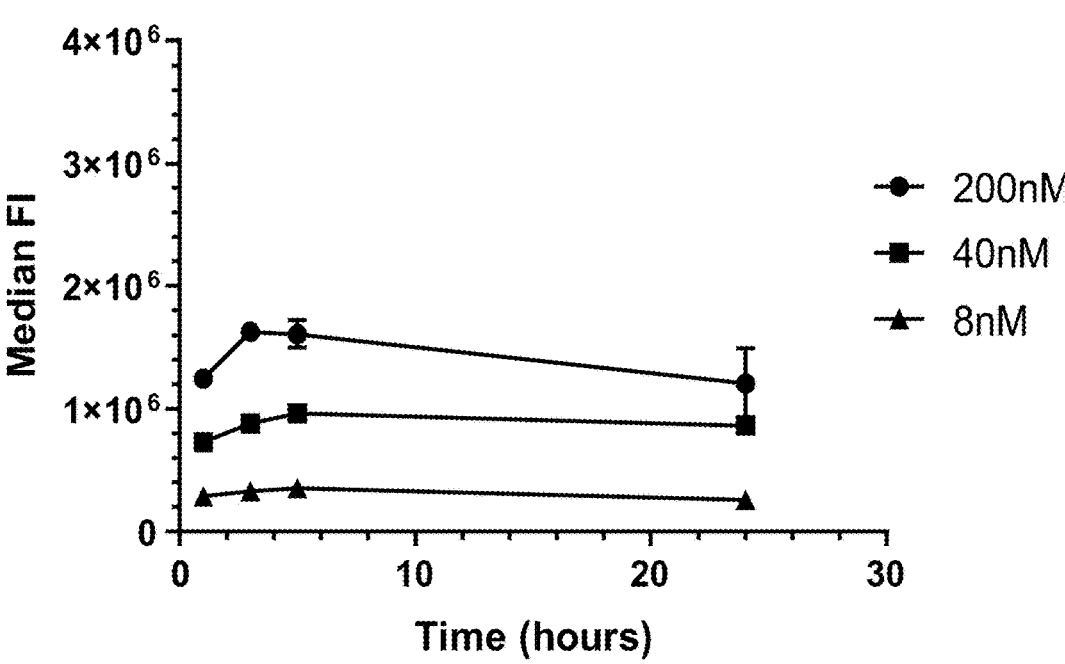
Figure 8C:
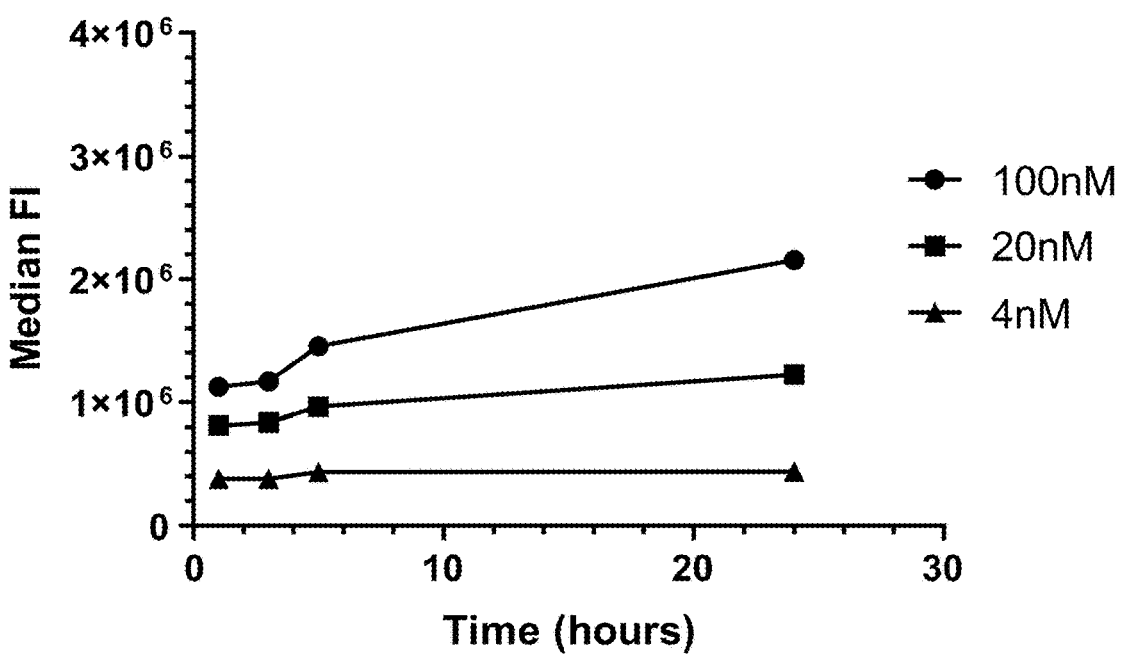
Figure 8D:
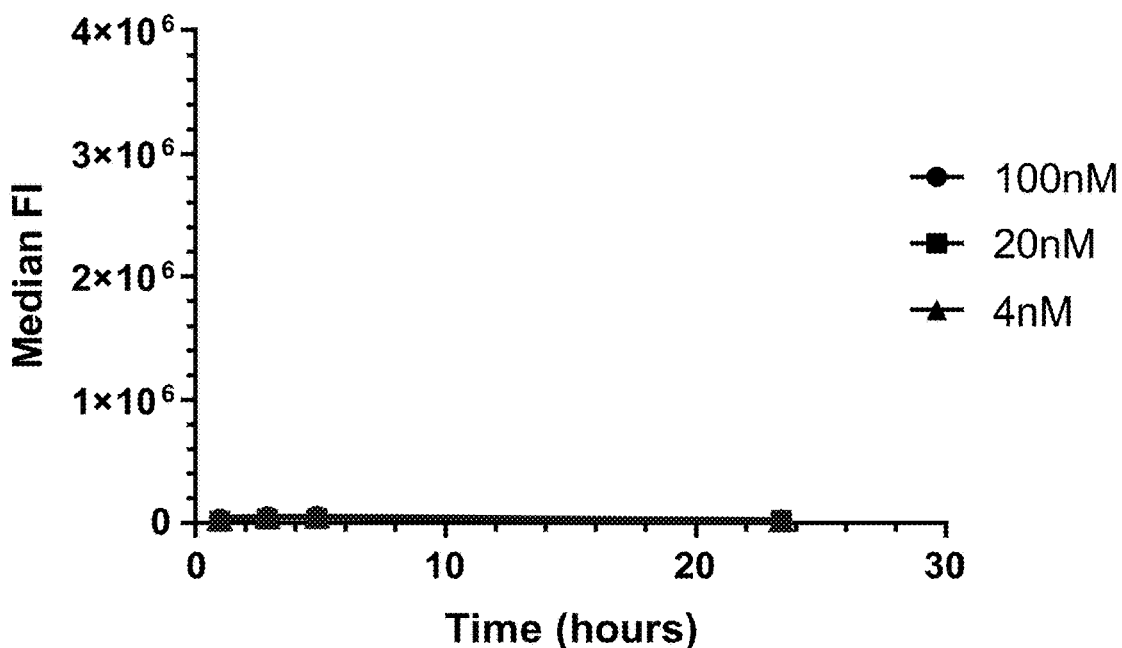
Figure 9A:
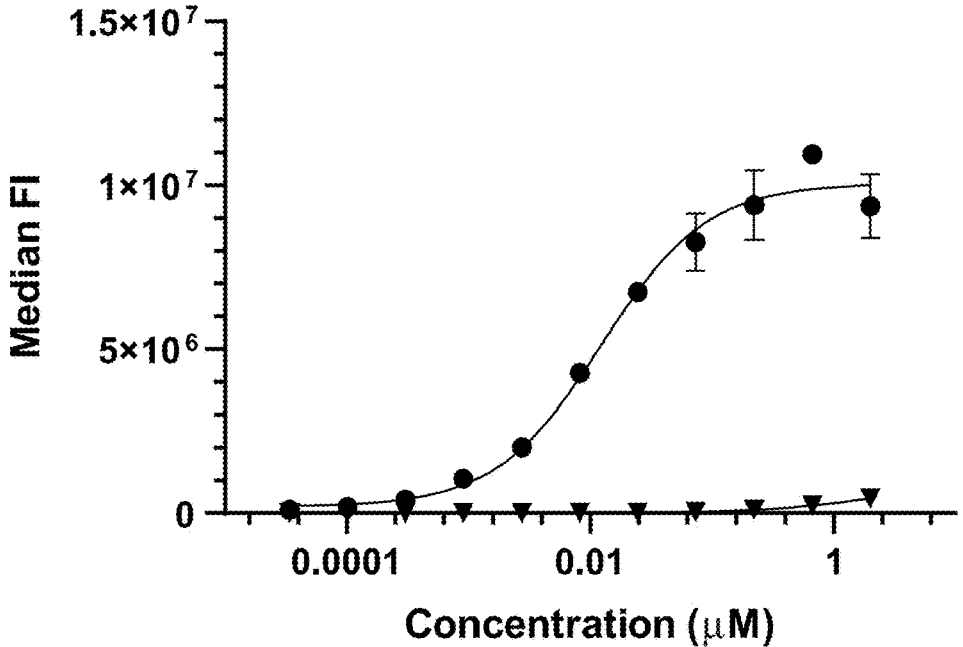
Figure 9B:
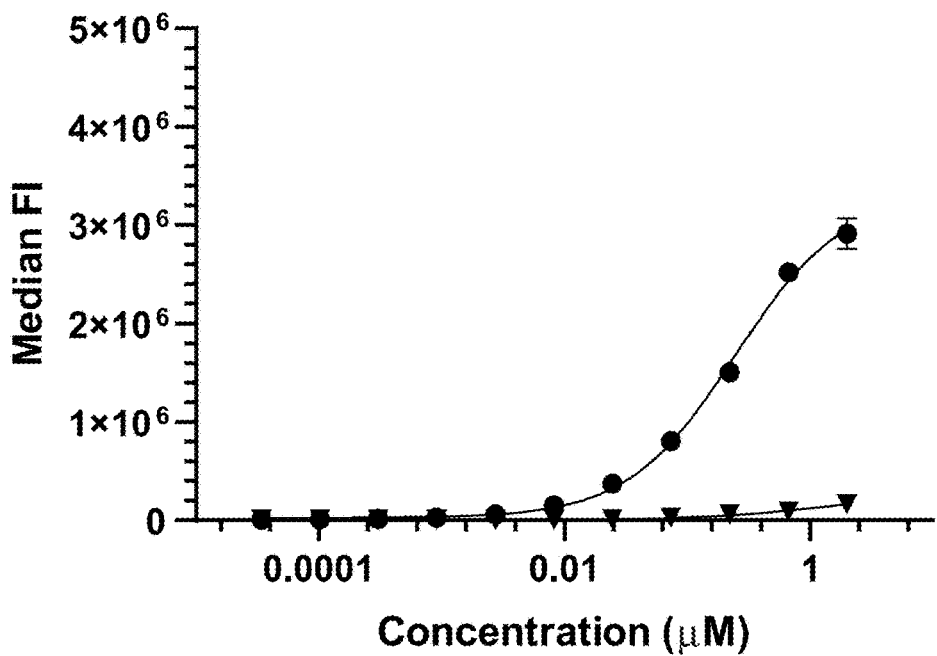
Figure 9C:
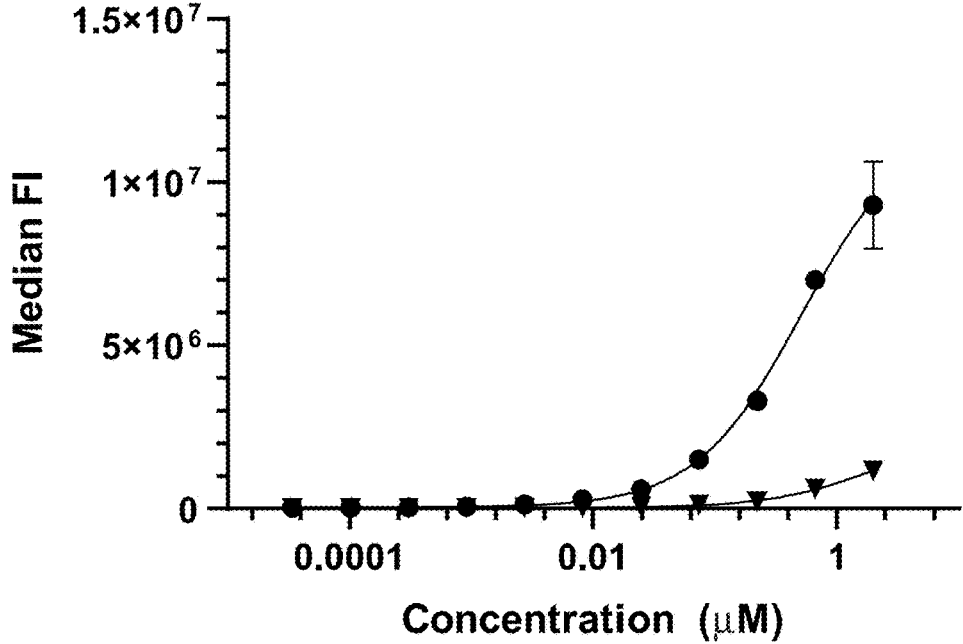
Figure 9D:
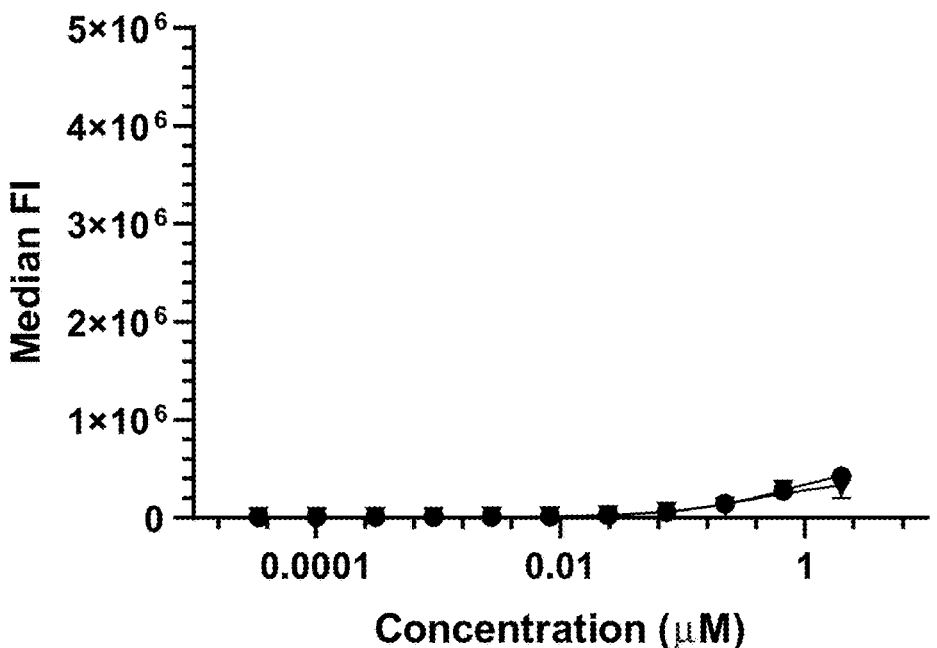

First, FACS-based binding for GPRC5D and BCMA binding arms of the trispecific molecule was determined by measuring the effective concentration (EC) range from a dose-response curve using a 4-parameter fit at 37° C. for 1 hr. This was assessed using an H929 suite of cells (WT, GPRC5D-KO, BCMA-KO, and GPRC5D/BCMA KO), and a similar MM.1R suite. Cell based $EC_{50}$ is approximately 13 nM for WT H929 (FIGS. 2A-2D, Table 7) and 2.4 nM for WT MM.1R (FIGS. 3A-3D, Table 8). A clear avidity affect is observed as $EC_{50}$ and Bmax are both reduced in GPRC5D-KO and BCMA-KO lines which test monovalent binding of target binding arms (Table 7). Next, cell-based $EC_{50}$ was determined for the CD3-binding Fab arm using purified Pan T cells from three random donors. As demonstrated in FIGS. 4A-4C, cell-based $EC_{50}$ for the CD3B376 (BGCB463) arm was approximately 329 nM (Table 9). Next, dose responsive binding was assessed at 4° C. to remove any potential biological effects. As shown in FIGS. 5A-5C, binding is stronger (50-100 nM) at 4° C., compared to 37° C., which may indicate internalization. Additionally, two expression lots of BGCB463 (BGCB463.003 from transient transfection and BGCB463.004 from a stable transfection pool), were directly compared with binding to H929, MM.1R, and Pan T cells and no differences were noted (FIGS. 6A-6C).

TABLE 7

H929 suite cell-based effective concentrations

| $EC_{50}$ (nM) | H929 | H929 GPRC5D KO | H929 BCMA KO | $EC_{90}$ (nM) | H929 | H929 GPRC5D KO | H929 BCMA KO |
|---|---|---|---|---|---|---|---|
| Run 1 | 14.0 | 106.4 | 195.4 | Run 1 | 240.1 | 722.6 | 1861.4 |
| Run 2 | 8.3 | 63.9 | 128.8 | Run 2 | 356.2 | 200.3 | 871.8 |
| Run 3 | 28.7 | 220.8 | 65.2 | Run 3 | 45776.5 | 1996.4 | 1237.5 |
| Run 4 | No fit | No fit | No fit | Run 4 | No fit | No fit | No fit |
| Run 5 | 2.4 | 456.8 | 48.8 | Run 5 | 9450.2 | 4130.3 | 281.2 |
| AVE | 13.3 | 212.0 | 109.5 | AVE | 13955.7 | 1762.4 | 1063.0 |

TABLE 8

MM.1R suite cell-based effective concentrations

| $EC_{50}$ (nM) | MM.1R | MM.1R GPRC5D KO | MM.1R BCMA KO | $EC_{90}$ (nM) | MM.1R | MM.1R GPRC5D KO | MM.1R BCMA KO |
|---|---|---|---|---|---|---|---|
| Run 1 | 3.2 | No fit | No fit | Run 1 | 128.1 | No fit | No fit |
| Run 2 | 1.2 | No fit | 16.6 | Run 2 | 13.9 | No fit | 198.7 |

TABLE 8-continued

| | MM.1R GPRC5D KO | MM.1R BCMA KO | | | MM.1R GPRC5D KO | MM.1R BCMA KO |
|---|---|---|---|---|---|---|
| $EC_{50}$ (nM) | MM.1R | | | $EC_{90}$ (nM) | MM.1R | |

MM.1R suite cell-based effective concentrations

| $EC_{50}$ (nM) | MM.1R | MM.1R GPRC5D KO | MM.1R BCMA KO | $EC_{90}$ (nM) | MM.1R | MM.1R GPRC5D KO | MM.1R BCMA KO |
|---|---|---|---|---|---|---|---|
| Run 3 | 3.4 | 141.6 | 35.3 | Run 3 | 75.5 | 2070.4 | 969.9 |
| Run 4 | 1.6 | 489.9 | 7.2 | Run 4 | 8.6 | 8298.7 | 38.2 |
| AVE | 2.4 | 315.8 | 19.7 | AVE | 56.5 | 5184.5 | 402.2 |

TABLE 9

T cell-based effective concentrations

| $EC_{50}$ (nM) | Donor 1 | Donor 2 | Donor 3 | $EC_{90}$ (nM) | Donor 1 | Donor 2 | Donor 3 |
|---|---|---|---|---|---|---|---|
| Run 1 | 769.8 | 572.5 | 548.9 | Run 1 | 10735.6 | 7046.4 | 6008.2 |
| Run 2 | No fit | No fit | No fit | Run 2 | No fit | No fit | No fit |
| Run 3 | 293.1 | 261.9 | 359.9 | Run 3 | 2864.8 | 2267.3 | 4148.3 |
| Run 4 | 209.9 | 192.1 | 254.8 | Run 4 | 1698.0 | 1418.4 | 2173.5 |
| Run 5 | 102.6 | 132.4 | 250.7 | Run 5 | 493 | 860 | 2600 |
| AVE | 343.9 | 289.7 | 353.6 | AVE | 3947.9 | 2898.0 | 3732.5 |
| Total AVE | 329.1 | | | Total AVE | 3526.1 | | |

Time Course Binding

Next, surface stability of the lead, BGCB463, was determined by assessing time course kinetic FACS binding on the H929 and MM.1R suites of cells. As demonstrated in FIGS. 7A-7D, binding kinetics are stable on H929 cells over the 24-hour period. Additionally, the bivalent binding of the trispecific molecule has a stronger signal compared to the monovalent binding arm assessed in the single KOs, which like above, is consistent with likely avidity effects. These results are echoed in the MM.1R suite (FIGS. 8A-8D).

Species Orthologs Cross Reactivity

Cross Reactivity to Cynomolgus Monkeys was Also Profiled for Both Target Binding scFv arms using FACS-based cell binding at 37° C. for 1 hr. To this end, K562 cells stably expressing human and cynomolgus GPRC5D or BCMA were utilized. As noted in FIGS. 9A-9E, cell based $EC_{50}$ for the GC5B680 scFv arm is approximately 30 nM for human GPRC5D and about 10-fold weaker at about 400 nM on cynomolgus GPRC5D. In contrast, cell based $EC_{50}$ for the BCMB519 scFv arm is approximately 145 nM for human BCMA, while there was no detectable binding to cynomolgus BCMA up to 2 μM.

Figure 10A:
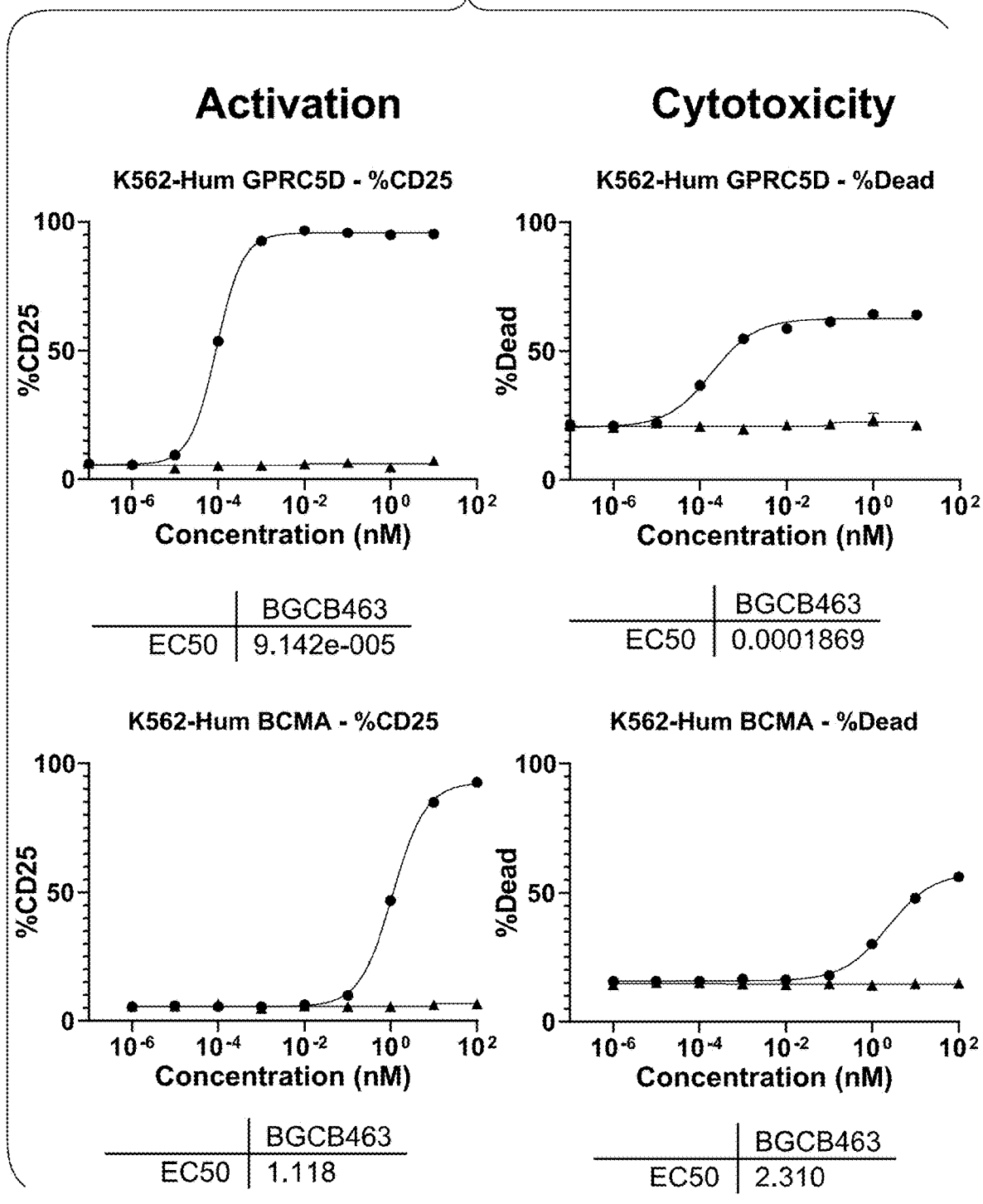
FIGS. 10A-10B. BGCB463 (circles) or negative control B23B251 (triangles) at a starting concentration of 10 nM were incubated with K562 cells expressing human or cynomolgus GPRC5D or 100 nM for K562 expressing human/cynomolgus BCMA as targets cells. Human activation and cytotoxicity in FIG. 10A. Cynomolgus activation and cytotoxicity in FIG. 10B. Human Pan T cells (1 donor) were added with an effector to target (E:T) ratio of 3:1 and incubated for 72 hr at 37° C. Cytotoxicity was determined using live/dead fixable dye and CD25 was measured using BV421-conjugated anti-CD25.
Figure 10B:
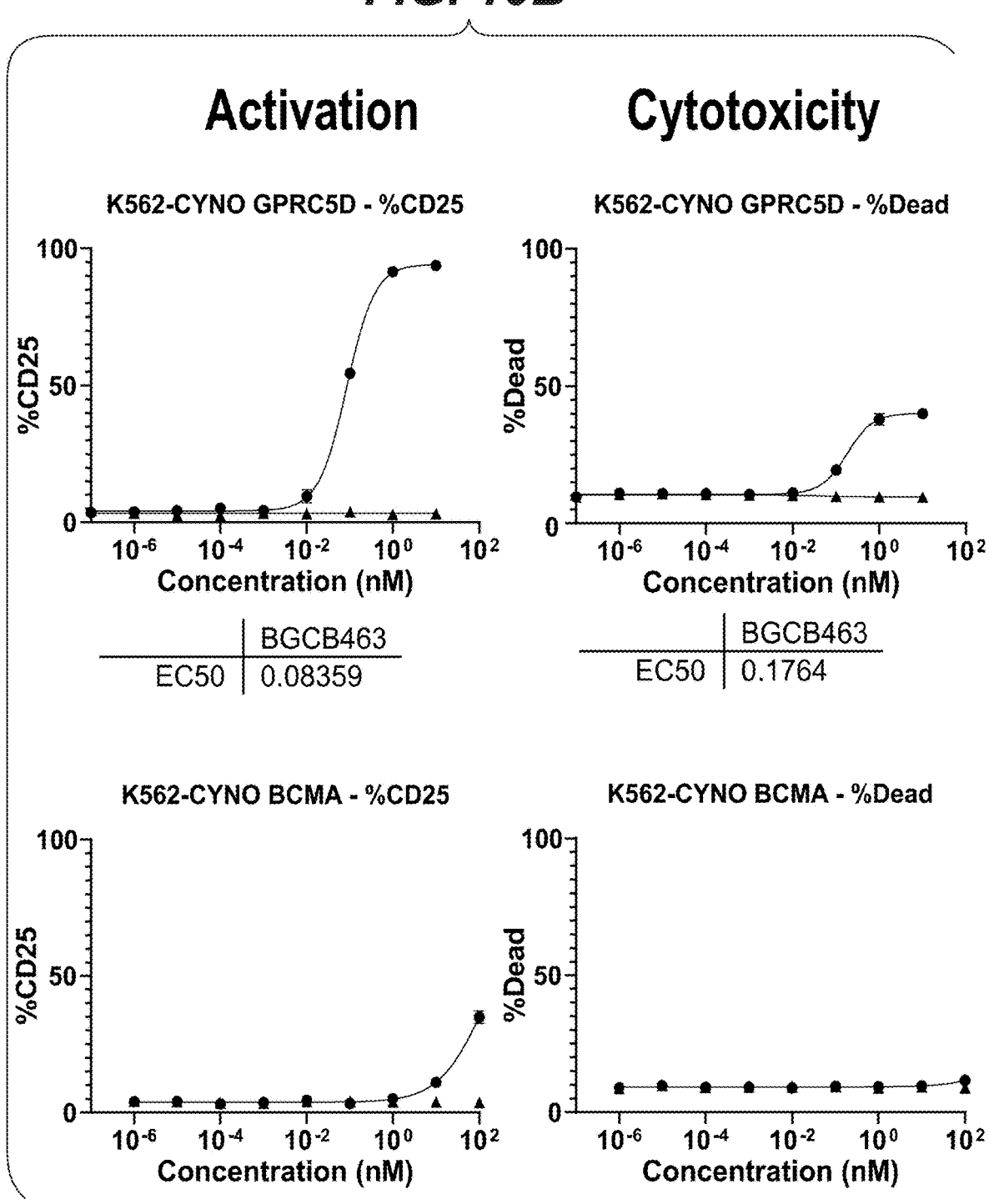

To further determine cynomolgus cross-reactivity, K562 cells that were used for binding were also utilized for cytotoxicity with human Pan T cells. As demonstrated in FIGS. 10A and 10B, weaker binding on cynomolgus GPRC5D compared to human GPRC5D correlates with weaker cytotoxicity and corresponding lower T cell activation with K562 expressing cyno GPRC5D. A similar pattern is observed with human and cyno BCMA, however, there is essentially no T cell response to cynomolgus BCMA.

Binding in 90% Human Serum

Figure 11:
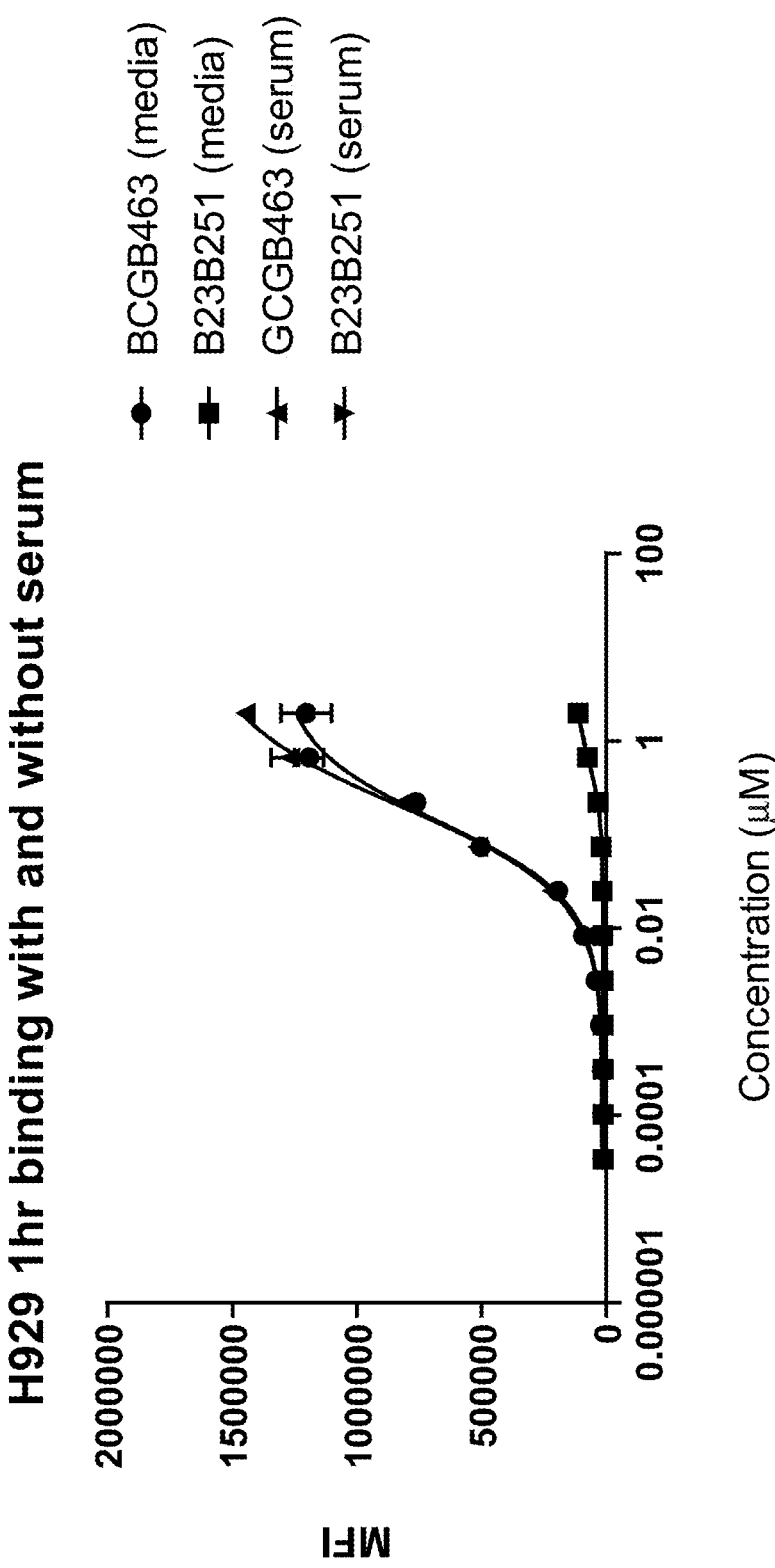
FIG. 11. H929 cells were incubated with increasing concentration of BGCB463 or negative control B23B251 for 1 hr at 37° C. with AF647-anti-human IgG in the presence of media (RPMI containing 10% FBS) or RPMI containing 90% human serum. BGCB463 binding is unaffected by the presence of serum.
Figure 12:
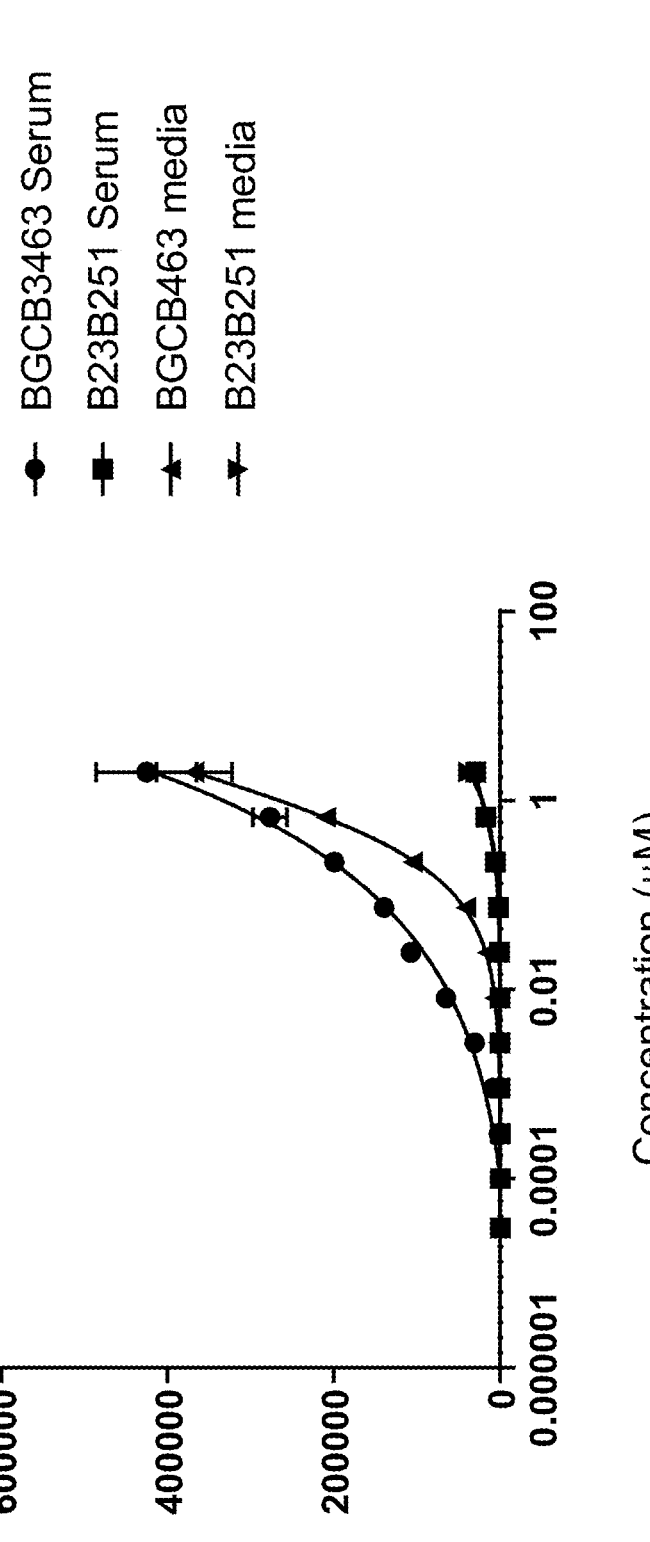
FIG. 12. T cells were incubated with increasing concentration of BGCB463 or negative control B23B251 for 1 hr at 37° C. with AF647-anti-human IgG in the presence of media (RPMI containing 10% FBS) or RPMI containing 90% human serum. Data are representative of three donors tested in two experiments. BGCB463 binding is unaffected by the presence of serum.

To better understand binding in vivo, binding was assessed for 1 hr at 37° C. in the presence of 90% human serum. The GPRC5D and BCMA binding scFv arms were tested with H929 cells (FIG. 11) while the CD3 binding Fab was tested with human pan-T cells (FIG. 12). In both cell types, BGCB463 binding is unaffected by the presence of serum.

Time Course Cytotoxicity

Figure 13A:
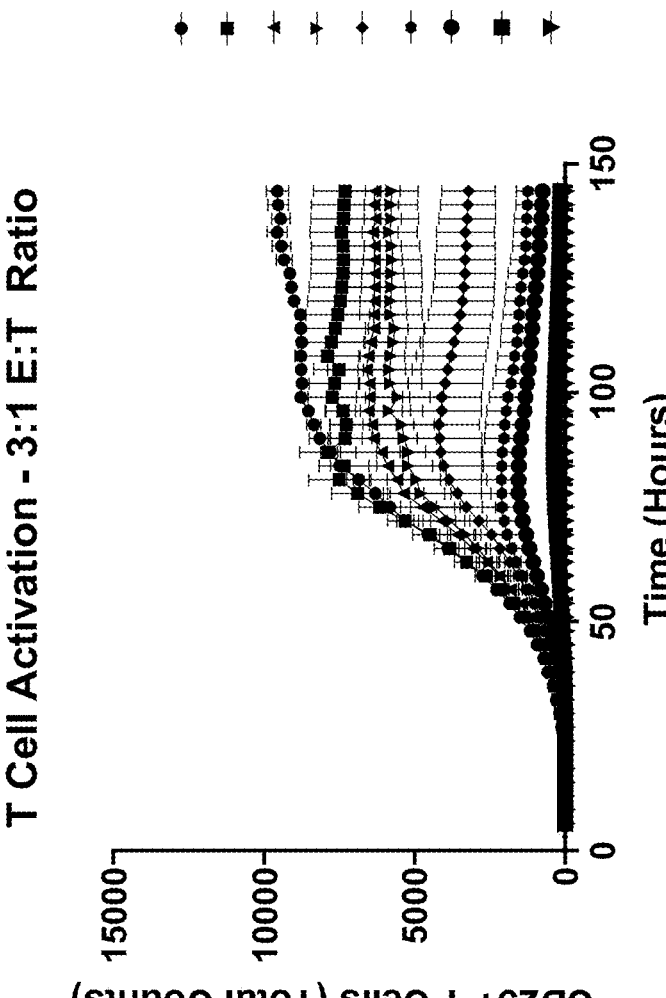
FIGS. 13A-13B. H929-GFP cells were incubated with BGCB463 and human Pan T cells from 3 donors at an E:T ratio of 3:1 with anti-CD25-AF647 added to track T cell activation (FIG. 13A). Percent cytolysis was calculated based on GFP signal in treated vs. untreated wells (FIG. 13B). The incubation lasted about 140 hours with images acquired every three hours.
Figure 13B:
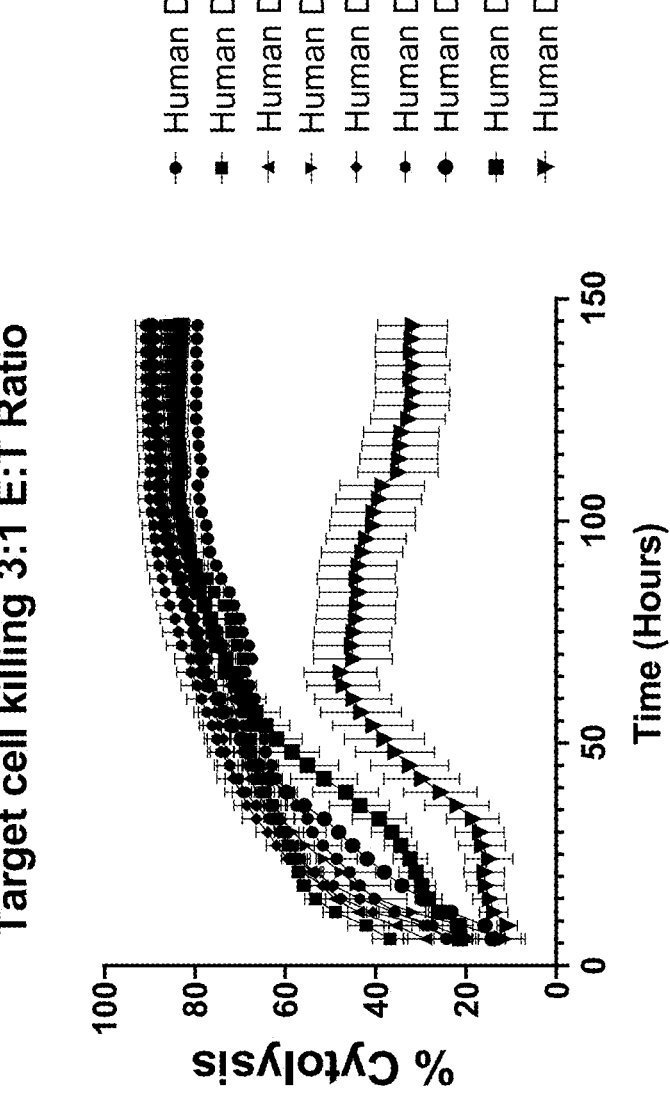
Figure 14A:
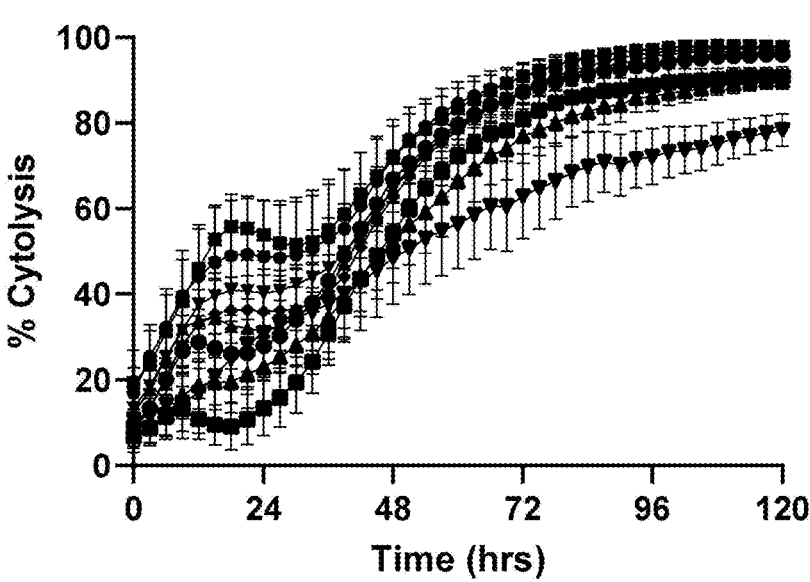
FIGS. 14A-14F. H929-GFP cells were incubated with BGCB463, or B23B251 (isotype control) molecules and human Pan T cells from four donors at an E:T ratio of 1:1 and 5:1 with anti-CD25-AF647 added to track T cell activation. Percent cytolysis was calculated based on GFP signal in treated vs. untreated wells. The incubation lasted about 140 hours with images acquired every three hours. BGCB463, 1:1 ratio, cytolysis (FIG. 14A). BGCB463, 1:1 ratio, total integrated intensity (FIG. 14B). BGCB463, 5:1 ratio, cytolysis (FIG. 14C). BGCB463, 5:1 ratio, total integrated intensity (FIG. 14D). B23B251, 5:1 ratio, cytolysis (FIG. 14E). B23B251, 5:1 ratio, total integrated intensity (FIG. 14F).
Figure 14B:
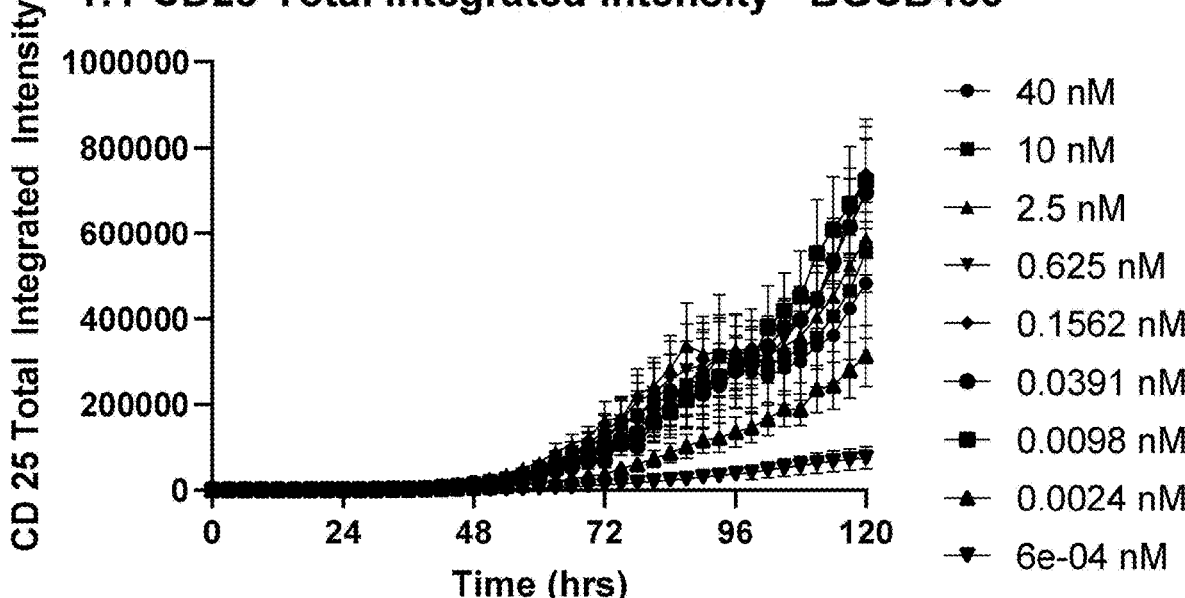
Figure 14C:
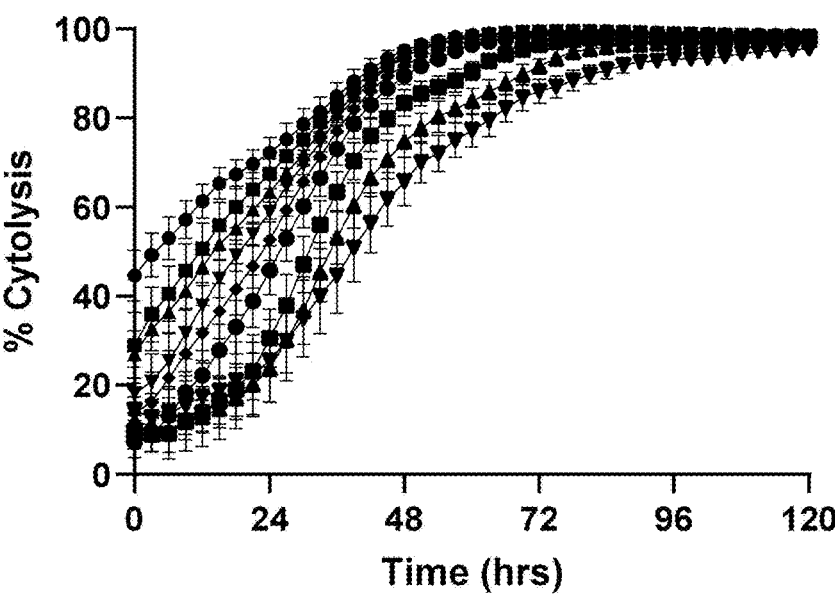
Figure 14D:
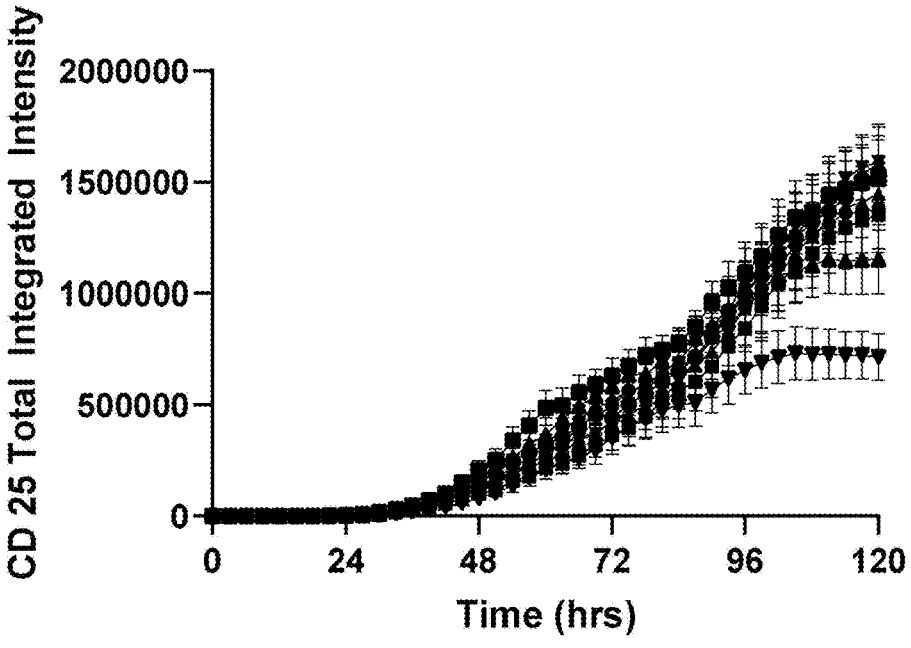
Figure 14E:
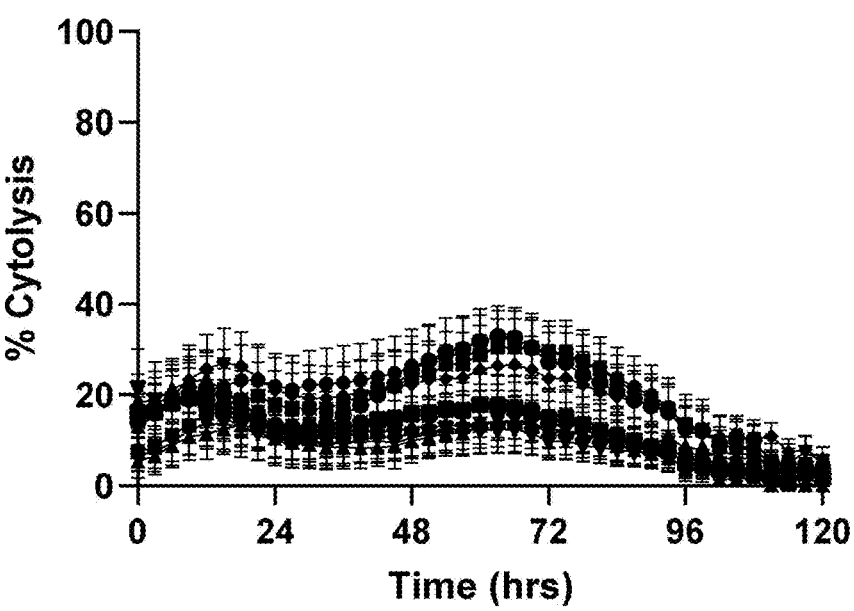
Figure 14F:
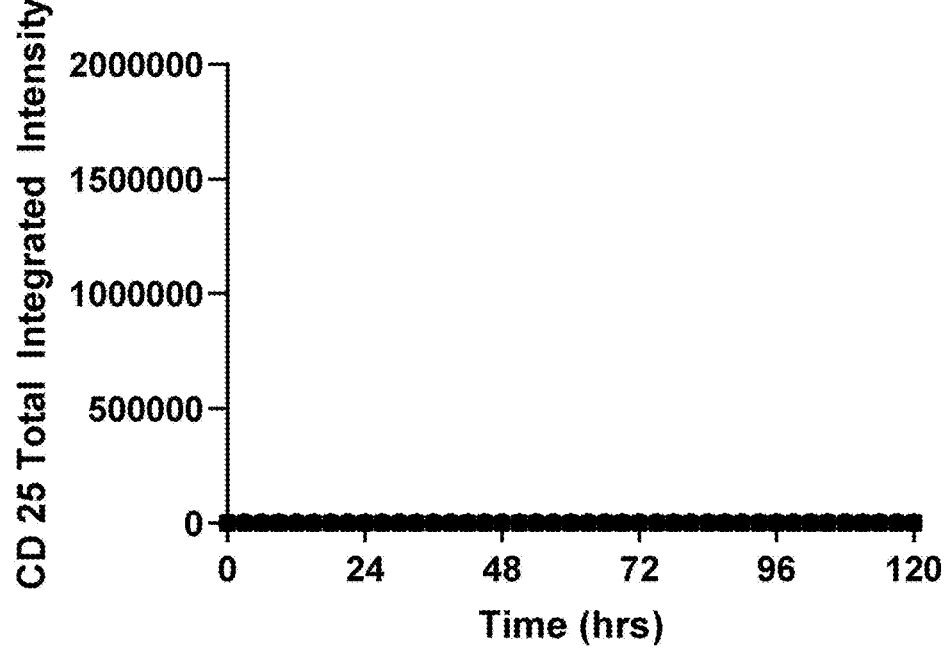
Figure 15A:
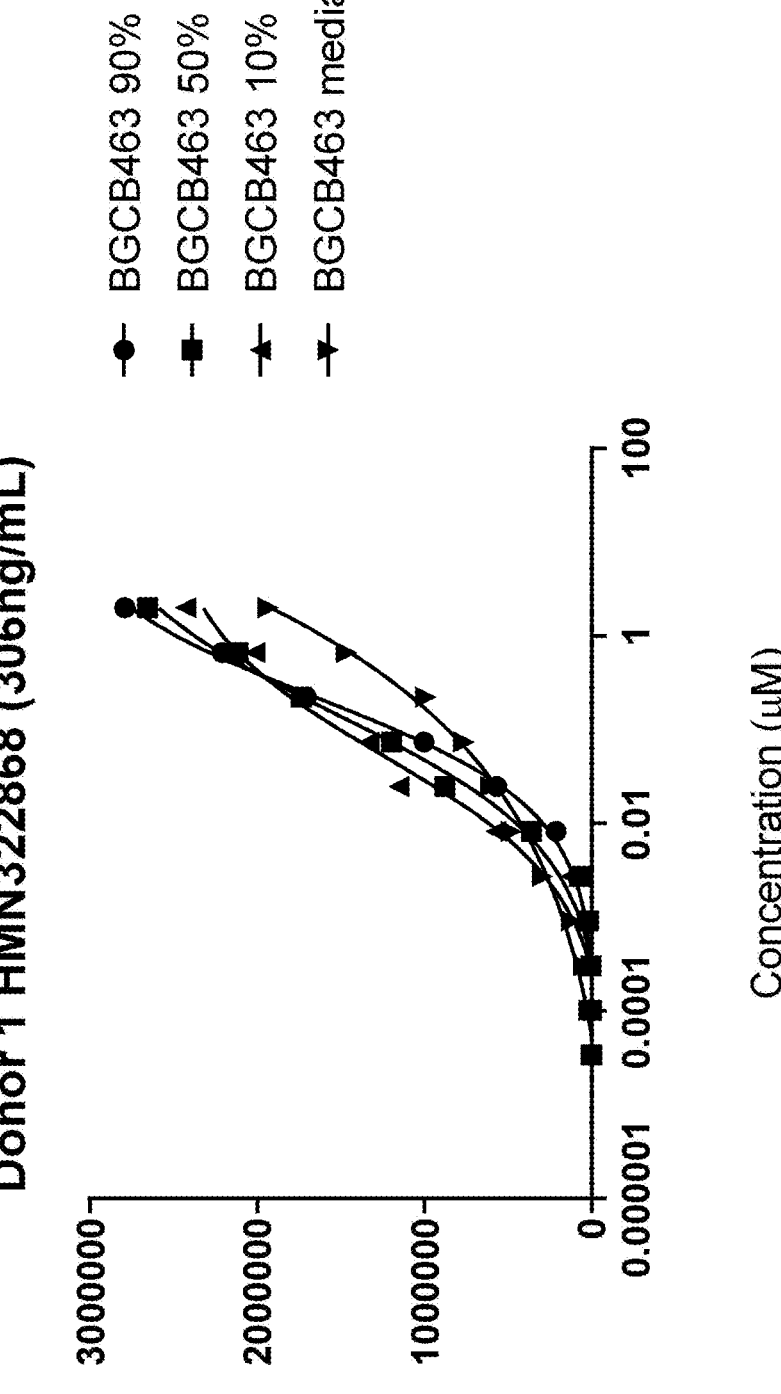
FIGS. 15A-15D. Determination of soluble BCMA interference using patient serums. Donor 1 (FIG. 15A); Donor 2 (FIG. 15B); Donor 3 (FIG. 15C); and normal serum (FIG. 15D). Patient serums with known levels of sBCMA were incubated (90% serum to 10% media) with directly labeled BGCB463-AF647 and B23B251-AF647 isotype control for 1 hr at 37° C. on H929 cells. 50% and 10% patient serum was diluted with normal serum to a final concentration of 50% and 10% respectively.
Figure 15B:
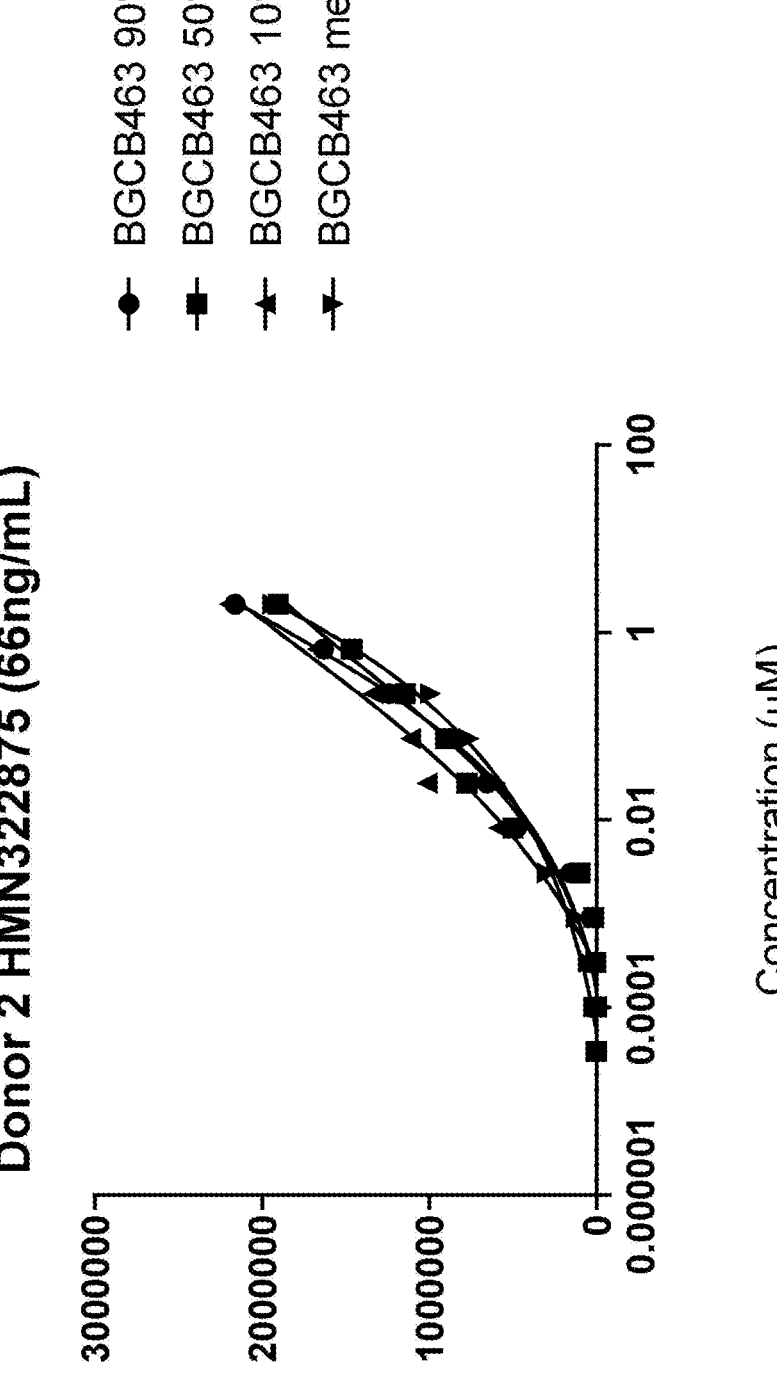
Figure 15C:
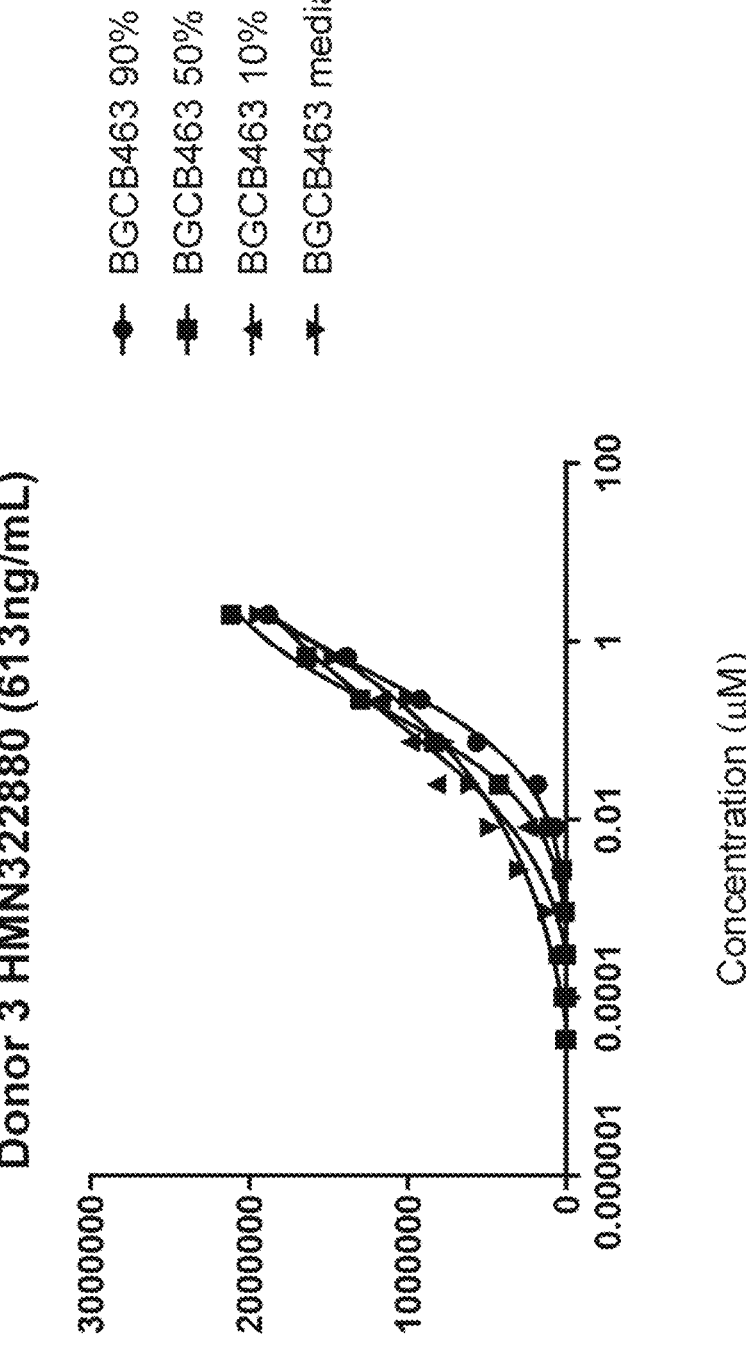
Figure 15D:
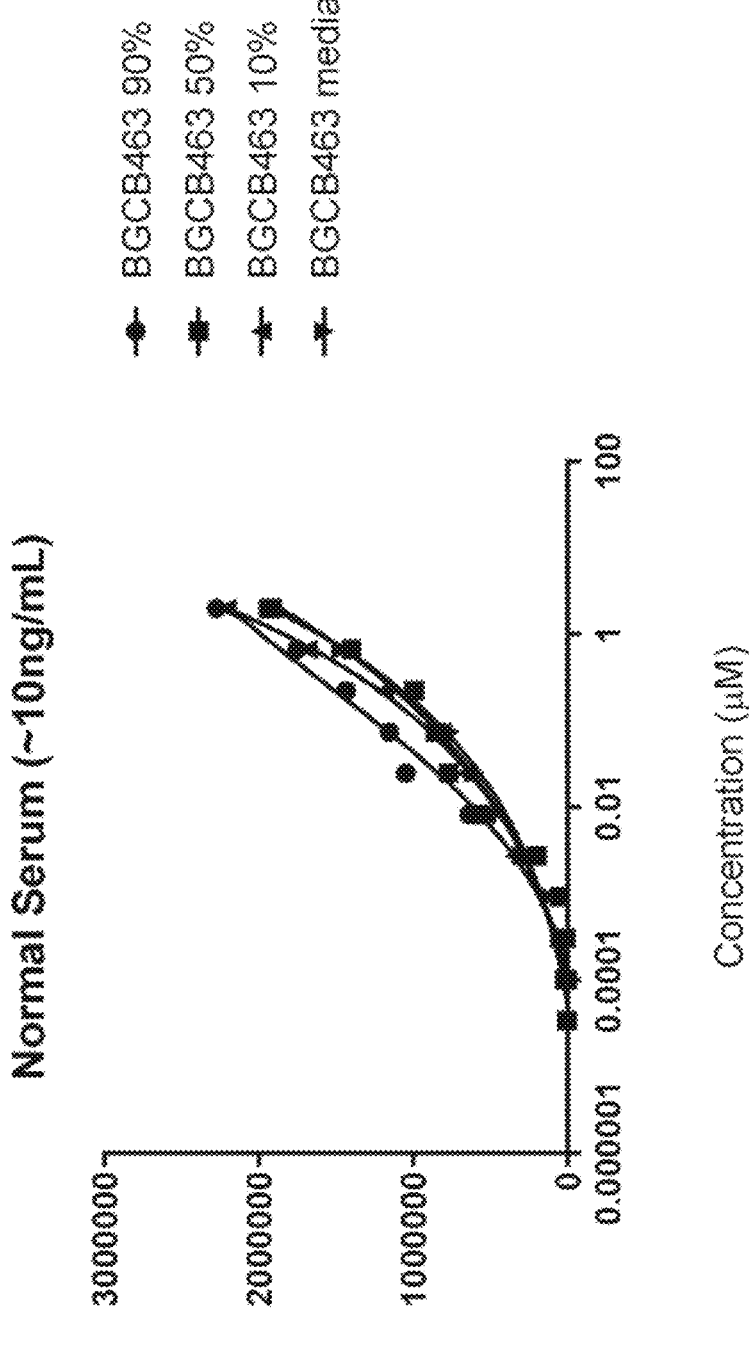

To assess in vitro killing kinetics, the Incucyte, an image-based platform, was utilized to acquire kinetic killing data. Tracking target cell killing and T cell activation over time gives a more detailed and qualitative readout of cytotoxic activity compared to standard FACS-based endpoint assays. As displayed in FIGS. 13A and 13B, BGCB463 reached a notable maximal kill at around 72 hr at all concentrations except for the lowest tested (1 pM) at a 3:1 E:T ratio. To expand on these data, 5:1 E:T and 1:1 E:T ratios were also tested (FIGS. 14A-14F). At 5:1 E:T, all concentrations tested reached maximum kill at 48-72 hr, where time to maximum kill inversely correlated with concentration. At 1:1 E:T, all concentrations also obtain maximum kill, but at later time points, with the same concentration dependence.

sBCMA Binding Interference Using Patient Serums

Assessment of potential interference with soluble BCMA (sBCMA) is necessary to support modeling and MABEL dose projection. Patient serums were chosen as a physiological source of soluble BCMA, and assayed by dilution in normal serum. As demonstrated in FIGS. 15A-15D, even the highest level of 613 ng/mL does not impact biding of BGCB463 to H929 cells. This is the case with all patient serum with varying levels of sBCMA.

Part 3. Discussion and Conclusions

The purpose of timecourse binding for a given panel is to determine if the molecule is stable on the surface of cells over a given time, taken with the caveat that this method is not capable of discerning internalization vs surface staining. BGCB463 maintains a stable or increasing signal at all concentrations tested on the H929 and MM.1R KO suites of cells. Thus, BGCB463 is stably presented on the surface of hematological cell targets.

Cross reactivity to cynomolgus BCMA and GPRC5D were also measured for BGCB463. GPRC5D binding was about 10-fold weaker on cyno compared to human which corresponded with cytotoxicity. On the other hand, BCMA binding was not cross-reactive up to 2 μM, which correlated with the observation of no functional activity.

Time course cytotoxicity was utilized to assess killing kinetics and give a more detailed view of how BGCB463 mediates T cell redirection. Killing was observed that approached maximum cytolysis with timing dependent on both concentration of molecule and E:T ratio.

Since BCMA exists in soluble form and it is elevated in patients, it was crucial to assess binding in the presence of patient serums with varying levels of sBCMA. The data demonstrated that sBCMA does not interfere with BGCB463 binding to surface BCMA on H929 cells.

Example 5: Biophysical Assessment for BGCB463 Trispecific Antibody

A range of biophysical assessments for BGCB463 were performed, including binding, protein characterizations, 2-week high concentration stability, and chemical and physical stability. A listing of the assessments and their results are shown in Table 10.

TABLE 10

| Biophysical Assessments and Results for BGCB463 | | |
|---|---|---|
| mAb TMP Characteristic | Results | Comments |
| Binding Affinity for human CD3 arm (SPR) | KD = 3.1E−8M Antigen: recombinant CD386 heterodimer construct | N/A |
| Binding Affinity for human BCMA arm (SPR) | KD = 8.4E−10M Antigen: BCMW37 | N/A |
| Fcγ Receptor Binding (SPR) | No measurable binding to human FcγR1, FcγRIIIa V158, FcγRIIIa F158, FcγRIIa or FcγRIIb. No measurable binding to cyno FcγR1, FcγRIII, FcγRIIa, or FcγRIIb | Silent Fc design confirmed |
| FcRn Binding (SPR) | pH 6.0: hFcRn KD = 954 nM cyFcRn KD = 826 nM Faster dissociation at pH 7.4 relative to pH 6.0 | N/A |
| Serum Interference (Octet) | No significant change in association rate in 50% human serum $k_a$ buffer/$k_a$ serum = 1.6-BCMA $k_a$ buffer/$k_a$ serum = 1.0-CD3 | N/A |
| GPRC5D Binding Epitope | Not determined | N/A |
| CD3 Binding Epitope | Linear epitope encompassing residues 22-35 (QDGNEEMGGITQTP (SEQ ID NO: 160)) of CD3ε chain | Epitope sequence determined for parent antibody CD3B376 against CD3εγ by HDX-MS |
| BCMA Binding Epitope | Linear epitope encompassing residues 17-26 (LLHACIPCQL (SEQ ID NO: 161)) of BCMA BCMW37 chain | HDX-MS data show residues 17-18 and 21-26 are protected by BGCB465. |
| Intact Abs mass, release (Mass Spec) | 156,431.5 Da | N/A |
| Glycoform profile (Mass Spec) | Typical IgG1 profile with main glycoform G0F/G0F | N/A |
| Level of HomoDimer(s) (Mass Spec) | No HD1 & HD2 detected | N/A |
| Levels of Other Product-Related Impurities (Mass Spec) | Minor clipping on HC2 (BCMA scFv) between AA 486-495. Minor losses of the CD3 LC and the combined VH + CH1 (pQ1-5222) of the CD3 arm. | N/A |
| N-link gly (non-Fc) (Mass Spec) | None predicted or observed | N/A |
| O-link gly sites (Mass Spec) | None observed | N/A |
| Glycation (% relative abundance) (Mass Spec) | HC1 (CD3)-9.5%, LC1 (CD3)-6.4%, HC2 (GPRC5D × BCMA)-7.5% | Glycation values represent upper limit due to over-estimation caused by non-zero baseline |
| Free Cys (Mass Spec) | None predicted or observed | N/A |
| N-terminal Elongation/Truncation (Mass Spec) | None observed | N/A |
| Conformational stability (DSC) | $Tm_1$ = 63.2° C. $Tm_2$ = 68.0° C. $Tm_3$ = 72.2° C. | Measured in 10 mM Histidine pH 6.5 |
| % Purity (2-step purification) (AUC) | 96.39% Monomer | Measured in 10 mM Histidine pH 6.4 |
| Serum stability (SEC-FDS) | 3.7% increase in aggregation at $t_0$ in human serum, 1.2% increase in aggregation after 2 days in human serum at 37° C. | Assessed by size exclusion chromatography using Alexa488 labeled GPRC5D × CD3 |
| IgG interactions (SPR) | No IgG interactions observed | N/A |
| Non-specific binding | No non-specific binding observed | N/A |
| Isoelectric point (cIEF) | pI = 9.51 % Acidic/Main/Basic peak area: 44.8/54.9/0.3 | N/A |
| Relative Hydrophobicity (aHIC) | Low surface hydrophobicity (hydrophobicity index <0.6) with broad peak | N/A |
| Viscosity | 5.48 cP | Determined at 150 mg/mL in 10 mM Histidine pH 6.5 |

TABLE 10-continued

| Biophysical Assessments and Results for BGCB463 | | |
|---|---|---|
| mAb TMP Characteristic | Results | Comments |
| Concentratability and % recovery in Histidine buffer pH 6.5 | Sample was concentrated to 176.5 mg/mL with 89.4% recovery | N/A |
| % Monomer (initial) (AUC) | 96.6% | Determined in Histidine pH 6.5 |
| % Monomer 2 weeks, 4° C. (AUC) | 84.7% | Determined in Histidine pH 6.5 |
| % Monomer 2 weeks, 40° C. (AUC) | 66.3% | Determined in Histidine pH 6.5 |
| Intact MS after Forced Degradation (Mass Spec) | All stress samples matched the expected mass. High pH stress resulted in minor BCMA scFv clipping along with minor loss of CD3 LC. Chemical oxidation treatment resulted in up to 3 oxidations on HC2 (scFv) arm and up to 2 oxidations on CD3 HC. | None |
| Size after Forced Degradation (aSEC) | Sample after physiological (2 wks 37 C.) and oxidation stress maintained >98% monomer; Samples after pH 8.5, 5, and 3.5 stresses showed 89-91% monomer; High concentration sample after 2 wks at 40 C. showed significant increase in HMW with only 63% monomer. | Increase in aggregation at high concentration was apparent over time and follow up formulation study is required to mitigate the aggregation propensity |
| Purity Forced Degradation (R and NR GXII) | NR GXII: All stressed samples maintained ≥99% monomer, except physiological (2 wks 37 C.) (97%), high concentration 40 C. 2 Wks (95.9%), and high pH (76.1%) samples. Reduced GXII: All stressed samples maintained ≥99% monomer, except 40 C. 2 Wks (97.9%) and high pH (89.7%). | None |
| Binding Affinity after Forced Degradation (SPR) | Affinity to CD3 is retained under all tested stress conditions. Affinity to BCMA was within error range of KD and % active species under all tested stress conditions. | N/A |
| Basal Oxidation level | 6.8% in M94 (GC5B680 scFv LCDR3) 4.7% in M232 (GC5B680 scFv HCDR3) <1% for all other CDRs residues | None |
| Met/Trp (change on oxidative stress) | 68.1% in M94 (GC5B680 scFv LCDR3) 15.1% in M232 (GC5B680 scFv HCDR3) 67.9% in M600 (BCMB519 scFv LCDR3) | None scFv scFv |
| Basal Deamidation level Deamidation sites (change on stress) | <1% in CDRs No significant change | None None |
| Basal isomerization level Isomerization sites (change on stress) | <1% in CDRs 20% D27 isomerization in HC-CDR1 CD3B2186 | None Note: D27 Isomerization under pH stress is observed all CD3B376 candidates and is thought not to impact activity. |

Example 6: Molecule Design, Sequence, and Structure of BGCB491 Trispecific Antibody BGCB491 is an immunoglobulin (Ig) G1 trispecific antibody that can bind simultaneously or independently to the epsilon subunit of the cluster of differentiation 3 receptor complex (CDRc) (Uniprot TD: P07766) on T lymphocytes (T cells), and to GPRC5D (G-protein coupled receptor family C group 5 member D, Uniprot TD: Q9NZD1) and BCMA (B cell maturation antigen, TNFRSF17, Uniprot ID: Q02223) on tumor cells. The antibody features mutations of L234A, L235A, and D265S in the constant region (Fc) to abolish interaction with Fc receptors and heterodimerization is enhanced using the knobs-into-holes platform mutations[1]. The anti-CD3ε "hole" chain also featured "RP" mutations (H435R, Y436F) to disrupt protein A binding of monomeric and homodimerized hole chains[2]. The molecule comprises an anti-CD3ε Fab region on the "hole, RP" chain and an anti-GPRC5D scFv v-region fused onto the C-terminus. The "knob" chain features the anti-BCMA scFv. The trispecific antibody was developed to evaluate the therapeutic potential of dual tumor targeting GPRC5D and BCMA and CD3 for T cell redirection. An illustration of BGCB491 is depicted in FIG. 16.

The trispecific BGCB491 antibody was generated by co-expression of the anti-CD3 heavy chain (HC) A fused to the C-terminal anti-GPRC5D scFv and anti-CD3 light chain (LC) with the anti-BCMA scFv fused to "knob" containing heavy chain B. The anti-CD3 variable region (VR000017350) was discovered by immunizing transgenic humanized rats [OmniRat (OMT™)] with recombinant CD38 protein. The anti-GPRC5d variable region (VR000038761) featured in BGCB491 is derived from the mAb GC5B680, discovered by immunizing transgenic humanized mice [Ablexis] with DNA encoding GPRC5d. The parent v-region (VR000029832) contained an "NSS" motif in the HC framework 3 region which presented a risk for N-linked glycosylation and which represented a mutation from the IGHV2-26*01 germline. The site was mutated back to the germline sequence "STS" to eliminate the risk for N-linked glycosylation, and this change resulted in the final variable region VR000038761. The anti-BCMA variable region (VR000003260) featured in BGCB491 is derived from the mAb BCMB519, discovered by immunizing transgenic humanized mice [Ablexis] with recombinant BCMA protein. No further modifications were made to this v-region. Both the anti-GPRC5D and anti-BCMA v-regions were formatted as single-chain fragment variable (scFv) in the final molecule.

The amino acid sequence for the BGCB491 heavy chains and light chain, as deduced from the cDNA sequence (SEQ ID Nos: 165, 166, and 167) of BGCB491 and confirmed by peptide mapping and mass spectrometry is shown below (Table 11). The 3 complementarity-determining regions (CDRs), defined according to ABM numbering, in each chain are bolded and underlined. The Gln residue at position 1 of BGCB491 heavy chain 1, Gln residue at position 1 of BGCB491 light chain, and Glu residue at position 1 of BGCB491 heavy chain 2 constitute the N-termini of the mature chains. Both heavy chains comprising BGCB491 IgG1 AAS have the following point mutations: L234A, L235A, and D265S. Heavy chain 1 from BGCB491 features the "hole" mutations: T366S, L368A, Y407V and the RF mutations: H435R, Y436F, while heavy chain 2 features the "knob" mutation: T366W. The knobs-into-holes mutations promote heterodimerization of the Fc[3]. The "RF" mutations disrupt binding to protein A. The mutations for FcγR receptor silencing (AAS) and the knobs-into-holes mutations are underlined in the sequences below.

TABLE 11

Amino Acid Sequence of BGCB491

| Area | AA Sequence | | | SEQ ID NO. |
|------|------|------|------|------|
| Light Chain 1 | QSALTQPASV TYKFVSWYQQ SSRFSGSKSG VSYAGSGTLL LFPPSSEELQ AWKADSSPVK YLSLTPEQWK APTECS | SGSPGQSITI HPDKAPKVLL NTASLTISGL FGGGTKLTVL ANKATLVCLI AGVETTTPSK SHRSYSCQVT | SCTGTSSNIG YEVSKRPSGV QAEDQADYHC GQPKAAPSVT SDFYPGAVTV QSNNKYAASS HEGSTVEKTV | 30 |

104

TABLE 11-continued

Amino Acid Sequence of BGCB491

| Area | AA Sequence | | | SEQ ID NO. |
|------|------|------|------|------|
| Heavy Chain 1 | QVQLQQSGPR NNNAAWSWIR YDYAVSVKSR PEDTALYYCA ASTKGPSVFP DYFPEPVTVS GLYSLSSVVT NTKVDKKVEP PSVFLFPPKP HEDPEVKFNW STYRVVSVLT LPAPIEKTIS MTKNQVSLSC ENNYKTTPPV QQGNVFSCSV GGGGSGGGGS SPVTLGQPAS LQQRPGQPPR GAGTDFTLKI HTFGQGTKLE GSQVTLKESG LTNIRMSVSW KSYSTSLKSR PVDTATYYCA S | LVRPSQTLSL QSPSRGLEWL ITVNPDTSRN RGYSSSFDYW LAPSSKSTSG WNSGALTSGV VPSSSLGTQT KSCDKTHTCP KDTLMISRTP YVDGVEVHNA VLHQDWLNGK KAKGQPREPQ AVKGFYPSDI LDSDGSFFLV MHEALHNRFT GGGGSGGGGS ISCRSSQSLV LLIYKISNRF SRVEAEDVGV IKGGSEGKSS PVLVKPTETL IRQPPGKALE LTISRDTSKS RMRLPYGMDV | TCAISGDSVF GRTYYRSKWL QFTLQLNSVT GQGTLVTVSS GTAALGCLVK HTFPAVLQSS YICNVNHKPS PCPAPEAAGG EVTCVVVSVS KTKPREEQYN EYKCKVSNKA VYTLPPSREE AVEWESNGQP SKLTVDKSRW QKSLSLSPGK DIVMTQTPLS HSDGNTYLSW FGVPDRFSGS YYCMQATQFP GSGSESKSTG TLTCTVSGFS WLAHIFSNDE QVVLTLTNVD WGQGTTVTVS | 29 |
| Heavy Chain 2 | EIVLTQSPGT SSFLTWYQQK DRFSGGGSGT HYGSSPMYTF SESKSTGGSE CAASGFTFSS SGSGGSTYYA QMNSLRAEDT VWGQGTTVTV AAGGPSVFLF VSVSHEDPEV EQYNSTYRVV SNKALPAPIE SREEMTKNQV NGQPENNYKT KSRWQQGNVF SPGK | LSLSPGERAT PGQAPRLLIY DFTLTISRLE GQGTKLEIKG VQLLESGGGL YAMSWVRQAP DSVKGRFTIS AVYYCAKDEG SSEPKSSDKT PPKPKDTLMI KFNWYVDGVE SVLTVLHQDW KTISKAKGQP SLWCLVKGFY TPPVLDSDGS SCSVMHEALH | LSCRASQSIS GASSRATGIP PEDFAVYYCQ GSEGKSSGSG VQPGGSLRLS GKGLEWVSAI RDNSKNTLYL YSSGHYYGMD HTCPPCPAPE SRTPEVTCVV VHNAKTKPRE LNGKEYKCKV REPQVYTLPP PSDIAVEWES FFLYSKLTVD NHYTQKSLSL | 31 |

Example 7: Immunogenicity Risk Assessment of BGCB491 Trispecific Antibody

The trispecific antibody sequences were analyzed for potential immunogenicity using the T-regulatory ($T_{reg}$) adjusted scores from the EpiVax Epimatrix in silico immunogenicity prediction program[4] (Table 12). EpiVax program computationally calculates the binding potential to the most common HLA molecules within each of the "supertypes". The report provides results that are representative of >90%0 of human populations worldwide without the necessity of testing each haplotype individually. The EpiVax score is calculated by aggregating the EpiMatrix scores of all predicted T-cell epitopes contained within a given protein sequence and adjusting for expected T-cell epitope content and protein length. The EpiVax score interpretation is as follows: an EpiVax score of <−20 is "Ideal"; an EpiVax score from −20 to +20 is "Acceptable"; and an EpiVax score of >+20 is "Unacceptable."

TABLE 12

| BGCB491 Chain info | Amino acid sequence of variable region | SEQ ID NO. | EpiVax score | EpiVax score interpretation |
|---|---|---|---|---|
| | Immunogenicity assessment for BGCB491 | | | |
| Light chain 1 (CD3B376) VL | QSALTQPASVSGSPGQSITISCTGTSSN IGTYKFVSWYQQHPDKAPKVLLYEVSKR PSGVSSRFSGSKSGNTASLTISGLQAED QADYHCVSYAGSGTLLFGGGTKLTVL | 7 | -44.88 | Ideal |
| Heavy Chain 1 (CD3B376) VH | QVQLQQSGPRLVRPSQTLSLTCAISGDS VFNNNAAWSWIRQSPSRGLEWLGRTYYR SKWLYDYAVSVKSRITVNPDTSRNQFTL QLNSVTPEDTALYYCARGYSSSFDYWGQ GTLVTVSS | 8 | +65.28 | Unacceptable |
| Heavy chain 2 N-terminal scFv (GC5B680 N68S, S69T) VL | DIVMTQTPLSSPVTLGQPASISCRSSQS LVHSDGNTYLSWLQQRPGQPPRLLIYKI SNRFFGVPDRFSGSGAGTDFTLKISRVE AEDVGVYYCMQATQFPHTFGQGTKLEIK | 15 | -3.12 | Acceptable |
| Heavy chain 2 N-terminal scFv (GC5B680 N68S, S69T) VH | QVTLKESGPVLVKPTETLTLTCTVSGFS LTNIRMSVSWIRQPPGKALEWLAHIFSN DEKSYSTSLKSRLTISRDTSKSQVVLTL TNVDPVDTATYYCARMRLPYGMDVWGQG TTVTVSS | 16 | -11.65 | Acceptable |
| Heavy chain 2 C-terminal scFv (BCMB519) VL | EIVLTQSPGTLSLSPGERATLSCRASQS ISSSFLTWYQQKPGQAPRLLIYGASSRA TGIPDRFSGGGSGTDFTLTISRLEPEDF AVYYCQHYGSSPMYTFGQGTKLEIK | 23 | -52.88 | Ideal |
| Heavy chain 2 C-terminal scFv (BCMB519) VH | EVQLLESGGGLVQPGGSLRLSCAASGFT FSSYAMSWVRQAPGKGLEWVSAISGSGG STYYADSVKGRFTISRDNSKNTLYLQMN SLRAEDTAVYYCAKDEGYSSGHYYGMDV WGQGTTVTVSS | 24 | -54.35 | Ideal |

Example 8: Trispecific Antibody Comparison Studies

BGCB463 and BGCB491, as described above, were tested in the series of following studies.

Trispecific Antibodies Mediate Killing of Target Positive Cells Only

Figure 17A:
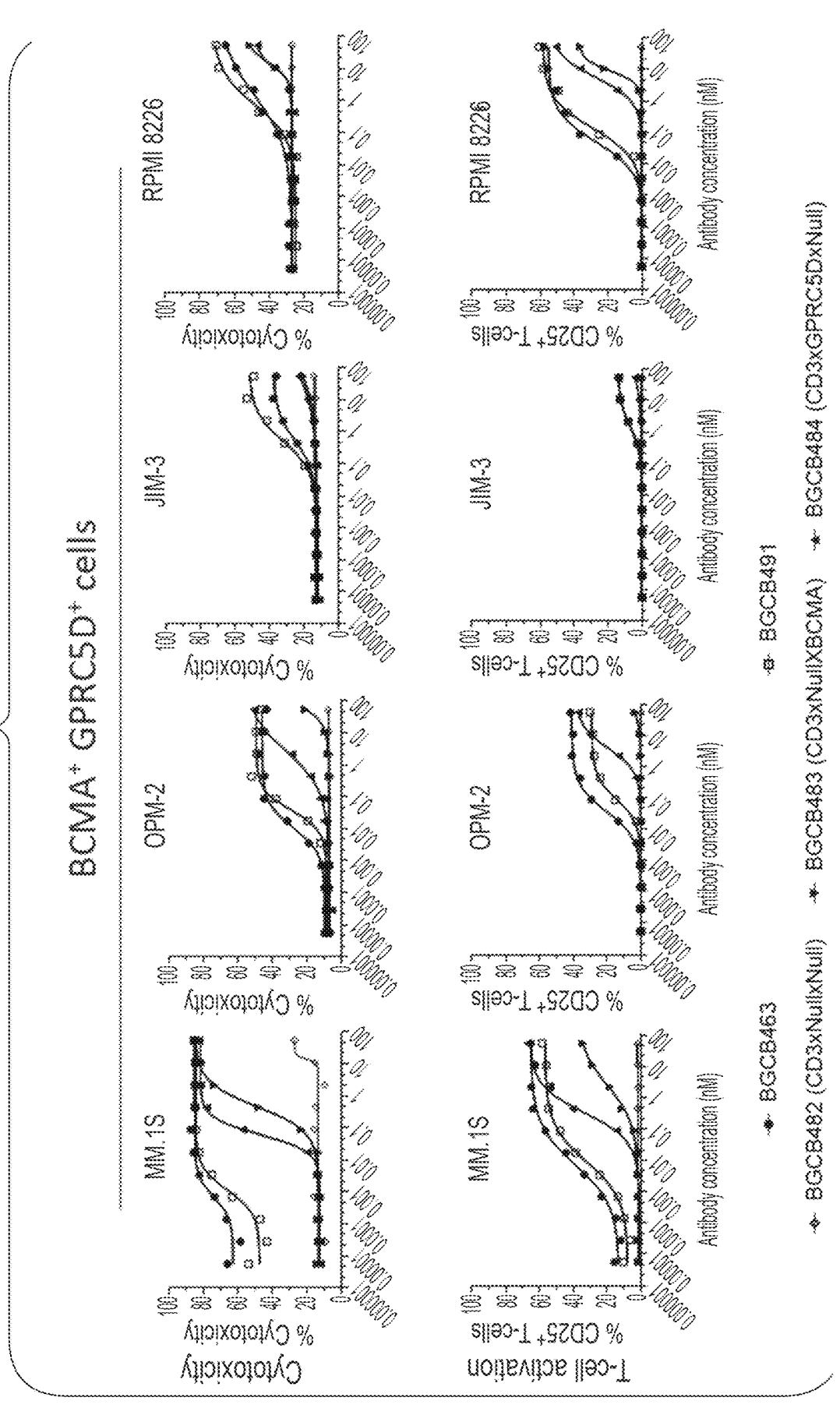
FIGS. 17A-17B. BGCB463, BGCB491, and three controls (BGCB482 (CD3×Null×Null), BGCB483 (CD3×Null×BCMA), BGCB484 (CD3×GPRC5D×Null)) were tested against $BCMA^+$ $GPRC5D^+$ cells (FIG. 17A) and $BCMA^-$ $GPRC5D^-$ cells (FIG. 17B). Effector to target (E:T) ratio of 3:1; n=1 T-cell donors, 72 hours incubation, top concentration 53 nM, 1-5 dilution. Tests were performed for both cytotoxicity and T-cell activation.
Figure 17B:
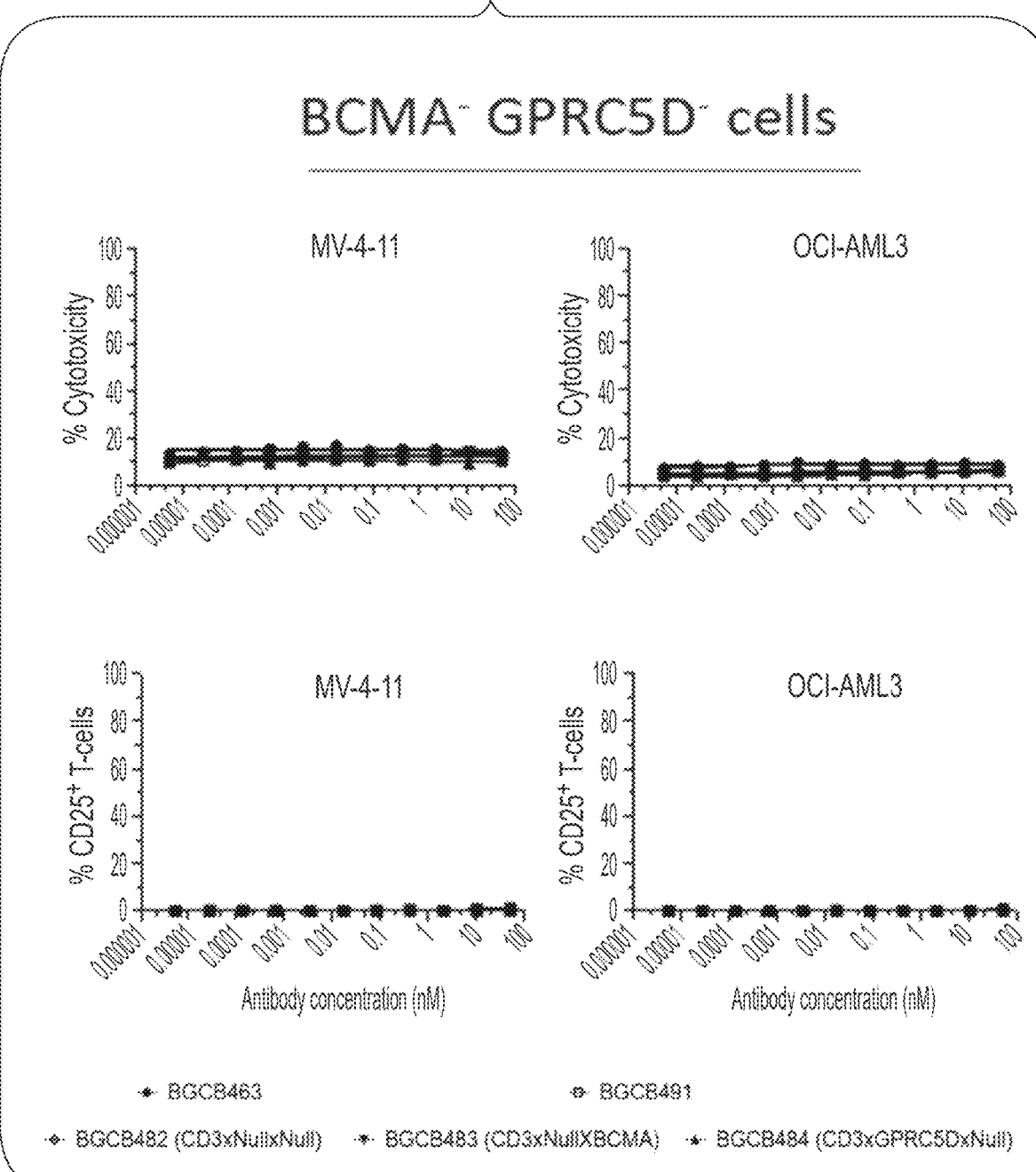

BGCB463, BGCB491, and three controls (BGCB4821 (CD3×Null×Null), BGCB483 (CD3×Null×BCMA), BGCB484 (CD3×GPRC5D×Null)) were tested against BCMA+ GPRC5D+ cells (FIG. 17A) and BCMA− GPRC5D− cells (FIG. 17B). Effector to target (E:T) ratio of 3:1; n=1 T-cell donors, 72 hours incubation, top concentration 53 nM, 1-5 dilution. Tests were performed for both cytotoxicity and T-cell activation. The results show that BGCB463 and BGCB491 only mediate the killing of the BCMA+ GPRC5D+ cells (as shown in FIG. 17A) while the BCMA− GPRC5D− cells were unaffected.

Trispecific Antibodies are Active in Depleting Clonal (CRISPR) Cell Lines

Figure 18A:
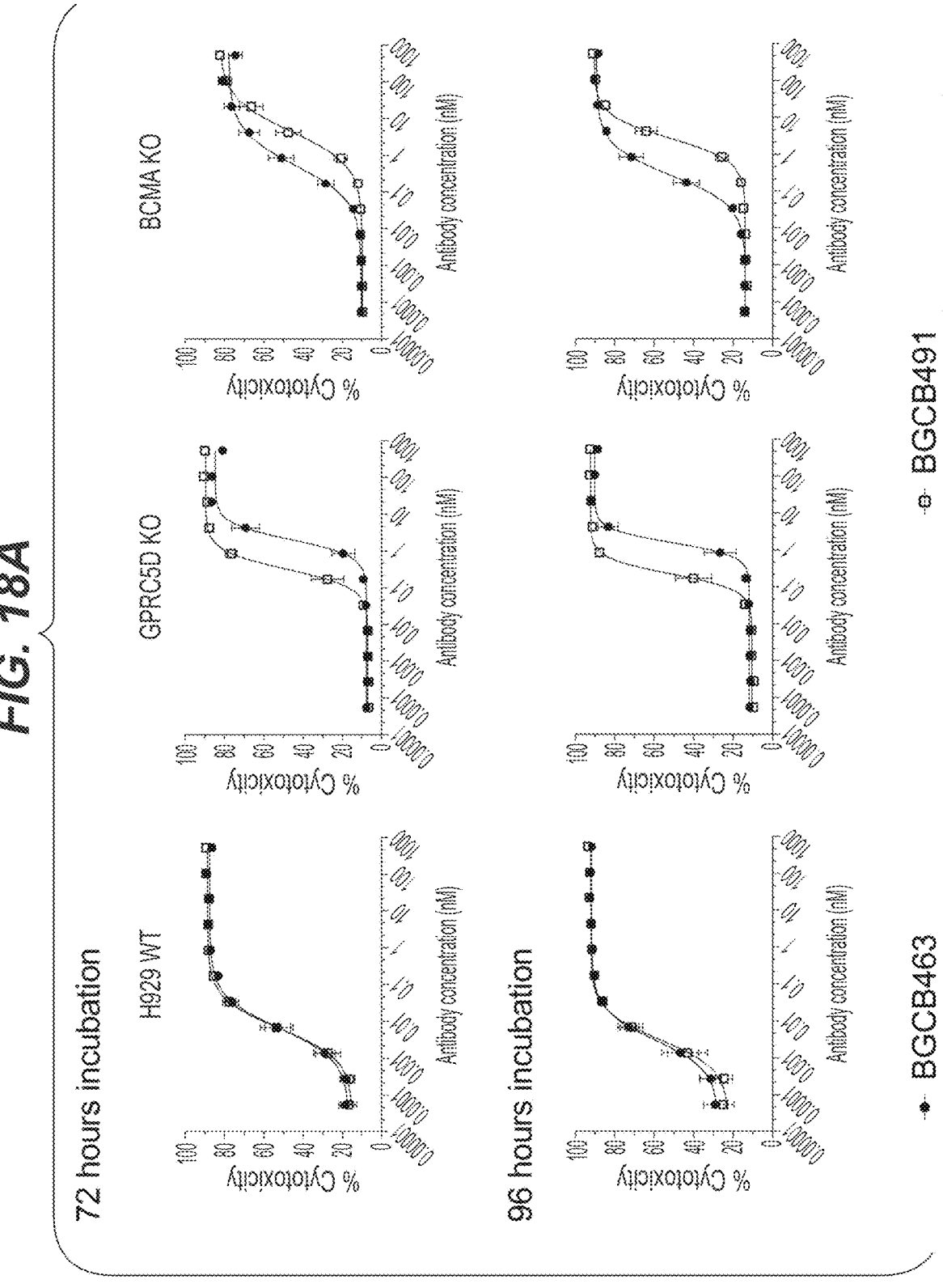
FIGS. 18A-18B. BGCB463 and BGCB491 depleted H929 WT, GPRC5D KO, and BCMA KO cell lines both 72 and 96 hours after primary incubation (FIG. 18A). The E:T ratio was 3:1, n=5 T-cell donors; 72(5) and 96(4) hours incubation; top concentration 532 mM, 1-5 dilution gradient. Both antibodies show increased T-cell activation both 72 and 96 hours in the same H929 WT, GPRC5D KO, and BCMA KO cells as above (FIG. 18B).

BGCB463 and BGCB491 depleted H929 WT, GPRC5D KO, and BCMA KO cell lines both 72 and 96 hours after primary incubation (FIG. 18A). The E:T ratio was 3:1, n=5 T-cell donors; 72(5) and 96(4) hours incubation; top concentration 532 mM, 1-5 dilution gradient. $EC_{50}$ values shown below in Table 13.

TABLE 13

| Incubation time | BGCB463 | BGCB491 | Cell Type |
|---|---|---|---|
| $EC_{50}$ values for 72/96 hour cytotoxicity test with BGCB463 and BGCB491 | | | |
| | Cytotoxicity | | |
| 72 hrs | | | |
| $EC_{50}$ value (nM) | 0.007 | 0.006 | H929 WT |
| | 2.055 | 0.322 | H929-GPRC5D KO |
| | 0.539 | 4.517 | H929-BCMA KO |
| 96 hrs | | | |
| $EC_{50}$ value (nM) | 0.003 | 0.003 | H929 WT |
| | 1.580 | 0.226 | H929-GPRC5D KO |
| | 0.269 | 2.759 | H929-BCMA KO |

Figure 18B:
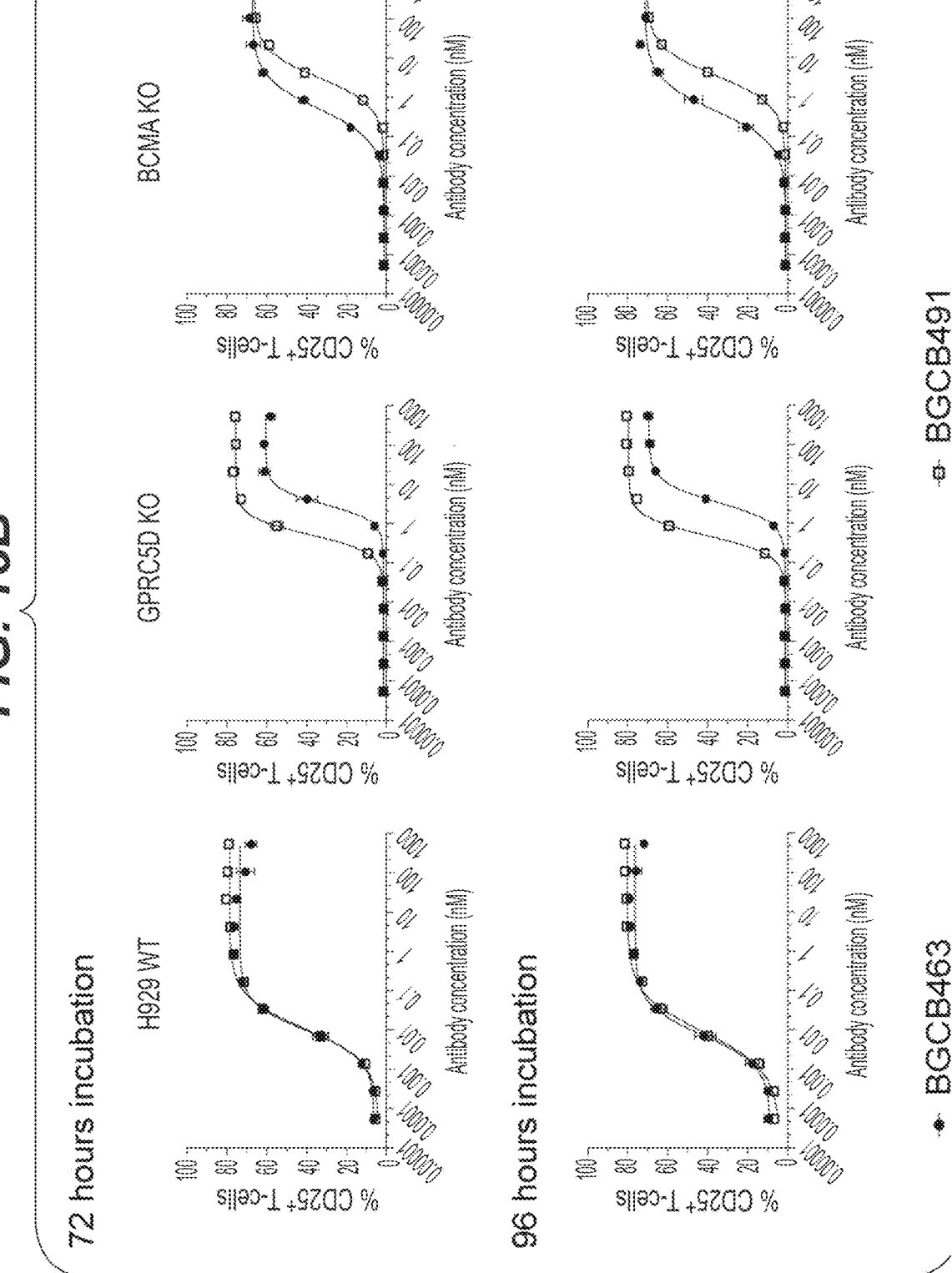

BGCB463 and BGCB491 also trigger T-cell activation while depleting CRISPR cells. Both antibodies show increased T-cell activation both 72 and 96 hours in the same H929 WT, GPRC5D KO, and BCMA KO cells as above (FIG. 18B and Table 14).

TABLE 14

EC$_{50}$ values for 72/96 hour T-cell test with BGCB463 and BGCB491

| Incubation time | BGCB463 | BGCB491 | Cell Type |
|---|---|---|---|
| T-cell activation | | | |
| 72 hrs | | | |
| EC$_{50}$ value (nM) | 0.009 | 0.011 | H929 WT |
| | 3.139 | 0.520 | H929-GPRC5D KO |
| | 0.517 | 3.110 | H929-BCMA KO |
| 96 hrs | | | |
| EC$_{50}$ value (nM) | 0.007 | 0.009 | H929 WT |
| | 3.507 | 0.480 | H929-GPRC5D KO |
| | 0.445 | 3.458 | H929-BCMA KO |

Trispecific Antibodies can Deplete Lymphoma (BCMA Only) Cell Lines

Figure 19:
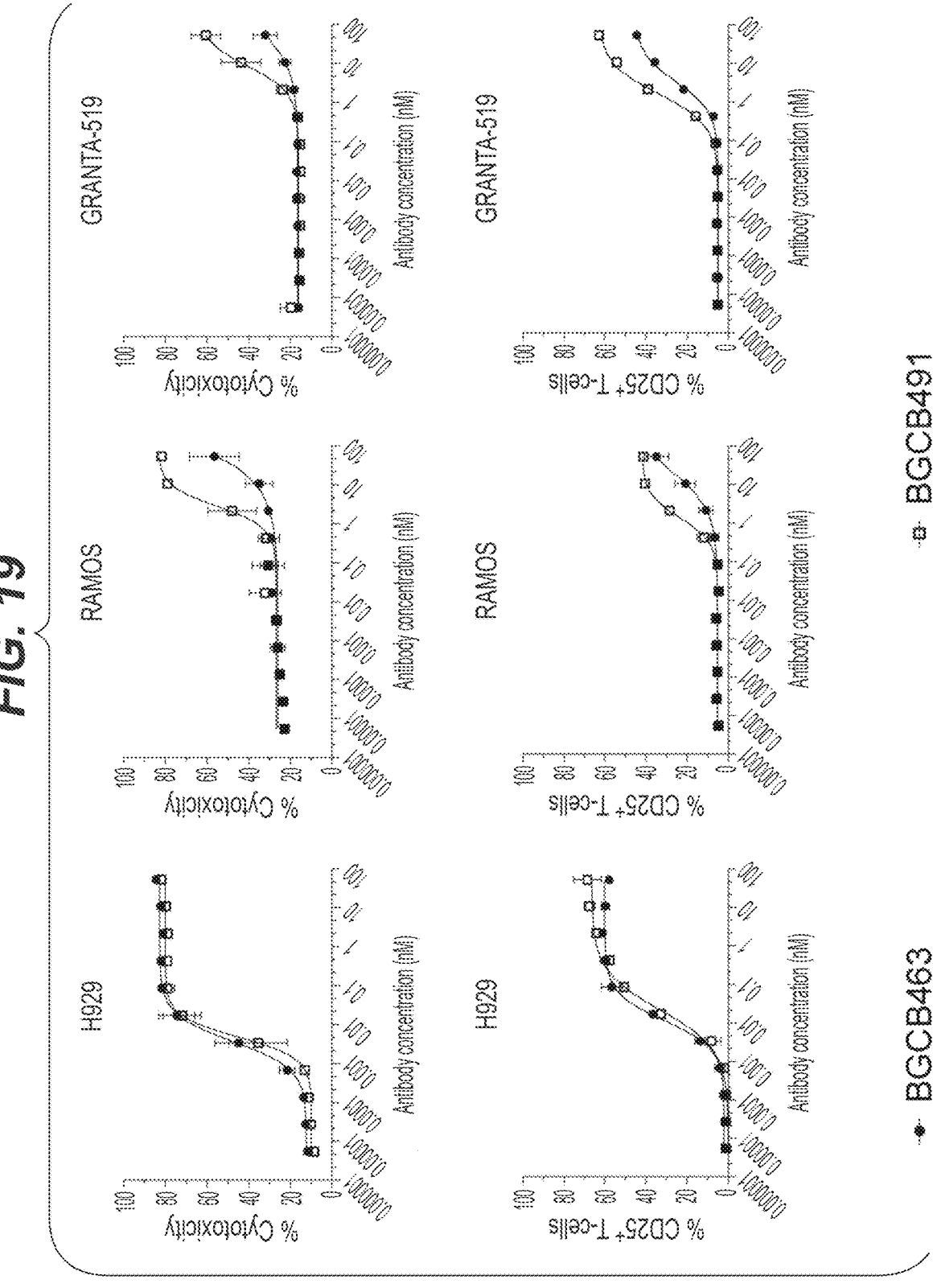
FIG. 19. BGCB463 and BGCB491 were testing in cytotoxicity and T-cell activation assays with H929, RAMOS and GRANTA-519 cells lines. E:T was 5:1, n=1 T-cell donors; 72 hours incubation only; top concentration of 53 nM; and a 1-5 dilution.

BGCB463 and BGCB491 were testing in cytotoxicity and T-cell activation assays with H929, RAMOS and GRANTA-519 cells lines. Results show both antibodies did deplete the RAMOS and GRANTA-519 lines, although higher concentrations of both antibodies were required (FIG. 19, with EC$_{50}$ values in Table 15). E:T was 5:1, n=1 T-cell donors; 72 hours incubation only; top concentration of 53 nM; and a 1-5 dilution.

TABLE 15

EC$_{50}$ values for lymphoma cell line depletion with BGCB463 and BGCB491

| | BGCB463 | BGCB491 | Cell Line |
|---|---|---|---|
| Cytotoxicity | | | |
| EC$_{50}$ value (nM) | 0.004 | 0.005 | H929 WT |
| | n/a | 2.813 | Ramos |
| | 80.980 | 8.584 | Granta-519 |
| T-cell activation | | | |
| EC$_{50}$ value (nM) | 0.012 | 0.022 | H929 WT |
| | 17.580 | 1.387 | Ramos |
| | 3.300 | 1.644 | Granta-519 |

Trispecific Antibodies Depletes Target Positive Cells in Whole Blood Assay

Figure 20:
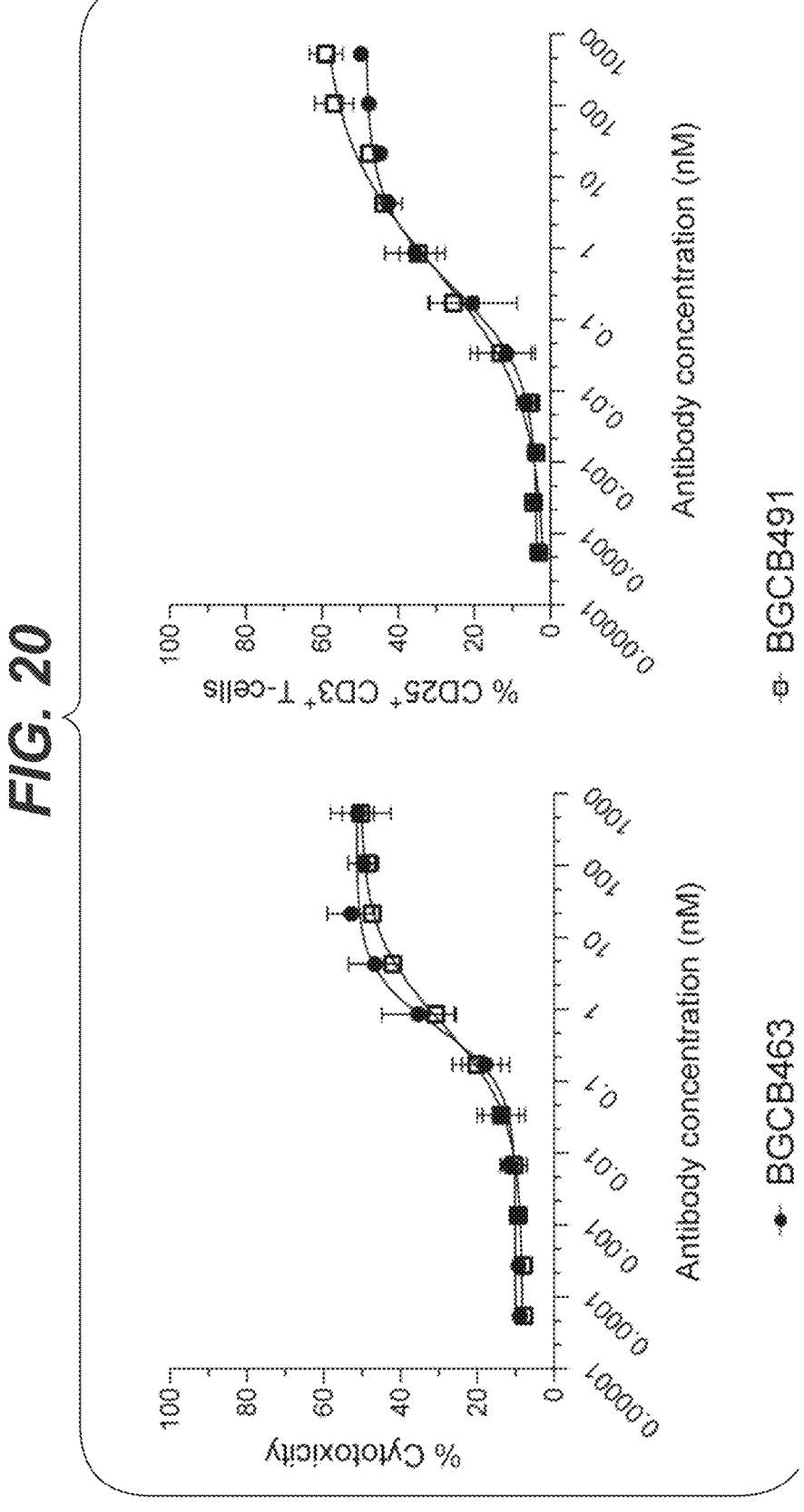
FIG. 20. BGCB463 and BGCB491 were testing in cytotoxicity and T-cell activation whole blood assays with H292 cells. E:T was 5:1, n=2 whole blood donors; 48 hours incubation; top concentration of 532 nM; and a 1-5 dilution.

BGCB463 and BGCB491 were testing in cytotoxicity and T-cell activation whole blood assays with H292 cells. Results show cytotoxicity and T-cell activation (FIG. 20 and EC50 values in Table 16). E:T was 5:1, n=2 whole blood donors; 48 hours incubation; top concentration of 532 nM; and a 1-5 dilution.

TABLE 16

EC values for whole blood cell depletion with BGCB463 and BGCB491

| EC value (nM) | BGCB463 | BGCB491 |
|---|---|---|
| Cytotoxicity | | |
| EC$_{20}$ | 0.159 | 0.084 |
| EC$_{50}$ | 0.574 | 0.648 |
| EC$_{90}$ | 4.412 | 16.380 |
| T-cell activation | | |
| EC$_{20}$ | 0.044 | 0.027 |
| EC$_{50}$ | 0.297 | 0.544 |
| EC$_{90}$ | 6.199 | 63.160 |

Trispecific Antibodies Regress Tumor Growth in Mice

Figure 21A:
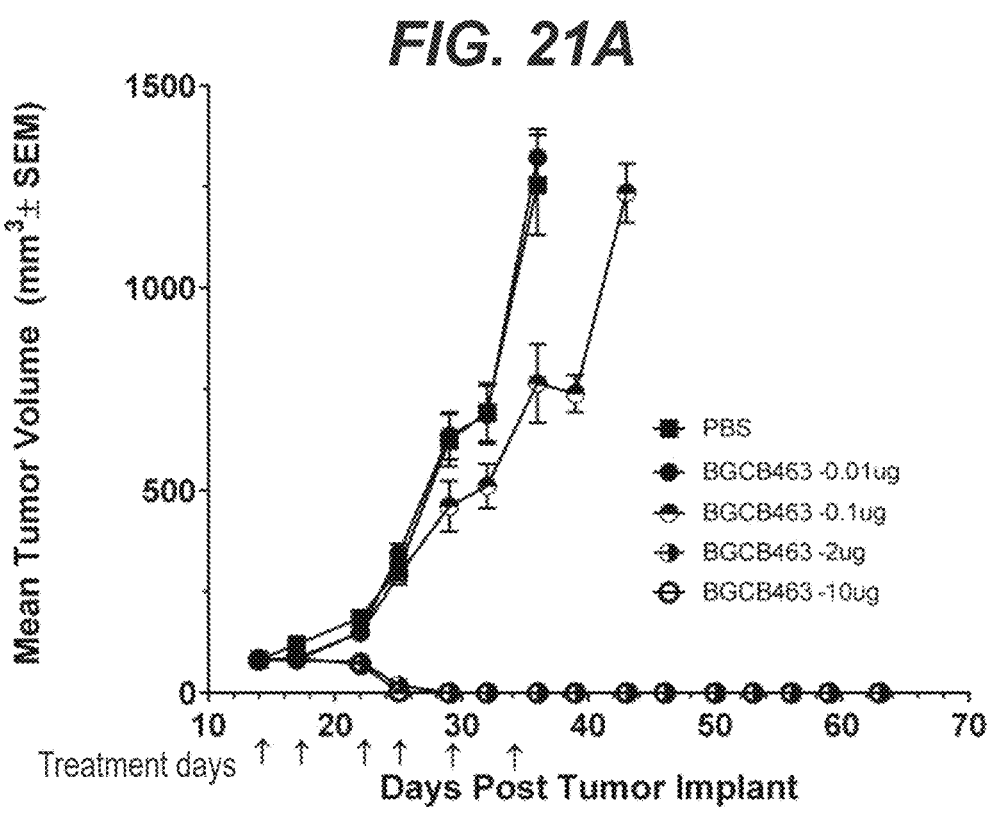
FIGS. 21A-21B. BGCB463 was shown to regress tumor growth in MM.1S and RPMI 8226 xenograft mouse models if given in a high enough dose: either 2 ug or 10 ug in the MM.1S model (FIG. 21A) or 5 ug or 10 ug in the RPMI 8226 model (FIG. 21B).
Figure 21B:
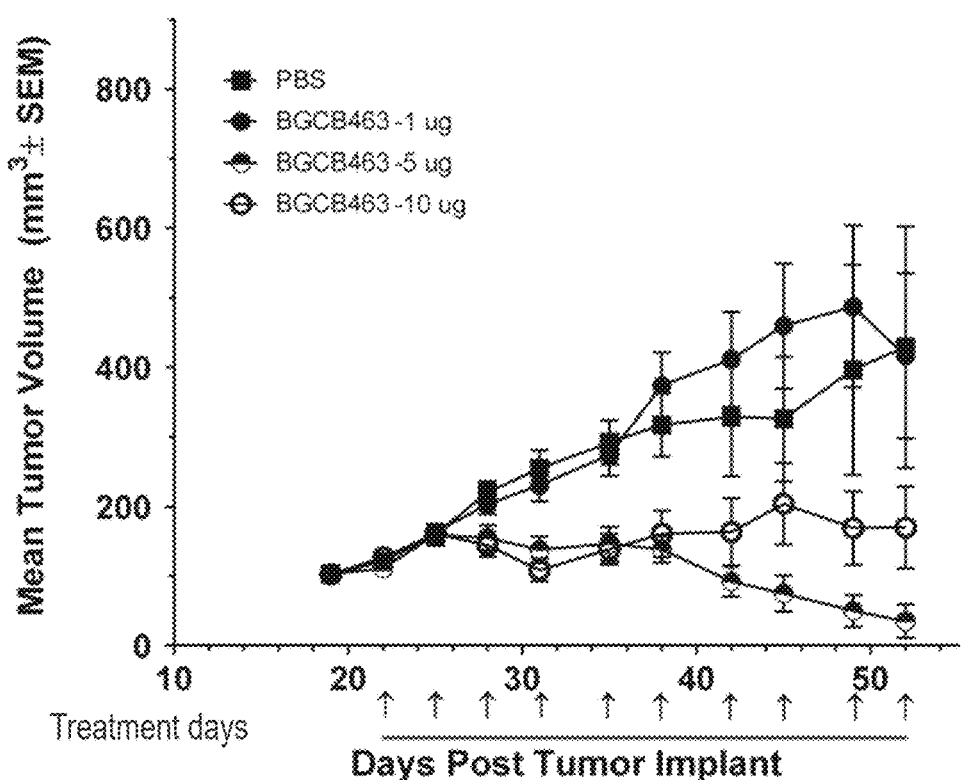

BGCB463 was shown to regress tumor growth in MM.1S and RPMI 8226 xenograft mouse models if given in a high enough dose: either 2 µg or 10 µg in the MM.1S model (FIG. 21A) or 5 µg or 10 µg in the RPMI 8226 model (FIG. 21). The tumors either stopped growing or showed a reduction in growth compared to control conditions.

Figure 22:
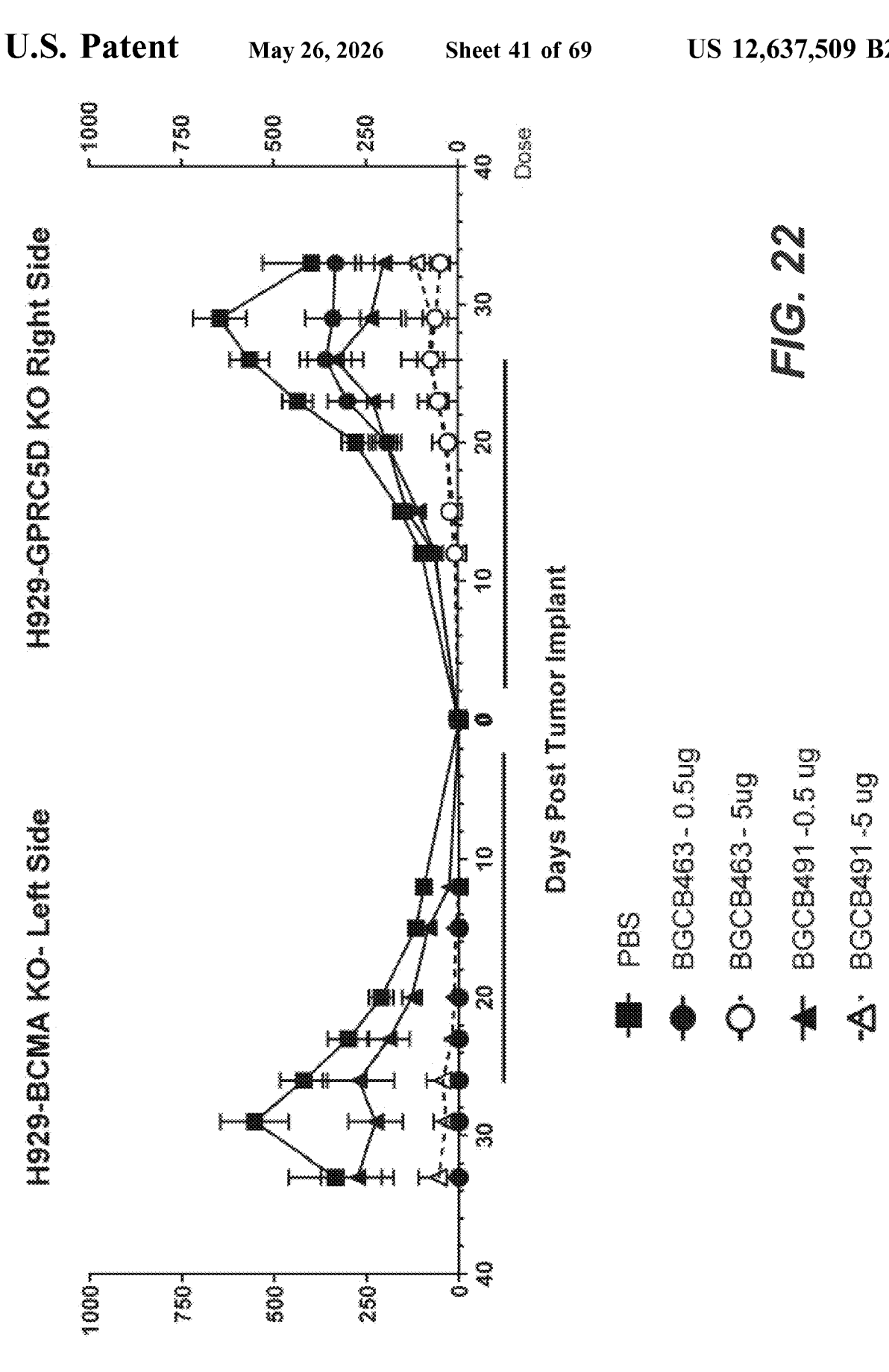
FIG. 22. BGCB463 and BGCB491 were shown to regress tumor growth in H929 prophylactic xenograft mouse models. Compared to PBS controls both 0.5 ug and 5 ug doses slowed tumor growth in both H929-BCMA KO and H929-GPRC5D KO models, with the higher 5 ug concentration showing more effect.

Additionally, both BGCB463 and BGCB491 were shown to regress tumor growth in H929 prophylactic xenograft mouse models. Compared to PBS controls both 0.5 µg and 5 µg doses slowed tumor growth in both H929-BCMA KO and H929-GPRC5D KO models, with the higher 5 µg concentration showing more effect (FIG. 22).

DRC Pan-T Binding

Figure 23:
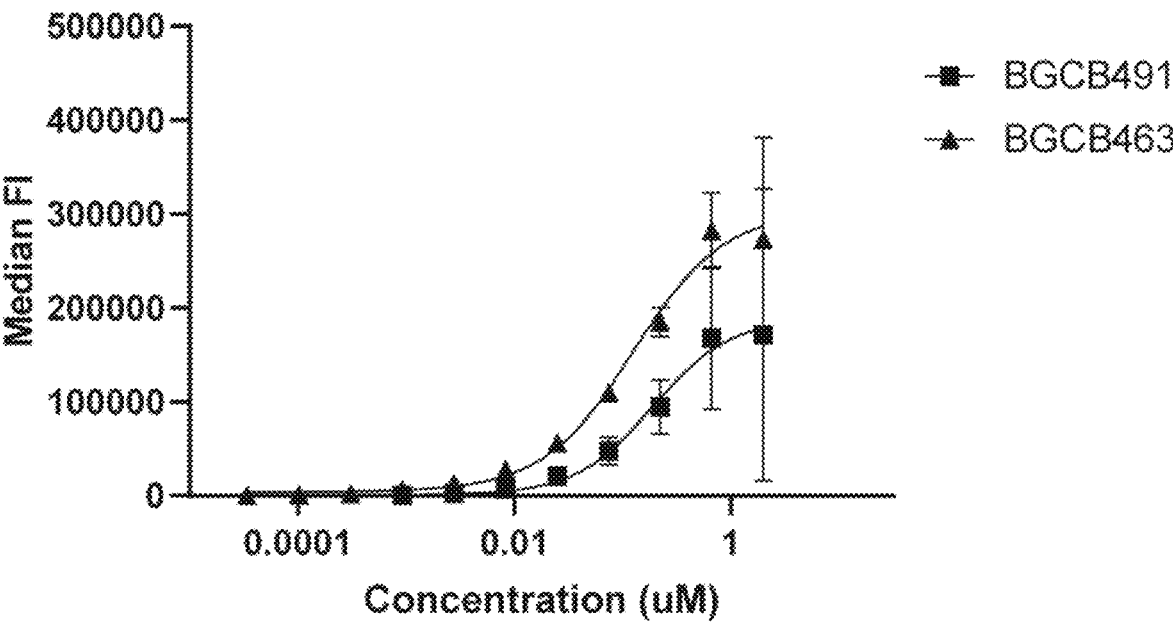
FIG. 23. BGCB463 and BGCB491 were tested in a 1 hr, 37° C. DRC Pan-T binding assay. Two human Pan-T cell donors were used, and test molecules had 2 uM starting concentrations with a 1:3 dilution and 11 point DRC.
Figure 24A:
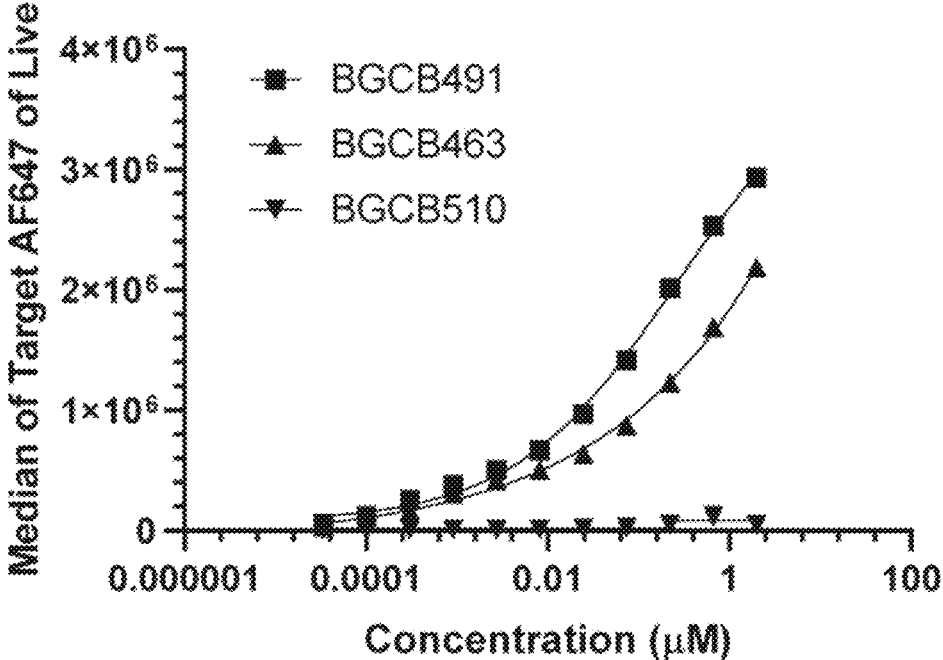
FIGS. 24A-24D. BGCB463, BGCB491, and a null control were tested against H929 WT (FIG. 24A), H929-BCMA KO (FIG. 24B), H929-GPRC5D KO (FIG. 24C), and H929-BCMA/GPRC5D double KO (FIG. 24D) cells in a 1 hour, 37° C. DRC suite binding assay.
Figure 24B:
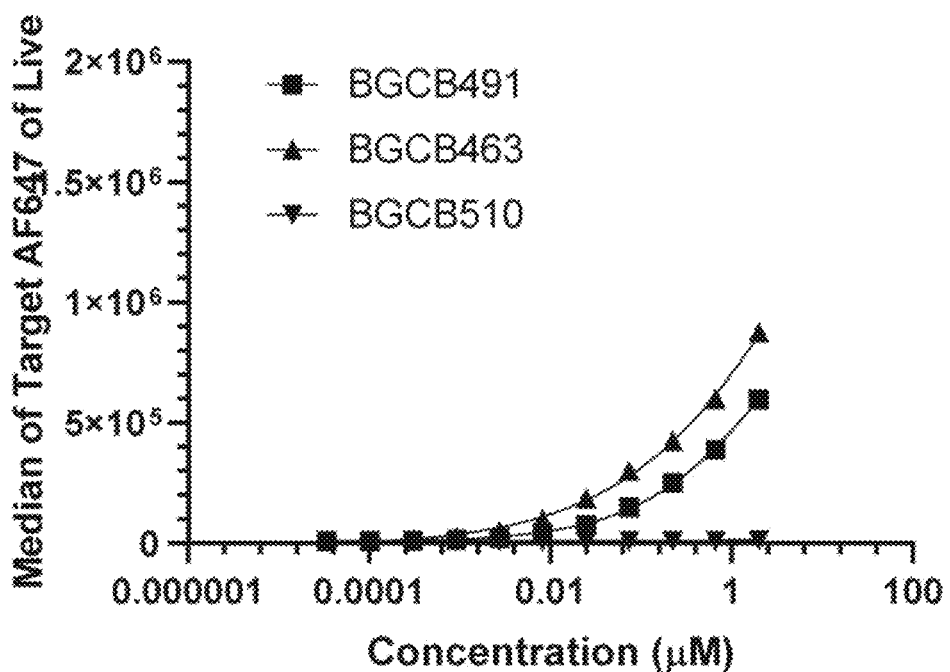
Figure 24C:
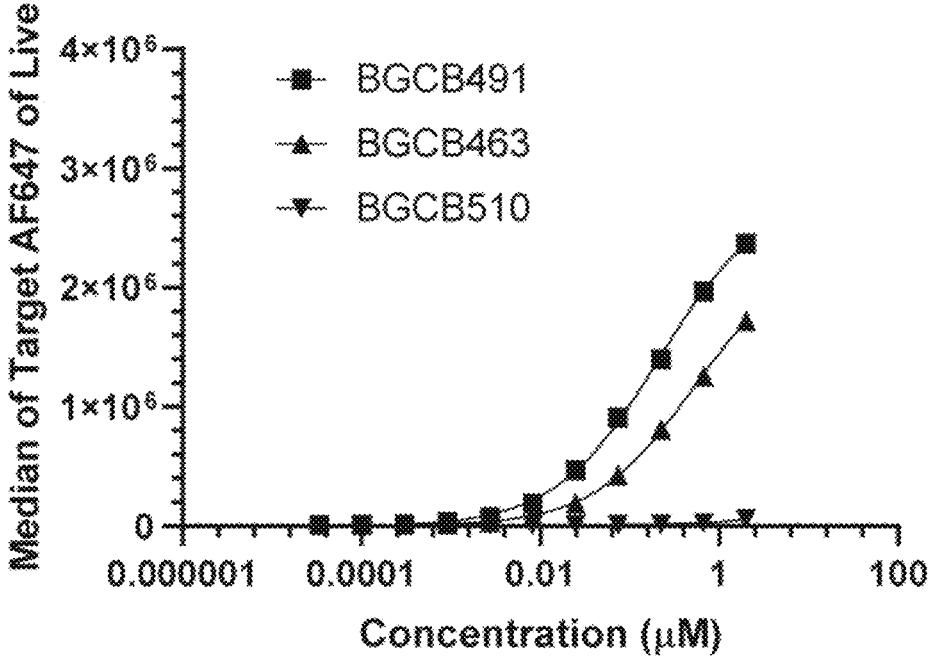
Figure 24D:
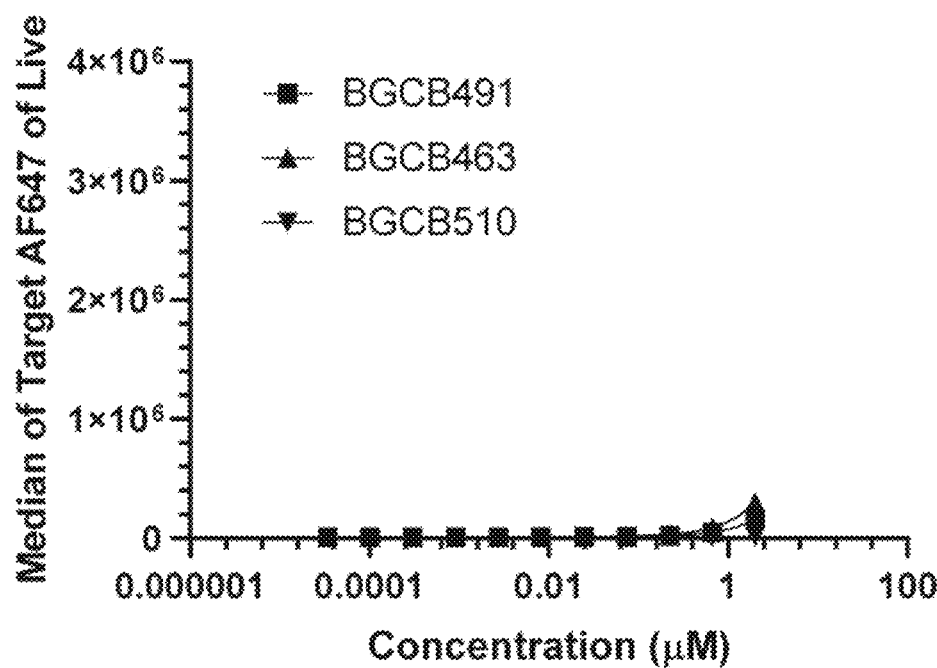

BGCB463 and BGCB491 were tested in a 1 hr, 37° C. DRC Pan-T binding assay. Two human Pan-T cell donors were used, and test molecules had 2 uM starting concentrations with a 1:3 dilution and 11 point DRC. Secondary detecting via Alexa Fluor® 647 AffiniPure Goat Anti-Human IgG (H+L). FACS was performed using Intellicyte Ique Screener plus. Results shown in FIG. 23, with BGCB491 having a EC$_{50}$ 0.1903 and top of 188194, and BGCB463 having a EC$_{50}$ of 0.1258 and top of 303269. The EC$_{50}$ values demonstrated are within expected parameters for the CD3 binding arm.

DRC H929 Suite Binding

BGCB463 and BGCB491 were tested against H929 WT, H929 BCMA-KO, H929 GPRC5D-KO, and H929 BCMA/GPRC5D double KO cells in a 1 hour, 37° C. DRC suite binding assay. Results shown in FIGS. 24A-24D, all with a null control (BGCB510). EC values shown in Table 17. Results showed that BGCB491 have increased BCMA-mediated binding and decreased GPRC5D-mediated binding compared to BGCB463.

TABLE 17

EC values (uM) for BGCB463 and BGCB491 in H929 suite binding

| | BGCB463 | BGCB491 |
|---|---|---|
| H929 WT | | |
| EC$_{50}$ | n/a | 0.270 |
| EC$_{90}$ | n/a | 25.049 |
| H929 BCMA-KO | | |
| EC$_{50}$ | 11.7 | 3.183 |
| EC$_{90}$ | n/a | n/a |
| H929 GPRC5D-KO | | |
| EC$_{50}$ | 0.504 | 0.210 |
| EC$_{90}$ | 8.385 | 3.896 |

Trispecific Antibody Analysis Studies

The follow Table 18 provides various analyses on BGCB463 and BGCB491.

TABLE 18

Analysis summary of BGCB463 and BGCB491 trispecific antibodies

| Analysis | BGCB463 | BGCB491 |
|---|---|---|
| Purity (AUC) (post 3-step purification) | 96.4% monomer | 98.9% monomer |
| Conformational stability (DSC, Histidine, pH 6.5) | Tms = 63° C., 68° C., 72° C. | Tms = 63° C., 68° C., 72° C. |
| Measured pI (cIEF) | pI: 9.51 | pI: 9.56 |
| Relative hydrophobicity | Moderate | Relative low |

TABLE 18-continued

Analysis summary of BGCB463 and BGCB491 trispecific antibodies

| Analysis | | BGCB463 | BGCB491 |
|---|---|---|---|
| by aHIC | | hydrophobicity | hydrophobicity (HI = 0.38) |
| PTMs analysis (LC-MS) | | <10% CDRs PTMs | <5% CDRs PTMs |
| Binding affinity (SPR) | | KD: CD3 (31.3 ± 8.7 nM); BCMA (844 ± 128 pM) | KD: BCMA (2.12E−10M); CD3 (2.51E−08M) |
| Serum Interference (Octet) | | Binding Unaffected | Binding Unaffected |
| Serum Stability (SEC-FDS, stable batch) | | ~12% increase in HMW after 7-day incubation at 37° C. | ~5% increase in HMW after 7-day incubation at 37° C. |
| Non-specific Binding (SPR) | | None | None |
| Concentratability | | ~180 mg/mL, 89% recovery, 97% monomer | ~180 mg/mL, 91% recovery, 97.5% monomer |
| Viscosity at 150 mg/mL | | 5.48 cP | 6.3 cP |
| HCLF: % Monomer after 2 wks @ 4° C. & 40° C. (AUC) | | Aggregation at 180 mg/mL increased to 15% and 34% after 2 wk at 4° C. & 40° C. | Aggregation at 180 mg/mL increased to 36% and 34% after 2 wk at 40° C., no increase in HMW at 4° C. |
| Physiological stress: 37° C., 2 mg/mL, PBS pH7.4 | | No physical/chemical/ affinity changes | No increase in HMW, significant increase in LMW (15% by SEC, ~18% by GXII): 18% lower binding activity to CD3, BCMA binding unaffected |
| PTMs Inducing Stress | pH 8.5, 1 wk, 40° C. | 20% D27 isomerization (CD3, HCDR1), binding unaffected; <10% deamidation/ isomerization in other CDRs residues | ~12% D27 isomerization (CD3, HCDR1); increase in LMW (~15% by SEC, ~20% by GXII): binding unaffected |
| | pH 5, 1 wk, 40° C. | No increase in CDRs PTMs | No significant changes |
| | pH 3.5, 6 h, rt | No increase in CDRs PTMs | No significant changes |
| | Chemical Oxidation | 68% M94 oxidation; 15% M232 oxidation; 68% M600; CD3 biding unaffected, BCMA binding with 2 folds of release | 97% M94 oxidation (GC5B680, LCDR3); 99% M600 (BCMB519 LCDR3); CD3 binding unaffected, BCMA binding affinity slightly affected (~2-3 folds of release) |
| | Metal Oxidation | No increase in CDRs PTMs | No significant changes |

Example 9: Biophysical Assessments of BGCB491 Trispecific Antibody

The trispecific molecule BGCB491 was selected as lead based on therapeutic efficacy in in vitro studies and in vivo studies and biophysical assessment. Table 19A provides recombinant antigen binding, species cross-reactivity, epitope identification, Fc receptor binding, and biophysical intrinsic property attributes of the lead candidate. Table 19B provides additional characteristics for BGCB491.

TABLE 19A

List of biophysical assessments and results for BGCB491

| mAb TAW characteristic | Result | Comments |
|---|---|---|
| Binding | | |
| Binding affinity for human CD3 arm (SPR) | $K_D$ = 2.5 × 10⁻⁸M | Antigen: recombinant CD3εγ heterodimer construct (CD3W200) |
| Binding affinity for human BCMA and GPRC5D arms (SPR) | Human BCMA: $K_D$ = 2.1 × 10⁻¹⁰M; Antigen: BCMW37. Human GPRC5D: no SPR data is available for GPRC5D due to lack of representative soluble reagent for this transmembrane target. Affinity binding was assessed using cell-based method on H929-BCMA-KO cells instead (see Example 11) | Parental BCMA binding using BCMW37 antigen: $K_D$ = 2.8 × 10⁻¹⁰M as scFv; $EC_{50}$ = 2.3-3.2 nM as scFv binding to H929 and MM.1R cells; Parental GPRC5D binding to H929 and MM.1R cells: $EC_{50}$ = 6-24 nM as Fab |
| Cross reactivity for BCMB519 scFv to cyno BCMA (SPR) | No/low binding up to 300 nM | Binding data were collected from BCMB601 containing BCMB519 scFv |
| Fcγ receptor binding (SPR) | No significant binding | As expected for hIgG1-AAS silent framework |
| FcRn binding (SPR) | pH 6.0: hFcRn $K_D$ = 485 nM; cyFcRn $K_D$ = 314 nM | Rapid dissociation at pH 7.4 |
| Serum interference (Octet) | $k_a$ buffer/$k_a$ serum < 2.0 | No significant change in association rate to bt-BCMA and bt-CD3 in 50% human serum. Not determined for GPRC5D due to lack of representative soluble reagent. |
| GPRC5D-binding epitope | Not determined | N/A |
| CD3-binding epitope | Linear epitope encompassing Residues 22-35 (QDGNEEMGGITQTP (SEQ ID NO: 160)) of CD3ε chain (P07766, CD3E_Human) | Epitope sequence determined for parent antibody CD3B376 against CD3W220 by HDX-MS |
| BCMA-binding epitope | Linear epitope encompassing Residues 17-26 (LLHACIPCQL (SEQ ID NO: 161)) of BCMA BCMW37 | HDX-MS data show Residues 17-18 and 21-26 of BCMW37 are protected by BGCB465 (contains same anti-BCMA scFv) |
| Protein characterization | | |
| Intact Abs mass, release (MS) | 155,978.8 Da | N/A |
| Glycoform profile (MS) | Typical IgG1 profile with main glycoform G0F/G0F | N/A |
| Level of homodimer(s) (MS) | No HD1 and HD2 detected | N/A |
| Levels of other product-related impurities (MS) | None observed | N/A |
| N-link gly (non-Fc) (MS) | None predicted or observed | N/A |

TABLE 19A-continued

List of biophysical assessments and results for BGCB491

| mAb TAW characteristic | Result | Comments |
|---|---|---|
| O-link gly sites (MS) | None observed | N/A |
| Glycation (% relative abundance) (MS) | HC1 (CD3), 16.7%; LC1 (CD3), 5.4%; HC2 (GPRC5DxBCMA), 8.1% | Glycation values represent upper limit due to over-estimation caused by non-zero baseline |
| Free Cys (MS) | None predicted or observed | N/A |
| N-terminal elongation/ truncation (MS) | None observed | N/A |
| Conformational stability (DSC) | $T_{m1}$ = 62.9° C.; $T_{m2}$ = 68.3° C.; $T_{m3}$ = 71.9° C. | Measured in 10 mM histidine pH 6.5; $T_{m1}$ was contributed by CD376-Fab domain; $T_{m2}$ was contributed by several parts of this molecule; $T_{m3}$ was contributed by CH3 domain |
| % Purity (2-step purification) (AUC) | 98.9% Monomer | Measured in 10 mM L-histidine pH 6.5 |
| Serum stability (SEC-FDS) | ~5% increase in HMW after 7-day incubation at 37° C. | Assessed by SEC using Alexa488-labeled BCMAxGPRC5DxCD3 trispecific |
| Non-specific binding | No non-specific binding observed | N/A |
| Isoelectric point (cIEF) | pI = 9.56; % acidic/main/basic peak area: 46/54/0 | N/A |
| Relative hydrophobicity (aHIC) | Low hydrophobicity (hydrophobicity index 0.38) but wide and tailing peak | N/A |
| Viscosity | 6.3 cP | Determined at 150 mg/mL in 10 mM L-histidine pH 6.5 |

2-week high concentration stability (4 and 40° C., target 150 mg/mL)

| | | |
|---|---|---|
| Concentratability and % recovery in L-histidine buffer pH 6.5 | Sample was concentrated to 183.5 mg/mL with 91% recovery | N/A |
| % Monomer (initial) (AUC) | 97.5% | Determined in 10 mM L-histidine pH 6.5 |
| % Monomer 2 weeks, 4° C. (AUC) | 95.4% | Determined in 10 mM L-histidine pH 6.5 |
| % Monomer 2 weeks, 40° C. (AUC) | 62.8% | Determined in 10 mM L-histidine pH 6.5 |

Chemical (PTM) and physical stability

| | | |
|---|---|---|
| Intact MS after forced degradation (MS) | Chemical oxidation treatment resulted in 4 oxidations on each HC. Under physiologic stress, fragments were observed from all domains Deamidation stress principally resulted in fragments from GPRC5D, although 2 fragments from the BCMA scFv were also observed. | N/A |
| Size after forced degradation (aSEC) | % Intact Monomer: Release = 100.0; *Physiological = 96.0; Thermal = 63.7; pH 8.5 = 83.2; pH 5.0 = 99.3; pH 3.5 = 100.0; | Increase in aggregation at high concentration at 40° C. was apparent over time and follow-up formulation study is required to mitigate the aggregation propensity. |

TABLE 19A-continued

List of biophysical assessments and results for BGCB491

| mAb TAW characteristic | Result | Comments |
|---|---|---|
| | Chem Ox = 98.5; Metal Ox = 97.6 | Clipping observed after pH 8.5 and physiological stress. |
| Purity forced degradation (R and NR GXII) | NR GXII % intact: Release = 100; Physiological = 82; Thermal = 99; pH 8.5 = 82; pH 5.0 = 99; pH 3.5 = 100; Chem Ox = 100; Metal Ox = 100 | Clipping observed after pH 8.5 and physiological stress. |
| CD3 binding after forced degradation (SPR) | Affinity (M)/% Active: Release = $2.51 \times 10^{-8}$/100; Physiological = $1.93 \times 10^{-8}$/82; Thermal = $2.58 \times 10^{-8}$/100; pH 8.5 = $2.16 \times 10^{-8}$/93; pH 5.0 = $2.26 \times 10^{-8}$/88; pH 3.5 = $2.17 \times 10^{-8}$/94; Chem Ox = $2.27 \times 10^{-8}$/93; Metal Ox = $2.33 \times 10^{-8}$/98 | Affinity to CD3 was retained under all tested stress conditions. Reduction in % active species after pH 8.5 stress. |
| BCMA binding after forced degradation (SPR) | Affinity (M)/% Active: Release = $2.12 \times 10^{-10}$/100; Physiological = $1.43 \times 10^{-10}$/110; Thermal = $2.81 \times 10^{-10}$/137; pH 8.5 = $1.60 \times 10^{-10}$/114; pH 5.0 = $2.07 \times 10^{-10}$/154; pH 3.5 = $1.75 \times 10^{-10}$/116; Chem Ox = $5.37 \times 10^{-10}$/131; Metal Ox = $2.15 \times 10^{-10}$/110 | N/A |
| Basal oxidation level | 2.4% in M94 (GC5B680 scFv LCDR3); 1.3% in M166 (GC5B680 scFv HCDR1); 1.9% in M232 (GC5B680 scFv HCDR3); 4.4% in M600 (BCMB519 scFv LCDR3) | N/A |
| Met/Trp (change on oxidative stress) | 96.9% in M94 (GC5B680 scFv LCDR3); 14.0% in M166 (GC5B680 scFv HCDR1); 14.3% in M232 (GC5B680 scFv HCDR3); 99.2% in M600 (BCMB519 scFv LCDR3) | N/A |
| Basal deamidation level | <1% in CDRs | N/A |
| Deamidation sites (change on stress) | No significant change | N/A |
| Basal isomerization level | <1% in CDRs | N/A |

TABLE 19A-continued

List of biophysical assessments and results for BGCB491

| mAb TAW characteristic | Result | Comments |
|---|---|---|
| Isomerization sites (change on stress) | 11.7% D27 isomerization in CD3B376 HCDR1; 5.3% D731 isomerization in BCMB519 scFv LCDR3 | Note: D27 isomerization under pH stress was observed in all CD3B376 candidates and is thought not to impact activity. |

AAS, L234A, L235A, and D265S;
Ab, antibody;
aHIC, analytical hydrophobic interaction chromatography;
aSEC, analytical size-exclusion chromatography;
AUC, analytical ultracentrifugation;
bt, biotinylated;
CDR, complementarity determining region;
Chem Ox, chemical oxidation;
cIEF, capillary isoelectric focusing;
cy or cyno, cynomolgus monkey;
Cys, cysteine,
DSC, differential scanning calorimetry;
$EC_{50}$, 50% effective concentration;
Fab, fragment antigen-binding;
Fc, fragment crystallizable;
FcRn, neonatal Fc receptor;
FDS, fluorescence detection system;
gly, glycosylation;
h, human;
HC, heavy chain;
HCDR, heavy chain complementarity determining region;
HD, homodimer;
HDX, hydrogen deuterium exchange;
HMW, higher molecular weight;
Ig, immunoglobulin;
$k_a$, association constant;
$K_D$, equilibrium dissociation constant;
LC, light chain;
LCDR, light chain complementarity determining region;
mAb, monoclonal antibody;
Met, methionine;
Metal Ox, oxidation with metal;
MS, mass spectrometry;
N/A, not assessed;
NME, new molecular entity;
NR GXII, non-reduced capillary electrophoresis;
PBS, phosphate-buffered saline;
pI, isoelectric point;
PS20, Polysorbate 20;
ref, reference;
R GXII, reduced capillary electrophoresis;
scFv, single-chain variable fragment;
SEC, size-exclusion chromatography;
SPR, surface plasmon resonance;
$T_m$, melting temperature;
TMP, target medicinal product;
Trp, tryptophan

TABLE 19B

Additional Characteristics for the binding arms in BGCB491

| Lead Parameters | | Characteristics |
|---|---|---|
| BCMA: BCMB519 | Affinity | $K_D$ = 0.28 nM as scFv (SPR) $EC_{50}$ = 2.3-3.2 nM as scFv (H929 & MM.1R) |
| | Epitope | Linear epitope a.a. 17-26 (LLHACIPCQL) |
| | Function | Blocks BAFF and APRIL binding[#] No agonistic activity[#] |
| GPRC5D: GC5B680 | Affinity | $EC_{50}$ = 6-24 nM as Fab (H929 & MM.1R) |
| CD3: CD3B376 | Affinity | $EC_{50}$ = 3.4 μM* (T-cell) |
| | Epitope | N-terminal epitope a.a. 22-35 (QDGNEEMGGITQTP) of CD3ε chain |

TABLE 19B-continued

Additional Characteristics for the binding arms in BGCB491

| Lead Parameters | | Characteristics |
|---|---|---|
| Off-target profile | Retrogenix | CLEAN, no off-target hits (BCMA & GPRC5D binders) |

*T cell: $EC_{50}$ determined based on fixed point extrapolation due to un-saturated binding curves at the highest tested 2 μM concentration

Example 10: Target Arm and CD3 Arm Binding Characterization of BGCB491

Endogenous Tumor Cell Line Binding of BGCB491

Flow cytometry was used to evaluate the BCMA and GPRC5D arm binding of BGCB491 in vitro. BGCB491 and isotype control were tested on a panel of H929-WT, H929-BCMA-KO, H929-GPRC5D-KO, and H929-BCMA/GPRC5D-KO cell lines after 1-hour 37° C. incubation.

Figure 25:
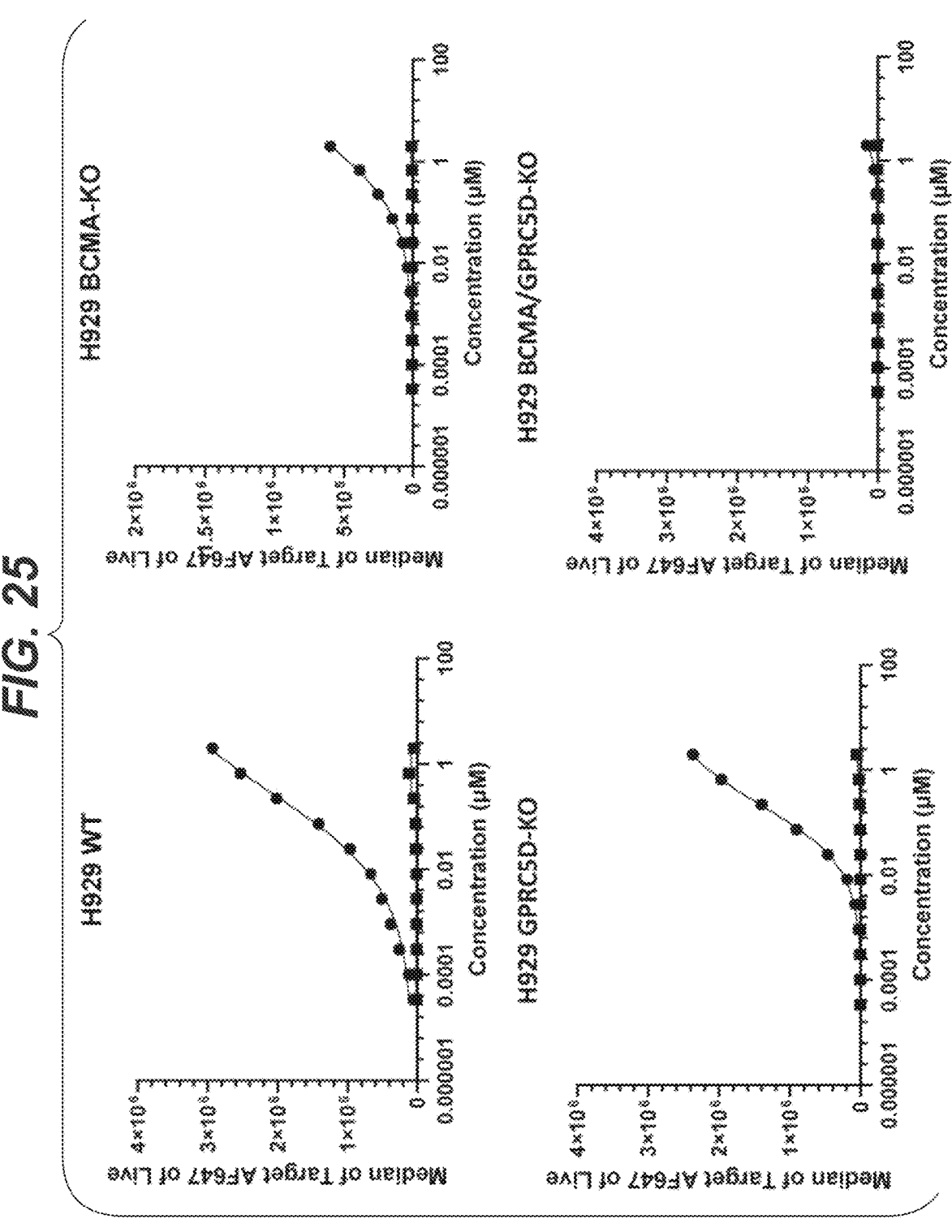
FIG. 25. Representative binding profiles of BGCB491 on H929 WT, H929-BCMA KO cells, H929-GPRC5D KO cells, and/or H929-BCMA/GPRC5D double KO cells after 1 hour 37° C. incubation. BGCB491 is indicated with ● and negative control CD3×Null×Null BGCB510 is indicated with ■. Curves are representative of 5 independent experiments. H929-GPRC5D-KO clone H15 is a heterozygous KO line with 2 copies of gene of 30% and 61% distribution. H929-BCMA-KO clone J8 is a heterozygous KO line with 2 copies of gene of equal 50% distribution.

BGCB491 showed specific binding on WT as well as each knock-out (KO) line verifying the binding of each individual target-binding arm (FIG. 25, Table 20).

TABLE 20

ECx values for H929 WT and KO suite binding of BGCB491 from 5 independent experiments

| | Run 1 | Run 2 | Run 3 | Run 4 | Run 5 | Med |
|---|---|---|---|---|---|---|
| | H929-WT | | | | | |
| $EC_{20}$ (nM) | 15 | NFC | N/A | 4 | 8 | 8 |
| $EC_{50}$ (nM) | 270 | NFC | N/A | 34 | 66 | 66 |
| $EC_{90}$ (nM) | 25,000 | NFC | N/A | 878 | 1,912 | 1,912 |
| | H929-BCMA-KO (GPRC5D arm) | | | | | |
| $EC_{20}$ (nM) | NFC | 19 | NFC | NFC | NFC | NFC |
| $EC_{50}$ (nM) | NFC | 66 | NFC | NFC | NFC | NFC |
| $EC_{90}$ (nM) | NFC | 489 | NFC | NFC | NFC | NFC |
| | H929-GPRC5D-KO (BCMA arm) | | | | | |
| $EC_{20}$ (nM) | 33 | 17 | 23 | 10 | 12 | 17 |
| $EC_{50}$ (nM) | 210 | 54 | 224 | 50 | 53 | 54 |
| $EC_{90}$ (nM) | 3,900 | 345 | 7,900 | 645 | 535 | 645 |

ECx, x % effective concentration;
KO, knock out;
Med, median;
N/A, not assessed;
NFC, not full curve;
WT, wild type.

Figure 40:
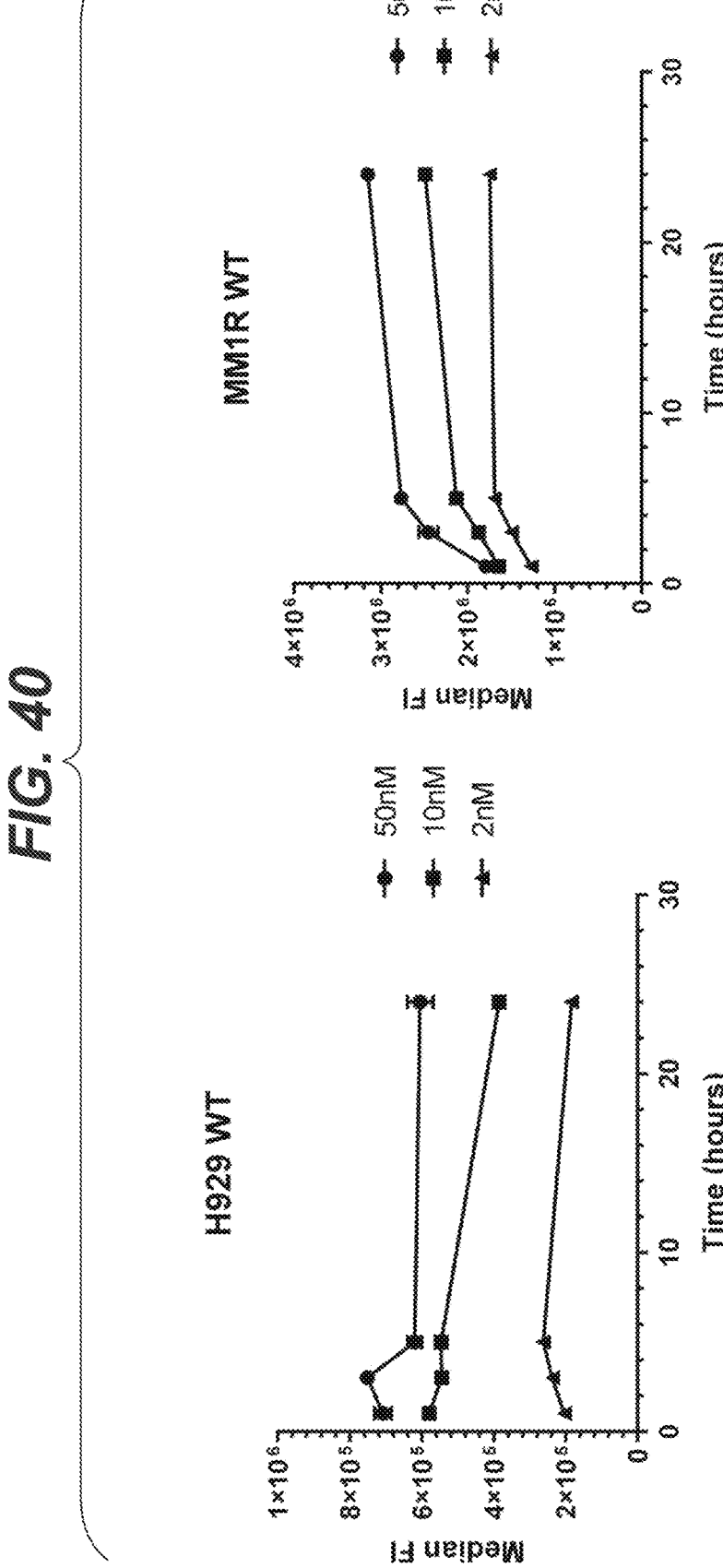
FIG. 40. Kinetic binding profiles of BGCB463 on H929 WT and MM.1R WT cell lines throughout 24 hour 37° C. incubation. MFI: mean fluorescence intensity.

The 24-hour kinetic binding experiment was performed on the trispecific antibody BGCB463. Flow cytometry was used to evaluate the binding kinetics on H929 WT and MM.1R WT cell lines at 50, 10, 2 nM throughout 24-hour 37° C. incubation (see FIG. 40). As demonstrated in FIG. 40, stable binding profiles were observed on both cell lines over the 24-hour period.

Primary T-Cell Binding of BGCB491

Figure 26:
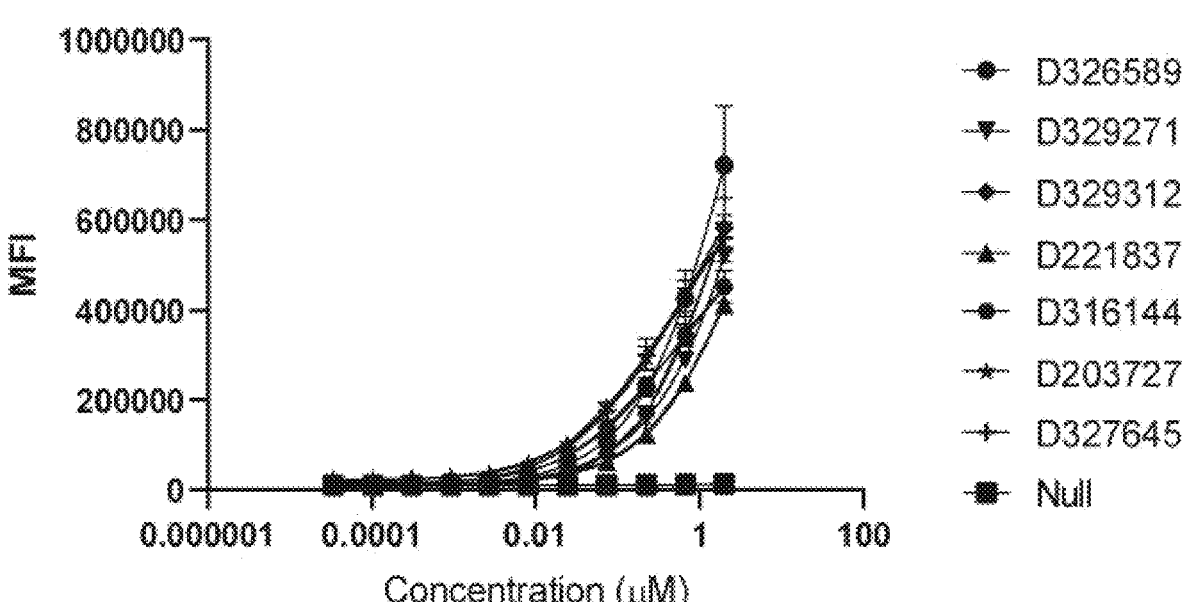
FIG. 26. Primary T cell binding profiles of BGCB491 on 7 donor cell preparations after 1 hour incubation at 37° C. MFI, mean fluorescence intensity.
Figure 27:
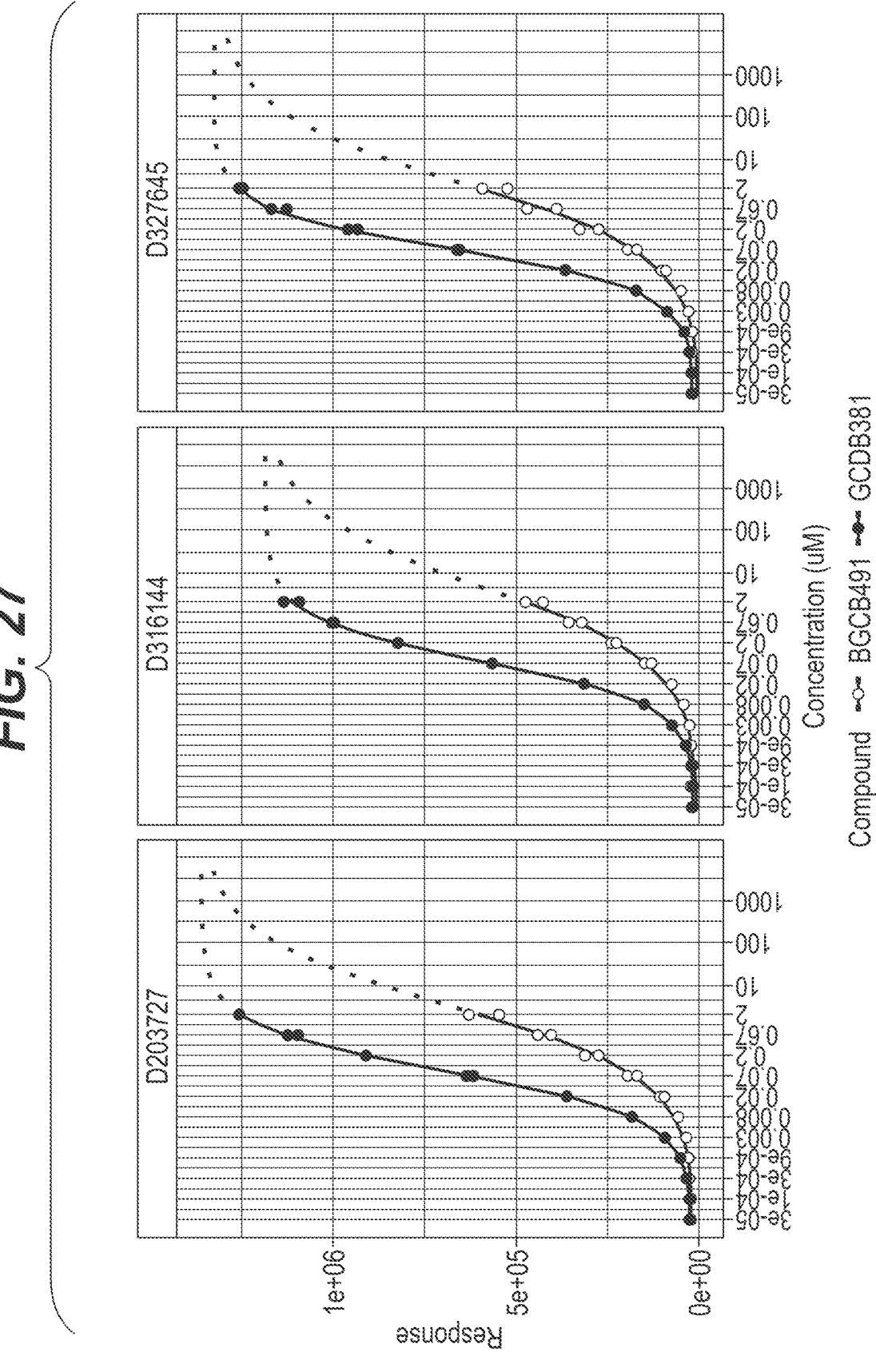
FIG. 27. Representative bioinformatic binding curve extrapolation with CD3B376×Null control antibody (GCDB381).

Flow cytometry was used to evaluate the CD3 arm (i.e., CD3B376) binding of BGCB491 to CD3$^+$ pan T cells from 7 different healthy human. Cell-based $EC_{50}$ for CD3B376 could not be determined due to lack of saturation kinetics at 1 hour (FIG. 26). Bioinformatic extrapolation was performed (FIG. 27) using the CD3B376×Null control antibody (i.e., GCDB381) molecule, which saturates within 2 μM top concentration dose-response to constrain the top of the non-linear regression curve to generate a full curve that enables estimation of $EC_x$ values (Table 21).

US 12,637,509 B2

115

TABLE 21

Estimation of ECx values of BGCB491 binding to T cells based on fixed
saturation point from bioinformatic extrapolation

| Donor | Estimated $EC_{20}$ (µM) | 95% confidence interval | Estimated $EC_{50}$ (µM) | 95% confidence interval |
|---|---|---|---|---|
| D203727 | 0.222 | (0.193, 0.255) | 3.37 | (3.01, 3.77) |
| D316144 | 0.279 | (0.237, 0.329) | 4.99 | (4.26, 5.85) |
| D327645 | 0.188 | (0.153, 0.230) | 3.36 | (2.86, 3.94) |
| Median | 0.222 | | 3.37 | |

$EC_x$, x % effective concentration;
D, donor.

Figure 42:
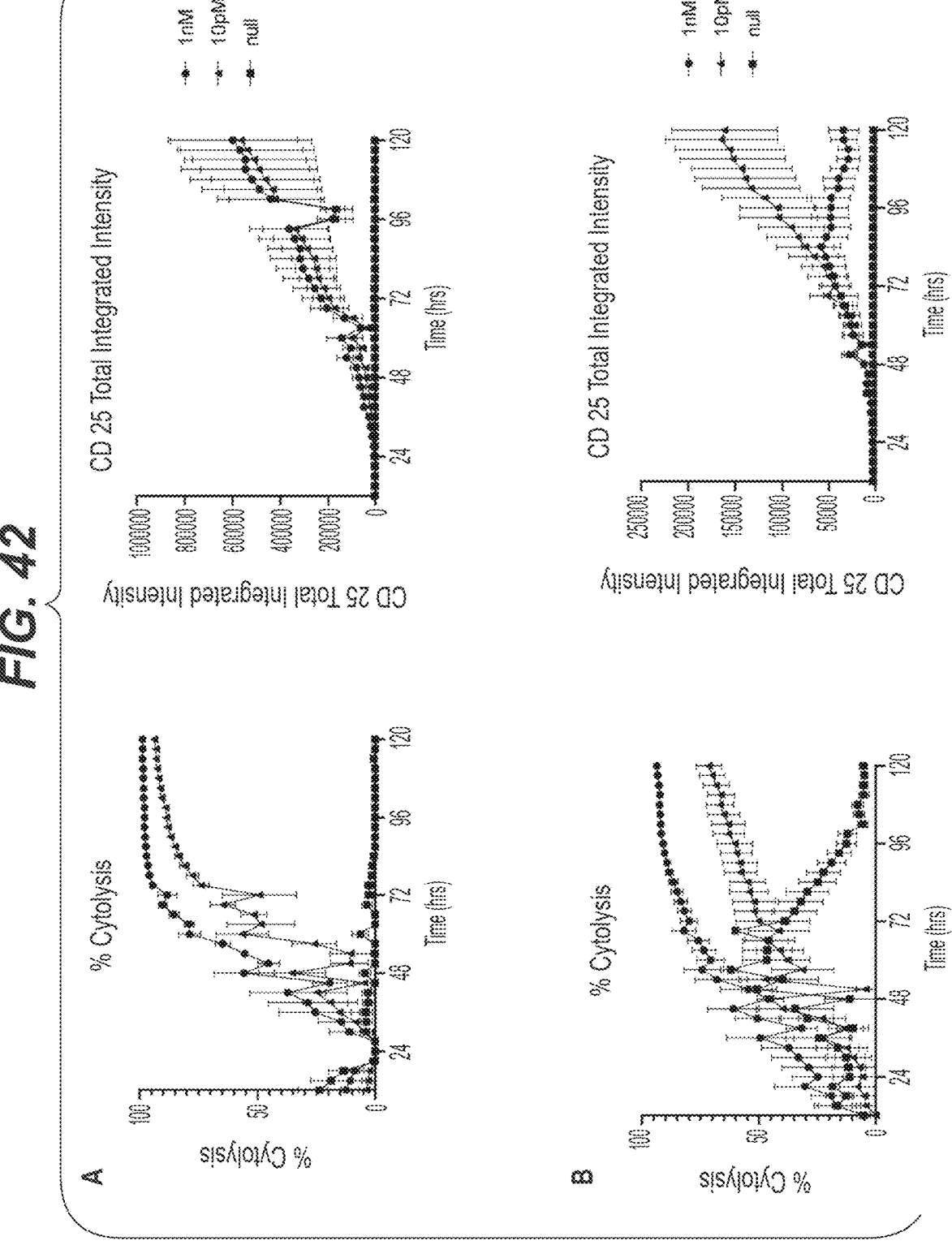
FIG. 42. Kinetic cytotoxicity and T-cell activation of BGCB491 and CD3B2271 (null control) using T cells from 3 T-cell donors at (FIG. 42A) 1:1 and (FIG. 42B) 1:3 E:T ratios. The CD25 measurement on the Incucyte is a measure of T cell count and CD25 expression (total integrated intensity). CD25 is a later marker of T cell activation, typically detectable 24 hours after activation and peaking around 96 hours. It does not necessarily line up with cytotoxicity with regards to timing. Percent cytolysis was calculated based on green fluorescent protein (GFP) signal in treated versus untreated wells.
Figure 44:
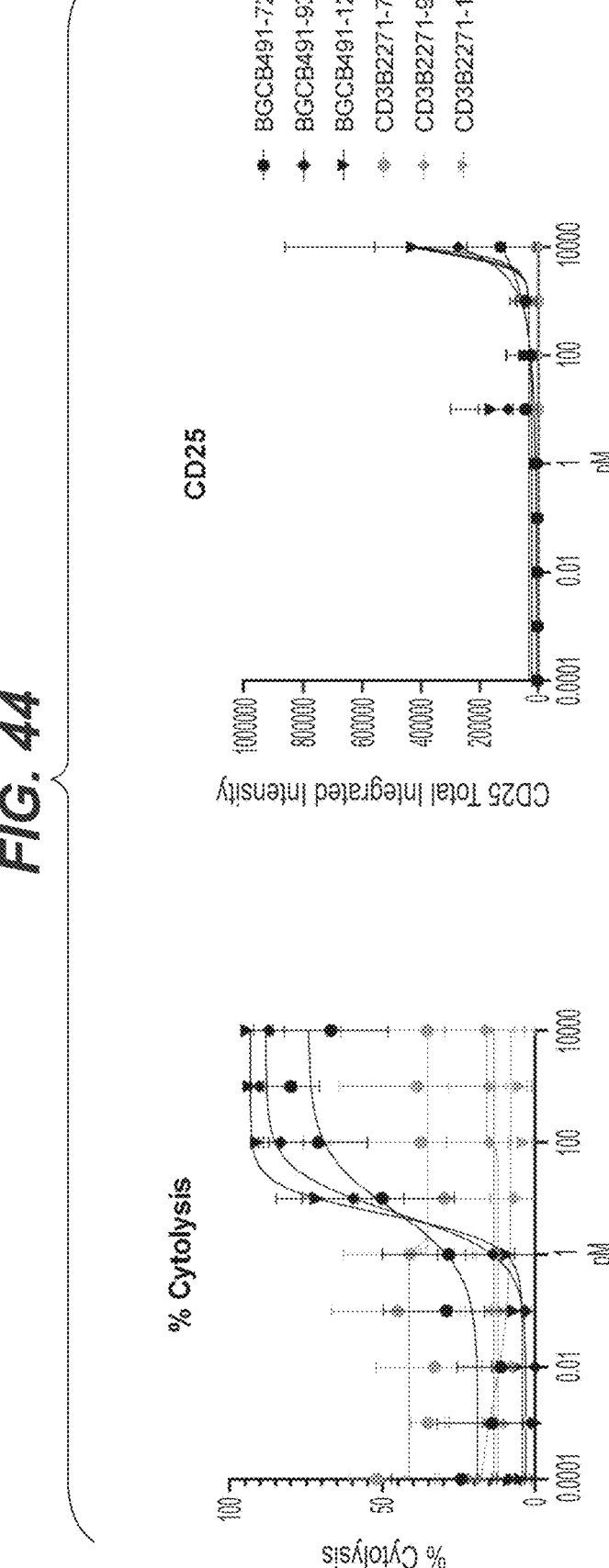
FIG. 44. Percent cytolysis and T-cell activation of BGCB491 and CD3B2271 (null control) at 72-, 93-, and 120-hour timepoints at 1:3 E:T ratio.

Despite use of a weak CD3-binding arm, BGCB491 showed robust subpicomolar potency with maximal cytotoxicity in both 1:1 and 1:3 E:T ratios in the kinetic cytotoxicity assay performed on the Incucyte across 3 pan T-cell donors throughout 120 hours. In a time-course cytotoxicity assay, Incucyte S3 was used to evaluate the kinetic target cytotoxicity and T-cell activation profiles of BGCB491 in H929-GFP cells across 3 pan T cell donors throughout 120 hours. BGCB491 reached a notable maximal cytotoxicity at around 72 hours at all concentrations except for the lowest concentration tested (10 pM) at a 1:3 E:T ratio (FIG. 42). From the kinetic plots, information for percent cytolysis and T-cell activation at 72-, 93-, and 120-hour timepoints was extracted for the 1:1 E:T ratio (FIG. 43) and the 1:3 E:T ratio (FIG. 44). BGCB491 showed robust subpicomolar killing potency in both E:T ratios (Table 22). More in-depth cytotoxicity characterizations are illustrated in Example 12.

TABLE 22

Average ECx values derived from H929-GFP percent cytolysis
in kinetic killing assay

| | E:T 1:1 | E:T 1:3 |
|---|---|---|
| | 72 hours | |
| $EC_{20}$ (pM) | 2.1 | 1.1 |
| $EC_{50}$ (pM) | 12.7 | 6.3 |
| $EC_{90}$ (pM) | 212.6 | 93 |

116

TABLE 22-continued

Average ECx values derived from H929-GFP percent cytolysis
in kinetic killing assay

| | E:T 1:1 | E:T 1:3 |
|---|---|---|
| | 93 hours | |
| $EC_{20}$ (pM) | 0.7 | 1.6 |
| $EC_{50}$ (pM) | 0.9 | 5.5 |
| $EC_{90}$ (pM) | 1.4 | 39 |
| | 120 hours | |
| $EC_{20}$ (pM) | 0.4 | 2.3 |
| $EC_{50}$ (pM) | 0.7 | 5.2 |
| $EC_{90}$ (pM) | 1.8 | 18.9 |

$EC_x$, x % effective concentration;
E:T, effector-to-target ratio;
GFP, green fluorescent protein.

In summary, BGCB491 is a fully human trispecific mAb targeting the TCR CD3 with 1 binding arm and tumor cell surface antigens BCMA or GPRC5D with the remaining 2 binding domains. BGCB491 showed acceptable intrinsic biophysical properties, and bound to all tested BCMA-, GPRC5D-, and dual BCMA-GPRC5D-expressing cell lines.

Example 11: Therapeutic Pharmacology

Part 1. In Vitro Studies
BCMA and GPRC5D Receptor Protein Surface Expression and Density in Test Cell Lines A subset of 4 dual target (i.e., BCMA-GPRC5D) positive cell lines (i.e., MM.1S, H929, JIM-3, and OPM-2) and 2 dual-target-negative cell lines (i.e., MV-4-11 and OCI-AML-3) were characterized for protein expression by fluorescence-activated cell sorting (FACS) using phycoerythrin (PE)-labeled commercial BCMA antibody and an in-house GPRC5D antibody. All target-positive cell lines had a significant shift in expression pattern compared to isotype control while target-negative cell lines failed to show any expression (Table 23). These 6 cell lines with various levels of target protein expression on their surface were selected for further in vitro and in vivo functional assays.

TABLE 23

Summary of BCMA and GPRC5D receptor densities in test cell lines

| Cell line | GPRC5D (Assay-1) | GPRC5D (Assay-2) | GPRC5D (Average) | BCMA (Assay-1) | BCMA (Assay-2) | BCMA (Average) |
|---|---|---|---|---|---|---|
| MM. 1S | 2,091 | 4,899 | 3,495 | 1,870 | 2,237 | 2,053 |
| H929 | 2,443 | 1,995 | 2,219 | 6,955 | 6,908 | 6,932 |
| OPM-2 | 12,109 | 8,159 | 10,134 | 5,703 | 4,411 | 5,057 |
| JIM-3 | 1,438 | 1,528 | 1,483 | 922 | 1,533 | 1,228 |
| MV-4-11 | 37 | 92 | 64 | 72 | 52 | 62 |
| OCI-AML-3 | 19 | 67 | 43 | 89 | 85 | 87 |

Target receptor densities quantified on target-positive and target-negative cells using a QuantiBRITE kit.
Individual values and average of 2 individual experiments listed above.

BGCB491 Binding to Endogenous BCMA-GPRC5D-Expressing Cell Lines

Figure 41:
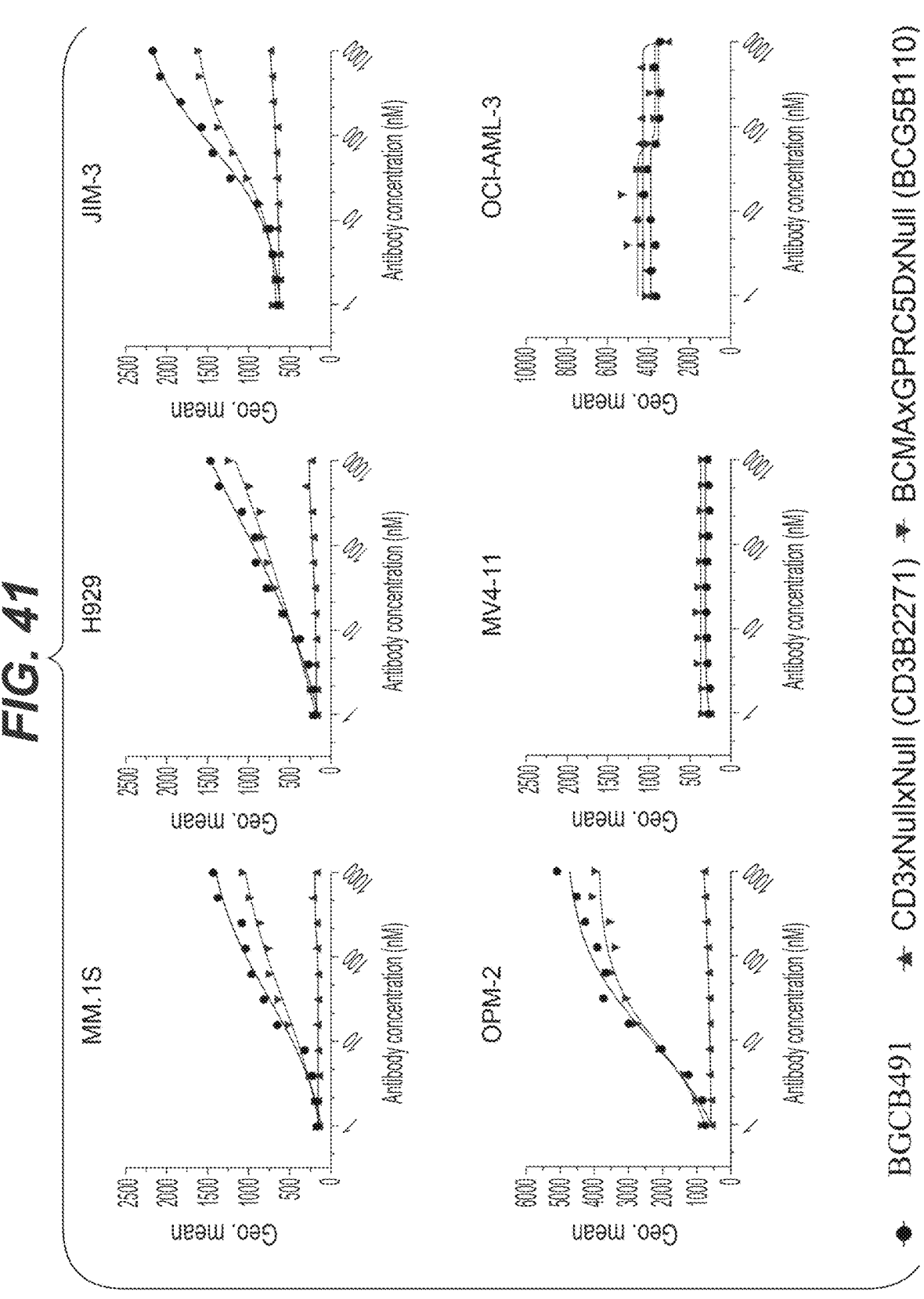
FIG. 41. BGCB491 binding to endogenous BCMA-GPRC5D-expressing cell lines. Geo, geometric. BGCB491, BCMA×GPRC5D×Null, and CD3×Null×Null were added at various concentrations (0.096 to 1,000 nM, X axis) and incubated for 1 hour at 37° C. The plots were generated using Prism 8 by fitting separate 4PL models to the observed data. Binding intensities expressed as geometrical mean (Y axis).

Next, BGCB491 (BCMA×GPRC5D×CD3 trispecific mAb) binding profiles were determined by applying flow cytometry methods. BGCB491 and BCMA×GPRC5D×Null control antibodies bound to BCMA-GPRC5D-expressing MM cells in a dose-dependent manner (EC$_{50}$ values: MM.1S, 33.39 nM; H929, 185.50 nM; JIM-3, 78.45 nM; OPM-2, 10.07 nM; FIG. 41) while CD3×Null×Null control antibodies showed no significant binding on these cells. None of the antibodies tested bound to dual-target-negative cell lines MV-4-11 and OCI-AML-3, indicating BGCB491 specificity.

Figure 28A:
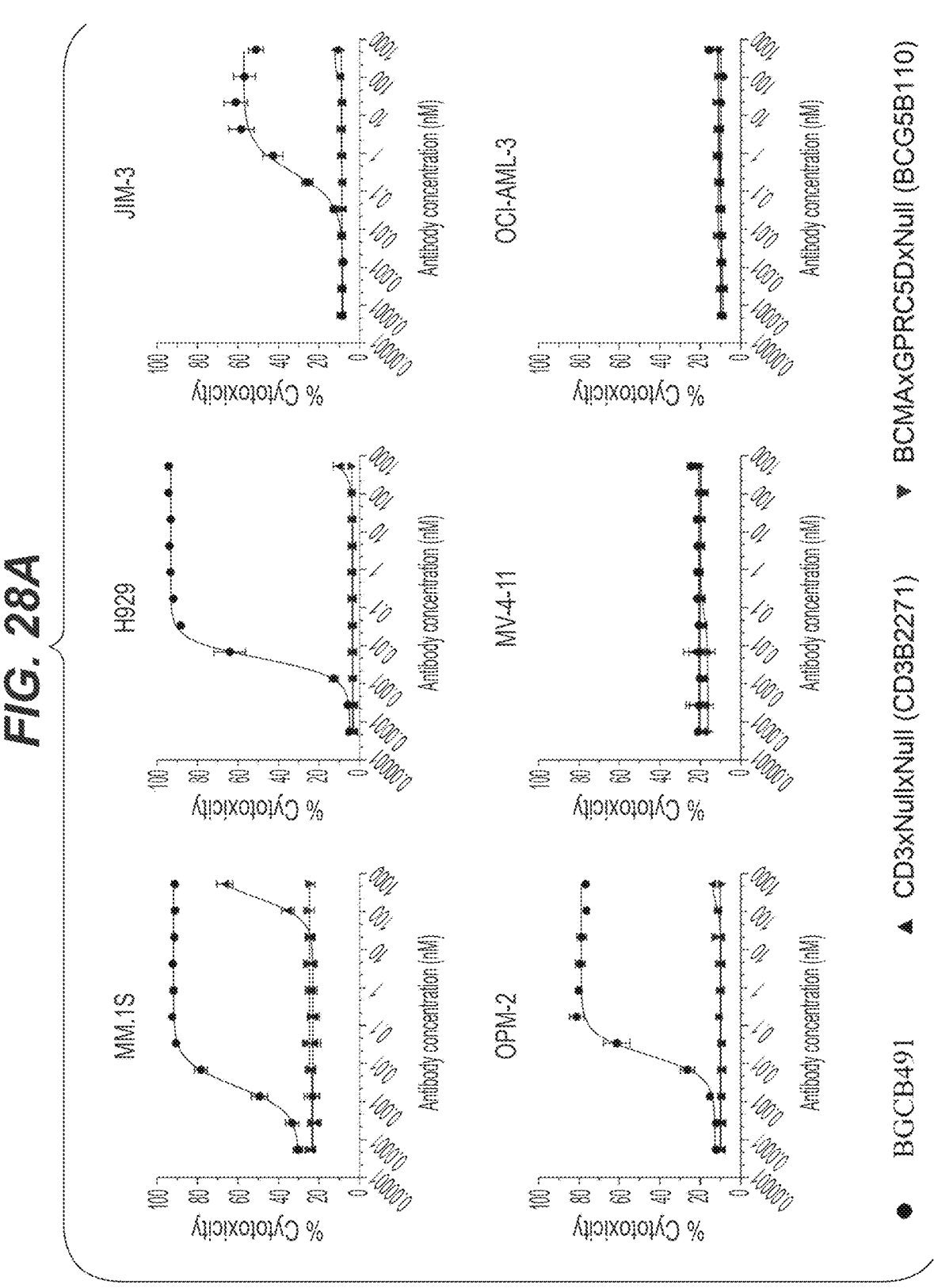
FIGS. 28A-28B. BGCB491-mediated (FIG. 28A) cell cytotoxicity and (FIG. 28B) T cell activation of BCMA-GPRCD-dual-positive and BCMA-GPRC5D-dual-negative cell lines. BGCB491, BCMA×GPRC5D×Null, and CD3× Null×Null were added at various concentrations (0.00005 to 533.33 nM, X axis) in the presence of pan T cells from 6 healthy donors (donor ID: 20063323, 20063309, 20062062, 20063310, 20062105, and 20061963) and Fc blocker (2 mg/mL) and incubated for 72 hours. The optimal E:T ratio of 3:1 was tested in these studies (for E:T ratio assessment see FIGS. 33A-33B). The plots were generated using Prism 8 by fitting separate 4PL models to the observed data. The data points aligned tightly along the generated fit curve and little variability was observed between T cell donors (6 donor averages plotted).
Figure 28B:
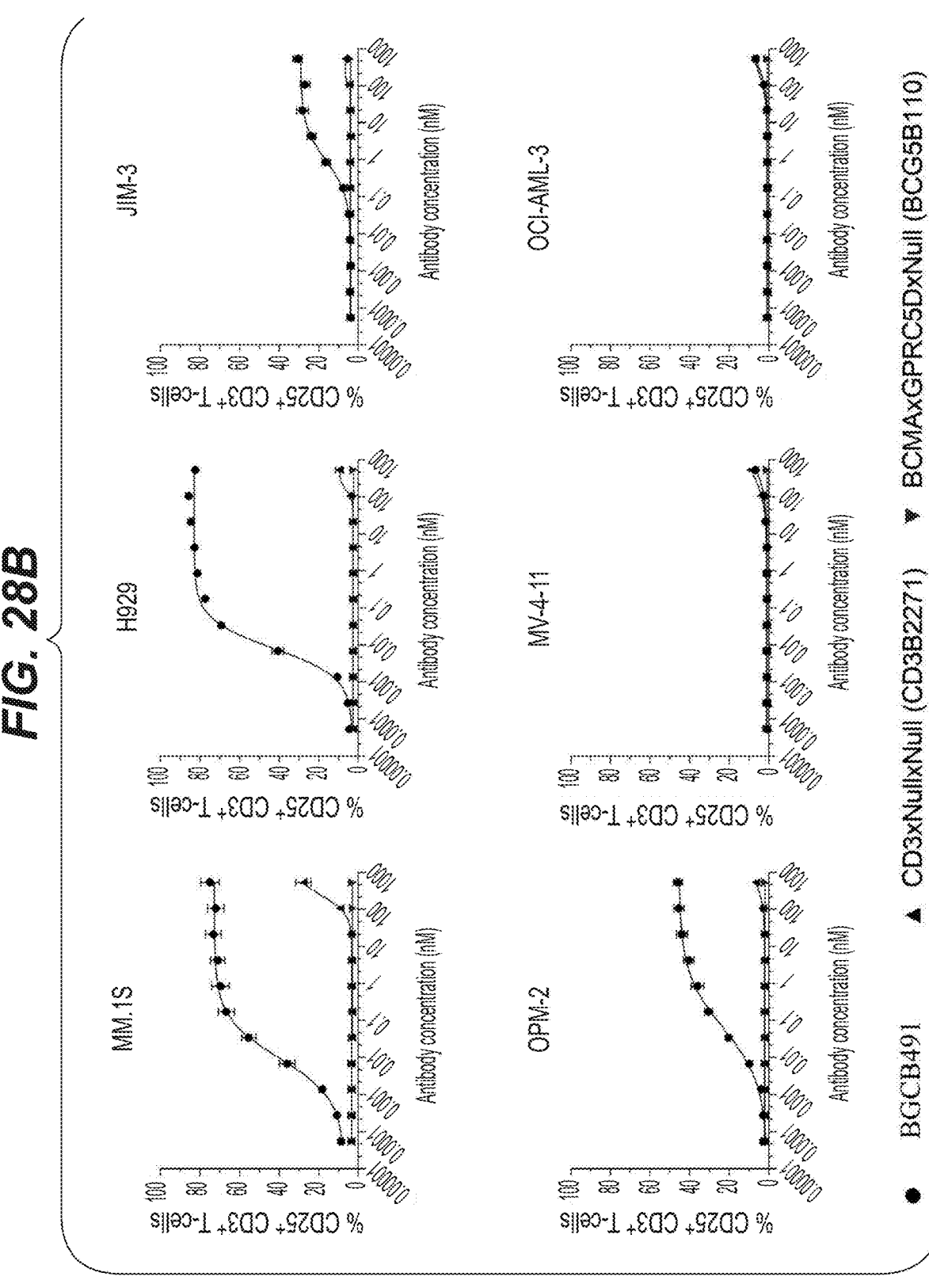

BGCB491-Mediated T-Cell-Dependent Cytotoxicity of MM Cell Lines and T-Cell Activation A T-cell-mediated cytotoxicity assay was used to evaluate the in vitro cytotoxicity and T-cell activation potential of BGCB491 using a FACS-based approach. BGCB491 was tested on various cell lines (BCMA-GPRC5D dual positive: MM.1S, H929, JIM-3, OPM-2; and BCMA-GPRC5D dual negative: MV-4-11 and OCI-AML-3) using pan T cells (CD3$^+$) from 6 healthy donors. Because the Fc receptor is expressed on some of the cells tested, 2 mg/mL of Fc blocker was added in the assay. Additionally, BCMA×GPRC5D× Null and CD3×Null×Null were used as negative controls. BGCB491 potently killed BCMA-GPRC5D-dual-positive cell lines in vitro after 72 hours of incubation (FIG. 28A, Table 24). BGCB491 was found to be a potent trispecific antibody with an EC$_{50}$ value range of 0.002 to 0.312 nM for cytotoxicity and 0.008 to 1.070 nM for T-cell activation as measured by CD3$^+$CD25$^+$ live T cells across all dual-target-positive cell lines. Concomitant T-cell activation was observed with only dual-target-positive cells as expected (FIG. 28B, Table 24). BGCB491 did not induce cytotoxicity or T-cell activation when tested with dual-target-negative cell lines MV-4-11 and OCI-AML-3, demonstrating the cytotoxic specificity. BCMA×GPRC5D×Null and CD3× Null×Null controls showed no significant cytotoxicity except for the MM.1S cell line where CD3×Null×Null antibody showed some activity at high concentrations (>100 nM).

TABLE 24

Summary of ECx values for cytotoxicity and T-cell activation using T cells from multiple healthy donors

|  | MM.1S | H929 | JIM-3 | OPM-2 | MV-4-11 | OCI-AML-3 |
|---|---|---|---|---|---|---|
| Cytotoxicity | | | | | | |
| EC$_{20}$ (nM) | 0.001 | 0.002 | 0.094 | 0.009 | NA | NA |
| EC$_{50}$ (nM) | 0.002 | 0.005 | 0.312 | 0.019 | NA | NA |
| EC$_{90}$ (nM) | 0.012 | 0.015 | 2.078 | 0.058 | NA | NA |
| Max cytotoxicity (%) | 92.580 | 94.470 | 61.220 | 81.320 | NA | NA |
| CD3 T-cell activation | | | | | | |
| EC$_{20}$ (nM) | 0.002 | 0.002 | 0.242 | 0.006 | NA | NA |
| EC$_{50}$ (nM) | 0.010 | 0.008 | 1.070 | 0.062 | NA | NA |
| EC$_{90}$ (nM) | 0.145 | 0.057 | 11.303 | 2.726 | NA | NA |
| Max activation (%) | 75.030 | 85.900 | 30.850 | 45.950 | NA | NA |

EC$_x$, x % effective concentration;

NA, not active.

Average EC$_x$ values from 6 T-cell donors for cytotoxicity and T-cell activation are shown for each cell line. EC$_x$ values were estimated post-hoc from a 4PL model with donor as a random effect. 95% confidence intervals were calculated using the delta method. The nonlinear mixed effects R package was used for model fitting.

Figure 29:
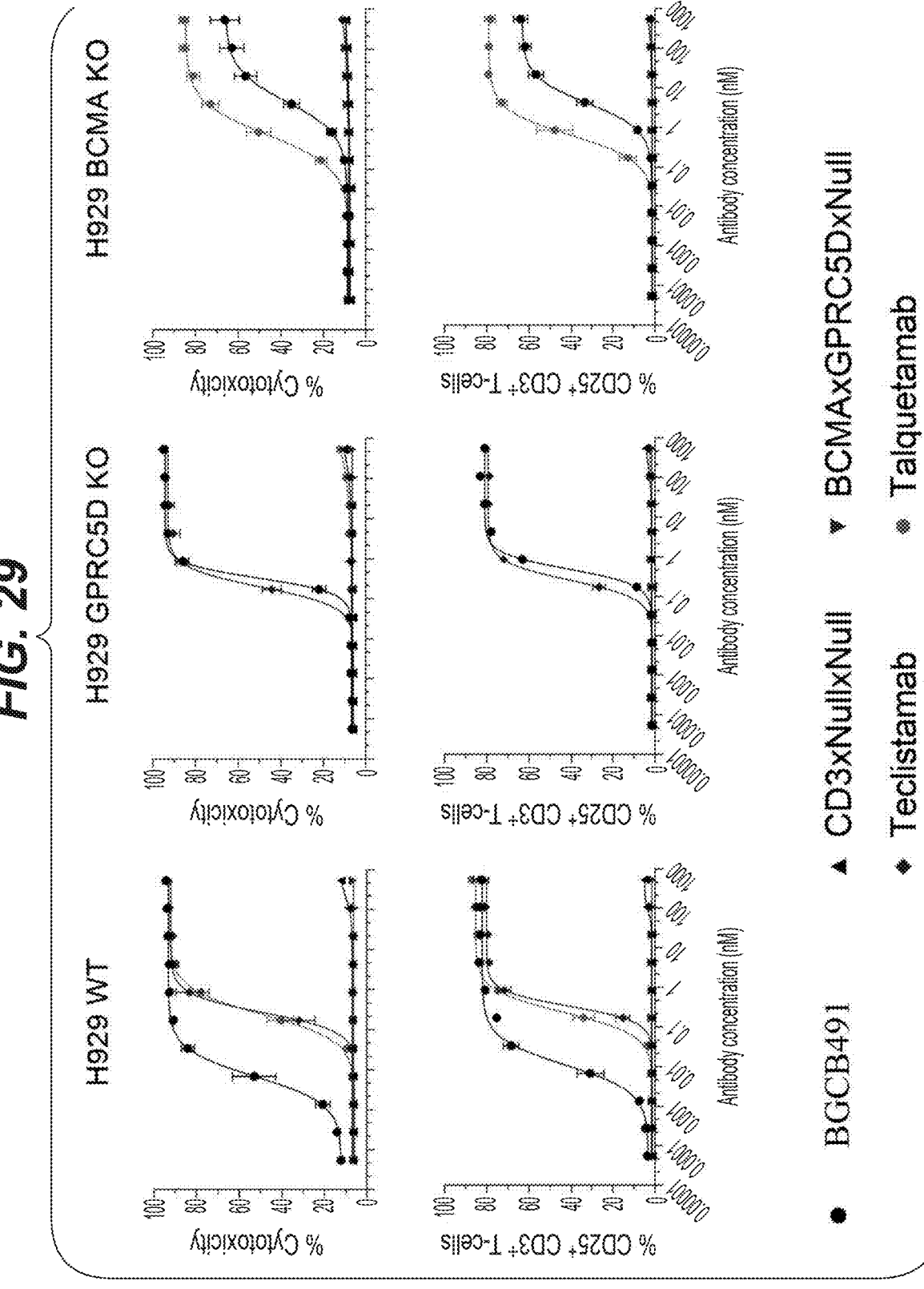
FIG. 29. BGCB491-mediated H929 CRISPR KO clonal cell cytotoxicity and T cell activation. BGCB491, BCMA× GPRC5D×Null, and CD3×Null×Null were added at various concentrations (0.00005 to 533.33 nM, X axis) in the presence of pan T cells from 4 healthy donors (donor ID: 20063323, 20063309, 20062062, and 20063310) and Fc blocker (2 mg/mL) and incubated for 72 hours. The E:T ratio of 3:1 was tested in these studies. The plots were generated using Prism 8 by fitting separate 4PL models to the observed data. The data points aligned tightly along the generated fit curve and little variability was observed between T cell donors (4-donor averages plotted). Target cell death was measured and expressed as percent cytotoxicity in the top row and T cell activation measured as percent CD25 expressing CD3+ positive cells was shown in the bottom row (Y axis).

H929 CRISPR Knockout Cell Generation and Target Expression
BCMA and GPRC5D Receptor Protein Expression and Density in CRISPR Knockout H929 Cell Lines Next, to evaluate BGCB491 potential to kill single-target-expressing cells, H929 clustered regularly interspaced short palindromic repeats (CRISPR) KO cell lines (i.e., H929-BCMA-KO and H929-GPRC5D-KO) were used in a cytotoxicity assay. These cells were sequence confirmed as described in the legend of FIG. 25 and were characterized for protein expression by FACS using PE-labeled commercial BCMA antibody and an in-house PE-labeled GPRC5D antibody. Expression profiles indicated complete knockout of BCMA expression in the H929-BCMA-KO cell line and of GPRC5D expression in the H929-GPRC5D-KO cell line.
BGCB491-Mediated Cytotoxicity of H929 CRISPR KO Clonal Cell Lines and T-Cell Activation Next, BGCB491 antibody was tested on CRISPR KO and wild-type (WT) cell lines (i.e., H929-WT, H929-GPRC5D-KO, and H929-BCMA-KO) using pan T cells ($CD3^+$) from 4 healthy donors to evaluate its clonal depletion potential using a FACS-based protocol. Additionally, BCMAx GPRC5DxNull and CD3xNullxNull were used as negative controls. BGCB491 potently killed all 3 cell lines (i.e., H929-WT, H929-GPRC5D-KO, and H929-BCMA-KO) and activated T cells in vitro after 72 hours of incubation (FIG. 29). BGCB491 exhibited significant potency in a dual-target-expressing H929-WT cells compared to single-target-expressing CRISPR KO cell lines due to avidity. BCMAx GPRC5DxNull and CD3xNullxNull showed no significant cytotoxicity or T-cell activation. Average $EC_{50}$ values using 4 different healthy T-cell donors are compiled in Table 25A. Teclistamab (BCMAxCD3 bispecific antibody) and talquetamab (GPRC5DxCD3 bispecific antibody) were used as positive controls and behaved as expected. Table 25B shows the receptor density values per cell of the H929 cells.

TABLE 25A

Summary of BGCB491 $EC_{50}$ values for cytotoxicity and T-cell activation using CRISPR KO H929 cells

| Estimate | BGCB491 | CD3xNull-xNull | BCMAxGP-RC5DxNull | Teclis-tamab | Talque-tamab |
|---|---|---|---|---|---|
| | | | Cytotoxicity H929-WT | | |
| $EC_{50}$ (nM) | 0.007 | NA | NA | 0.275 | 0.243 |
| Max cytotoxicity (%) | 93.012 | NA | NA | 92.072 | 92.741 |
| | | | H929-GPRC5D-KO | | |
| $EC_{50}$ (nM) | 0.330 | NA | NA | 0.198 | NA |
| Max cytotoxicity (%) | 94.243 | NA | NA | 93.017 | NA |
| | | | H929-BCMA-KO | | |
| $EC_{50}$ (nM) | 4.789 | NA | NA | NA | 0.761 |
| Max cytotoxicity (%) | 65.822 | NA | NA | NA | 84.664 |
| | | | CD3 T-cell activation H929-WT | | |
| $EC_{50}$ (nM) | 0.011 | NA | NA | 0.334 | 0.233 |
| Max cytotoxicity (%) | 82.147 | NA | NA | 80.196 | 85.399 |

TABLE 25A-continued

Summary of BGCB491 $EC_{50}$ values for cytotoxicity and T-cell activation using CRISPR KO H929 cells

| Estimate | BGCB491 | CD3xNull-xNull | BCMAxGP-RC5DxNull | Teclis-tamab | Talque-tamab |
|---|---|---|---|---|---|
| | | | H929-GPRC5D-KO | | |
| $EC_{50}$ (nM) | 0.487 | NA | NA | 0.253 | NA |
| Max cytotoxicity (%) | 81.084 | NA | NA | 79.450 | NA |
| | | | H929-BCMA-KO | | |
| $EC_{50}$ (nM) | 4.131 | NA | NA | NA | 0.633 |
| Max cytotoxicity (%) | 63.379 | NA | NA | NA | 78.888 |

CRISPR, clustered regularly interspaced short palindromic repeats;

$EC_{50}$, 50% effective concentration;

E:T, effector to target;

Fc, fragment crystallizable;

KO, knock out;

NA, not active.

Average $EC_{50}$ values from 4 T-cell donors for cytotoxicity and T-cell activation are shown for each cell line (H929-WT, H929-GPRC5D-KO, and H929-BCMA-KO). $EC_{50}$ values were estimated post-hoc from a 4PL model with donor as a random effect. 95% confidence intervals were calculated using the delta method. The nonlinear mixed effects R package was used for model fitting. Teclistamab and talquetamab were used as positive controls.

TABLE 25B

Receptor density of H929 cells

| Cells | | H929-WT | H929-GPRC5D-KO | H929-BCMA-KO |
|---|---|---|---|---|
| Receptor density | BCMA | 5381 | 3926 | 1 |
| | GPRC5D | 1574 | 19 | 957 |

Cytotoxicity and T-Cell Activation Potential of BGCB491 Against Dual-Target-Positive H929 Cells Spiked in Healthy Human Whole Blood (MABEL Assay)

Figure 30:
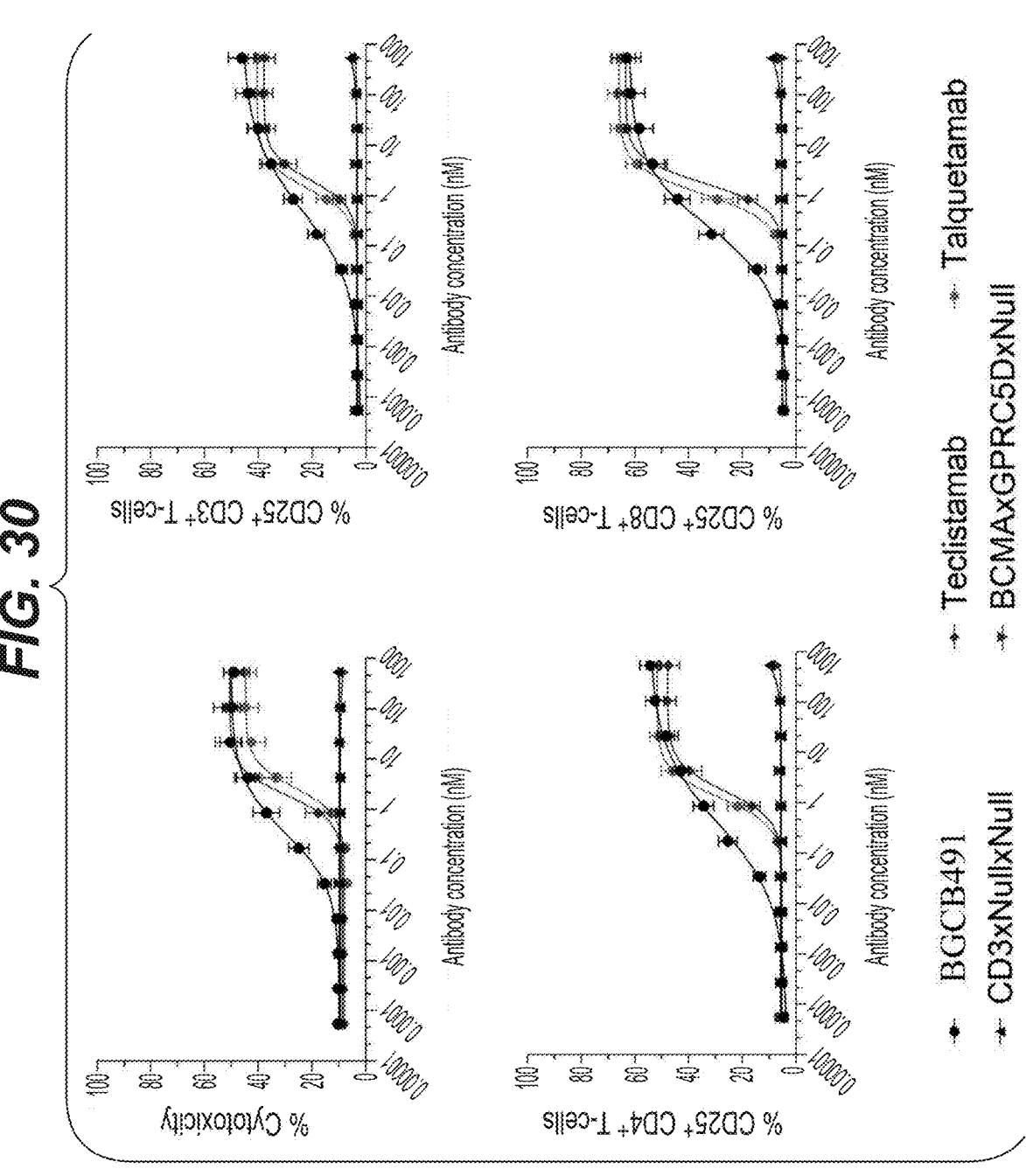
FIG. 30. BGCB491-mediated target cell cytotoxicity in whole blood spiked with H929 MM cells (MABEL assay). MABEL, minimum anticipated biological effect level. BGCB491, BCMA×GPRC5D×Null, and CD3×Null×Null were added at various concentrations (0.00005 to 533.33 nM, X axis) to whole blood from 7 healthy donors (donor ID: 10145, 10403, 10420, 10083, 10463, 10493, and 10145; T cell source) in presence of H929 target myeloma cells at an adjusted E:T ratio of 5:1 for 48 hours. The plots were generated using Prism 8 by fitting separate 4PL models to the observed data. The data points aligned tightly along the generated fit curve and little variability was observed between T cell donors (7 donor averages plotted). Target cell death was measured and expressed as percent cytotoxicity and T cell activation measured as percent CD25+CD3+ cells. In this experiment teclistamab and talquetamab were tested as positive controls.
Figure 31:
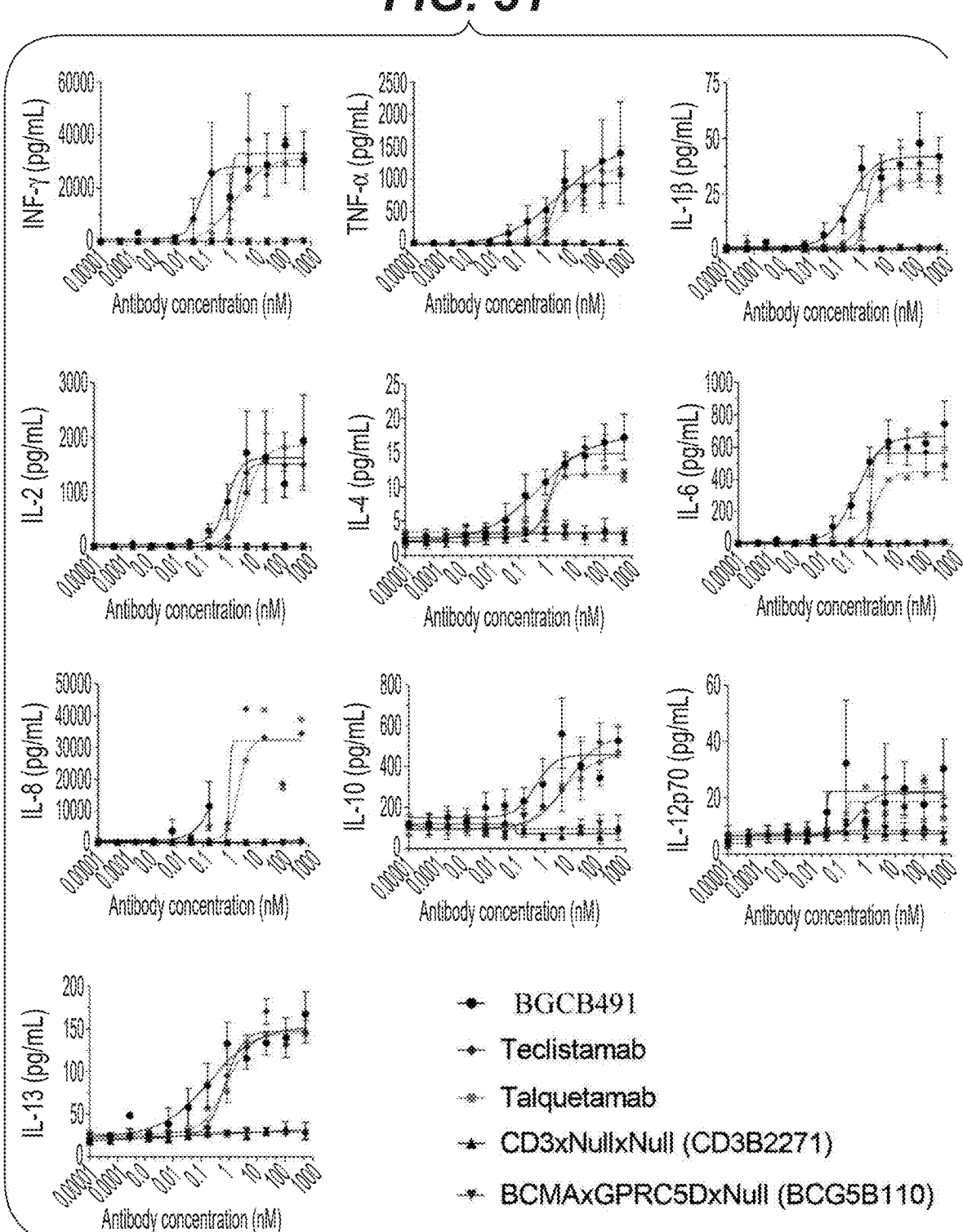
FIG. 31. Cytokine profiles of BGCB491 from MABEL assay. MSD, Meso Scale Discovery. BGCB491, BCMA× GPRC5D×Null, and CD3×Null×Null were added at various concentrations (0.00005 to 533.33 nM, X axis) to whole blood from 3 healthy donors. H929 cell supernatants from the above cytotoxicity experiment (FIG. 7; 3 T cell donors; donor ID: 10083, 10463, and 10493) were collected and analyzed for cytokine levels using an MSD-based multiplex assay (Cat #: K15049D). Cytokine levels were measured as pg/mL. The plots were generated using Prism 8 by fitting separate 4PL models to the observed data. The data points aligned tightly along the generated fit curve and little variability was observed between T cell donors (3 donor averages plotted). In this experiment teclistamab and talquetamab were tested as positive controls.

The MABEL assay was used to characterize the effects of BGCB491 in a more physiologically relevant environment. Here, dual-target-positive H929 cells were added to human healthy whole blood to establish cytotoxicity, T-cell activation, and cytokine parameters. The H929 cell line was selected based on its compatibility in a human whole-blood environment for 48 hours. BGCB491 potently killed dual-target-positive H929 cells and activated T cells in this cocultured whole-blood assay after 48 hours of incubation (FIG. 30). BGCB491 had a mean average $EC_{50}$ value of 0.274 nM for cytotoxicity and of 0.376 nM for $CD3^+$ T-cell activation when tested using whole blood from 7 different healthy donors (Table 26). BCMAxGPRC5DxNull and CD3xNullxNull showed no significant cytotoxicity or T-cell activation. Cytokines were quantified using a 10-plex Meso Scale Discovery (MSD)-based protocol from 3 different whole-blood donors (FIG. 31, Table 27). Positive controls teclistamab and talquetamab showed specific activity.

TABLE 26

Cytotoxicity and T-cell activation ECx values (nM) for MABEL assay

| | BGCB491 | CD3x Nullx Null | BCMAx GPRC5Dx Null | Teclistamab | Talquetamab |
|---|---|---|---|---|---|
| Cytotoxicity | | | | | |
| EC$_{20}$ | 0.063 (0.027, 0.146) | NA | NA | 1.273 (0.715, 2.268) | 1.272 (0.843, 1.919) |
| EC$_{30}$ | 0.112 (0.049, 0.253) | NA | NA | 1.549 (0.877, 2.733) | 1.744 (1.186, 2.566) |
| EC$_{50}$ | 0.274 (0.123, 0.612) | NA | NA | 2.106 (1.196, 3.707) | 2.866 (1.978, 4.151) |
| EC$_{90}$ | 2.804 (1.142, 6.883) | NA | NA | 4.675 (2.513, 8.699) | 10.379 (6.471, 16.646) |
| Max | 49.765 (41.946, 57.583) | NA | NA | 50.309 (41.780, 58.837) | 44.761 (35.940, 53.582) |
| CD3$^+$ T-cell activation | | | | | |
| EC$_{20}$ | 0.042 (0.018, 0.098) | NA | NA | 1.043 (0.692, 1.574) | 0.677 (0.436, 1.050) |
| EC$_{30}$ | 0.098 (0.043, 0.223) | NA | NA | 1.378 (0.926, 2.051) | 0.927 (0.624, 1.377) |
| EC$_{50}$ | 0.376 (0.168, 0.839) | NA | NA | 2.135 (1.446, 3.152) | 1.521 (1.052, 2.199) |
| EC$_{90}$ | 12.150 (4.684, 31.514) | NA | NA | 6.641 (4.249, 10.378) | 5.491 (3.196, 9.436) |
| Max | 43.685 (34.087, 53.282) | NA | NA | 37.993 (31.416, 44.570) | 40.780 (33.202, 48.357) |
| CD4$^+$ T-cell activation | | | | | |
| EC$_{20}$ | 0.031 (0.013, 0.071) | NA | NA | 0.830 (0.529, 1.302) | 0.585 (0.370, 0.924) |
| EC$_{30}$ | 0.069 (0.030, 0.156) | NA | NA | 1.124 (0.733, 1.725) | 0.812 (0.540, 1.220) |

TABLE 26-continued

Cytotoxicity and T-cell activation ECx values (nM) for MABEL assay

| | BGCB491 | CD3x Nullx Null | BCMAx GPRC5Dx Null | Teclistamab | Talquetamab |
|---|---|---|---|---|---|
| EC$_{50}$ | 0.248 (0.110, 0.556) | NA | NA | 1.814 (1.199, 2.744) | 1.361 (0.934, 1.982) |
| EC$_{90}$ | 6.820 (2.815, 16.522) | NA | NA | 6.263 (3.781, 10.375) | 5.191 (2.921, 9.224) |
| Max | 52.423 (44.614, 60.232) | NA | NA | 48.005 (41.702, 54.308) | 52.079 (45.784, 58.374) |
| CD8$^+$ T-cell activation | | | | | |
| EC$_{20}$ | 0.034 (0.016, 0.071) | NA | NA | 0.903 (0.632, 1.291) | 0.506 (0.337, 0.760) |
| EC$_{30}$ | 0.068 (0.034, 0.138) | NA | NA | 1.189 (0.840, 1.683) | 0.693 (0.472, 1.018) |
| EC$_{50}$ | 0.206 (0.105, 0.406) | NA | NA | 1.831 (1.300, 2.577) | 1.137 (0.784, 1.648) |
| EC$_{90}$ | 3.674 (1.550, 8.708) | NA | NA | 5.610 (3.837, 8.201) | 4.102 (2.585, 6.508) |
| Max | 61.800 (51.931, 71.669) | NA | NA | 63.628 (57.194, 70.062) | 66.038 (59.506, 72.571) |

EC$_x$, x % effective concentration;
E:T, effector to target;
MABEL, minimum anticipated biological effect level;
Max, maximal value;
NA, not active.
BGCB491 was added to whole blood at various concentrations in the presence of target cells (H929) and incubated for 48 hours. The target cells were spiked into whole blood at an optimal ET ratio of 5:1. The study was conducted using 7 healthy human donor whole-blood samples (donor ID: 10145, 10403, 10420, 10083, 10463, 10493, and 10145). EC$_x$ values were estimated post-hoc from a 4PL model with donor as a random effect. 95% confidence intervals (indicated between brackets) were calculated using the delta method. The nonlinear mixed effects R package was used for model fitting. Maximal cytotoxicity/ activation values are percentages.

TABLE 27

Individual cytokine EC$_{50}$ values for MABEL assay.

| | BGCB491 | | Teclistamab | | Talquetamab | |
|---|---|---|---|---|---|---|
| Cytokine | EC$_{50}$ (nM) | Max (95% CI) (pg/mL) | EC$_{50}$ (nM) | Max (95% CI) (pg/mL) | EC$_{50}$ (nM) | Max (95% CI) (pg/mL) |
| INF-γ | 0.172 | 24,856.5 | 0.994 | 32,357.6 | 2.144 | 35,384.7 |
| TNF-α | 0.398 | 886.8 | 1.721 | 819.9 | 3.474 | 935.7 |
| IL-1β | 0.156 | 36.5 | 1.621 | 35.1 | 1.336 | 30.2 |
| IL-2 | 0.585 | 1,385.4 | 1.409 | 1,270.2 | 3.911 | 1,725.4 |
| IL-4 | 0.156 | 14.4 | 1.529 | 15.1 | 1.408 | 11.9 |
| IL-6 | 0.104 | 572.3 | 1.235 | 549.8 | 1.209 | 440.7 |
| IL-10 | 0.924 | 472.6 | 7.694 | 495.6 | 1.2 | 365.8 |
| IL-13 | 0.254 | 144.4 | 0.769 | 146.3 | 0.832 | 145.7 |

95% CI, 95% confidence interval;

EC$_{50}$, 50% effective concentration;

IL, interleukin;

IFN, interferon;

MABEL, minimum anticipated biological effect level;

Max, maximal concentration;

MSD, Meso Scale Discovery;

TNF, tumor necrosis factor.

H929 cell supernatants from the above cytotoxicity experiment (FIG. 30, 3 T-cell donors) were collected and analyzed for cytokine levels using an MSD-based multiplex assay (Cat #: K15049D) Maximal cytokine levels were expressed as pg/mL (with 95% confidence intervals between brackets).

BGCB491-mediated Cytotoxicity of MM Patient Bone Marrow CD138+ Cells

Figure 32:
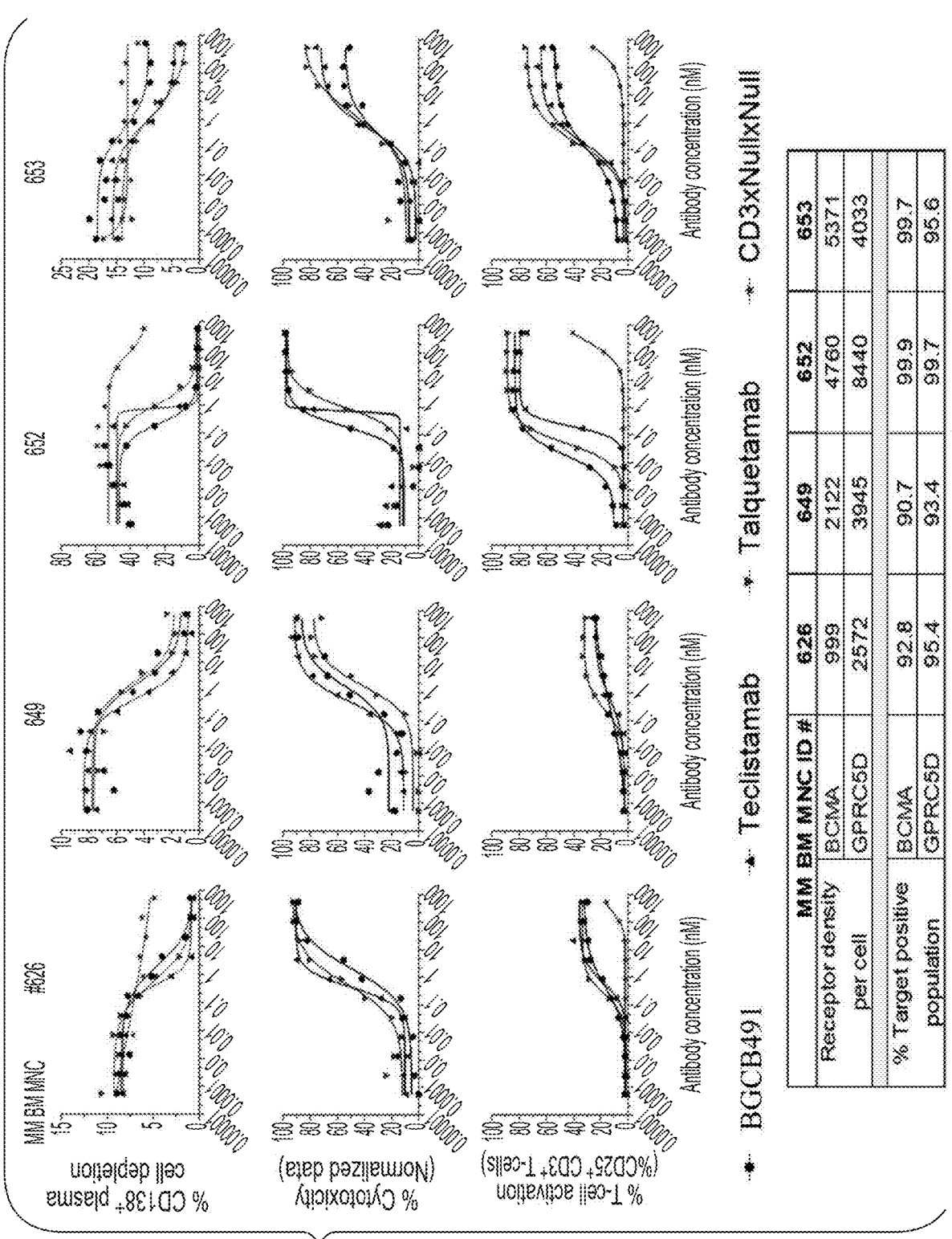
FIG. 32. Cytotoxic potency of BGCB491 against human primary MM CD138+ cells. MNC, mononuclear cell. Frozen bone-marrow-derived mononuclear cells from 4 different myeloma patients (MM BM MNC-626, 649, 652, and 653) were used to assess BGCB491 plasma cell depletion (top row) and T cell activation (bottom row) potential. T cells from a normal healthy donor (donor ID: 20063309) were exogenously added to patient BM MNC samples (E:T ratio of 1:1) and incubated with BGCB491, CD3×Null× Null, teclistamab, or talquetamab (0.00005 to 533.33 nM, X axis) for 48 hours. The loss of live plasma cells (CD138+) and the concomitant upregulation of CD25 on T cells in response to BGCB491 treatment is observed. Variability in total initial plasma cell count was observed between the donors. Individual target receptor density values and percentage target-positive population are listed.

To evaluate the potency of BGCB491 in primary samples from MM patients, this trispecific mAb was tested in a cytotoxic assay using frozen bone marrow mononuclear cells from 4 different MM patients and T cells from a healthy donor. Equal numbers of exogenous T cells and bone marrow mononuclear cells (i.e., 100,000; E:T ratio=1:1) were mixed and incubated with BGCB491, CD3×Null×Null, teclistamab, or talquetamab for 48 hours. Antibody-mediated plasma cell depletion and T-cell activation potential were measured using a flow-cytometry-based approach. BGCB491 induced CD138$^+$ plasma cell depletion of all patient samples in a dose-dependent manner after 48 hours of coculture with healthy normal T cells (FIG. 32). T-cell activation data correlated well with the cytotoxicity data, as expected. This data confirms that BGCB491 is cytotoxic to primary MM bone marrow cells in an ex vivo coculture assay. The donor-specific EC$_x$ values for plasma cell depletion and T-cell activation are listed in Table 28. CD3×Null× Null control antibody was tested in 3 samples that had enough cells for all 4 molecules, and showed some minimal non-specific plasma cell depletion and T-cell activation at higher concentrations (>1 nM). Teclistamab and talquetamab were used as positive controls and behaved as expected.

TABLE 28

Summary of BGCB491 ECx values for cytotoxicity and T-cell activation using primary MM bone marrow mononuclear cells

| | Cytotoxicity | | | T-cell activation | | |
|---|---|---|---|---|---|---|
| EC$_x$ | BGCB491 | Teclistamab | Talquetamab | BGCB491 | Teclistamab | Talquetamab |
| BM MNC ID # 626 | | | | | | |
| EC$_{20}$ (nM) | 0.281 | 0.164 | 0.080 | 0.062 | 0.196 | 0.081 |
| EC$_{30}$ (nM) | 0.598 | 0.242 | 0.169 | 0.139 | 0.320 | 0.126 |
| EC$_{50}$ (nM) | 1.961 | 0.443 | 0.545 | 0.488 | 0.689 | 0.255 |
| EC$_{90}$ (nM) | 42.630 | 2.138 | 11.300 | 12.760 | 5.047 | 1.582 |
| BM MNC ID # 649 | | | | | | |
| EC$_{20}$ (nM) | 0.345 | 0.111 | 0.387 | 0.005 | 0.090 | 0.068 |
| EC$_{30}$ (nM) | 0.650 | 0.200 | 0.713 | 0.028 | 0.201 | 0.118 |
| EC$_{50}$ (nM) | 1.762 | 0.506 | 1.858 | 0.381 | 0.712 | 0.278 |
| EC$_{90}$ (nM) | 23.400 | 5.599 | 22.310 | 330.900 | 19.050 | 2.586 |
| BM MNC ID # 652 | | | | | | |
| EC$_{20}$ (nM) | 0.073 | ~0.6316 | 0.304 | 0.005 | 0.106 | 0.015 |
| EC$_{30}$ (nM) | 0.108 | ~0.7015 | 0.482 | 0.009 | 0.137 | 0.024 |
| EC$_{50}$ (nM) | 0.202 | ~0.7440 | 0.990 | 0.019 | 0.204 | 0.051 |
| EC$_{90}$ (nM) | 1.017 | ~0.9663 | 6.421 | 0.153 | 0.576 | 0.334 |
| BM MNC ID # 653 | | | | | | |
| EC$_{20}$ (nM) | 0.071 | 0.114 | 0.203 | 0.013 | 0.033 | 0.028 |
| EC$_{30}$ (nM) | 0.145 | 0.223 | 0.482 | 0.030 | 0.064 | 0.058 |
| EC$_{50}$ (nM) | 0.446 | 0.641 | 1.877 | 0.120 | 0.179 | 0.181 |
| EC$_{90}$ (nM) | 8.183 | 9.900 | 63.680 | 4.355 | 2.627 | 3.407 |
| Average | | | | | | |
| EC$_{20}$ (nM) | 0.192 | 0.130 | 0.244 | 0.021 | 0.106 | 0.048 |
| EC$_{30}$ (nM) | 0.375 | 0.222 | 0.461 | 0.051 | 0.180 | 0.082 |

TABLE 28-continued

| Summary of BGCB491 ECx values for cytotoxicity and T-cell activation using primary MM bone marrow mononuclear cells | | | | | |
|---|---|---|---|---|---|
| | Cytotoxicity | | | T-cell activation | |
| $EC_x$ | BGCB491 | Teclistamab | Talquetamab | BGCB491 | Teclistamab | Talquetamab |
| $EC_{50}$ (nM) | 1.093 | 0.530 | 1.317 | 0.252 | 0.446 | 0.191 |
| $EC_{90}$ (nM) | 18.808 | 5.879 | 25.928 | 87.042 | 6.825 | 1.977 |

BM, bone marrow;
$EC_x$, x % effective concentration;
E:T, effector to target;
MM, multiple myeloma;
MNC, mononuclear cell.
BGCB491 was added to MM BM MNCs at various concentrations in the presence of healthy T cells at 1:1 E:T ratio and incubated for 48 hours. The study was conducted using 4 MM patient bone marrow samples (donor ID: MM BM MNC-626, 649, 652, and 653). In this experiment teclistamab and talquetamab were used as positive controls. $EC_x$ values were estimated post-hoc from a 4PL model with donor as a random effect. 95% confidence intervals were calculated using the delta method. The nonlinear mixed effects R package was used for model fitting.

BGCB491 Cytotoxicity Potential at Various E: T Ratios and Incubation Times

Figure 33A:
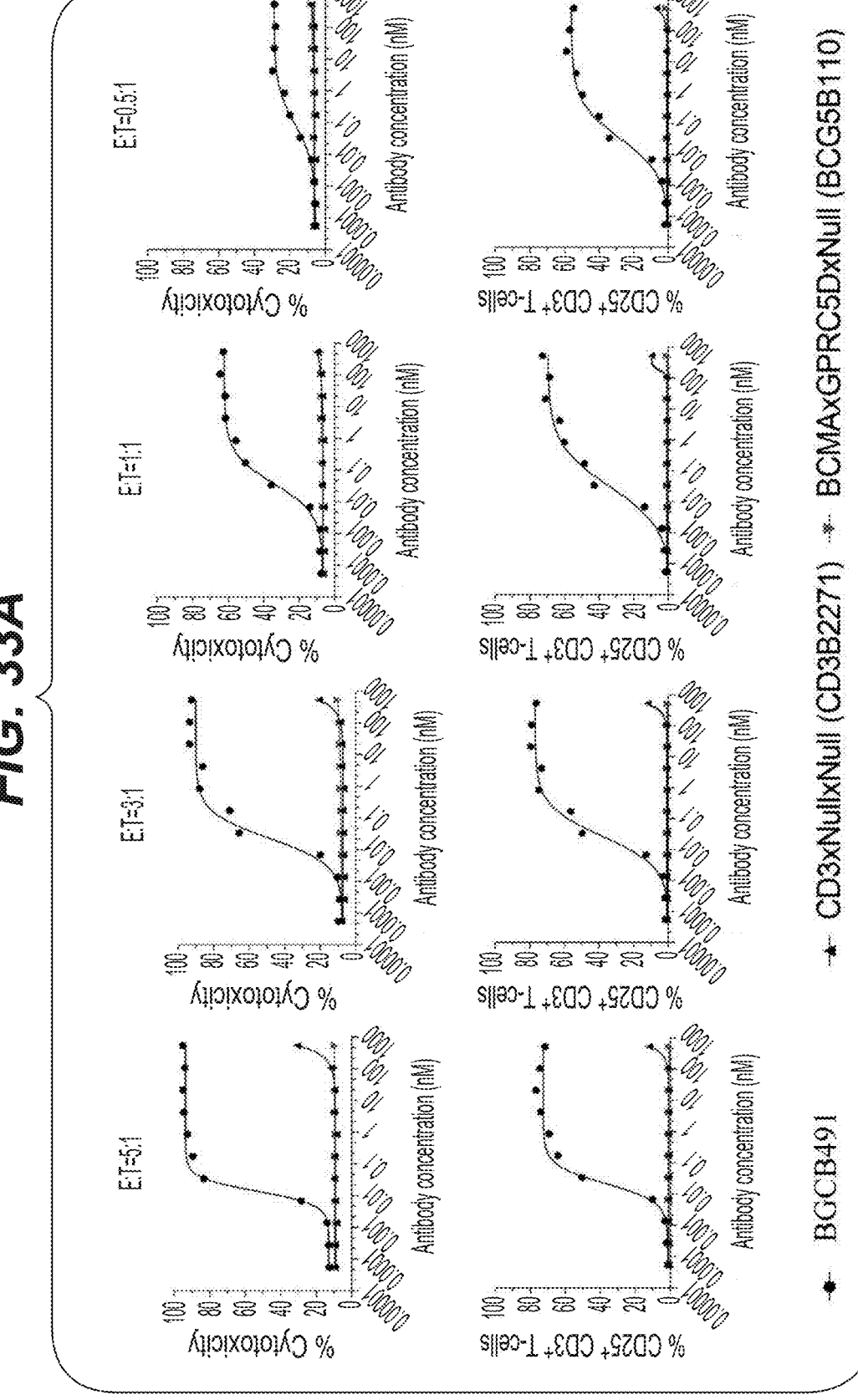
FIGS. 33A-33B. BGCB491 cytotoxicity potential at various E:T ratios and incubation times (H929 cell line).
Figure 33B:
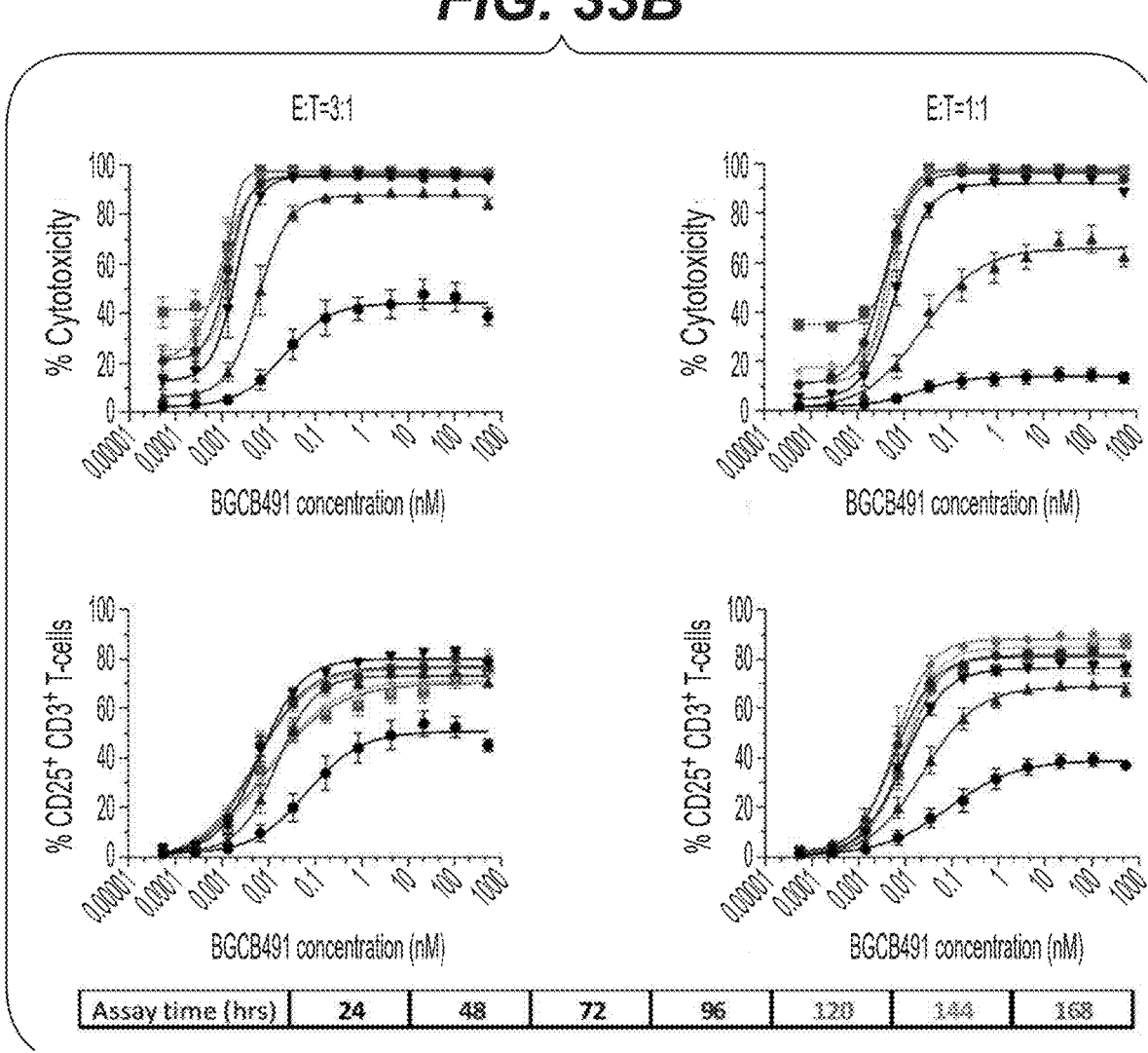

Further, BGCB491 target cell cytotoxicity potential was tested using a T-cell-mediated cytotoxicity assay with several E:T ratios and different incubation times to understand its ability to deplete myeloma cells in a clinical setting. As test cell lines, H929 cells were mixed with T cells (donor ID: 20063323) to attain a E:T ratios of 5:1, 3:1, 1:1, and 0.5:1 in presence of BGCB491, BCMA×GPRC5D×Null, and CD3×Null×Null, and incubations were performed for 72 hours. For a time-course experiment, 3:1 and 1:1 E:T ratios were selected for testing at 24, 48, 72, 96, 120, 144 and 168 hours of incubation. The receptor density per cell for BCMA and GPRC5D is 5381 and 1574, respectively, in H929 cells. BGCB491 potently killed H929 cells at all E:T ratios tested with comparable $EC_{50}$ values for cytotoxicity and for T-cell activation (FIG. 33A, Table 29). BGCB491 initiated target cell cytotoxicity from the earliest time point tested (24 hours) and its potency and efficacy increased with time till 72 hours of incubation where it almost reached a plateau (FIG. 33B). BGCB491 potently killed H929 cells at all time points tested with $EC_{50}$ values ranging between 0.001 and 0.022 nM for cytotoxicity and between 0.005 and 0.067 nM for T-cell activation (3:1 E:T ratio). For the 1:1 E:T ratio assay, the $EC_{50}$ values ranged between 0.004 and 0.025 nM for cytotoxicity and between 0.006 and 0.083 nM for T-cell activation (FIG. 33B, Table 30). This data indicates that the trispecific mAb BGCB491 is very efficient and can benefit in situations where T-cell count is limiting. However, at a lower E:T ratio of 0.5:1 the maximal cytotoxicity percentage was much lower (~20%) than at other conditions tested in the 72-hour incubation assay. It would be interesting to see if longer incubation times can improve the maximum cytotoxicity at these lower T-cell counts. In a separate study, BGCB491 showed measurable, low-affinity binding to primary human T cells expressing CD3 from multiple donors (FIG. 26) with robust cytotoxicity of H929 cells at both 1:1 and 1:3 E:T ratios (FIG. 43, FIG. 44).

TABLE 29

| Summary of BGCB491 ECx values for cytotoxicity and T-cell activation in E:T ratio assay | | | |
|---|---|---|---|
| E:T ratio | $EC_x$ | Cytotoxicity | $CD3^+$ T-cell activation |
| 5:1 | $EC_{20}$ (nM) | 0.007 | 0.008 |
| | $EC_{50}$ (nM) | 0.014 | 0.022 |
| | $EC_{90}$ (nM) | 0.040 | 0.097 |
| 3:1 | $EC_{20}$ (nM) | 0.006 | 0.005 |
| | $EC_{50}$ (nM) | 0.023 | 0.027 |
| | $EC_{90}$ (nM) | 0.192 | 0.343 |
| 1:1 | $EC_{20}$ (nM) | 0.008 | 0.004 |
| | $EC_{50}$ (nM) | 0.038 | 0.031 |
| | $EC_{90}$ (nM) | 0.445 | 0.993 |
| 0.5:1 | $EC_{20}$ (nM) | 0.013 | 0.005 |
| | $EC_{50}$ (nM) | 0.088 | 0.033 |
| | $EC_{90}$ (nM) | 1.919 | 0.662 |

CD, cluster of differentiation;
$EC_x$, x % effective concentration;
E:T, effector to target.
BGCB491 was tested in presence of pan T cells from 1 healthy donor (donor ID: 20063323) at various E:T ratios (5:1, 3:1, 1:1, and 0.5:1) for 72 hours. Target cell death and T-cell activation was measured and expressed as percent cytotoxicity and percent $CD25^+CD3^+$ T cells. $EC_x$ values were estimated post-hoc from a 4PL model with donor as a random effect. 95% confidence intervals were calculated using the delta method. The nonlinear mixed effects R package was used for model fitting.

TABLE 30

| Summary of BGCB491 ECx values for cytotoxicity and T-cell activation in time-course assay | | | | | | | | |
|---|---|---|---|---|---|---|---|---|
| | | Incubation time (hours) | | | | | | |
| Endpoint | $EC_x$ | 24 | 48 | 72 | 96 | 120 | 144 | 168 |
| | | E:T ratio 3:1 | | | | | | |
| Cytotoxicity | $EC_{20}$ (nM) | 0.005 | 0.002 | 0.001 | 0.001 | 0 | 0.001 | 0.001 |
| | $EC_{50}$ (nM) | 0.022 | 0.006 | 0.002 | 0.001 | 0.001 | 0.002 | 0.001 |
| | $EC_{90}$ (nM) | 0.258 | 0.033 | 0.007 | 0.004 | 0.005 | 0.004 | 0.003 |

TABLE 30-continued

| | | Summary of BGCB491 ECx values for cytotoxicity and T-cell activation in time-course assay | | | | | | |
|---|---|---|---|---|---|---|---|---|
| | | Incubation time (hours) | | | | | | |
| Endpoint | $EC_x$ | 24 | 48 | 72 | 96 | 120 | 144 | 168 |
| CD3$^+$ T-cell activation | $EC_{20}$ (nM) | 0.011 | 0.004 | 0.002 | 0.001 | 0.001 | 0.001 | 0.001 |
| | $EC_{50}$ (nM) | 0.067 | 0.015 | 0.007 | 0.006 | 0.005 | 0.01 | 0.008 |
| | $EC_{90}$ (nM) | 1.255 | 0.121 | 0.064 | 0.087 | 0.102 | 0.307 | 0.385 |
| | | E:T ratio 1:1 | | | | | | |
| Cytotoxicity | $EC_{20}$ (nM) | 0.004 | 0.003 | 0.002 | 0.001 | 0.002 | 0.003 | 0.003 |
| | $EC_{50}$ (nM) | 0.019 | 0.025 | 0.007 | 0.004 | 0.004 | 0.006 | 0.006 |
| | $EC_{90}$ (nM) | 0.224 | 0.585 | 0.039 | 0.017 | 0.013 | 0.017 | 0.019 |
| CD3$^+$ T-cell activation | $EC_{20}$ (nM) | 0.008 | 0.004 | 0.002 | 0.002 | 0.002 | 0.003 | 0.003 |
| | $EC_{50}$ (nM) | 0.083 | 0.024 | 0.009 | 0.006 | 0.006 | 0.009 | 0.01 |
| | $EC_{90}$ (nM) | 3.117 | 0.448 | 0.086 | 0.047 | 0.04 | 0.056 | 0.066 |

CD, cluster of differentiation;
$EC_x$, x % effective concentration;
E:T, effector to target.
For time-course assay, BGCB491 was tested at an E:T ratio of 3:1 and 1:1 for various time points (24, 48, 72, 96, 120, 144, and 168 hours) using 4 different T-cell donors (donor ID: 20062105, 20063309, 20061963, and 20063310). Target cell death and T-cell activation was measured and expressed as percent cytotoxicity and percent CD25$^+$CD3$^+$ T cells. $EC_x$ values were estimated post-hoc from a 4PL model with donor as a random effect. 95% confidence intervals were calculated using the delta method. The nonlinear mixed effects R package was used for model fitting.

Effect of BGCB491 on T-Cell Activation in the Absence of Target Cells

Figures 34A, 34B:
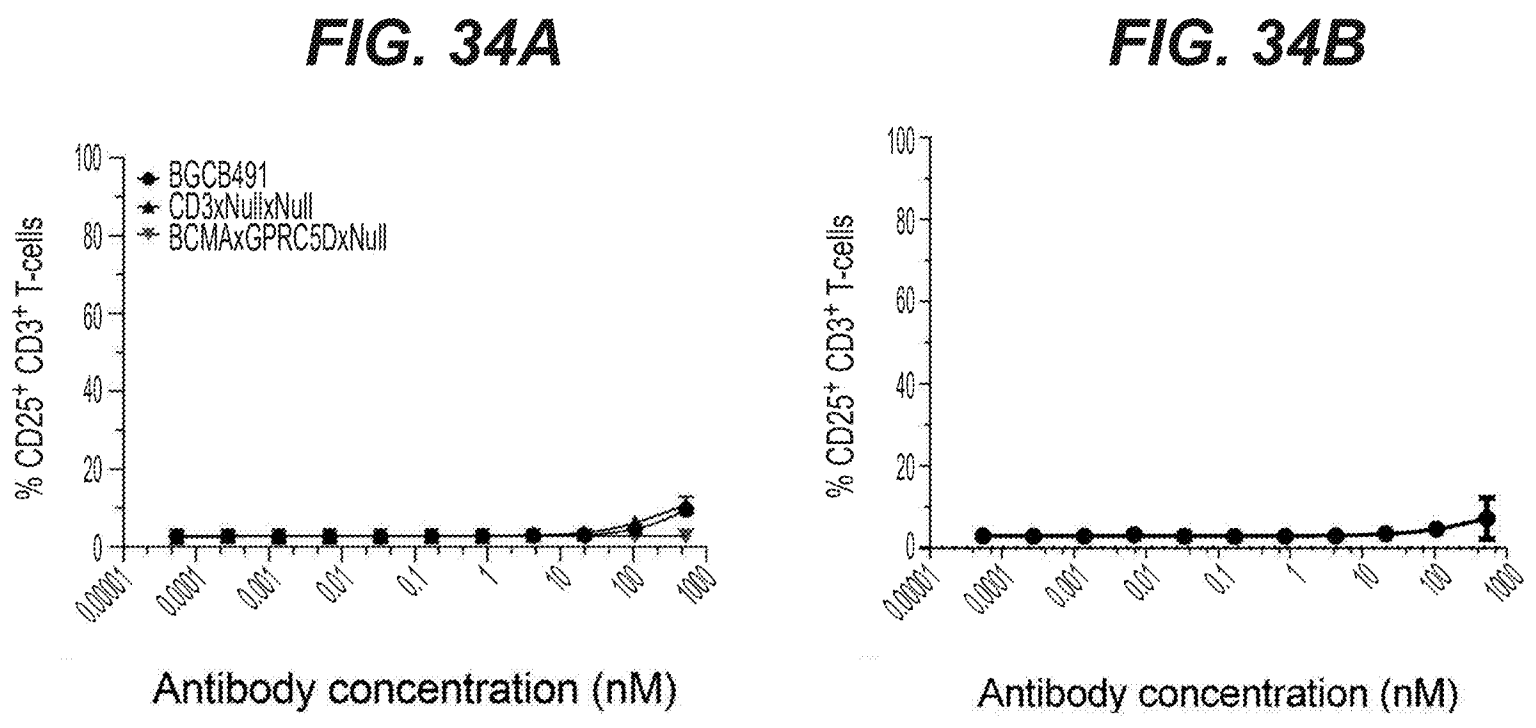
Figure 34C:
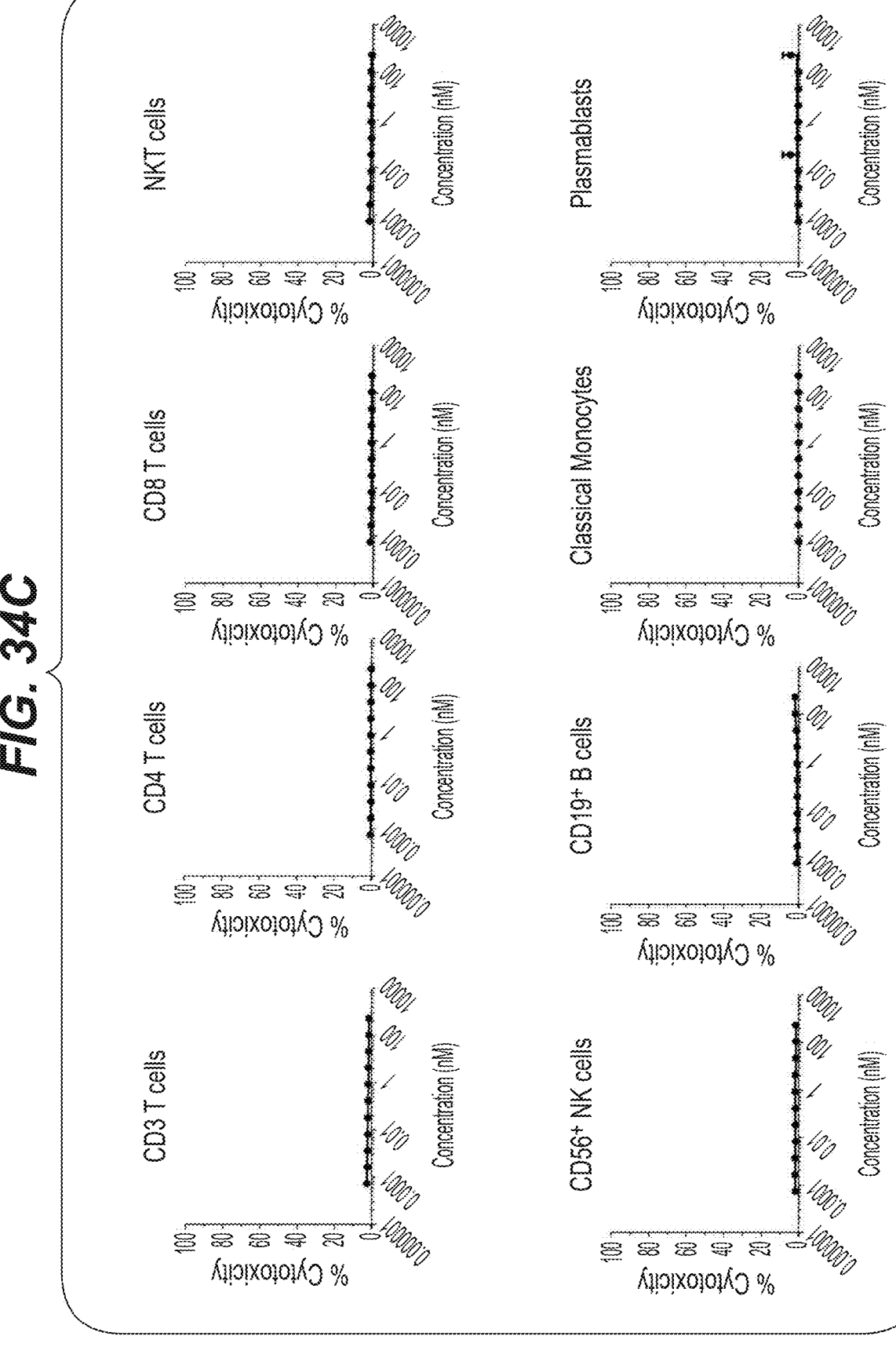

To assess whether BGCB491 promotes unwanted T-cell activation in the absence of target engagement, the effect of BGCB491 in a T-cell activation assay was tested. In the first study, 6 normal healthy donor T-cell samples were incubated in the presence of various concentrations of BGCB491 for 72 hours (FIG. 34A). In the second study a more physiologically relevant assay format was used where BCMA-GPRC5D-positive cells are absent in healthy human whole blood, and here BGCB491 was added in 6 normal healthy donor whole-blood samples at various concentrations for 48 hours (FIG. 34B). T-cell activation and cytotoxicity effects were then measured by scoring CD25-positive CD3$^+$, CD4$^+$, and CD8$^+$ T cells or percent cell death of various blood cells (FIG. 34C; neutrophils, monocytes, B cells, NK cells, plasmablasts) by flow cytometry. BGCB491 had no significant impact on the activation of T cells or on non-specific cell death in the absence of BCMA-GPRC5D-expressing target cells (FIGS. 34B and C). Minimal T-cell activation was observed at concentrations >10 nM.

Part 2. In Vivo Studies

The antitumor efficacy of BGCB491 was evaluated in RPMI 8226 (Study A) and H929-CRISPR-KO (Study B) human MM xenografts. To provide a suitable host for engrafting human tumors and human T cells, female NSG (i.e., non-obese diabetic [NOD] severe combined immunodeficiency [scid] gamma or NOD.Cg-Prkdc$^{scid}$ Il2rg$^{tm1Wjl}$/SzJ) mice were used for both studies.

In Study A, mice were implanted SC with RPMI 8226 cells on Day 0. Human pan T cells were engrafted intraperitoneally (IP) on Day 18 post tumor cell engraftment. Treatments with vehicle, BGCB491, teclistamab, or talquetamab were administered IP starting on Day 19 and continued twice weekly for a total of 8 treatments. Study B was performed as a prevention study injecting human expanded pan T cells IP on Day −1. H929-BCMA-KO cells were implanted SC in the left flank of NSG mice, while H929-GPRC5D-KO cells were implanted SC in the right flank on Day 0. Treatments with vehicle (i.e., phosphate-buffered saline [PBS]), BGCB491, teclistamab, and talquetamab were initiated on Day 1, and administered twice weekly for 7 treatments.

Figure 35:
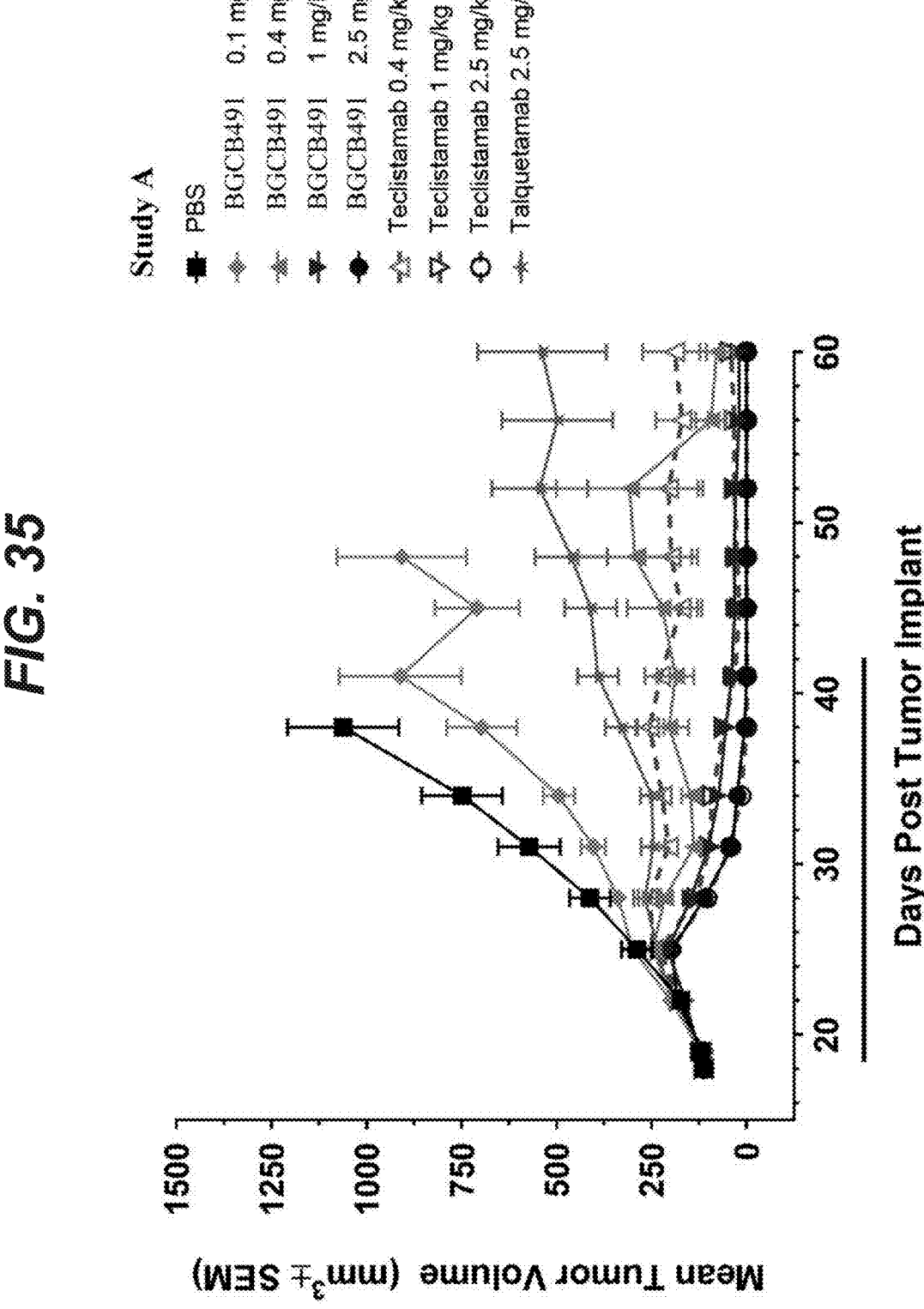
FIG. 35. Antitumor efficacy of BGCB491, teclistamab, and talquetamab in subcutaneous (SC) RPMI 8226 xenografts in T cell-humanized NSG mice (Study A). KO, knock-out; NSG, non-obese diabetic (NOD) severe combined immunodeficiency (scid) gamma or NOD.Cg Prkdc$^{scid}$ Il2rg$^{tm1Wjl}$/SzJ; PBS, phosphate-buffered saline; SEM, standard error of the mean. T cell-humanized NSG mice bearing established SC RPMI 8226 tumors were intraperitoneally (IP) dosed with BGCB491 at 0.1, 0.4, 1, and 2.5 mg/kg. Teclistamab was IP dosed at 0.4, 1, and 2.5 mg/kg. Talquetamab was IP dosed at 2.5 mg/kg. Treatments were administered on Days 19, 21, 25, 28, 31, 34, 38, and 41 (indicated by black line beneath X axis). Tumor volume was measured twice weekly, and the results presented as the mean tumor volume±SEM for each group. Data graphically represented for each group with at least 70% of animals remaining in the study.

In Study A (regression model) percent A tumor growth inhibition (TGI) of RPMI 8226 xenografts was calculated on Day 38, when >70% of vehicle-treated control animals remained on study. The receptor density per cell for BCMA and GPRC5D is 2317 and 486, respectively, in RPMI 8226 cells. Statistically significant ΔTGI was observed with BGCB491 at 0.4 mg/kg (equivalent to approximately 8 μg for a 20-gram mouse), 1 mg/kg (20 μg/mouse), and 2.5 mg/kg (50 μg/mouse), resulting in ΔTGI values of 90.5%, 106.2%, and 111.2%, respectively (p<0.05 for all groups versus vehicle controls) (FIG. 35). The lowest dose of 0.1 mg/kg (2 μg/mouse) resulted in 38.4% ΔTGI (p=0.035), which was deemed not efficacious. Teclistamab inhibited tumor growth with 85% ΔTGI at 0.4 mg/kg, 105.6% ΔTGI at 1 mg/kg, and 111.9% ΔTGI at 2.5 mg/kg, respectively, as compared to PBS-treated control mice, whereas talquetamab dosed at 2.5 mg/kg inhibited RPMI 8226 tumor growth by 77.2% ΔTGI (p<0.05 for all groups versus PBS-treated controls).

In the RPMI 8226 model, BGCB491-mediated tumor regressions continued to be observed for more than 2 weeks post treatment cessation. Percent tumor regression (TR) as compared to initial tumor burden was evaluated on Day 60, which was 19 days post last dose. Tumor regression was observed with BGCB491 at 1 and 2.5 mg/kg resulting in TR values of 80.27% (p<0.0001) and 100% (p<0.0001), respectively. The 0.4 mg/kg dose had 28.7% TR on Day 60 but was not statistically significant. Teclistamab, likewise, elicited TR with 68.88% (p=0.0025) at 1 mg/kg and 100% (p<0.0001) at 2.5 mg/kg. In in vitro testing using RPMI 8226 cells in a 72-hours incubation assay, BGCB491 showed a similar cytotoxicity profile with no additive effect compared to teclistamab or talquetamab individually.

Figure 36:
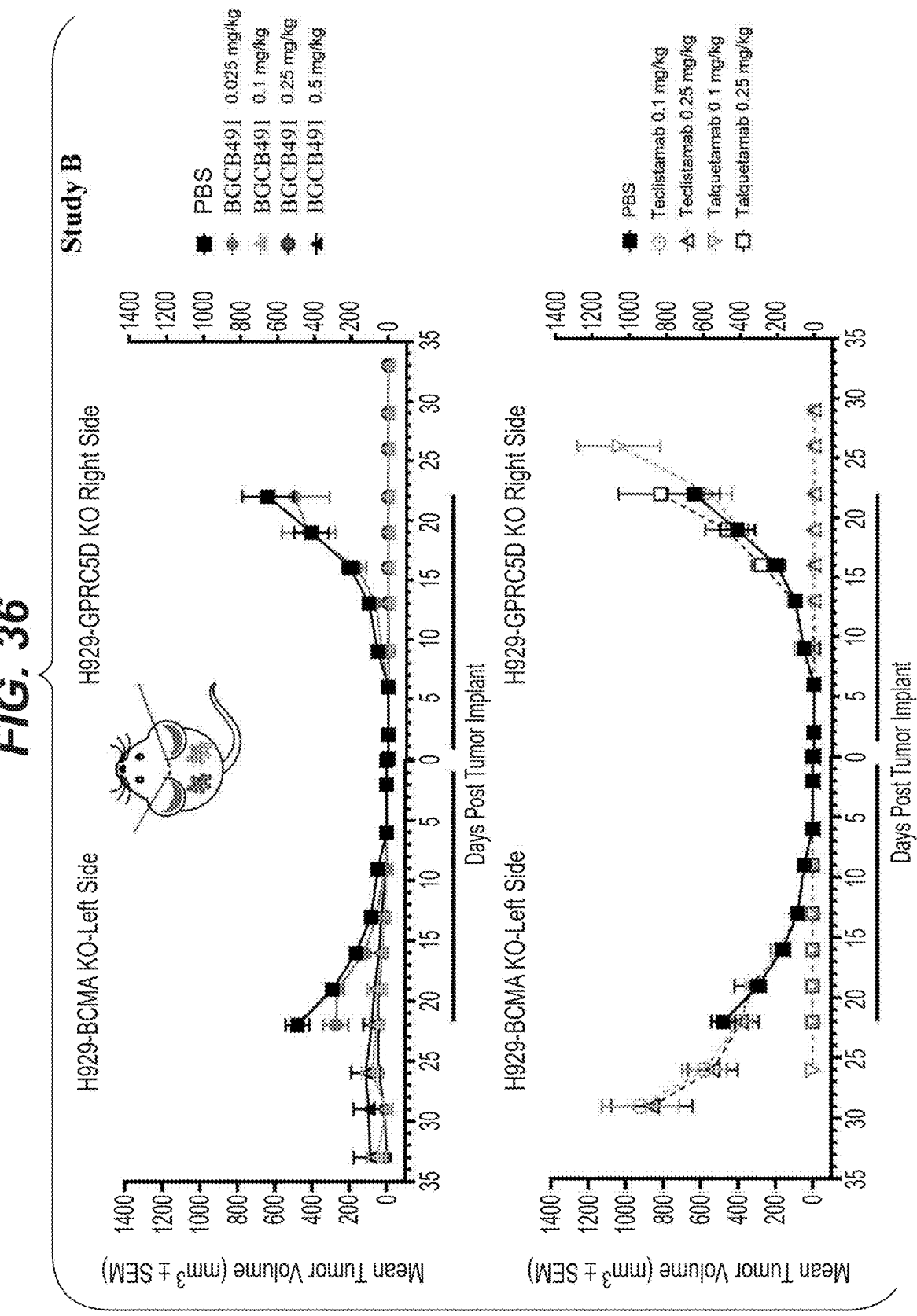
FIG. 36. Antitumor efficacy of BGCB491, teclistamab, and talquetamab in subcutaneous (SC) H929-BCMA-KO and H929-GPRC5D-KO xenografts in T cell-humanized NSG mice (Study B). KO, knock-out; NSG, non-obese diabetic (NOD) severe combined immunodeficiency (scid) gamma or NOD.Cg Prkdc$^{scid}$ Il2rg$^{tm1 Wjl}$/SzJ; PBS, phosphate-buffered saline; SEM, standard error of the mean. T cell humanized NSG mice bearing H929-BCMA-KO (left flank) and H929-GPRC5D-KO (right flank) tumors were dosed intraperitoneally (IP) with BGCB491 at 0.025, 0.1, 0.25, and 0.5 mg/kg. Teclistamab and talquetamab were IP dosed at 0.1 and 0.25 mg/kg. Treatments were administered on Days 1, 5, 9, 13, 16, 19, and 22 (indicated by black line beneath X axis). Tumor volume was measured twice weekly, and the results presented as the mean tumor volume±SEM for each group. Data graphically represented for each group with at least 70% of animals remaining in the study.

In Study B (prophylactic model), percent TGI was calculated on Day 22 post tumor implantation, when >70% of animals remained on study. Statistically significant TGI against BCMA-KO tumors was observed with BGCB491 at 0.1, 0.25, and 0.5 mg/kg resulting in 89.2%, 91.1%, and 83.6% TGI, respectively, as compared with PBS-treated controls (all p-values <0.05; FIG. 36). Teclistamab had no efficacy at both dose levels tested (0.1 mg/kg, 17.2% TGI; and 0.25 mg/kg, 19.9% TGI), while talquetamab inhibited tumor growth 100% at both the 0.1 and 0.25 mg/kg dose levels (p<0.05). Against GPRC5D-KO tumors, BGCB491 treatment resulted in significant efficacy with 100% TGI at 0.1, 0.25, and 0.5 mg/kg dose levels (p<0.05 for all groups). The 0.025 mg/kg dose had a minor effect of 22.09% TGI that was not considered biologically significant (34). Teclistamab inhibited H929-GPRC5D-KO tumor growth by 100% TGI at both the 0.1 and 0.25 mg/kg dose levels (p<0.05), talquetamab had no effect. The receptor density per cell for BCMA and GPRC5D is 1 and 957, respectively, in H929 BCMA-KO cells. The receptor density per cell for BCMA and GPRC5D is 3926 and 19, respectively, in H929 GPRC5D-KO cells.

Animals were monitored post treatment until signs of graft-versus-host disease (GvHD)-related morbidity manifested at which time the animals were euthanized and the study was concluded.

In summary, the trispecific mAb BGCB491 exhibited efficacy in numerous MM cell lines and was able to deplete a clonal population that expressed either single targets or dual targets. BGCB491 was also able to kill target-expressing cells in a more physiological setting like the whole-blood assay. Importantly, BGCB491 was able to deplete MM patient plasma cells in a dose-dependent manner. BGCB491 efficacy was also reflected in significant reductions in tumor growth in in vivo mouse xenograft models. Finally, there was no non-specific T-cell activation or cytotoxicity of target-negative cells. These results indicate that BGCB491 may have significant therapeutic potential in treating MM patients.

In a further in vivo study, the antitumor efficacy of BGCB491 was evaluated in MM.1S (Study C) human MM xenografts. To provide a suitable host for engrafting human tumors and human T cells, female NSG (i.e., non-obese diabetic [NOD] severe combined immunodeficiency [scid] gamma or NOD.Cg-Prkdc$^{scid}$ Il2rg$^{tm1 Wjl}$/SzJ) mice were used for the study.

In Study C, mice were implanted SC with MM.1 S cells on Day 0. Human expanded pan T cells were engrafted intraperitoneally (IP) on Day 13 post tumor cell engraftment, and treatments with vehicle, BGCB491, teclistamab, or talquetamab were administered IP starting on Day 15 and continued twice weekly for a total of 7 treatments.

The percent tumor growth inhibition (TGI) was calculated on Day 34 post tumor implantation, when >70% of animals remained on study. Statistically significant TGI against MM.1 S tumors was observed with BGCB491 at 0.025, 0.1, 0.5, and 1 mg/kg resulting in 66.9%, 91.2%, 99.7% and 100% TGI, respectively, as compared with PBS-treated controls (all p-values <0.05; FIG. 45). Teclistamab inhibited tumor growth at both dose levels tested (0.1 mg/kg, 73.7% TGI; and 0.5 mg/kg, 92.3% TGI (p<0.05). Talquetamab was efficacious with 90.9% TGI at 0.025 mg/kg and 99.4% at 0.1 mg/kg (p<0.05).

BGCB491-mediated tumor regressions for 2 weeks post treatment cessation. Percent tumor regression (TR) as compared to initial tumor burden was evaluated on Day 51, 14 days post last dose. Tumor regression was observed with BGCB491 at 0.5 and 1 mg/kg resulting in TR values of 100% each (8 out of 8 complete regression of established tumors). The 0.4 mg/kg dose had 28.7% TR on Day 60 but was not statistically significant. Teclistamab did not elicit any tumor regression, but talquetamab at 0.1 mg/kg resulted in 100% TR of established MM.1S tumors.

Example 12: Affinity of Therapeutic to Human and Other Species

The CD3-binding arm (i.e., CD3B376) binds to cynomolgus monkey CD3. Briefly, binding was measured by flow cytometry after incubating human and cynomolgus monkey peripheral blood mononuclear cells (PBMCs) with GCDB381 (i.e., CD3B376 Fab in bivalent IgG1-AAS antibody), CD3B891 (i.e., CD3B376×Null, IgG1-AAS bispecific antibody), or null control.

The BCMA (BCMB601, containing BCMB519 scFv) binding arm did not bind to cynomolgus monkey BCMA (Table 19A).

The GPRC5D (i.e., GC5B680) and BCMA binding arms were assessed for cross-reactivity to cynomolgus monkey as part of the BGCB463 molecule, which uses the identical binding arms as BGCB491. Cross reactivity to cynomolgus monkeys was profiled for both target-binding scFv arms using FACS-based cell binding at 37° C. for 1 hour with K562 stably expressing human or cynomolgus monkey GPRC5D or BCMA. The cell-based $EC_{50}$ value for the GC5B680 scFv arm was approximately 30 nM against human GPRC5D-expressing cells and about 10-fold weaker (approximately 400 nM) on cynomolgus monkey GPRC5D-expressing cells. In contrast, the cell-based $EC_{50}$ value for the BCMB519 scFv arm was approximately 145 nM for human BCMA, while there was no detectable binding to cynomolgus BCMA up to 2 μM.

Example 13: Off-Target Toxicity Assessment

The potential for risks due to off-target binding or functional activity associated with the tumor-antigen-binding arms was assessed using the Retrogenix™ cell microarray (no off-target liabilities were observed) and the functional selectivity TAA cell line assay, respectively.

Selectivity of the CD3 arm of BGCB491 was demonstrated by the lack of cytotoxicity and T-cell activation in the absence of target-expressing cells (FIGS. 34A-34C; see Example 12).

GPRC5D Off-Target Binding Assessment

The GPRC5D binder (GC5B1257.001, anti-GPRC5D GC5B680 scFv-Fc) when screened for binding against fixed HEK293 cells individually expressing a library of 5,868 full-length human plasma membrane and cell-surface-tethered human secreted proteins (including all known G-protein-coupled receptor Family C Group 5 [GPRC5] family members) and 371 heterodimers, was determined to bind specifically to its primary target, GPRC5D. No off-target interactions were identified, demonstrating the target specificity of the GPRC5D-binding domain contained in BGCB491.

BCMA Off-Target Binding Assessment

The BCMA binder (BCMB601.001, anti-BCMA BCMB519 scFv-Fc) when screened for binding against fixed HEK293 cells individually expressing a library of 5,475 full-length human plasma membrane and cell-surface-tethered human secreted proteins and 371 heterodimers, was determined to bind specifically to its primary target, BCMA (TNFRSF17). No off-target interactions were identified, demonstrating the target specificity of the BCMA-binding domain contained in BGCB491.

Functional Selectivity in Tumor-Associated Antigen-Negative Cell Lines

The antigen specificity of BGCB491 is further characterized in an in vitro functional assay using a panel of 5 cancer cell lines that lack expression of GPRC5D, BCMA, and CD3 (as confirmed by flow cytometry), but by transcriptomics are predicted to express >50% of the known cell surface proteins. In coculture studies with healthy donor-derived T cells, BGCB491 is assessed for the induction of antibody-dependent, T-cell-mediated cytokine release of granzyme B, interferon (IFN)-7, tumor necrosis factor (TNF)-α, and interleukin (IL)-2 when added to cocultures with target cells that express GPRC5D and BCMA (i.e., H929 cells). These data can support the antigen specificity of BGCB491 to GPRC5D and BCMA.

Example 14: Local Tolerance

Skin reactions were assessed in a PK study in minipigs treated with 0.1 or 0.01 mg/kg BGCB491 SC in 2 to 2.5 mL at 0.05 and 0.5 mg/mL, respectively (see Gottingen minipig pharmacokinetics in Example 16). No skin reactions were observed.

Example 15: Pharmacokinetics in Preclinical Species

Mouse Pharmacokinetics

The serum and tumor PK properties of BGCB491 is characterized in a NSG MM.1S xenograft mouse model following a single IV injection at 0.5 and 0.1 mg/kg.

Cynomolgus Monkey Pharmacokinetics

Figure 37:
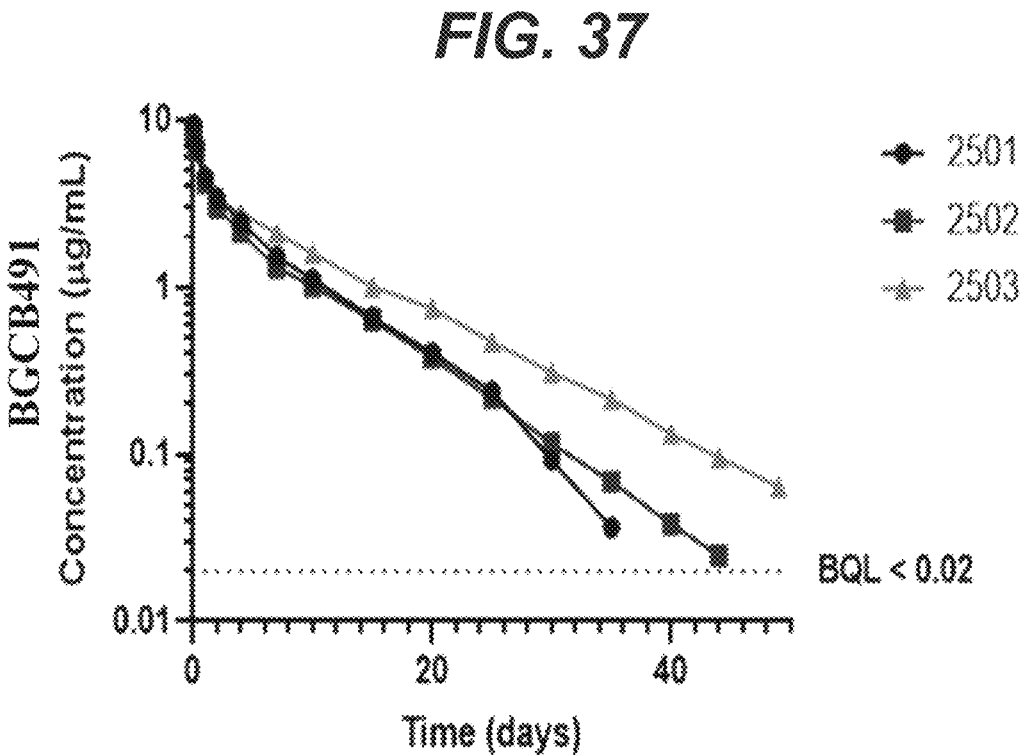
FIGS. 37-38. Individual BGCB491 serum concentration—time profiles following a single intravenous (IV) 0.5 mg/kg dose in female cynomolgus monkey (FIG. 37) and predicted model (FIG. 38). BQL, below quantification limit. Data points with concentrations below the lowest quantifiable concentration are not shown in the graph.
Figure 38:
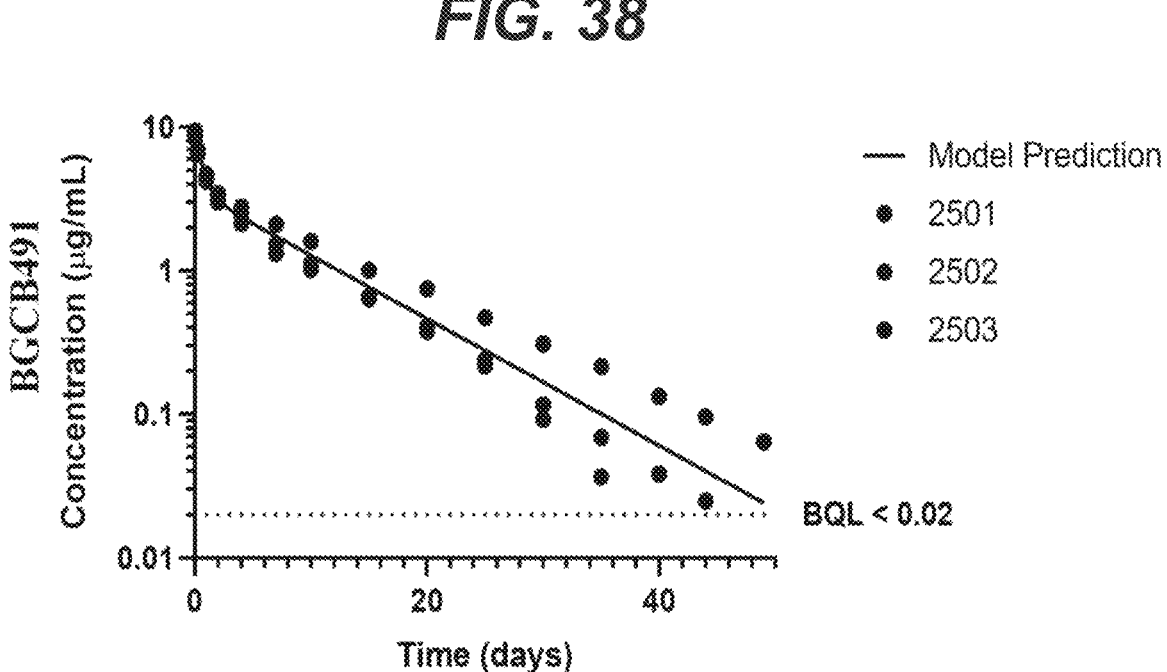

The PK properties of BGCB491 were characterized following a single-dose non-GLP PK study in female cynomolgus monkeys (n=3). BGCB491 was administered IV to cynomolgus monkeys at a dose level of 0.5 mg/kg (10 mM histidine, pH 6.5). A qualified electrochemiluminescence immunoassay (ECLIA) from MSD was used to quantitate concentrations of total BGCB491. BGCB491 systemic drug exposure assessed by maximum serum concentration ($C_{max}$) and area under the serum concentration versus time curve (AUC) of 1 dose interval is shown in Table 31, and BGCB491 serum concentrations are illustrated in FIG. 37.

TABLE 31

Individual and mean (SD) total BGCB491 PK parameter estimates following a single IV dose of 0.5 mg/kg in cynomolgus monkeys (Group 2; n = 3/group)

| ID | $C_{max}$ (µg/mL) | $AUC_{last}$ (µg · day/mL) | $AUC_{inf}$ (µg · day/mL) | CL (mL/day/kg) | $V_z$ (mL/kg) | $T_{1/2}$ (day) |
|---|---|---|---|---|---|---|
| 2501 | 9.39 | 35.61 | 35.81 | 13.96 | 74.51 | 3.70 |
| 2502 | 8.49 | 32.73 | 32.95 | 15.17 | 137.01 | 6.26 |
| 2503 | 9.22 | 47.95 | 48.74 | 10.26 | 126.52 | 8.55 |
| Mean | 9.03 | 38.76 | 39.17 | 13.13 | 112.68 | 6.17 |
| SD | 0.48 | 8.08 | 8.41 | 2.56 | 33.47 | 2.43 |

$AUC_{inf}$, area under the serum concentration-time curve extrapolated to infinity;

$AUC_{last}$, area under the serum concentration-time curve up to the last sampling point;

CL, systemic clearance;

$C_{max}$, maximum serum concentration;

IV, intravenous;

PK, pharmacokinetics;

SD, standard deviation;

$T_{1/2}$, terminal phase elimination half-life;

$V_z$, total systemic clearance.

Gottingen Minipig Pharmacokinetics

Figure 39A:
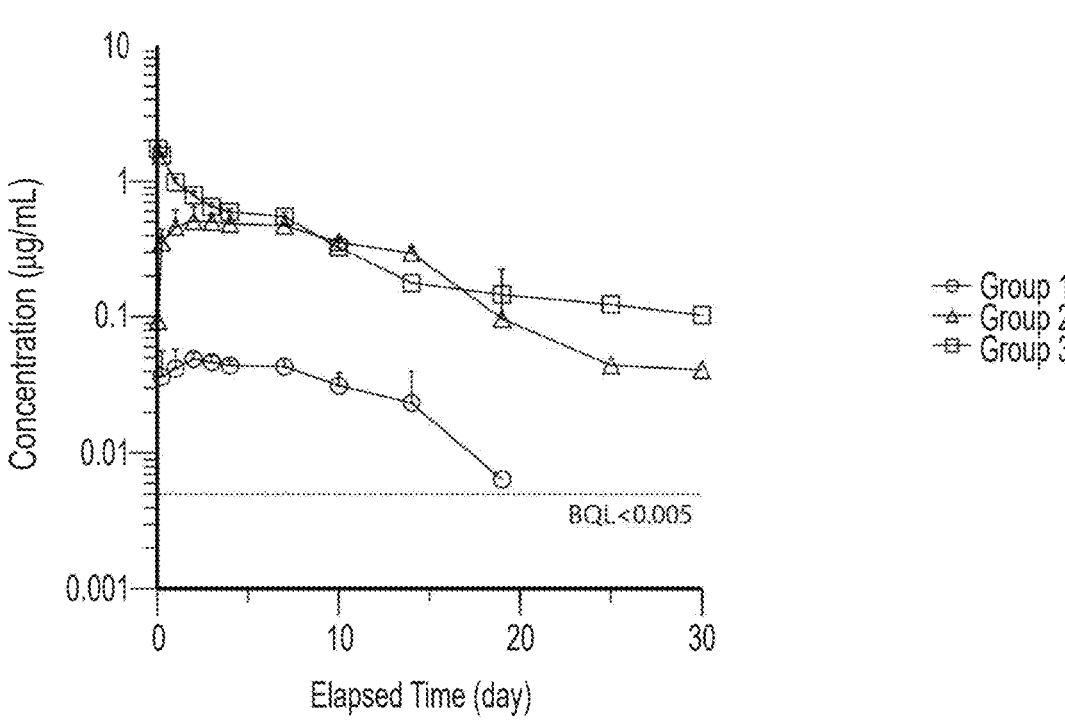
FIG. 39A-39B. Mean (SD) BGCB491 concentration—time profiles following a single dose of BGCB491 in male minipigs and model prediction. BQL, below quantification limit; SD, standard deviation. Data points with concentrations below the lowest quantifiable concentration are not shown in the graph. Group 1: Dose=0.01 mg/kg, subcutaneous (SC) administration. Group 2: Dose=0.1 mg/kg, SC. Group 3: Dose=0.1 mg/kg, IV.
Figure 39B:
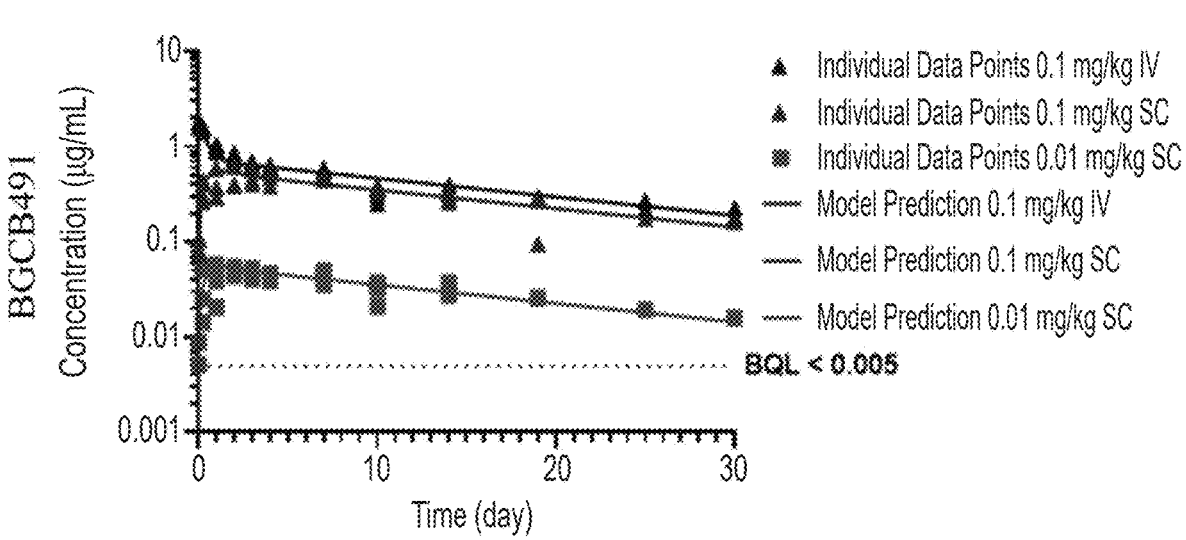

The PK properties of BGCB491 were characterized following a single-dose non-GLP PK study in male Gottingen minipigs (n=4/group). BGCB491 was administered IV to minipigs at a dose level of 0.1 mg/kg or SC at dose levels of 0.1 or 0.01 mg/kg (10 mM histidine, pH 6.5). A qualified ECLIA from MSD was used to quantitate concentrations of total BGCB491. The minipig PK study was used to estimate absorption rate (ka) and SC bioavailability (F) parameters for BGCB491. Drug exposure ($C_{max}$ and $AUC_{inf}$) increased with dose in an approximately dose-proportional manner in the dose range of 0.01 to 0.1 mg/kg. BGCB491 systemic drug exposure assessed by $C_{max}$ and AUC of 1 dose interval is shown in Table 32, and BGCB491 serum concentrations are illustrated in FIG. 39A.

opability: quality by molecular design. *MAbs* 5, 646-654, doi:10.4161/mabs.25632 (2013).

4 De Groot, A. S. & Martin, W. Reducing risk, improving outcomes: bioengineering less immunogenic protein therapeutics. *Clinical immunology* 131, 189-201, doi: 10.1016/j.clim.2009.01.009 (2009).

5. Usmani S Z, Berdeja J G, Truppel-Hartmann A, et al. KarMMa-4: Idecabtagene vicleucel (ide-cel, bb2121), a BCMA-directed CAR T-cell therapy in high-risk newly diagnosed multiple myeloma. J Clin Oncol. 2021; 39(15_suppl):TPS8053. doi: 10.1200/ JCO.2021.39.15_suppl.TPS8053

6. Berdeja J G, Krishnan A Y, Oriol A, et al. Updated results of a phase 1, first-in-human study of talquetamab, a G protein-coupled receptor family C group 5 member D

TABLE 32

Individual and mean (SD) total BGCB491 PK parameter estimates
following a single dose of BGCB491 in male minipigs (n = 4/group)

| ID | $C_{max}$ (µg/mL) | $T_{max}^{a}$ (day) | $AUC_{last}$ (µg · day/mL) | $AUC_{inf}$ (µg · day/mL) | CL (mL/day/kg) | $V_z$ (mL/kg) | $T_{1/2}$ (day) |
|---|---|---|---|---|---|---|---|
| | | | Group 1: 0.01 mg/kg SC | | | | |
| 1001 | 0.0512 | 2.00 | 0.9688 | 1.3280 | — | — | 15.80 |
| 1002 | 0.0515 | 0.25 | 0.3699 | 0.5884 | — | — | 6.73 |
| 1003 | 0.0473 | 3.00 | 0.5145 | 1.0341 | — | — | 12.54 |
| 1004 | 0.0587 | 1.00 | 0.5769 | 0.9630 | — | — | 10.12 |
| Mean | 0.0522 | 1.50 | 0.6075 | 0.9784 | — | — | 11.30 |
| SD | 0.0047 | 0.25-3.00 | 0.2560 | 0.3042 | — | — | 3.83 |
| | | | Group 2: 0.1 mg/kg SC | | | | |
| 2001 | 0.6308 | 2.00 | 10.1287 | 13.5595 | — | — | 15.22 |
| 2002 | 0.6264 | 2.00 | 7.1009 | 9.1614 | — | — | 8.23 |
| 2003 | 0.4533 | 7.00 | 5.4560 | 7.9707 | — | — | 9.52 |
| 2004 | 0.4717 | 4.00 | 5.9607 | 11.4536 | — | — | 14.90 |
| Mean | 0.5455 | 3.00 | 7.1616 | 10.5363 | — | — | 11.97 |
| SD | 0.0962 | 2.00-7.00 | 2.0943 | 2.4802 | — | — | 3.61 |
| | | | Group 3: 0.1 mg/kg IV | | | | |
| 3001 | 1.6311 | — | 6.1690 | 8.5061 | 11.7563 | 97.0290 | 5.72 |
| 3002 | 1.8074 | — | 13.3265 | 20.4865 | 4.8813 | 154.0263 | 21.87 |
| 3003 | 1.8519 | — | 6.7074 | 9.8693 | 10.1324 | 95.3027 | 6.52 |
| 3004 | 1.6333 | — | 11.7039 | 16.0389 | 6.2348 | 148.9873 | 16.56 |
| Mean | 1.7309 | — | 9.4767 | 13.7252 | 8.2512 | 123.8363 | 12.67 |
| SD | 0.1154 | — | 3.5773 | 5.5730 | 3.2273 | 32.0250 | 7.87 |

$AUC_{inf}$, area under the serum concentration-time curve extrapolated to infinity;
$AUC_{last}$, area under the serum concentration-time curve up to the last sampling point;
CL, systemic clearance;
$C_{max}$, maximum serum concentration;
IV, intravenous;
PK, pharmacokinetics;
SD, standard deviation;
$T_{1/2}$, terminal phase elimination half-life;
$T_{max}$, time to maximum serum concentration;
$V_z$, total systemic clearance.
Extrapolated AUC was > 20% for all animals.
$^{a}$Median and range are presented for $T_{max}$.

REFERENCES

1 Ridgway, J. B., Presta, L. G. & Carter, P. 'Knobs-into-holes' engineering of antibody CH3 domains for heavy chain heterodimerization. *Protein Eng* 9, 617-621, doi: 10.1093/protein/9.7.617 (1996).

2 Tustian, A. D., Endicott, C., Adams, B., Mattila, J. & Bak, H. Development of purification processes for fully human bispecific antibodies based upon modification of protein A binding avidity. *MAbs* 8, 828-838, doi:10.1080/ 19420862.2016.1160192 (2016).

3 Von Kreudenstein, T. S. et al. Improving biophysical properties of a bispecific antibody scaffold to aid devel- (GPRC5D)×CD3 bispecific antibody, in relapsed/refractory multiple myeloma (M M). J Clin Oncol. 2021; 39(15_suppl):8008. doi: 10.1200/ JCO.2021.39.15_suppl.8008

7. Usmani S Z, Berdeja J G, Madduri D, et al. Ciltacabtagene autoleucel, a B-cell maturation antigen (BCMA)-directed chimeric antigen receptor T-cell (CAR-T) therapy, in relapsed/refractory multiple myeloma (R/RMM): updated results from CARTITUDE-1. J Clin Oncol. 2021; 39(15_suppl):8005. doi: 10.1200/ JCO.2021.39.15_suppl.8005

8. Maus M V, June C H. Zoom Zoom: racing CARs for multiple myeloma. Clin Cancer Res. 2013; 19(8):1917-1919. doi:10.1158/1078-0432.CCR-13-0168

9. Darce J R, Arendt B K, Chang S K, Jelinek D F. Divergent effects of BAFF on human memory B cell differentiation into Ig-secreting cells. J Immunol. 2007; 178(9):5612-5622. doi:10.4049/jimmunol.178.9.5612

10. Tai Y T, Anderson K C. Targeting B-cell maturation antigen in multiple myeloma. Immunotherapy. 2015; 7(11):1187-1199. doi:10.2217/imt.15.77

11. Patel D R, Wallweber H J, Yin J, et al. Engineering an APRIL-specific B cell maturation antigen. J Biol Chem. 2004; 279(16):16727-16735. doi:10.1074/jbc.M312316200

12. Laurent S A, Hoffmann F S, Kuhn P H, et al. γ-Secretase directly sheds the survival receptor BCMA from plasma cells. Nat Commun. 2015; 6:7333. Published 2015 Jun. 11. doi:10.1038/ncomms8333

13. Pillarisetti K, Powers G, Luistro L, et al. Teclistamab is an active T cell-redirecting bispecific antibody against B-cell maturation antigen for multiple myeloma. Blood Adv. 2020; 4(18):4538-4549. doi:10.1182/bloodadvances.2020002393

14. Sanchez E, Li M, Kitto A, et al. Serum B-cell maturation antigen is elevated in multiple myeloma and correlates with disease status and survival. Br J Haematol. 2012; 158(6):727-738. doi:10.1111/j.1365-2141.2012.09241.x 15. Huehls A M, Coupet T A, Sentman C L. Bispecific T-cell engagers for cancer immunotherapy. Immunol Cell Biol. 2015; 93(3):290-296. doi:10.1038/icb.2014.93

16. Strohl W R, Naso M. Bispecific T-cell redirection versus chimeric antigen receptor (CAR)-T cells as approaches to kill cancer cells. Antibodies (Basel). 2019; 8(3):41. Published 2019 Jul. 3. doi:10.3390/antib8030041

17. Shah N, Chari A, Scott E, Mezzi K, Usmani S Z. B-cell maturation antigen (BCMA) in multiple myeloma: rationale for targeting and current therapeutic approaches. Leukemia. 2020; 34(4):985-1005. doi:10.1038/s41375-020-0734-z 18. Bräuner-Osborne H, Jensen A A, Sheppard P O, Brodin B, Krogsgaard-Larsen P, O'Hara P. Cloning and characterization of a human orphan family C G-protein coupled receptor GPRC5D. Biochim Biophys Acta. 2001; 1518 (3):237-248. doi:10.1016/s0167-4781(01)00197-x 19. Atamaniuk J, Gleiss A, Porpaczy E, et al. Overexpression of G protein-coupled receptor 5D in the bone marrow is associated with poor prognosis in patients with multiple myeloma. Eur J Clin Invest. 2012; 42(9):953-960. doi:10.1111/j.1365-2362.2012.02679.x 20. Frigyesi I, Adolfsson J, Ali M, et al. Robust isolation of malignant plasma cells in multiple myeloma. Blood. 2014; 123(9):1336-1340. doi:10.1182/blood-2013-09-529800

21. Smith E L, Harrington K, Staehr M, et al. GPRC5D is a target for the immunotherapy of multiple myeloma with rationally designed CAR T cells. Sci Transl Med. 2019; 11(485):eaau7746. doi:10.1126/scitranslmed.aau7746

22. Pillarisetti K, Edavettal S, Mendonga M, et al. A T-cell-redirecting bispecific G-protein-coupled receptor class 5 member DxCD3 antibody to treat multiple myeloma. Blood. 2020; 135(15):1232-1243. doi:10.1182/blood.2019003342

23. Verkleij C P M, Broekmans M E C, van Duin M, et al. Preclinical activity and determinants of response of the GPRC5DxCD3 bispecific antibody talquetamab in multiple myeloma. Blood Adv. 2021; 5(8):2196-2215. doi:10.1182/bloodadvances.2020003805

24. Kodama T, Kochi Y, Nakai W, et al. Anti-GPRC5D/CD3 bispecific T-cell-redirecting antibody for the treatment of multiple myeloma. Mol Cancer Ther. 2019; 18(9):1555-1564. doi:10.1158/1535-7163.MCT-18-1216

25. Carpenter R O, Evbuomwan M O, Pittaluga S, et al. B-cell maturation antigen is a promising target for adoptive T-cell therapy of multiple myeloma. Clin Cancer Res. 2013; 19(8):2048-2060. doi:10.1158/1078-0432.CCR-12-2422

26. Seckinger A, Delgado J A, Moser S, et al. Target Expression, Generation, Preclinical Activity, and Pharmacokinetics of the BCMA-T Cell Bispecific Antibody EM801 for Multiple Myeloma Treatment. Cancer Cell. 2017; 31(3):396-410. doi:10.1016/j.ccell.2017.02.002

27. Inoue S, Nambu T, Shimomura T. The RAIG family member, GPRC5D, is associated with hard-keratinized structures. J Invest Dermatol. 2004; 122(3):565-573. doi:10.1046/j.0022-202X.2004.12628.x 28. Rajkumar S V, Harousseau J L, Durie B, et al. Consensus recommendations for the uniform reporting of clinical trials: report of the International Myeloma Workshop Consensus Panel 1. Blood. 2011; 117(18):4691-4695. doi:10.1182/blood-2010-10-299487

29. Rodriguez-Abreu D, Bordoni A, Zucca E. Epidemiology of hematological malignancies. Ann Oncol. 2007; 18 Suppl 1:i3-i8. doi:10.1093/annonc/md1443

30. Michels T C, Petersen K E. Multiple myeloma: diagnosis and treatment. Am Fam Physician. 2017; 95(6):373-383.

31. Gandhi U H, Cornell R F, Lakshman A, et al. Outcomes of patients with multiple myeloma refractory to CD38-targeted monoclonal antibody therapy. Leukemia. 2019; 33(9):2266-2275. doi:10.1038/s41375-019-0435-7

32. Dimopoulos M A, San-Miguel J, Belch A, et al. Daratumumab plus lenalidomide and dexamethasone versus lenalidomide and dexamethasone in relapsed or refractory multiple myeloma: updated analysis of POLLUX. Haematologica. 2018; 103(12):2088-2096. doi:10.3324/haematol.2018.194282

33. Kumar S K, Callander N S, Adekola K, et al. Multiple Myeloma, Version 3.2021, NCCN clinical practice guidelines in oncology. J Natl Compr Canc Netw. 2020; 18(12): 1685-1717. Published 2020 Dec. 2. doi:10.6004/jnccn.2020.0057

34. Johnson J I, Decker S, Zaharevitz D, et al. Relationships between drug activity in NCI preclinical in vitro and in vivo models and early clinical trials. Br J Cancer. 2001; 84(10):1424-1431. doi:10.1054/bjoc.2001.1796

35. Chiu A, Xu W, He B, et al. Hodgkin lymphoma cells express TACI and BCMA receptors and generate survival and proliferation signals in response to BAFF and APRIL. Blood. 2007; 109(2):729-739. doi:10.1182/blood-2006-04-015958

36. Avery D T, Kalled S L, Ellyard J I, et al. BAFF selectively enhances the survival of plasmablasts generated from human memory B cells [published correction appears in J Clin Invest. 2004 April; 113(7):1069]. J Clin Invest. 2003; 112(2):286-297. doi:10.1172/JCI18025

37. O'Connor B P, Raman V S, Erickson L D, et al. BCMA is essential for the survival of long-lived bone marrow plasma cells. J Exp Med. 2004; 199(1):91-98. doi:10.1084/jem.20031330

38. Bu D X, Singh R, Choi E E, et al. Pre-clinical validation of B cell maturation antigen (BCMA) as a target for T cell immunotherapy of multiple myeloma. Oncotarget. 2018; 9(40):25764-25780. Published 2018 May 25. doi:10.18632/oncotarget.25359

39. Carpenter R O, Evbuomwan M O, Pittaluga S, et al. B-cell maturation antigen is a promising target for adoptive T-cell therapy of multiple myeloma. Clin Cancer Res. 2013; 19(8):2048-2060. doi:10.1158/1078-0432.CCR-12-2422

40. Laabi Y, Gras M P, Carbonnel F, et al. A new gene, BCM, on chromosome 16 is fused to the interleukin 2 gene by a t(4; 16)(q26; p13) translocation in a malignant T cell lymphoma. EMBO J. 1992; 11(11):3897-3904.

41. Laabi Y, Gras M P, Brouet J C, Berger R, Larsen C J, Tsapis A. The BCMA gene, preferentially expressed during B lymphoid maturation, is bidirectionally transcribed. Nucleic Acids Res. 1994; 22(7):1147-1154. doi:10.1093/nar/22.7.1147

42. Kalled S L. The role of BAFF in immune function and implications for autoimmunity. Immunol Rev. 2005; 204:43-54. doi:10.1111/j.0105-2896.2005.00219.x 43. Ng L G, Sutherland A P, Newton R, et al. B cell-activating factor belonging to the TNF family (BAFF)-R is the principal BAFF receptor facilitating BAFF costimulation of circulating T and B cells. J Immunol. 2004; 173(2):807-817. doi:10.4049/jimmunol.173.2.807

44. Venkateshaiah S U, Bam R, Li X, Khan S, Ling W, Randal S S, Yaccoby S. GPRC5D is a cell surface plasma cell marker whose expression is high in myeloma cells and reduced following coculture with osteoclasts. Blood. 2013; 122(21):3099. doi: 10.1182/blood.V122.21.3099.3099

45. Kamperschroer C, Shenton J, Lebrec H, Leighton J K, Moore P A, Thomas O. Summary of a workshop on preclinical and translational safety assessment of CD3 bispecifics. J Immunotoxicol. 2020; 17(1):67-85. doi:10.1080/1547691X.2020.1729902

46. Li J, Piskol R, Ybarra R, et al. CD3 bispecific antibody-induced cytokine release is dispensable for cytotoxic T cell activity. Sci Transl Med. 2019; 11(508):eaax8861. doi:10.1126/scitranslmed.aax8861

47. Leong S R, Sukumaran S, Hristopoulos M, et al. An anti-CD3/anti-CLL-1 bispecific antibody for the treatment of acute myeloid leukemia. Blood. 2017; 129(5):609-618. doi:10.1182/blood-2016-08-735365

48. Singh A, Dees S, Grewal I S. Overcoming the challenges associated with CD3+ T-cell redirection in cancer. Br J Cancer. 2021; 124(6):1037-1048. doi:10.1038/s41416-020-01225-5

49. Jain T, Litzow M R. Management of toxicities associated with novel immunotherapy agents in acute lymphoblastic leukemia. Ther Adv Hematol. 2020; 11:2040620719899897. Published 2020 Jan. 20. doi:10.1177/2040620719899897

50. Ling J, Zhou H, Jiao Q, Davis H M. Interspecies scaling of therapeutic monoclonal antibodies: initial look. J Clin Pharmacol. 2009; 49(12):1382-1402. doi:10.1177/0091270009337134

51. Woo S, Jusko W J. Interspecies comparisons of pharmacokinetics and pharmacodynamics of recombinant human erythropoietin. Drug Metab Dispos. 2007; 35(9):1672-1678. doi:10.1124/dmd.107.015248

52. Li J, Stagg N J, Johnston J, et al. Membrane-proximal epitope facilitates efficient T cell synapse formation by anti-FcRH5/CD3 and is a requirement for myeloma cell killing. Cancer Cell. 2017; 31(3):383-395. doi:10.1016/j.ccell.2017.02.001

53. ClinicalTrials.gov. NCT02879695: Blinatumomab and nivolumab with or without ipilimumab in treating patients with poor-risk relapsed or refractory CD19+ precursor B-lymphoblastic leukemia. https://clinicaltrials.gov/ct2/show/NCT02879695. Accessed: 23 Jun. 2021.

54. Guillerey C, Nakamura K, Pichler A C, et al. Chemotherapy followed by anti-CD137 mAb immunotherapy improves disease control in a mouse myeloma model. JCI Insight. 2019; 5(14):e125932. Published 2019 Jun. 13. doi:10.1172/jci.insight.125932

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

```
List of Sequences
CD3B376 LCDR1
                                            SEQ ID NO: 1
TGTSSNIGTYKFVS

CD3B376 LCDR2
                                            SEQ ID NO: 2
EVSKRPS

CD3B376 LCDR3
                                            SEQ ID NO: 3
VSYAGSGTLL

CD3B376 HCDR1
                                            SEQ ID NO: 4
GDSVFNNNAAWS

CD3B376 HCDR2
                                            SEQ ID NO: 5
RTYYRSKWLYD

CD3B376 HCDR3
                                            SEQ ID NO: 6
GYSSSFDY
```

-continued

CD3B376 VL
SEQ ID NO: 7
QSALTQPASVSGSPGQSITISCTGTSSNIGTYKFVSWYQQHPDKAPKVLLYEVSKRP

SGVSSRFSGSKSGNTASLTISGLQAEDQADYHCVSYAGSGTLLFGGGTKLTVL

CD3B376 VH
SEQ ID NO: 8
QVQLQQSGPRLVRPSQTLSLTCAISGDSVFNNNAAWSWIRQSPSRGLEWLGRTYY

RSKWLYDYAVSVKSRITVNPDTSRNQFTLQLNSVTPEDTALYYCARGYSSSFDYW

GQGTLVTVSS

GC5B680 LCDR1
SEQ ID NO: 9
RSSQSLVHSDGNTYLS

GC5B680 LCDR2
SEQ ID NO: 10
KISNRFF

GC5B680 LCDR3
SEQ ID NO: 11
MQATQFPHT

GC5B680 HCDR1
SEQ ID NO: 12
GFSLTNIRMSVS

GC5B680 HCDR2
SEQ ID NO: 13
HIFSNDEKS

GC5B680 HCDR3
SEQ ID NO: 14
MRLPYGMDV

GC5B680 VL
SEQ ID NO: 15
DIVMTQTPLSSPVTLGQPASISCRSSQSLVHSDGNTYLSWLQQRPGQPPRLLIYKIS

NRFFGVPDRFSGSGAGTDFTLKISRVEAEDVGVYYCMQATQFPHTFGQGTKLEIK

GC5B680 VH
SEQ ID NO: 16
QVTLKESGPVLVKPTETLTLTCTVSGFSLTNIRMSVSWIRQPPGKALEWLAHIFSND

EKSYSTSLKSRLTISRDTSKSQVVLTLTNVDPVDTATYYCARMRLPYGMDVWGQ

GTTVTVSS

BCMB519 LCDR1
SEQ ID NO: 17
RASQSISSSFLT

BCMB519 LCDR2
SEQ ID NO: 18
GASSRAT

BCMB519 LCDR3
SEQ ID NO: 19
QHYGSSPMYT

BCMB519 HCDR1
SEQ ID NO: 20
GFTFSSYAMS

BCMB519 HCDR2
SEQ ID NO: 21
AISGSGGSTY

BCMB519 HCDR3
SEQ ID NO: 22
DEGYSSGHYYGMDV

-continued

BCMB519 VL
```
                                         SEQ ID NO: 23
EIVLTQSPGTLSLSPGERATLSCRASQSISSSFLTWYQQKPGQAPRLLIYGASSRATG

IPDRFSGGGSGTDFTLTISRLEPEDFAVYYCQHYGSSPMYTEGQGTKLEIK
```

BCMB519 VH
```
                                         SEQ ID NO: 24
EVQLLESGGGLVQPGGSLRLSCAASGFTESSYAMSWVRQAPGKGLEWVSAISGSG

GSTYYADSVKGRETISRDNSKNTLYLQMNSLRAEDTAVYYCAKDEGYSSGHYYG

MDVWGQGTTVTVSS
``` linker
```
                                         SEQ ID NO: 25
GGSEGKSSGSGSESKSTGGS
```

BGCB463 Heavy chain 1
```
                                         SEQ ID NO: 26
QVQLQQSGPRLVRPSQTLSLTCAISGDSVENNNAAWSWIRQSPSRGLEWLGRTYY

RSKWLYDYAVSVKSRITVNPDTSRNQFTLQLNSVTPEDTALYYCARGYSSSFDYW

GQGTLVTVSSASTKGPSVFPLAPSSKSTSGGTAALGCLVKDYFPEPVTVSWNSGAL

TSGVHTFPAVLQSSGLYSLSSVVTVPSSSLGTQTYICNVNHKPSNTKVDKKVEPKS

CDKTHTCPPCPAPEAAGGPSVFLEPPKPKDTLMISRTPEVTCVVVSVSHEDPEVKF

NWYVDGVEVHNAKTKPREEQYNSTYRVVSVLTVLHQDWLNGKEYKCKVSNKA

LPAPIEKTISKAKGQPREPQVYTLPPSREEMTKNQVSLSCAVKGFYPSDIAVEWESN

GQPENNYKTTPPVLDSDGSFFLVSKLTVDKSRWQQGNVFSCSVMHEALHNRFTQ

KSLSLSPGK
```

BGCB463 Light chain 1
```
                                         SEQ ID NO: 27
QSALTQPASVSGSPGQSITISCTGTSSNIGTYKFVSWYQQHPDKAPKVLLYEVSKRP

SGVSSRFSGSKSGNTASLTISGLQAEDQADYHCVSYAGSGTLLFGGGTKLTVLGQP

KAAPSVTLFPPSSEELQANKATLVCLISDFYPGAVTVAWKADSSPVKAGVETTTPS

KQSNNKYAASSYLSLTPEQWKSHRSYSCQVTHEGSTVEKTVAPTECS
```

BGCB463 Heavy chain 2
```
                                         SEQ ID NO: 28
DIVMTQTPLSSPVTLGQPASISCRSSQSLVHSDGNTYLSWLQQRPGQPPRLLIYKIS

NRFFGVPDRFSGSGAGTDFTLKISRVEAEDVGVYYCMQATQFPHTFGQGTKLEIK

GGSEGKSSGSGSESKSTGGSQVTLKESGPVLVKPTETLTLTCTVSGFSLTNIRMSVS

WIRQPPGKALEWLAHIFSNDEKSYSTSLKSRLTISRDTSKSQVVLTLTNVDPVDTA

TYYCARMRLPYGMDVWGQGTTVTVSSEPKSSDKTHTCPPCPAPEAAGGPSVFLFP

PKPKDTLMISRTPEVTCVVVSVSHEDPEVKFNWYVDGVEVHNAKTKPREEQYNST

YRVVSVLTVLHQDWLNGKEYKCKVSNKALPAPIEKTISKAKGQPREPQVYTLPPS

REEMTKNQVSLWCLVKGFYPSDIAVEWESNGQPENNYKTTPPVLDSDGSFFLYSK

LTVDKSRWQQGNVFSCSVMHEALHNHYTQKSLSLSPGKGGSEGKSSGSGSESKST

GGSEIVLTQSPGTLSLSPGERATLSCRASQSISSSFLTWYQQKPGQAPRLLIYGASSR

ATGIPDRFSGGGSGTDFTLTISRLEPEDFAVYYCQHYGSSPMYTFGQGTKLEIKGGS

EGKSSGSGSESKSTGGSEVQLLESGGGLVQPGGSLRLSCAASGFTFSSYAMSWVR

QAPGKGLEWVSAISGSGGSTYYADSVKGRETISRDNSKNTLYLQMNSLRAEDTAV

YYCAKDEGYSSGHYYGMDVWGQGTTVTVSS
```

-continued

BGCB491 Heavy chain 1

SEQ ID NO: 29

QVQLQQSGPRLVRPSQTLSLTCAISGDSVFNNNAAWSWIRQSPSRGLEWLGRTYY

RSKWLYDYAVSVKSRITVNPDTSRNQFTLQLNSVTPEDTALYYCARGYSSSFDYW

GQGTLVTVSSASTKGPSVFPLAPSSKSTSGGTAALGCLVKDYFPEPVTVSWNSGAL

TSGVHTFPAVLQSSGLYSLSSVVTVPSSSLGTQTYICNVNHKPSNTKVDKKVEPKS

CDKTHTCPPCPAPEAAGGPSVFLEPPKPKDTLMISRTPEVTCVVVSVSHEDPEVKF

NWYVDGVEVHNAKTKPREEQYNSTYRVVSVLTVLHQDWLNGKEYKCKVSNKA

LPAPIEKTISKAKGQPREPQVYTLPPSREEMTKNQVSLSCAVKGFYPSDIAVEWESN

GQPENNYKTTPPVLDSDGSFFLVSKLTVDKSRWQQGNVFSCSVMHEALHNRFTQ

KSLSLSPGKGGGGSGGGGSGGGGSGGGGSDIVMTQTPLSSPVTLGQPASISCRSSQ

SLVHSDGNTYLSWLQQRPGQPPRLLIYKISNREFGVPDRFSGSGAGTDFTLKISRVE

AEDVGVYYCMQATQFPHTFGQGTKLEIKGGSEGKSSGSGSESKSTGGSQVTLKES

GPVLVKPTETLTLTCTVSGFSLTNIRMSVSWIRQPPGKALEWLAHIFSNDEKSYSTS

LKSRLTISRDTSKSQVVLTLTNVDPVDTATYYCARMRLPYGMDVWGQGTTVTVS

S

BGCB491 Light chain

SEQ ID NO: 30

QSALTQPASVSGSPGQSITISCTGTSSNIGTYKFVSWYQQHPDKAPKVLLYEVSKRP

SGVSSRFSGSKSGNTASLTISGLQAEDQADYHCVSYAGSGTLLFGGGTKLTVLGQP

KAAPSVTLFPPSSEELQANKATLVCLISDFYPGAVTVAWKADSSPVKAGVETTTPS

KQSNNKYAASSYLSLTPEQWKSHRSYSCQVTHEGSTVEKTVAPTECS

BGCB491 Heavy chain 2

SEQ ID NO: 31

EIVLTQSPGTLSLSPGERATLSCRASQSISSSFLTWYQQKPGQAPRLLIYGASSRATG

IPDRFSGGGSGTDFTLTISRLEPEDFAVYYCQHYGSSPMYTFGQGTKLEIKGGSEGK

SSGSGSESKSTGGSEVQLLESGGGLVQPGGSLRLSCAASGFTFSSYAMSWVRQAPG

KGLEWVSAISGSGGSTYYADSVKGRETISRDNSKNTLYLQMNSLRAEDTAVYYCA

KDEGYSSGHYYGMDVWGQGTTVTVSSEPKSSDKTHTCPPCPAPEAAGGPSVFLFP

PKPKDTLMISRTPEVTCVVVSVSHEDPEVKFNWYVDGVEVHNAKTKPREEQYNST

YRVVSVLTVLHQDWLNGKEYKCKVSNKALPAPIEKTISKAKGQPREPQVYTLPPS

REEMTKNQVSLWCLVKGFYPSDIAVEWESNGQPENNYKTTPPVLDSDGSFFLYSK

LTVDKSRWQQGNVFSCSVMHEALHNHYTQKSLSLSPGK

BCMA CDR

SEQ ID NO: 32

SGSYFWG

BCMA CDR

SEQ ID NO: 33

SIYYSGITYYNPSLKS

BCMA CDR

SEQ ID NO: 34

HDGAVAGLFDY

BCMA CDR

SEQ ID NO: 35

SSSYYWG

BCMA CDR

SEQ ID NO: 36

SIYYSGSTYYNPSLKS

-continued

```
BCMA CDR
                                     SEQ ID NO: 37
HDGATAGLFDY

BCMA CDR
                                     SEQ ID NO: 38
SSSYFWG

BCMA CDR
                                     SEQ ID NO: 39
GGNNIGSKSVH

BCMA CDR
                                     SEQ ID NO: 40
DDSDRPS

BCMA CDR
                                     SEQ ID NO: 41
QVWDSSSDHVV

BCMA VH
                                     SEQ ID NO: 42
QLQLQESGPGLVKPSETLSLTCTVSGGSISSGSYFWGWIRQPPGKGLEWIGSIYYSG

ITYYNPSLKSRVTISVDTSKNQFSLKLSSVTAADTAVYYCARHDGAVAGLFDYWG

QGTLVTVSSA

BCMA VH
                                     SEQ ID NO: 43
QLQLQESGPGLVKPSETLSLTCTVSGGSISSSSYFWGWIRQPPGKGLEWIGSIYYSGI

TYYNPSLKSRVTISVDTSKNQFSLKLSSVTAADTAVYYCARHDGAVAGLFDYWG

QGTLVTVSSA

BCMA VH
                                     SEQ ID NO: 44
QLQLQESGPGLVKPSETLSLTCTVSGGSISSGSYFWGWIRQPPGKGLEWIGSIYYSG

ITYYNPSLKSRVTISVDTSKNQFSLKLSSVTAADTAVYYCARHDGATAGLFDYWG

QGTLVTVSSA

BCMA VH
                                     SEQ ID NO: 45
QLQLQESGPGLVKPSETLSLTCTVSGGSISSGSYFWGWIRQPPGKGLEWIGSIYYSG

STYYNPSLKSRVTISVDTSKNQFSLKLSSVTAADTAVYYCARHDGAVAGLFDYWG

QGTLVTVSSA

BCMA VH
                                     SEQ ID NO: 46
QLQLQESGPGLVKPSETLSLTCTVSGGSISSSSYFWGWIRQPPGKGLEWIGSIYYSGI

TYYNPSLKSRVTISVDTSKNQFSLKLSSVTAADTAVYYCARHDGATAGLFDYWG

QGTLVTVSSA

BCMA VH
                                     SEQ ID NO: 47
QLQLQESGPGLVKPSETLSLTCTVSGGSISSSSYFWGWIRQPPGKGLEWIGSIYYSG

RTYYNPSLKSRVTISVDTSKNQFSLKLSSVTAADTAVYYCARHDGATAGLFDYWG

QGTLVTVSSA

BCMA VL
                                     SEQ ID NO: 48
SYVLTQPPSVSVAPGQTARITCGGNNIGSKSVHWYQQPPGQAPVVVVYDDSDRPS

GIPERFSGSNSGNTATLTISRVEAGDEAVYYCQVWDSSSDHVVFGGGTKLTVL

GPRC5D CDR
                                     SEQ ID NO: 49
SYAIS

GPRC5D CDR
                                     SEQ ID NO: 50
NYWMS
```

-continued

```
GPRC5D CDR
                                    SEQ ID NO: 51
SYFIG

GPRC5D CDR
                                    SEQ ID NO: 52
GYTMN

GPRC5D CDR
                                    SEQ ID NO: 53
GIIPIFGTANYAQKFQG

GPRC5D CDR
                                    SEQ ID NO: 54
GISYSGGSKYYASSVKG

GPRC5D CDR
                                    SEQ ID NO: 55
IIYPGKSDTRYSPSFQG

GPRC5D CDR
                                    SEQ ID NO: 56
LINPYNSDTNYAQKLQG

GPRC5D CDR
                                    SEQ ID NO: 57
ESRWRGYKLD

GPRC5D CDR
                                    SEQ ID NO: 58
AAFDFGRRAVRLD

GPRC5D CDR
                                    SEQ ID NO: 59
VYSFGGRHKALFDY

GPRC5D CDR
                                    SEQ ID NO: 60
VALRVALDY

GPRC5D CDR
                                    SEQ ID NO: 61
RASQSISSYLN

GPRC5D CDR
                                    SEQ ID NO: 62
RASQSVSSYLA

GPRC5D CDR
                                    SEQ ID NO: 63
KASQNVATHVG

GPRC5D CDR
                                    SEQ ID NO: 64
AASSLQS

GPRC5D CDR
                                    SEQ ID NO: 65
DASNRAT

GPRC5D CDR
                                    SEQ ID NO: 66
SASYRYS

GPRC5D CDR
                                    SEQ ID NO: 67
QQSYSTPLT

GPRC5D CDR
                                    SEQ ID NO: 68
QQRSNWPLT

GPRC5D CDR
                                    SEQ ID NO: 69
QQYNRYPYT

GPRC5D CDR
                                    SEQ ID NO: 70
DYGMH
```

-continued

GPRC5D CDR
SEQ ID NO: 71
SYWIG

GPRC5D CDR
SEQ ID NO: 72
GYAMS

GPRC5D CDR
SEQ ID NO: 73
SYGIS

GPRC5D CDR
SEQ ID NO: 74
GYSFTGYTMN

GPRC5D CDR
SEQ ID NO: 75
SYAMS

GPRC5D CDR
SEQ ID NO: 76
GFSLTSYNVH

GPRC5D CDR
SEQ ID NO: 77
AIKYSGGSTYYADSVKG

GPRC5D CDR
SEQ ID NO: 78
GISYSGGSKYYADSVKG

GPRC5D CDR
SEQ ID NO: 79
IIYPGDSDTRYSPSFQG

GPRC5D CDR
SEQ ID NO: 80
AISGSGGSTYYADSVKG

GPRC5D CDR
SEQ ID NO: 81
GIIPIFGNINYAQKFQG

GPRC5D CDR
SEQ ID NO: 82
LINPYNGDTN

GPRC5D CDR
SEQ ID NO: 83
VIWAGGSTNYNSALMS

GPRC5D CDR
SEQ ID NO: 84
RAESGPGLDY

GPRC5D CDR
SEQ ID NO: 85
AAWDFGRRAVRLDY

GPRC5D CDR
SEQ ID NO: 86
IGFYGRSFRIFDY

GPRC5D CDR
SEQ ID NO: 87
VDRSFGRSRYTLDY

GPRC5D CDR
SEQ ID NO: 88
VSRRFKRFAYYFDY

GPRC5D CDR
SEQ ID NO: 89
SNFLPVVFDY

GPRC5D CDR
SEQ ID NO: 90
DGIRLRFAY

-continued

GPRC5D CDR
                                        SEQ ID NO: 91
KSSQSVLYSSNNKNYLA

GPRC5D CDR
                                        SEQ ID NO: 92
RASQSVRKSLA

GPRC5D CDR
                                        SEQ ID NO: 93
WASTRES

GPRC5D CDR
                                        SEQ ID NO: 94
TASNRAT

GPRC5D CDR
                                        SEQ ID NO: 95
QQYYSTPLT

GPRC5D CDR
                                        SEQ ID NO: 96
QQYFRAPIT

GPRC5D VH
                                        SEQ ID NO: 97
QVQLVQSGAEVKKPGSSVKVSCKASGGTFSSYAISWVRQAPGQGLEWMGGIIPIF

GTANYAQKFQGRVTITADESTSTAYMELSSLRSEDTAVYYCARESRWRGYKLDY

WGQGTLVTVSS

GPRC5D VH
                                        SEQ ID NO: 98
EVQLLESGGGLVQPGGSLRLSCAASGFTFSNYWMSWVRQAPGKGLEWVSGISYS

GGSKYYASSVKGRFTISRDNSKNTLYLQMNSLRAEDTAVYYCAKAAFDFGRRAV

RLDYWGQGTLVTVSS

GPRC5D VH
                                        SEQ ID NO: 99
EVQLVQSGAEVKKPGESLKISCKGSGYSFTSYFIGWVRQMPGKGLEWMGITYPGK

SDTRYSPSFQGQVTISADKSISTAYLQWSSLKASDTAMYYCARVYSFGGRHKALF

DYWGQGTLVTVSS

GPRC5D VH
                                        SEQ ID NO: 100
QVQLVQSGAEVKKPGASVKVSCKASGYSFTGYTMNWVRQAPGQGLEWMGLINP

YNSDTNYAQKLQGRVTMTTDTSTSTAYMELRSLRSDDTAVYYCARVALRVALD

YWGQGTLVTVSS

GPRC5D VL
                                        SEQ ID NO: 101
DIQMTQSPSSLSASVGDRVTITCRASQSISSYLNWYQQKPGKAPKLLIYAASSLQSG

VPSRFSGSGSGTDFTLTISSLQPEDFATYYCQQSYSTPLTFGQGTKVEIK

GPRC5D VL
                                        SEQ ID NO: 102
EIVLTQSPATLSLSPGERATLSCRASQSVSSYLAWYQQKPGQAPRLLIYDASNRAT

GIPARFSGSGSGTDFTLTISSLEPEDFAVYYCQQRSNWPLTFGQGTKVEIK

GPRC5D VL
                                        SEQ ID NO: 103
DIQMTQSPSSLSASVGDRVTITCKASQNVATHVGWYQQKPGKAPKRLIYSASYRY

SGVPSRFSGSGSGTEFTLTISNLQPEDFATYYCQQYNRYPYTFGQGTKLEIK

-continued

GPRC5D VH
```
                                       SEQ ID NO: 104
EVQLLESGGGLVQPGGSLRLSCAASGFTFSDYGMHWVRQAPGKGLEWVSAIKYS

GGSTYYADSVKGRFTISRDNSKNTLYLQMNSLRAEDTAVYYCAKRAESGPGLDY

WGQGTLVTVSS
```

GPRC5D VH
```
                                       SEQ ID NO: 105
EVQLLESGGGLVQPGGSLRLSCAASGFTFSNYWMSWVRQAPGKGLEWVSGISYS

GGSKYYADSVKGRFTISRDNSKNTLYLQMNSLRAEDTAVYYCAKAAWDFGRRA

VRLDYWGQGTLVTVSS
```

GPRC5D VH
```
                                       SEQ ID NO: 106
EVQLVQSGAEVKKPGESLKISCKGSGYSFTSYWIGWVRQMPGKGLEWMGIIYPGD

SDTRYSPSFQGQVTISADKSISTAYLQWSSLKASDTAMYYCARIGFYGRSFRIFDY

WGQGTLVTVSS
```

GPRC5D VH
```
                                       SEQ ID NO: 107
EVQLVQSGAEVKKPGESLKISCKGSGYSFTSYWIGWVRQMPGKGLEWMGIIYPGD

SDTRYSPSFQGQVTISADKSISTAYLQWSSLKASDTAMYYCARVYSFGGRHKALF

DYWGQGTLVTVSS
```

GPRC5D VH
```
                                       SEQ ID NO: 108
EVQLLESGGGLVQPGGSLRLSCAASGFTFSGYAMSWVRQAPGKGLEWVSAISGSG

GSTYYADSVKGRFTISRDNSKNTLYLQMNSLRAEDTAVYYCAKVDRSFGRSRYTL

DYWGQGTLVTVSS
```

GPRC5D VH
```
                                       SEQ ID NO: 109
QVQLVQSGAEVKKPGSSVKVSCKASGGTFSSYGISWVRQAPGQGLEWMGGIIPIF

GNINYAQKFQGRVTITADESTSTAYMELSSLRSEDTAVYYCARVSRRFKRFAYYF

DYWGQGTLVTVSS
```

GPRC5D VH
```
                                       SEQ ID NO: 110
QVQLVQSGAEVKKPGASVKVSCKASGYSFTGYTMNWVRQAPGQGLEWMGLINP

YNGDTNYAQKLQGRVTMTTDTSTSTAYMELRSLRSDDTAVYYCARVALRVALD

YWGQGTLVTVSS
```

GPRC5D VH
```
                                       SEQ ID NO: 111
EVQLLESGGGLVQPGGSLRLSCAASGFTFSSYAMSWVRQAPGKGLEWVSAISGSG

GSTYYADSVKGRFTISRDNSKNTLYLQMNSLRAEDTAVYYCAKSNFLPVVFDYW

GQGTLVTVSS
```

GPRC5D VH
```
                                       SEQ ID NO: 112
QVTLKESGPVLVKPTETLTLTCTVSGFSLTSYNVHWIRQPPGKALEWLAVIWAGG

STNYNSALMSRLTISKDTSKSQVVLTMTNMRAEDTATYYCARDGIRLRFAYWGQ

GTLVTVSS
```

GPRC5D VL
```
                                       SEQ ID NO: 113
DIVMTQSPDSLAVSLGERATINCKSSQSVLYSSNNKNYLAWYQQKPGQPPKLLIY

WASTRESGVPDRFSGSGSGTDFTLTISSLQAEDVAVYYCQQYYSTPLTFGQGTKVE

IK
```

GPRC5D VL

SEQ ID NO: 114

EIVLTQSPATLSLSPGERATLSCRASQSVRKSLAWYQQKPGQAPRLLIYTASNRAT

GIPARFSGSGSGTDFTLTISSLEPEDFAVYYCQQYFRAPITFGQGTKVEIKK

GPRC5D VL

SEQ ID NO: 115

EIVMTQSPATLSVSPGERATLSCKASQNVATHVGWYQQKPGQAPRLLIYSASYRY

SGIPARFSGSGSGTEFTLTISSLQSEDFAVYYCQQYNRYPYTFGQGTKLEIK

GPRC5D

SEQ ID NO: 116

MYKDCIESTGDYFLLCDAEGPWGIILESLAILGIVVTILLLLAFLFLMRKIQDCSQW

NVLPTQLLELLSVLGLEGLAFAFIIELNQQTAPVRYFLEGVLFALCFSCLLAHASNL

VKLVRGCVSFSWTTILCIAIGCSLLQIIIATEYVTLIMTRGMMFVNMTPCQLNVDFV

VLLVYVLFLMALTFFVSKATECGPCENWKQHGRLIFITVLFSIIIWVVWISMLLRGN

PQFQRQPQWDDPVVCIALVTNAWVFLLLYIVPELCILYRSCRQECPLQGNACPVTA

YQHSFQVENQELSRARDSDGAEEDVALTSYGTPIQPQTVDPTQECEIPQAKLSPQQ

DAGGV

CD3 CDR 1

SEQ ID NO: 117

TYAMN

CD3 CDR 2

SEQ ID NO: 118

RIRSKYNNYATYYAASVKG

CD3 CDR 3

SEQ ID NO: 119

HGNFGNSYVSWFAY

CD3 VH

SEQ ID NO: 120

EVQLVESGGGLVQPGGSLRLSCAASGFTENTYAMNWVRQAPGKGLEWVARIRSK

YNNYATYYAASVKGRFTISRDDSKNSLYLQMNSLKTEDTAVYYCARHGNFGNSY

VSWFAYWGQGTLVTVSS

CD3 Heavy chain

SEQ ID NO: 121

EVQLVESGGGLVQPGGSLRLSCAASGFTENTYAMNWVRQAPGKGLEWVARIRSK

YNNYATYYAASVKGRFTISRDDSKNSLYLQMNSLKTEDTAVYYCARHGNFGNSY

VSWFAYWGQGTLVTVSSASTKGPSVFPLAPCSRSTSESTAALGCLVKDYFPEPVTV

SWNSGALTSGVHTFPAVLQSSGLYSLSSVVTVPSSSLGTKTYTCNVDHKPSNTKV

DKRVESKYGPPCPPCPAPEAAGGPSVFLEPPKPKDTLMISRTPEVTCVVVDVSQED

PEVQFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFYPSDIAVE

WESNGQPENNYKTTPPVLDSDGSFLLYSKLTVDKSRWQEGNVFSCSVMHEALHN

HYTQKSLSLSLGK

CD3 CDR 1

SEQ ID NO: 122

RSSTGAVTTSNYAN

CD3 CDR 2

SEQ ID NO: 123

GTNKRAP

CD3 CDR 3

SEQ ID NO: 124

ALWYSNLWV

-continued

CD3 VL

SEQ ID NO: 125

QTVVTQEPSLTVSPGGTVTLTCRSSTGAVTTSNYANWVQQKPGQAPRGLIGGTNK

RAPGTPARFSGSLLGGKAALTLSGVQPEDEAEYYCALWYSNLWVFGGGTKLTVL

CD3 Light chain

SEQ ID NO: 126

QTVVTQEPSLTVSPGGTVTLTCRSSTGAVTTSNYANWVQQKPGQAPRGLIGGTNK

RAPGTPARFSGSLLGGKAALTLSGVQPEDEAEYYCALWYSNLWVFGGGTKLTVL

GQPKAAPSVTLFPPSSEELQANKATLVCLISDFYPGAVTVAWKADSSPVKAGVETT

TPSKQSNNKYAASSYLSLTPEQWKSHRSYSCQVTHEGSTVEKTVAPTECS linker

SEQ ID NO: 127

GGGSGGGS linker

SEQ ID NO: 128

GGGSGGGSGGGS linker

SEQ ID NO: 129

GGGSGGGSGGGSGGGS linker

SEQ ID NO: 130

GGGSGGGSGGGSGGGSGGGS linker

SEQ ID NO: 131

GGGGSGGGGSGGGGS linker

SEQ ID NO: 132

GGGGSGGGGSGGGGSGGGGSGGGGS linker

SEQ ID NO: 133

GSTSGSGKPGSGEGSTKG linker

SEQ ID NO: 134

IRPRAIGGSKPRVA linker

SEQ ID NO: 135

GKGGSGKGGSGKGGS linker

SEQ ID NO: 136

GGKGSGGKGSGGKGS linker

SEQ ID NO: 137

GGGKSGGGKSGGGKS linker

SEQ ID NO: 138

GKGKSGKGKSGKGKS linker

SEQ ID NO: 139

GGGKSGGKGSGKGGS linker

SEQ ID NO: 140

GKPGSGKPGSGKPGS linker

SEQ ID NO: 141

GKPGSGKPGSGKPGSGKPGS linker

SEQ ID NO: 142

GKGKSGKGKSGKGKSGKGKS linker

SEQ ID NO: 143

STAGDTHLGGEDFD linker

SEQ ID NO: 144

GEGGSGEGGSGEGGS linker

SEQ ID NO: 145

GGEGSGGEGSGGEGS linker

SEQ ID NO: 146

GEGESGEGESGEGES linker

SEQ ID NO: 147

GGGESGGEGSGEGGS linker

SEQ ID NO: 148

GEGESGEGESGEGESGEGES linker

SEQ ID NO: 149

GSTSGSGKPGSGEGSTKG linker

SEQ ID NO: 150

PRGASKSGSASQTGSAPGS linker

SEQ ID NO: 151

GTAAAGAGAAGGAAAGAAG linker

SEQ ID NO: 152

GTSGSSGSGSGGSGSGGGG linker

SEQ ID NO: 153

GKPGSGKPGSGKPGSGKPGS linker

SEQ ID NO: 154

GSGS linker

SEQ ID NO: 155

APAPAPAPAP linker

SEQ ID NO: 156

APAPAPAPAPAPAPAPAPAP linker

SEQ ID NO: 157

AEAAAKEAAAKEAAAAKEAAAAKEAAAAKAAA

Ig1

SEQ ID NO: 158

ASTKGPSVFPLAPSSKSTSGGTAALGCLVKDYFPEPVTVSWNSGALTSGVHTFPAV

LQSSGLYSLSSVVTVPSSSLGTQTYICNVNHKPSNTKVDKKVEPKSCDKTHTCPPC

PAPELLGGPSVFLFPPKPKDTLMISRTPEVTCVVVDVSHEDPEVKFNWYVDGVEV

HNAKTKPREEQYNSTYRVVSVLTVLHQDWLNGKEYKCKVSNKALPAPIEKTISKA

KGQPREPQVYTLPPSREEMTKNQVSLTCLVKGFYPSDIAVEWESNGQPENNYKTT

PPVLDSDGSFFLYSKLTVDKSRWQQGNVFSCSVMHEALHNHYTQKSLSLSPGK

Ig1

SEQ ID NO: 159

ASTKGPSVFPLAPSSKSTSGGTAALGCLVKDYFPEPVTVSWNSGALTSGVHTFPAV

LQSSGLYSLSSVVTVPSSSLGTQTYICNVNHKPSNTKVDKKVEPKSCDKTHTCPPC

PAPEAAGGPSVFLFPPKPKDTLMISRTPEVTCVVVSVHEDPEVKFNWYVDGVEV

-continued

HNAKTKPREEQYNSTYRVVSVLTVLHQDWLNGKEYKCKVSNKALPAPIEKTISKA

KGQPREPQVYTLPPSREEMTKNQVSLTCLVKGFYPSDIAVEWESNGQPENNYKTT

PPVLDSDGSFFLYSKLTVDKSRWQQGNVFSCSVMHEALHNHYTQKSLSLSPGK

Ig4

SEQ ID NO: 160

ASTKGPSVFPLAPCSRSTSESTAALGCLVKDYFPEPVTVSWNSGALTSGVHTFPAV

LQSSGLYSLSSVVTVPSSSLGTKTYTCNVDHKPSNTKVDKRVESKYGPPCPPCPAP

EAAGGPSVFLFPPKPKDTLMISRTPEVTCVVVDVSQEDPEVQFNWYVDGVEVHNA

KTKPREEQFNSTYRVVSVLTVLHQDWLNGKEYKCKVSNKGLPSSIEKTISKAKGQ

PREPQVYTLPPSQEEMTKNQVSLTCLVKGFYPSDIAVEWESNGQPENNYKTTPPVL

DSDGSFFLYSRLTVDKSRWQEGNVFSCSVMHEALHNHYTQKSLSLSLGK

CD3 epitope

SEQ ID NO: 161

QDGNEEMGGITQTP

BCMA epitope

SEQ ID NO: 162

LLHACIPCQL linker

SEQ ID NO: 163

GGGGSGGGGSGGGGSGGGGS

BCMA CDR

SEQ ID NO: 164

SIYYSGRTYYNPSLKS

Nucleotide sequence of the BGCB491 Heavy Chain 1 gene with
signal peptide coding region underlined.

SEQ ID NO: 165

<u>ATGGCCAGGAAGTCCGCTCTGCTCGCTCTGGCACTTCTGCTTCTGGGATTTGGACCTGCT</u>

<u>TGGGCT</u>CAGGTGCAGCTGCAGCAGTCTGGCCCTAGACTCGTGCGGCCTTCCCAGACCCTG

TCTCTGACCTGTGCCATCTCCGGCGACTCCGTGTTCAACAACAACGCCGCCTGGTCCTGG

ATCCGGCAGTCTCCATCTCGCGGTCTGGAGTGGCTCGGTCGCACCTACTACCGCTCTAAA

TGGCTGTACGACTACGCCGTGTCCGTGAAGTCCCGGATCACCGTGAACCCTGACACCTCC

CGGAACCAGTTCACCCTGCAGCTGAACTCCGTGACCCCTGAGGACACCGCCCTGTACTAC

TGCGCCAGAGGCTACTCCTCCTCCTTCGACTATTGGGGCCAAGGCACCCTCGTGACCGTG

TCCTCTGCCTCCACCAAGGGCCCATCGGTCTTCCCCCTGGCACCCTCCTCCAAGAGCACC

TCTGGGGGCACAGCGGCCCTGGGCTGCCTGGTCAAGGACTACTTCCCCGAACCGGTGACG

GTGTCGTGGAACTCAGGCGCCCTGACCAGCGGCGTGCACACCTTCCCGGCTGTCCTACAG

TCCTCAGGACTCTACTCCCTCAGCAGCGTGGTGACCGTGCCCTCCAGCAGCTTGGGCACC

CAGACCTACATCTGCAACGTGAATCACAAGCCCAGCAACACCAAGGTGGACAAGAAAGTT

GAGCCCAAATCTTGTGACAAAACTCACACATGCCCACCGTGCCCAGCACCTGAAGCCGCC

GGGGGACCGTCAGTCTTCCTCTTCCCCCCAAAACCCAAGGACACCCTCATGATCTCCCGG

ACCCCTGAGGTCACATGCGTGGTGGTGAGCGTGAGCCACGAAGACCCTGAGGTCAAGTTC

AACTGGTACGTGGACGGCGTGGAGGTGCATAATGCCAAGACAAAGCCGCGGGAGGAGCAG

TACAACAGCACGTACCGTGTGGTCAGCGTCCTCACCGTCCTGCACCAGGACTGGCTGAAT

GGCAAGGAGTACAAGTGCAAGGTGTCGAACAAAGCCCTCCCAGCCCCCATCGAGAAAACC

ATCTCCAAAGCCAAAGGGCAGCCCCGAGAACCACAGGTGTACACCCTGCCCCCATCCCGG

GAGGAGATGACCAAGAACCAGGTCAGCCTGTCCTGCGCCGTCAAAGGCTTCTATCCCAGC

GACATCGCCGTGGAGTGGGAGAGCAATGGGCAGCCGGAGAACAACTACAAGACCACGCCT

-continued

CCCGTGCTGGACTCCGACGGCTCCTTCTTCCTCGTGAGCAAGCTCACCGTGGACAAGAGC

AGATGGCAGCAGGGGAACGTCTTCTCATGCTCCGTGATGCATGAGGCTCTGCACAACCGG

TTCACGCAGAAGTCTCTCTCCCTGTCTCCGGGAAAAGGAGGCGGAGGATCTGGCGGAGGT

GGAAGTGGCGGAGGCGGTTCTGGTGGTGGTGGATCTGACATCGTGATGACCCAGACACCT

CTGAGCAGCCCCGTTACATTGGGCCAGCCTGCCTCCATCTCCTGCAGATCCTCTCAGTCC

CTGGTGCACTCTGACGGCAACACCTACCTCTCTTGGCTGCAGCAGAGGCCTGGACAGCCT

CCTAGACTGCTGATCTACAAGATCTCCAACCGGTTCTTCGGCGTGCCCGACAGATTTTCT

GGATCTGGCGCTGGCACCGACTTCACCCTGAAGATTTCCAGAGTGGAAGCCGAGGACGTG

GGCGTGTACTACTGTATGCAGGCCACACAGTTCCCTCACACCTTTGGCCAGGGCACCAAG

CTGGAAATCAAGGGCGGATCTGAGGGAAAGTCCAGCGGCTCCGGCAGCGAAAGCAAGTCC

ACCGGCGGAAGCCAAGTGACCCTGAAAGAAAGCGGCCCTGTGCTGGTCAAGCCCACCGAA

ACACTGACCCTGACCTGTACCGTGTCCGGCTTCTCCCTGACCAATATCCGGATGTCCGTG

TCCTGGATCAGACAGCCTCCTGGCAAGGCTCTGGAATGGCTGGCCCACATCTTCTCCAAC

GACGAGAAGTCCTACTCCACCAGCCTGAAGTCCCGGCTGACCATCTCCAGAGACACCTCC

AAGTCTCAGGTGGTGCTGACACTGACCAACGTGGACCCTGTGGATACCGCCACCTACTAC

TGCGCCAGAATGAGACTGCCCTACGGCATGGATGTGTGGGGCCAGGGAACAACCGTGACC

GTTTCTTCT

Nucleotide sequence of the BGCB491 Light gene with signal
peptide coding region underlined.
                                                    SEQ ID NO: 166
<u>ATGGCTAGATCCGCACTGCTCATTCTGGCTCTGCTTCTGCTTGGACTGTTCTCTCCTGGA</u>

<u>GCATGGGGA</u>CAGTCTGCTCTGACCCAGCCTGCCTCCGTGTCTGGCTCTCCCGGCCAGTCC

ATCACCATCAGCTGTACCGGCACCTCCTCCAACATCGGCACCTACAAGTTCGTGTCCTGG

TATCAGCAACACCCCGACAAGGCCCCCAAAGTGCTGCTGTACGAGGTGTCCAAGCGGCCC

TCTGGCGTGTCCTCCAGATTCTCCGGCTCCAAGTCTGGCAACACCGCCTCCCTGACCATC

AGCGGACTGCAGGCTGAGGACCAGGCCGACTACCACTGTGTGTCCTACGCTGGCTCTGGC

ACCCTGCTGTTTGGCGGAGGCACCAAGCTGACTGTCCTGGGTCAGCCCAAGGCTGCACCC

AGTGTCACTCTGTTCCCGCCCTCCTCTGAGGAGCTTCAAGCCAACAAGGCCACACTGGTG

TGTCTCATAAGTGACTTCTACCCGGGAGCCGTGACAGTGGCCTGGAAGGCCGATAGCAGC

CCCGTCAAGGCGGGAGTCGAAACCACCACACCCTCCAAACAAAGCAACAACAAGTACGCG

GCCAGCAGCTATCTGAGCCTGACGCCTGAGCAGTGGAAGTCCCACAGAAGCTACAGCTGC

CAGGTCACGCATGAAGGGAGCACCGTGGAGAAGACAGTGGCCCCTACAGAATGTTCA

Nucleotide sequence of the BGCB491 Heavy Chain 2 gene with
signal peptide coding region underlined.
                                                    SEQ ID NO: 167
<u>ATGGCCAGGAAGTCCGCTCTGCTCGCTCTGGCACTTCTGCTTCTGGGATTTGGACCTGCT</u>

<u>TGGGCT</u>GAGATCGTGCTGACCCAGTCTCCTGGCACACTGTCACTGTCTCCAGGCGAGAGA

GCTACCCTGTCCTGTAGAGCCAGCCAGTCTATCTCCTCCTCCTTCCTGACCTGGTATCAG

CAGAAGCCTGGACAGGCCCCTCGGCTGTTGATCTACGGTGCTTCTTCCAGAGCCACAGGC

ATCCCTGACAGATTCTCTGGCGGCGGATCTGGCACCGACTTCACCCTGACAATCTCCCGG

CTGGAACCTGAGGACTTCGCCGTGTACTACTGCCAGCACTACGGCAGCAGCCCCATGTAC

ACATTTGGCCAGGGCACCAAGCTGGAAATCAAGGGCGGATCTGAGGGAAAGTCCAGCGGC

TCCGGCAGCGAAAGCAAGTCCACCGGCGGAAGCGAGGTTCAGCTGCTGGAATCTGGCGGA

-continued

GGATTGGTTCAGCCTGGCGGTTCTCTGAGACTGTCTTGTGCCGCTTCCGGCTTCACCTTC

TCCAGCTACGCTATGTCCTGGGTCCGACAGGCTCCTGGCAAAGGACTGGAATGGGTGTCC

GCCATCTCTGGCTCTGGCGGCAGCACCTACTACGCCGATTCTGTGAAGGGCAGATTCACC

ATCAGCCGGGACAACTCCAAGAACACCCTGTACCTGCAGATGAACTCCCTGAGAGCCGAG

GACACCGCCGTGTACTACTGTGCTAAGGACGAGGGCTACTCCTCCGGCCACTACTACGGA

ATGGATGTGTGGGGCCAGGGCACCACAGTGACAGTCTCTTCTGAGCCCAAATCTAGCGAC

AAAACTCACACATGCCCACCGTGCCCAGCACCTGAAGCCGCCGGGGGACCGTCAGTCTTC

CTCTTCCCCCCAAAACCCAAGGACACCCTCATGATCTCCCGGACCCCTGAGGTCACATGC

GTGGTGGTGAGCGTGAGCCACGAAGACCCTGAGGTCAAGTTCAACTGGTACGTGGACGGC

GTGGAGGTGCATAATGCCAAGACAAAGCCGCGGGAGGAGCAGTACAACAGCACGTACCGT

GTGGTCAGCGTCCTCACCGTCCTGCACCAGGACTGGCTGAATGGCAAGGAGTACAAGTGC

AAGGTGTCGAACAAAGCCCTCCCAGCCCCCATCGAGAAAACCATCTCCAAAGCCAAAGGG

CAGCCCCGAGAACCACAGGTGTACACCCTGCCCCCATCCCGGGAGGAGATGACCAAGAAC

CAGGTCAGCCTGTGGTGCCTGGTCAAAGGCTTCTATCCCAGCGACATCGCCGTGGAGTGG

GAGAGCAATGGGCAGCCGGAGAACAACTACAAGACCACGCCTCCCGTGCTGGACTCCGAC

GGCTCCTTCTTCCTCTACAGCAAGCTCACCGTGGACAAGAGCAGATGGCAGCAGGGGAAC

GTCTTCTCATGCTCCGTGATGCATGAGGCTCTGCACAACCACTACACGCAGAAGTCTCTC

TCCCTGTCTCCGGGAAAA

List of Sequences SEQ ID NO: 1 CD3B376 LCDR1
TGTSSNIGTYKFVS

---

We claim:

1. A trispecific antibody, comprising:
   (a) a first antigen-binding arm comprising a first heavy chain variable domain (VH1) and a first light chain variable domain (VL1), wherein the VH1 comprises the heavy chain complementarity determining region 1 (HCDR1), the HCDR2, and the HCDR3 of the VH1 of SEQ ID NO: 8 and the VL1 comprises the light chain complementarity determining region 1 (LCDR1), the LCDR2, and the LCDR3 of the VL1 of SEQ ID NO: 7;
   (b) a second antigen-binding arm comprising a second heavy chain variable domain (VH2) and a second light chain variable domain (VL2), wherein the VH2 comprises the HCDR1, the HCDR2, and the HCDR3 of the VH2 of SEQ ID NO: 16 and the VL2 comprises the LCDR1, the LCDR2, and the LCDR3 of the VL2 of SEQ ID NO: 15;
   (c) a third antigen-binding arm comprising a third heavy chain variable domain (VH3) and a third light chain variable domain (VL3), wherein the VH3 comprises the HCDR1, the HCDR2, and the HCDR3 of the VH3 of SEQ ID NO: 24 and the VL3 comprises the LCDR1, the LCDR2, and the LCDR3 of the VL3 of SEQ ID NO: 23;

wherein the first antigen-binding arm binds to an epitope on cluster of differentiation 3 (CD3), the second antigen-binding arm binds to an epitope on G-protein coupled receptor family C group 5 member D (GPRC5D), and the third antigen-binding arm binds to an epitope on B cell maturation antigen (BCMA).

2. The trispecific antibody of claim 1, wherein the first antigen-binding arm comprises a HCDR1 comprising the amino acid sequence of SEQ ID NO: 4, a HCDR2 comprising the amino acid sequence of SEQ ID NO: 5, a HCDR3 comprising the amino acid sequence of SEQ ID NO: 6, a LCDR1 comprising the amino acid sequence of SEQ ID NO: 1, a LCDR2 comprising the amino acid sequence of SEQ ID NO: 2, and a LCDR3 comprising the amino acid sequence of SEQ ID NO: 3.

3. The trispecific antibody of claim 2, wherein the first antigen-binding arm comprises the VH1 of SEQ ID NO: 8 and the VL1 of SEQ ID NO: 7.

4. The trispecific antibody of claim 1, wherein the second antigen-binding arm comprises a HCDR1 comprising the amino acid sequence of SEQ ID NO: 12, a HCDR2 comprising the amino acid sequence of SEQ ID NO: 13, a HCDR3 comprising the amino acid sequence of SEQ ID NO: 14, a LCDR1 comprising the amino acid sequence of SEQ ID NO: 9, a LCDR2 comprising the amino acid sequence of SEQ ID NO: 10, and a LCDR3 comprising the amino acid sequence of SEQ ID NO: 11.

5. The trispecific antibody of claim 4, wherein the second antigen-binding arm comprises the VH2 of SEQ ID NO: 16 and the VL2 of SEQ ID NO: 15.

6. The trispecific antibody of claim 1, wherein the third antigen-binding arm comprises a HCDR1 comprising the amino acid sequence of SEQ ID NO: 20, a HCDR2 comprising the amino acid sequence of SEQ ID NO: 21, a HCDR3 comprising the amino acid sequence of SEQ ID NO: 22, a LCDR1 comprising the amino acid sequence of SEQ ID NO: 17, a LCDR2 comprising the amino acid sequence of SEQ ID NO: 18, and a LCDR3 comprising the amino acid sequence of SEQ ID NO: 19.

7. The trispecific antibody of claim 6, wherein the third antigen-binding arm comprises the VH3 of SEQ ID NO: 24 and the VL3 of SEQ ID NO: 23.

8. The trispecific antibody of claim 1, wherein:
the first antigen-binding arm comprises the HCDR1, the HCDR2, the HCDR3, the LCDR1, the LCDR2, and the LCDR3 of SEQ ID NOs: 4, 5, 6, 1, 2, and 3, respectively;
the second antigen-binding arm comprises the HCDR1, the HCDR2, the HCDR3, the LCDR1, the LCDR2, and the LCDR3 of SEQ ID NOs: 12, 13, 14, 9, 10, and 11, respectively; and
the third antigen-binding arm comprises the HCDR1, the HCDR2, the HCDR3, the LCDR1, the LCDR2, and the LCDR3 of SEQ ID NOs: 20, 21, 22, 17, 18, and 19, respectively.

9. The trispecific antibody of claim 8, wherein:
the first antigen-binding arm comprises the VH1 of SEQ ID NO: 8 and the VL1 of SEQ ID NO: 7;
the second antigen-binding arm comprises the VH2 of SEQ ID NO: 16 and the VL2 of SEQ ID NO: 15; and
the third antigen-binding arm comprises the VH3 of SEQ ID NO: 24 and the VL3 of SEQ ID NO: 23.

10. The trispecific antibody of claim 1, wherein the first antigen-binding arm comprises a Fragment crystallizable (Fc) domain comprising the amino acid sequence of SEQ ID NO: 158 wherein the Fc domain comprises one or more mutations selected from T366S, L368A, T366W, and Y407V according to EU numbering.

11. The trispecific antibody of claim 10, wherein the Fc domain further comprises one or more mutations selected from L234A, L235A, and D265S according to EU numbering.

12. The trispecific antibody of claim 10, wherein the Fc domain comprises mutations H435R and/or Y436F according to EU numbering.

13. The trispecific antibody of claim 1, wherein the first antigen-binding arm specifically binds to SEQ ID NO: 161.

14. The trispecific antibody of claim 1, wherein the third antigen-binding arm specifically binds to SEQ ID NO: 162.

15. The trispecific antibody of claim 1, wherein the first antigen-binding arm comprises a first heavy chain (HC1) comprising the amino acid sequence of SEQ ID NO: 26.

16. The trispecific antibody of claim 15, wherein the first antigen-binding arm comprises a light chain (LC) comprising the amino acid sequence of SEQ ID NO: 27.

17. The trispecific antibody of claim 1, wherein a single polypeptide comprises the second antigen-binding arm and the third antigen-binding arm, the single polypeptide comprising the amino acid sequence of SEQ ID NO: 28.

18. The trispecific antibody of claim 17, wherein the first antigen-binding arm comprises an HC1 comprising the amino acid sequence of SEQ ID NO: 26 and a LC comprising the amino acid sequence of SEQ ID NO: 27.

19. A synthetic polynucleotide encoding the trispecific antibody or trispecific binding fragment of claim 1.

20. A pharmaceutical composition for treating multiple myeloma comprising the trispecific antibody of claim 1 and a pharmaceutically acceptable carrier.

21. A cell expressing the trispecific antibody of claim 1.

22. The cell of claim 21, wherein the cell is a hybridoma.

23. The cell of claim 21, wherein the trispecific antibody is recombinantly produced.

24. A method for treating multiple myeloma in a subject in need thereof, the method comprising administering to the subject a therapeutically effective amount of the pharmaceutical composition of claim 20.

25. The method of claim 24, wherein the pharmaceutical composition is administered for a time sufficient to treat the multiple myeloma.

26. The method of claim 24, wherein the multiple myeloma expresses BCMA and/or GPRC5D.

27. The method of claim 26, wherein the multiple myeloma is smoldering multiple myeloma (SMM).

28. The method of claim 24, wherein the multiple myeloma is relapsed, refractory, or any combination thereof.

29. The method of claim 28, wherein the subject has received a prior treatment, wherein the prior treatment comprises a proteasome inhibitor, an immunomodulatory drug, a CD38 antibody, a bispecific agent, a CAR-T therapy, or a combination thereof.

30. A method for generating a trispecific antibody, wherein the method comprises culturing the cell of claim 21 and isolating the trispecific antibody.

31. A trispecific antibody, comprising:
a polypeptide comprising the amino acid sequence of SEQ 1D NO: 29,
a polypeptide comprising the amino acid sequence of SEQ 1D NO: 30, and
a polypeptide comprising the amino acid sequence of SEQ 11) NO: 31.

32. A trispecific antibody, comprising:
a polypeptide comprising the amino acid sequence of SEQ 1D NO: 26,
a polypeptide comprising the amino acid sequence of SEQ 1D NO: 27, and
a polypeptide comprising the amino acid sequence of SEQ 11) NO: 28.

33. A trispecific antibody, comprising:
a polypeptide comprising the amino acid sequence of SEQ 1D NO: 29,
a polypeptide comprising the amino acid sequence of SEQ 1D NO: 30, and
a polypeptide comprising the amino acid sequence of SEQ 11) NO: 31.

34. A trispecific antibody, comprising:
a polypeptide comprising the amino acid sequence of SEQ 1D NO: 26,
a polypeptide comprising the amino acid sequence of SEQ 1D NO: 27, and
a polypeptide comprising the amino acid sequence of SEQ 11) NO: 28.

35. A method for treating multiple myeloma in a subject in need thereof, the method comprising administering to the subject a therapeutically effective amount of the trispecific antibody of claim 31.

36. The method of claim 35, wherein the trispecific antibody is administered for a time sufficient to treat the multiple myeloma.

37. The method of claim 35, wherein the multiple myeloma expresses BCMA and/or GPRC5D.

38. The method of claim 37, wherein the multiple myeloma is smoldering multiple myeloma (SMM).

39. The method of claim 35, wherein the multiple myeloma is relapsed, refractory, or any combination thereof.

40. The method of claim 39, wherein the subject has received a prior treatment, wherein the prior treatment comprises a proteasome inhibitor, an immunomodulatory drug, a CD38 antibody, a bispecific agent, a CAR-T therapy, or a combination thereof.

41. A method for treating multiple myeloma in a subject in need thereof, the method comprising administering to the subject a therapeutically effective amount of the trispecific antibody of claim 33.

42. The method of claim 41, wherein the trispecific antibody is administered for a time sufficient to treat the multiple myeloma.

43. The method of claim 41, wherein the multiple myeloma expresses BCMA and/or GPRC5D.

44. The method of claim 43, wherein the multiple myeloma is smoldering multiple myeloma (SMM).

45. The method of claim 41, wherein the multiple myeloma is relapsed, refractory, or any combination thereof.

46. The method of claim 45, wherein the subject has received a prior treatment, wherein the prior treatment comprises a proteasome inhibitor, an immunomodulatory drug, a CD38 antibody, a bispecific agent, a CAR-T therapy, or a combination thereof.

\* \* \* \* \*

SEQUENCE LISTING

<160> NUMBER OF SEQ ID NOS: 167

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Thr Gly Thr Ser Ser Asn Ile Gly Thr Tyr Lys Phe Val Ser
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Val Ser Lys Arg Pro Ser
1               5

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 3

Val Ser Tyr Ala Gly Ser Gly Thr Leu Leu
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Asp Ser Val Phe Asn Asn Asn Ala Ala Trp Ser
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Thr Tyr Tyr Arg Ser Lys Trp Leu Tyr Asp
1               5                   10

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Tyr Ser Ser Ser Phe Asp Tyr
1               5

<210> SEQ ID NO 7
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asn Ile Gly Thr Tyr
            20                  25                  30

Lys Phe Val Ser Trp Tyr Gln Gln His Pro Asp Lys Ala Pro Lys Val
        35                  40                  45

Leu Leu Tyr Glu Val Ser Lys Arg Pro Ser Gly Val Ser Ser Arg Phe
    50                  55                  60

Ser Gly Ser Lys Ser Gly Asn Thr Ala Ser Leu Thr Ile Ser Gly Leu
65                  70                  75                  80

Gln Ala Glu Asp Gln Ala Asp Tyr His Cys Val Ser Tyr Ala Gly Ser
                85                  90                  95

Gly Thr Leu Leu Phe Gly Gly Gly Thr Lys Leu Thr Val Leu

```
                 100              105              110

<210> SEQ ID NO 8
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Gln Gln Ser Gly Pro Arg Leu Val Arg Pro Ser Gln
1               5                   10                  15

Thr Leu Ser Leu Thr Cys Ala Ile Ser Gly Asp Ser Val Phe Asn Asn
            20                  25                  30

Asn Ala Ala Trp Ser Trp Ile Arg Gln Ser Pro Ser Arg Gly Leu Glu
        35                  40                  45

Trp Leu Gly Arg Thr Tyr Tyr Arg Ser Lys Trp Leu Tyr Asp Tyr Ala
    50                  55                  60

Val Ser Val Lys Ser Arg Ile Thr Val Asn Pro Asp Thr Ser Arg Asn
65                  70                  75                  80

Gln Phe Thr Leu Gln Leu Asn Ser Val Thr Pro Glu Asp Thr Ala Leu
                85                  90                  95

Tyr Tyr Cys Ala Arg Gly Tyr Ser Ser Ser Phe Asp Tyr Trp Gly Gln
            100                 105                 110

Gly Thr Leu Val Thr Val Ser Ser
        115                 120

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Ser Ser Gln Ser Leu Val His Ser Asp Gly Asn Thr Tyr Leu Ser
1               5                   10                  15

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Ile Ser Asn Arg Phe Phe
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Met Gln Ala Thr Gln Phe Pro His Thr
1               5
```

```
<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Phe Ser Leu Thr Asn Ile Arg Met Ser Val Ser
1               5                   10

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

His Ile Phe Ser Asn Asp Glu Lys Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Met Arg Leu Pro Tyr Gly Met Asp Val
1               5

<210> SEQ ID NO 15
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Phe Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro His Thr Phe Gly Gln Gly Thr Lys Leu Glu Ile Lys
            100                 105                 110

<210> SEQ ID NO 16
<211> LENGTH: 119
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 16

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Asn Ile
            20                  25                  30

Arg Met Ser Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Arg Asp Thr Ser Lys Ser Gln Val
65                  70                  75                  80

Val Leu Thr Leu Thr Asn Val Asp Pro Val Asp Thr Ala Thr Tyr Tyr
                85                  90                  95

Cys Ala Arg Met Arg Leu Pro Tyr Gly Met Asp Val Trp Gly Gln Gly
            100                 105                 110

Thr Thr Val Thr Val Ser Ser
        115

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Ala Ser Gln Ser Ile Ser Ser Ser Phe Leu Thr
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Ala Ser Ser Arg Ala Thr
1               5

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln His Tyr Gly Ser Ser Pro Met Tyr Thr
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
        peptide

<400> SEQUENCE: 20

Gly Phe Thr Phe Ser Ser Tyr Ala Met Ser
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 21

Ala Ile Ser Gly Ser Gly Gly Ser Thr Tyr
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 22

Asp Glu Gly Tyr Ser Ser Gly His Tyr Tyr Gly Met Asp Val
1               5                   10

<210> SEQ ID NO 23
<211> LENGTH: 109
<212> TYPE: PRT
<213> ORGANISM: Artificial Sequence
<220> FEATURE:
<223> OTHER INFORMATION: Description of Artificial Sequence: Synthetic
        polypeptide

<400> SEQUENCE: 23

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Ser
            20                  25                  30

Phe Leu Thr Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Gly Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Ser Ser Pro
                85                  90                  95

Met Tyr Thr Phe Gly Gln Gly Thr Lys Leu Glu Ile Lys
            100                 105

<210> SEQ ID NO 24
<211> LENGTH: 123
<212> TYPE: PRT
<213> ORGANISM: Artificial Sequence
<220> FEATURE:
<223> OTHER INFORMATION: Description of Artificial Sequence: Synthetic
        polypeptide

<400> SEQUENCE: 24

Glu Val Gln Leu Leu Glu Ser Gly Gly Gly Leu Val Gln Pro Gly Gly
```

```
1               5               10              15
Ser Leu Arg Leu Ser Cys Ala Ala Ser Gly Phe Thr Phe Ser Ser Tyr
            20              25              30

Ala Met Ser Trp Val Arg Gln Ala Pro Gly Lys Gly Leu Glu Trp Val
            35              40              45

Ser Ala Ile Ser Gly Ser Gly Gly Ser Thr Tyr Tyr Ala Asp Ser Val
        50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Lys Asp Glu Gly Tyr Ser Ser Gly His Tyr Tyr Gly Met Asp Val
            100             105             110

Trp Gly Gln Gly Thr Thr Val Thr Val Ser Ser
        115             120
```

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 25

```
Gly Gly Ser Glu Gly Lys Ser Ser Gly Ser Gly Ser Glu Ser Lys Ser
1               5               10              15

Thr Gly Gly Ser
            20
```

<210> SEQ ID NO 26
<211> LENGTH: 450
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 26

```
Gln Val Gln Leu Gln Gln Ser Gly Pro Arg Leu Val Arg Pro Ser Gln
1               5               10              15

Thr Leu Ser Leu Thr Cys Ala Ile Ser Gly Asp Ser Val Phe Asn Asn
            20              25              30

Asn Ala Ala Trp Ser Trp Ile Arg Gln Ser Pro Ser Arg Gly Leu Glu
            35              40              45

Trp Leu Gly Arg Thr Tyr Tyr Arg Ser Lys Trp Leu Tyr Asp Tyr Ala
        50              55              60

Val Ser Val Lys Ser Arg Ile Thr Val Asn Pro Asp Thr Ser Arg Asn
65              70              75              80

Gln Phe Thr Leu Gln Leu Asn Ser Val Thr Pro Glu Asp Thr Ala Leu
                85              90              95

Tyr Tyr Cys Ala Arg Gly Tyr Ser Ser Ser Phe Asp Tyr Trp Gly Gln
            100             105             110

Gly Thr Leu Val Thr Val Ser Ser Ala Ser Thr Lys Gly Pro Ser Val
            115             120             125

Phe Pro Leu Ala Pro Ser Ser Lys Ser Thr Ser Gly Gly Thr Ala Ala
        130             135             140

Leu Gly Cys Leu Val Lys Asp Tyr Phe Pro Glu Pro Val Thr Val Ser
```

-continued

```
145                150                155                160

Trp Asn Ser Gly Ala Leu Thr Ser Gly Val His Thr Phe Pro Ala Val
                165                170                175

Leu Gln Ser Ser Gly Leu Tyr Ser Leu Ser Ser Val Val Thr Val Pro
                180                185                190

Ser Ser Ser Leu Gly Thr Gln Thr Tyr Ile Cys Asn Val Asn His Lys
                195                200                205

Pro Ser Asn Thr Lys Val Asp Lys Lys Val Glu Pro Lys Ser Cys Asp
    210                215                220

Lys Thr His Thr Cys Pro Pro Cys Pro Ala Pro Glu Ala Ala Gly Gly
225                230                235                240

Pro Ser Val Phe Leu Phe Pro Pro Lys Pro Lys Asp Thr Leu Met Ile
                245                250                255

Ser Arg Thr Pro Glu Val Thr Cys Val Val Val Ser Val Ser His Glu
                260                265                270

Asp Pro Glu Val Lys Phe Asn Trp Tyr Val Asp Gly Val Glu Val His
                275                280                285

Asn Ala Lys Thr Lys Pro Arg Glu Glu Gln Tyr Asn Ser Thr Tyr Arg
    290                295                300

Val Val Ser Val Leu Thr Val Leu His Gln Asp Trp Leu Asn Gly Lys
305                310                315                320

Glu Tyr Lys Cys Lys Val Ser Asn Lys Ala Leu Pro Ala Pro Ile Glu
                325                330                335

Lys Thr Ile Ser Lys Ala Lys Gly Gln Pro Arg Glu Pro Gln Val Tyr
                340                345                350

Thr Leu Pro Pro Ser Arg Glu Glu Met Thr Lys Asn Gln Val Ser Leu
                355                360                365

Ser Cys Ala Val Lys Gly Phe Tyr Pro Ser Asp Ile Ala Val Glu Trp
    370                375                380

Glu Ser Asn Gly Gln Pro Glu Asn Asn Tyr Lys Thr Thr Pro Pro Val
385                390                395                400

Leu Asp Ser Asp Gly Ser Phe Phe Leu Val Ser Lys Leu Thr Val Asp
                405                410                415

Lys Ser Arg Trp Gln Gln Gly Asn Val Phe Ser Cys Ser Val Met His
                420                425                430

Glu Ala Leu His Asn Arg Phe Thr Gln Lys Ser Leu Ser Leu Ser Pro
                435                440                445

Gly Lys
    450

<210> SEQ ID NO 27
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Ser Ala Leu Thr Gln Pro Ala Ser Val Ser Gly Ser Pro Gly Gln
1                5                10                15

Ser Ile Thr Ile Ser Cys Thr Gly Thr Ser Ser Asn Ile Gly Thr Tyr
                20                25                30

Lys Phe Val Ser Trp Tyr Gln Gln His Pro Asp Lys Ala Pro Lys Val
                35                40                45
```

```
Leu Leu Tyr Glu Val Ser Lys Arg Pro Ser Gly Val Ser Ser Arg Phe
    50              55                  60
```

```
Ser Gly Ser Lys Ser Gly Asn Thr Ala Ser Leu Thr Ile Ser Gly Leu
65              70                  75                  80
```

```
Gln Ala Glu Asp Gln Ala Asp Tyr His Cys Val Ser Tyr Ala Gly Ser
                85                  90                  95
```

```
Gly Thr Leu Leu Phe Gly Gly Gly Thr Lys Leu Thr Val Leu Gly Gln
            100                 105                 110
```

```
Pro Lys Ala Ala Pro Ser Val Thr Leu Phe Pro Pro Ser Ser Glu Glu
            115                 120                 125
```

```
Leu Gln Ala Asn Lys Ala Thr Leu Val Cys Leu Ile Ser Asp Phe Tyr
    130                 135                 140
```

```
Pro Gly Ala Val Thr Val Ala Trp Lys Ala Asp Ser Ser Pro Val Lys
145                 150                 155                 160
```

```
Ala Gly Val Glu Thr Thr Thr Pro Ser Lys Gln Ser Asn Asn Lys Tyr
                165                 170                 175
```

```
Ala Ala Ser Ser Tyr Leu Ser Leu Thr Pro Glu Gln Trp Lys Ser His
            180                 185                 190
```

```
Arg Ser Tyr Ser Cys Gln Val Thr His Glu Gly Ser Thr Val Glu Lys
            195                 200                 205
```

```
Thr Val Ala Pro Thr Glu Cys Ser
    210                 215
```

```
<210> SEQ ID NO 28
<211> LENGTH: 755
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 28
```

```
Asp Ile Val Met Thr Gln Thr Pro Leu Ser Ser Pro Val Thr Leu Gly
1               5                   10                  15
```

```
Gln Pro Ala Ser Ile Ser Cys Arg Ser Ser Gln Ser Leu Val His Ser
                20                  25                  30
```

```
Asp Gly Asn Thr Tyr Leu Ser Trp Leu Gln Gln Arg Pro Gly Gln Pro
            35                  40                  45
```

```
Pro Arg Leu Leu Ile Tyr Lys Ile Ser Asn Arg Phe Phe Gly Val Pro
    50                  55                  60
```

```
Asp Arg Phe Ser Gly Ser Gly Ala Gly Thr Asp Phe Thr Leu Lys Ile
65              70                  75                  80
```

```
Ser Arg Val Glu Ala Glu Asp Val Gly Val Tyr Tyr Cys Met Gln Ala
                85                  90                  95
```

```
Thr Gln Phe Pro His Thr Phe Gly Gln Gly Thr Lys Leu Glu Ile Lys
            100                 105                 110
```

```
Gly Gly Ser Glu Gly Lys Ser Ser Gly Ser Gly Ser Glu Ser Lys Ser
            115                 120                 125
```

```
Thr Gly Gly Ser Gln Val Thr Leu Lys Glu Ser Gly Pro Val Leu Val
    130                 135                 140
```

```
Lys Pro Thr Glu Thr Leu Thr Leu Thr Cys Thr Val Ser Gly Phe Ser
145                 150                 155                 160
```

```
Leu Thr Asn Ile Arg Met Ser Val Ser Trp Ile Arg Gln Pro Pro Gly
                165                 170                 175
```

```
Lys Ala Leu Glu Trp Leu Ala His Ile Phe Ser Asn Asp Glu Lys Ser
            180                 185                 190
```

-continued

```
Tyr Ser Thr Ser Leu Lys Ser Arg Leu Thr Ile Ser Arg Asp Thr Ser
        195                 200                 205

Lys Ser Gln Val Val Leu Thr Leu Thr Asn Val Asp Pro Val Asp Thr
        210                 215                 220

Ala Thr Tyr Tyr Cys Ala Arg Met Arg Leu Pro Tyr Gly Met Asp Val
225                 230                 235                 240

Trp Gly Gln Gly Thr Thr Val Thr Val Ser Ser Glu Pro Lys Ser Ser
                245                 250                 255

Asp Lys Thr His Thr Cys Pro Pro Cys Pro Ala Pro Glu Ala Ala Gly
                260                 265                 270

Gly Pro Ser Val Phe Leu Phe Pro Pro Lys Pro Lys Asp Thr Leu Met
                275                 280                 285

Ile Ser Arg Thr Pro Glu Val Thr Cys Val Val Val Ser Val Ser His
        290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
                340                 345                 350

Lys Glu Tyr Lys Cys Lys Val Ser Asn Lys Ala Leu Pro Ala Pro Ile
        355                 360                 365

Glu Lys Thr Ile Ser Lys Ala Lys Gly Gln Pro Arg Glu Pro Gln Val
        370                 375                 380

Tyr Thr Leu Pro Pro Ser Arg Glu Glu Met Thr Lys Asn Gln Val Ser
385                 390                 395                 400

Leu Trp Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
                420                 425                 430

Val Leu Asp Ser Asp Gly Ser Phe Phe Leu Tyr Ser Lys Leu Thr Val
                435                 440                 445

Asp Lys Ser Arg Trp Gln Gln Gly Asn Val Phe Ser Cys Ser Val Met
        450                 455                 460

His Glu Ala Leu His Asn His Tyr Thr Gln Lys Ser Leu Ser Leu Ser
465                 470                 475                 480

Pro Gly Lys Gly Gly Ser Glu Gly Lys Ser Ser Gly Ser Gly Ser Glu
                485                 490                 495

Ser Lys Ser Thr Gly Gly Ser Glu Ile Val Leu Thr Gln Ser Pro Gly
                500                 505                 510

Thr Leu Ser Leu Ser Pro Gly Glu Arg Ala Thr Leu Ser Cys Arg Ala
                515                 520                 525

Ser Gln Ser Ile Ser Ser Ser Phe Leu Thr Trp Tyr Gln Gln Lys Pro
        530                 535                 540

Gly Gln Ala Pro Arg Leu Leu Ile Tyr Gly Ala Ser Ser Arg Ala Thr
545                 550                 555                 560

Gly Ile Pro Asp Arg Phe Ser Gly Gly Gly Ser Gly Thr Asp Phe Thr
                565                 570                 575

Leu Thr Ile Ser Arg Leu Glu Pro Glu Asp Phe Ala Val Tyr Tyr Cys
                580                 585                 590

Gln His Tyr Gly Ser Ser Pro Met Tyr Thr Phe Gly Gln Gly Thr Lys
                595                 600                 605
```

-continued

```
Leu Glu Ile Lys Gly Gly Ser Glu Gly Lys Ser Ser Gly Ser Gly Ser
    610             615             620

Glu Ser Lys Ser Thr Gly Gly Ser Glu Val Gln Leu Leu Glu Ser Gly
625             630             635             640

Gly Gly Leu Val Gln Pro Gly Gly Ser Leu Arg Leu Ser Cys Ala Ala
            645             650             655

Ser Gly Phe Thr Phe Ser Ser Tyr Ala Met Ser Trp Val Arg Gln Ala
            660             665             670

Pro Gly Lys Gly Leu Glu Trp Val Ser Ala Ile Ser Gly Ser Gly Gly
            675             680             685

Ser Thr Tyr Tyr Ala Asp Ser Val Lys Gly Arg Phe Thr Ile Ser Arg
    690             695             700

Asp Asn Ser Lys Asn Thr Leu Tyr Leu Gln Met Asn Ser Leu Arg Ala
705             710             715             720

Glu Asp Thr Ala Val Tyr Tyr Cys Ala Lys Asp Glu Gly Tyr Ser Ser
            725             730             735

Gly His Tyr Tyr Gly Met Asp Val Trp Gly Gln Gly Thr Thr Val Thr
            740             745             750

Val Ser Ser
    755
```

```
<210> SEQ ID NO 29
<211> LENGTH: 721
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Gln Gln Ser Gly Pro Arg Leu Val Arg Pro Ser Gln
1               5               10              15

Thr Leu Ser Leu Thr Cys Ala Ile Ser Gly Asp Ser Val Phe Asn Asn
            20              25              30

Asn Ala Ala Trp Ser Trp Ile Arg Gln Ser Pro Ser Arg Gly Leu Glu
        35              40              45

Trp Leu Gly Arg Thr Tyr Tyr Arg Ser Lys Trp Leu Tyr Asp Tyr Ala
    50              55              60

Val Ser Val Lys Ser Arg Ile Thr Val Asn Pro Asp Thr Ser Arg Asn
65              70              75              80

Gln Phe Thr Leu Gln Leu Asn Ser Val Thr Pro Glu Asp Thr Ala Leu
            85              90              95

Tyr Tyr Cys Ala Arg Gly Tyr Ser Ser Ser Phe Asp Tyr Trp Gly Gln
            100             105             110

Gly Thr Leu Val Thr Val Ser Ser Ala Ser Thr Lys Gly Pro Ser Val
            115             120             125

Phe Pro Leu Ala Pro Ser Ser Lys Ser Thr Ser Gly Gly Thr Ala Ala
    130             135             140

Leu Gly Cys Leu Val Lys Asp Tyr Phe Pro Glu Pro Val Thr Val Ser
145             150             155             160

Trp Asn Ser Gly Ala Leu Thr Ser Gly Val His Thr Phe Pro Ala Val
            165             170             175

Leu Gln Ser Ser Gly Leu Tyr Ser Leu Ser Ser Val Val Thr Val Pro
            180             185             190

Ser Ser Ser Leu Gly Thr Gln Thr Tyr Ile Cys Asn Val Asn His Lys
            195             200             205
```

```
Pro Ser Asn Thr Lys Val Asp Lys Lys Val Glu Pro Lys Ser Cys Asp
    210             215             220

Lys Thr His Thr Cys Pro Pro Cys Pro Ala Pro Glu Ala Ala Gly Gly
225             230             235             240

Pro Ser Val Phe Leu Phe Pro Pro Lys Pro Lys Asp Thr Leu Met Ile
            245             250             255

Ser Arg Thr Pro Glu Val Thr Cys Val Val Val Ser Val Ser His Glu
            260             265             270

Asp Pro Glu Val Lys Phe Asn Trp Tyr Val Asp Gly Val Glu Val His
        275             280             285

Asn Ala Lys Thr Lys Pro Arg Glu Glu Gln Tyr Asn Ser Thr Tyr Arg
290             295             300

Val Val Ser Val Leu Thr Val Leu His Gln Asp Trp Leu Asn Gly Lys
305             310             315             320

Glu Tyr Lys Cys Lys Val Ser Asn Lys Ala Leu Pro Ala Pro Ile Glu
            325             330             335

Lys Thr Ile Ser Lys Ala Lys Gly Gln Pro Arg Glu Pro Gln Val Tyr
            340             345             350

Thr Leu Pro Pro Ser Arg Glu Glu Met Thr Lys Asn Gln Val Ser Leu
            355             360             365

Ser Cys Ala Val Lys Gly Phe Tyr Pro Ser Asp Ile Ala Val Glu Trp
    370             375             380

Glu Ser Asn Gly Gln Pro Glu Asn Asn Tyr Lys Thr Thr Pro Pro Val
385             390             395             400

Leu Asp Ser Asp Gly Ser Phe Phe Leu Val Ser Lys Leu Thr Val Asp
            405             410             415

Lys Ser Arg Trp Gln Gln Gly Asn Val Phe Ser Cys Ser Val Met His
            420             425             430

Glu Ala Leu His Asn Arg Phe Thr Gln Lys Ser Leu Ser Leu Ser Pro
            435             440             445

Gly Lys Gly Gly Gly Gly Ser Gly Gly Gly Gly Ser Gly Gly Gly Gly
    450             455             460

Ser Gly Gly Gly Gly Ser Asp Ile Val Met Thr Gln Thr Pro Leu Ser
465             470             475             480

Ser Pro Val Thr Leu Gly Gln Pro Ala Ser Ile Ser Cys Arg Ser Ser
            485             490             495

Gln Ser Leu Val His Ser Asp Gly Asn Thr Tyr Leu Ser Trp Leu Gln
            500             505             510

Gln Arg Pro Gly Gln Pro Pro Arg Leu Leu Ile Tyr Lys Ile Ser Asn
        515             520             525

Arg Phe Phe Gly Val Pro Asp Arg Phe Ser Gly Ser Gly Ala Gly Thr
    530             535             540

Asp Phe Thr Leu Lys Ile Ser Arg Val Glu Ala Glu Asp Val Gly Val
545             550             555             560

Tyr Tyr Cys Met Gln Ala Thr Gln Phe Pro His Thr Phe Gly Gln Gly
            565             570             575

Thr Lys Leu Glu Ile Lys Gly Gly Ser Glu Gly Lys Ser Ser Gly Ser
            580             585             590

Gly Ser Glu Ser Lys Ser Thr Gly Gly Ser Gln Val Thr Leu Lys Glu
        595             600             605

Ser Gly Pro Val Leu Val Lys Pro Thr Glu Thr Leu Thr Leu Thr Cys
    610             615             620
```

```
Thr Val Ser Gly Phe Ser Leu Thr Asn Ile Arg Met Ser Val Ser Trp
625             630             635             640

Ile Arg Gln Pro Pro Gly Lys Ala Leu Glu Trp Leu Ala His Ile Phe
            645             650             655

Ser Asn Asp Glu Lys Ser Tyr Ser Thr Ser Leu Lys Ser Arg Leu Thr
            660             665             670

Ile Ser Arg Asp Thr Ser Lys Ser Gln Val Val Leu Thr Leu Thr Asn
            675             680             685

Val Asp Pro Val Asp Thr Ala Thr Tyr Tyr Cys Ala Arg Met Arg Leu
            690             695             700

Pro Tyr Gly Met Asp Val Trp Gly Gln Gly Thr Thr Val Thr Val Ser
705             710             715             720

Ser
```

```
<210> SEQ ID NO 30
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Ser Ala Leu Thr Gln Pro Ala Ser Val Ser Gly Ser Pro Gly Gln
1               5               10              15

Ser Ile Thr Ile Ser Cys Thr Gly Thr Ser Ser Asn Ile Gly Thr Tyr
            20              25              30

Lys Phe Val Ser Trp Tyr Gln Gln His Pro Asp Lys Ala Pro Lys Val
            35              40              45

Leu Leu Tyr Glu Val Ser Lys Arg Pro Ser Gly Val Ser Ser Arg Phe
    50              55              60

Ser Gly Ser Lys Ser Gly Asn Thr Ala Ser Leu Thr Ile Ser Gly Leu
65              70              75              80

Gln Ala Glu Asp Gln Ala Asp Tyr His Cys Val Ser Tyr Ala Gly Ser
            85              90              95

Gly Thr Leu Leu Phe Gly Gly Gly Thr Lys Leu Thr Val Leu Gly Gln
            100             105             110

Pro Lys Ala Ala Pro Ser Val Thr Leu Phe Pro Pro Ser Ser Glu Glu
            115             120             125

Leu Gln Ala Asn Lys Ala Thr Leu Val Cys Leu Ile Ser Asp Phe Tyr
    130             135             140

Pro Gly Ala Val Thr Val Ala Trp Lys Ala Asp Ser Ser Pro Val Lys
145             150             155             160

Ala Gly Val Glu Thr Thr Thr Pro Ser Lys Gln Ser Asn Asn Lys Tyr
            165             170             175

Ala Ala Ser Ser Tyr Leu Ser Leu Thr Pro Glu Gln Trp Lys Ser His
            180             185             190

Arg Ser Tyr Ser Cys Gln Val Thr His Glu Gly Ser Thr Val Glu Lys
            195             200             205

Thr Val Ala Pro Thr Glu Cys Ser
    210             215
```

```
<210> SEQ ID NO 31
<211> LENGTH: 484
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 31

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Ser
            20                  25                  30

Phe Leu Thr Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Gly Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Ser Ser Pro
                85                  90                  95

Met Tyr Thr Phe Gly Gln Gly Thr Lys Leu Glu Ile Lys Gly Gly Ser
            100                 105                 110

Glu Gly Lys Ser Ser Gly Ser Gly Ser Glu Ser Lys Ser Thr Gly Gly
        115                 120                 125

Ser Glu Val Gln Leu Leu Glu Ser Gly Gly Gly Leu Val Gln Pro Gly
        130                 135                 140

Gly Ser Leu Arg Leu Ser Cys Ala Ala Ser Gly Phe Thr Phe Ser Ser
145                 150                 155                 160

Tyr Ala Met Ser Trp Val Arg Gln Ala Pro Gly Lys Gly Leu Glu Trp
                165                 170                 175

Val Ser Ala Ile Ser Gly Ser Gly Gly Ser Thr Tyr Tyr Ala Asp Ser
            180                 185                 190

Val Lys Gly Arg Phe Thr Ile Ser Arg Asp Asn Ser Lys Asn Thr Leu
            195                 200                 205

Tyr Leu Gln Met Asn Ser Leu Arg Ala Glu Asp Thr Ala Val Tyr Tyr
    210                 215                 220

Cys Ala Lys Asp Glu Gly Tyr Ser Ser Gly His Tyr Tyr Gly Met Asp
225                 230                 235                 240

Val Trp Gly Gln Gly Thr Thr Val Thr Val Ser Ser Glu Pro Lys Ser
                245                 250                 255

Ser Asp Lys Thr His Thr Cys Pro Pro Cys Pro Ala Pro Glu Ala Ala
            260                 265                 270

Gly Gly Pro Ser Val Phe Leu Phe Pro Pro Lys Pro Lys Asp Thr Leu
            275                 280                 285

Met Ile Ser Arg Thr Pro Glu Val Thr Cys Val Val Val Ser Val Ser
    290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Asn Ser Thr
            325                 330                 335

Tyr Arg Val Val Ser Val Leu Thr Val Leu His Gln Asp Trp Leu Asn
            340                 345                 350

Gly Lys Glu Tyr Lys Cys Lys Val Ser Asn Lys Ala Leu Pro Ala Pro
        355                 360                 365

Ile Glu Lys Thr Ile Ser Lys Ala Lys Gly Gln Pro Arg Glu Pro Gln
    370                 375                 380

Val Tyr Thr Leu Pro Pro Ser Arg Glu Glu Met Thr Lys Asn Gln Val
385                 390                 395                 400

```
Ser Leu Trp Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
                420                 425                 430

Pro Val Leu Asp Ser Asp Gly Ser Phe Phe Leu Tyr Ser Lys Leu Thr
            435                 440                 445

Val Asp Lys Ser Arg Trp Gln Gln Gly Asn Val Phe Ser Cys Ser Val
        450                 455                 460

Met His Glu Ala Leu His Asn His Tyr Thr Gln Lys Ser Leu Ser Leu
465                 470                 475                 480

Ser Pro Gly Lys

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ser Gly Ser Tyr Phe Trp Gly
1               5

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ser Ile Tyr Tyr Ser Gly Ile Thr Tyr Tyr Asn Pro Ser Leu Lys Ser
1               5                   10                  15

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

His Asp Gly Ala Val Ala Gly Leu Phe Asp Tyr
1               5                   10

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ser Ser Ser Tyr Tyr Trp Gly
1               5

<210> SEQ ID NO 36
<211> LENGTH: 16
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 36

Ser Ile Tyr Tyr Ser Gly Ser Thr Tyr Tyr Asn Pro Ser Leu Lys Ser
1               5                   10                  15

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

His Asp Gly Ala Thr Ala Gly Leu Phe Asp Tyr
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ser Ser Ser Tyr Phe Trp Gly
1               5

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Gly Asn Asn Ile Gly Ser Lys Ser Val His
1               5                   10

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Asp Ser Asp Arg Pro Ser
1               5

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gln Val Trp Asp Ser Ser Ser Asp His Val Val
1               5                   10
```

-continued

<210> SEQ ID NO 42
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Ser Tyr Phe Trp Gly Trp Ile Arg Gln Pro Pro Gly Lys Gly Leu Glu
        35                  40                  45

Trp Ile Gly Ser Ile Tyr Tyr Ser Gly Ile Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Asp Gly Ala Val Ala Gly Leu Phe Asp Tyr Trp Gly
            100                 105                 110

Gln Gly Thr Leu Val Thr Val Ser Ser Ala
        115                 120

<210> SEQ ID NO 43
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Phe Trp Gly Trp Ile Arg Gln Pro Pro Gly Lys Gly Leu Glu
        35                  40                  45

Trp Ile Gly Ser Ile Tyr Tyr Ser Gly Ile Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Asp Gly Ala Val Ala Gly Leu Phe Asp Tyr Trp Gly
            100                 105                 110

Gln Gly Thr Leu Val Thr Val Ser Ser Ala
        115                 120

<210> SEQ ID NO 44
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 44

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Ser Tyr Phe Trp Gly Trp Ile Arg Gln Pro Pro Gly Lys Gly Leu Glu
        35                  40                  45

Trp Ile Gly Ser Ile Tyr Tyr Ser Gly Ile Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Asp Gly Ala Thr Ala Gly Leu Phe Asp Tyr Trp Gly
            100                 105                 110

Gln Gly Thr Leu Val Thr Val Ser Ser Ala
        115                 120

<210> SEQ ID NO 45
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Ser Tyr Phe Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Asp Gly Ala Val Ala Gly Leu Phe Asp Tyr Trp Gly
            100                 105                 110

Gln Gly Thr Leu Val Thr Val Ser Ser Ala
        115                 120

<210> SEQ ID NO 46
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Phe Trp Gly Trp Ile Arg Gln Pro Pro Gly Lys Gly Leu Glu
```

-continued

```
            35                  40                  45

Trp Ile Gly Ser Ile Tyr Tyr Ser Gly Ile Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Asp Gly Ala Thr Ala Gly Leu Phe Asp Tyr Trp Gly
                100                 105                 110

Gln Gly Thr Leu Val Thr Val Ser Ser Ala
        115                 120
```

<210> SEQ ID NO 47
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Gln Leu Gln Leu Gln Glu Ser Gly Pro Gly Leu Val Lys Pro Ser Glu
1                   5                   10                  15

Thr Leu Ser Leu Thr Cys Thr Val Ser Gly Gly Ser Ile Ser Ser Ser
                20                  25                  30

Ser Tyr Phe Trp Gly Trp Ile Arg Gln Pro Pro Gly Lys Gly Leu Glu
            35                  40                  45

Trp Ile Gly Ser Ile Tyr Tyr Ser Gly Arg Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Asp Gly Ala Thr Ala Gly Leu Phe Asp Tyr Trp Gly
                100                 105                 110

Gln Gly Thr Leu Val Thr Val Ser Ser Ala
        115                 120
```

<210> SEQ ID NO 48
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Ser Tyr Val Leu Thr Gln Pro Pro Ser Val Ser Val Ala Pro Gly Gln
1                   5                   10                  15

Thr Ala Arg Ile Thr Cys Gly Gly Asn Asn Ile Gly Ser Lys Ser Val
                20                  25                  30

His Trp Tyr Gln Gln Pro Pro Gly Gln Ala Pro Val Val Val Val Tyr
            35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Val Tyr Tyr Cys Gln Val Trp Asp Ser Ser Ser Asp His
```

-continued

```
                 85              90              95
Val Val Phe Gly Gly Gly Thr Lys Leu Thr Val Leu
            100             105

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ser Tyr Ala Ile Ser
1               5

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Asn Tyr Trp Met Ser
1               5

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ser Tyr Phe Ile Gly
1               5

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Tyr Thr Met Asn
1               5

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Ile Ile Pro Ile Phe Gly Thr Ala Asn Tyr Ala Gln Lys Phe Gln
1               5                  10                  15

Gly

<210> SEQ ID NO 54
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Ile Ser Tyr Ser Gly Gly Ser Lys Tyr Tyr Ala Ser Ser Val Lys
1               5                   10                  15

Gly

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ile Ile Tyr Pro Gly Lys Ser Asp Thr Arg Tyr Ser Pro Ser Phe Gln
1               5                   10                  15

Gly

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Leu Ile Asn Pro Tyr Asn Ser Asp Thr Asn Tyr Ala Gln Lys Leu Gln
1               5                   10                  15

Gly

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Glu Ser Arg Trp Arg Gly Tyr Lys Leu Asp
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ala Ala Phe Asp Phe Gly Arg Arg Ala Val Arg Leu Asp
1               5                   10

<210> SEQ ID NO 59
<211> LENGTH: 14
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 59

Val Tyr Ser Phe Gly Gly Arg His Lys Ala Leu Phe Asp Tyr
1               5                   10

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Val Ala Leu Arg Val Ala Leu Asp Tyr
1               5

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Arg Ala Ser Gln Ser Ile Ser Ser Tyr Leu Asn
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Arg Ala Ser Gln Ser Val Ser Ser Tyr Leu Ala
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Lys Ala Ser Gln Asn Val Ala Thr His Val Gly
1               5                   10

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ala Ala Ser Ser Leu Gln Ser
1               5

-continued

```
<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Asp Ala Ser Asn Arg Ala Thr
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ser Ala Ser Tyr Arg Tyr Ser
1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Gln Ser Tyr Ser Thr Pro Leu Thr
1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gln Gln Arg Ser Asn Trp Pro Leu Thr
1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gln Gln Tyr Asn Arg Tyr Pro Tyr Thr
1               5

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 70

Asp Tyr Gly Met His
1               5

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ser Tyr Trp Ile Gly
1               5

<210> SEQ ID NO 72
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Tyr Ala Met Ser
1               5

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ser Tyr Gly Ile Ser
1               5

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Tyr Ser Phe Thr Gly Tyr Thr Met Asn
1               5                   10

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ser Tyr Ala Met Ser
1               5

<210> SEQ ID NO 76
<211> LENGTH: 10
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 76

Gly Phe Ser Leu Thr Ser Tyr Asn Val His
1               5                   10

<210> SEQ ID NO 77
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ala Ile Lys Tyr Ser Gly Gly Ser Thr Tyr Tyr Ala Asp Ser Val Lys
1               5                   10                  15

Gly

<210> SEQ ID NO 78
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Ile Ser Tyr Ser Gly Gly Ser Lys Tyr Tyr Ala Asp Ser Val Lys
1               5                   10                  15

Gly

<210> SEQ ID NO 79
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ile Ile Tyr Pro Gly Asp Ser Asp Thr Arg Tyr Ser Pro Ser Phe Gln
1               5                   10                  15

Gly

<210> SEQ ID NO 80
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ala Ile Ser Gly Ser Gly Gly Ser Thr Tyr Tyr Ala Asp Ser Val Lys
1               5                   10                  15

Gly

<210> SEQ ID NO 81
<211> LENGTH: 17
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 81

Gly Ile Ile Pro Ile Phe Gly Asn Ile Asn Tyr Ala Gln Lys Phe Gln
1               5                   10                  15

Gly

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Leu Ile Asn Pro Tyr Asn Gly Asp Thr Asn
1               5                   10

<210> SEQ ID NO 83
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Val Ile Trp Ala Gly Gly Ser Thr Asn Tyr Asn Ser Ala Leu Met Ser
1               5                   10                  15

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Arg Ala Glu Ser Gly Pro Gly Leu Asp Tyr
1               5                   10

<210> SEQ ID NO 85
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ala Ala Trp Asp Phe Gly Arg Arg Ala Val Arg Leu Asp Tyr
1               5                   10

<210> SEQ ID NO 86
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ile Gly Phe Tyr Gly Arg Ser Phe Arg Ile Phe Asp Tyr
```

```
1               5                    10
```

<210> SEQ ID NO 87
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Val Asp Arg Ser Phe Gly Arg Ser Arg Tyr Thr Leu Asp Tyr
1               5                    10

<210> SEQ ID NO 88
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Val Ser Arg Arg Phe Lys Arg Phe Ala Tyr Tyr Phe Asp Tyr
1               5                    10

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ser Asn Phe Leu Pro Val Val Phe Asp Tyr
1               5                    10

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Asp Gly Ile Arg Leu Arg Phe Ala Tyr
1               5

<210> SEQ ID NO 91
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Lys Ser Ser Gln Ser Val Leu Tyr Ser Ser Asn Asn Lys Asn Tyr Leu
1               5                    10                   15

Ala

<210> SEQ ID NO 92
<211> LENGTH: 11
<212> TYPE: PRT
<213> ORGANISM: Artificial Sequence -continued
<220> FEATURE:
<223> OTHER INFORMATION: Description of Artificial Sequence: Synthetic
      peptide

<400> SEQUENCE: 92

Arg Ala Ser Gln Ser Val Arg Lys Ser Leu Ala
1               5                   10

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Trp Ala Ser Thr Arg Glu Ser
1               5

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Thr Ala Ser Asn Arg Ala Thr
1               5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gln Gln Tyr Tyr Ser Thr Pro Leu Thr
1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gln Gln Tyr Phe Arg Ala Pro Ile Thr
1               5

<210> SEQ ID NO 97
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
        20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Arg Trp Arg Gly Tyr Lys Leu Asp Tyr Trp Gly Gln
                100                 105                 110

Gly Thr Leu Val Thr Val Ser Ser
        115                 120

<210> SEQ ID NO 98
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Glu Val Gln Leu Leu Glu Ser Gly Gly Gly Leu Val Gln Pro Gly Gly
1                   5                   10                  15

Ser Leu Arg Leu Ser Cys Ala Ala Ser Gly Phe Thr Phe Ser Asn Tyr
        20                  25                  30

Trp Met Ser Trp Val Arg Gln Ala Pro Gly Lys Gly Leu Glu Trp Val
        35                  40                  45

Ser Gly Ile Ser Tyr Ser Gly Ser Lys Tyr Tyr Ala Ser Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Ala Phe Asp Phe Gly Arg Arg Ala Val Arg Leu Asp Tyr
                100                 105                 110

Trp Gly Gln Gly Thr Leu Val Thr Val Ser Ser
        115                 120

<210> SEQ ID NO 99
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Glu Val Gln Leu Val Gln Ser Gly Ala Glu Val Lys Lys Pro Gly Glu
1                   5                   10                  15

Ser Leu Lys Ile Ser Cys Lys Gly Ser Gly Tyr Ser Phe Thr Ser Tyr
        20                  25                  30

Phe Ile Gly Trp Val Arg Gln Met Pro Gly Lys Gly Leu Glu Trp Met
        35                  40                  45

Gly Ile Ile Tyr Pro Gly Lys Ser Asp Thr Arg Tyr Ser Pro Ser Phe
    50                  55                  60

```
Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Tyr Ser Phe Gly Gly Arg His Lys Ala Leu Phe Asp Tyr
            100                 105                 110

Trp Gly Gln Gly Thr Leu Val Thr Val Ser Ser
        115                 120

<210> SEQ ID NO 100
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
                20                  25                  30

Thr Met Asn Trp Val Arg Gln Ala Pro Gly Gln Gly Leu Glu Trp Met
            35                  40                  45

Gly Leu Ile Asn Pro Tyr Asn Ser Asp Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Ala Leu Arg Val Ala Leu Asp Tyr Trp Gly Gln Gly Thr
            100                 105                 110

Leu Val Thr Val Ser Ser
        115

<210> SEQ ID NO 101
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105
```

-continued

```
<210> SEQ ID NO 102
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys
            100                 105

<210> SEQ ID NO 103
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Ala Thr His
                20                  25                  30

Val Gly Trp Tyr Gln Gln Lys Pro Gly Lys Ala Pro Lys Arg Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Gln Gln Tyr Asn Arg Tyr Pro Tyr
                85                  90                  95

Thr Phe Gly Gln Gly Thr Lys Leu Glu Ile Lys
            100                 105

<210> SEQ ID NO 104
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
```

-continued

```
                20              25              30

Gly Met His Trp Val Arg Gln Ala Pro Gly Lys Gly Leu Glu Trp Val
        35              40              45

Ser Ala Ile Lys Tyr Ser Gly Gly Ser Thr Tyr Tyr Ala Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Lys Arg Ala Glu Ser Gly Pro Gly Leu Asp Tyr Trp Gly Gln Gly
                100             105             110

Thr Leu Val Thr Val Ser Ser
        115
```

```
<210> SEQ ID NO 105
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Glu Val Gln Leu Leu Glu Ser Gly Gly Gly Leu Val Gln Pro Gly Gly
1               5               10              15

Ser Leu Arg Leu Ser Cys Ala Ala Ser Gly Phe Thr Phe Ser Asn Tyr
                20              25              30

Trp Met Ser Trp Val Arg Gln Ala Pro Gly Lys Gly Leu Glu Trp Val
        35              40              45

Ser Gly Ile Ser Tyr Ser Gly Gly Ser Lys Tyr Tyr Ala Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Lys Ala Ala Trp Asp Phe Gly Arg Arg Ala Val Arg Leu Asp Tyr
                100             105             110

Trp Gly Gln Gly Thr Leu Val Thr Val Ser Ser
        115             120
```

```
<210> SEQ ID NO 106
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Glu Val Gln Leu Val Gln Ser Gly Ala Glu Val Lys Lys Pro Gly Glu
1               5               10              15

Ser Leu Lys Ile Ser Cys Lys Gly Ser Gly Tyr Ser Phe Thr Ser Tyr
                20              25              30

Trp Ile Gly Trp Val Arg Gln Met Pro Gly Lys Gly Leu Glu Trp Met
        35              40              45

Gly Ile Ile Tyr Pro Gly Asp Ser Asp Thr Arg Tyr Ser Pro Ser Phe
    50              55              60

Gln Gly Gln Val Thr Ile Ser Ala Asp Lys Ser Ile Ser Thr Ala Tyr
```

-continued

```
65                70                75                80

Leu Gln Trp Ser Ser Leu Lys Ala Ser Asp Thr Ala Met Tyr Tyr Cys
            85                90                95

Ala Arg Ile Gly Phe Tyr Gly Arg Ser Phe Arg Ile Phe Asp Tyr Trp
            100               105               110

Gly Gln Gly Thr Leu Val Thr Val Ser Ser
        115               120
```

<210> SEQ ID NO 107
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

```
Glu Val Gln Leu Val Gln Ser Gly Ala Glu Val Lys Lys Pro Gly Glu
1                5                10                15

Ser Leu Lys Ile Ser Cys Lys Gly Ser Gly Tyr Ser Phe Thr Ser Tyr
            20                25                30

Trp Ile Gly Trp Val Arg Gln Met Pro Gly Lys Gly Leu Glu Trp Met
            35                40                45

Gly Ile Ile Tyr Pro Gly Asp Ser Asp Thr Arg Tyr Ser Pro Ser Phe
        50                55                60

Gln Gly Gln Val Thr Ile Ser Ala Asp Lys Ser Ile Ser Thr Ala Tyr
65                70                75                80

Leu Gln Trp Ser Ser Leu Lys Ala Ser Asp Thr Ala Met Tyr Tyr Cys
            85                90                95

Ala Arg Val Tyr Ser Phe Gly Gly Arg His Lys Ala Leu Phe Asp Tyr
            100               105               110

Trp Gly Gln Gly Thr Leu Val Thr Val Ser Ser
        115               120
```

<210> SEQ ID NO 108
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

```
Glu Val Gln Leu Leu Glu Ser Gly Gly Gly Leu Val Gln Pro Gly Gly
1                5                10                15

Ser Leu Arg Leu Ser Cys Ala Ala Ser Gly Phe Thr Phe Ser Gly Tyr
            20                25                30

Ala Met Ser Trp Val Arg Gln Ala Pro Gly Lys Gly Leu Glu Trp Val
        35                40                45

Ser Ala Ile Ser Gly Ser Gly Gly Ser Thr Tyr Tyr Ala Asp Ser Val
        50                55                60

Lys Gly Arg Phe Thr Ile Ser Arg Asp Asn Ser Lys Asn Thr Leu Tyr
65                70                75                80

Leu Gln Met Asn Ser Leu Arg Ala Glu Asp Thr Ala Val Tyr Tyr Cys
            85                90                95

Ala Lys Val Asp Arg Ser Phe Gly Arg Ser Arg Tyr Thr Leu Asp Tyr
            100               105               110

Trp Gly Gln Gly Thr Leu Val Thr Val Ser Ser
```

```
                115                     120
```

```
<210> SEQ ID NO 109
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Gly Ile Ser Trp Val Arg Gln Ala Pro Gly Gln Gly Leu Glu Trp Met
            35                  40                  45

Gly Gly Ile Ile Pro Ile Phe Gly Asn Ile Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Ser Arg Arg Phe Lys Arg Phe Ala Tyr Tyr Phe Asp Tyr
                100                 105                 110

Trp Gly Gln Gly Thr Leu Val Thr Val Ser Ser
            115                 120

<210> SEQ ID NO 110
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
                20                  25                  30

Thr Met Asn Trp Val Arg Gln Ala Pro Gly Gln Gly Leu Glu Trp Met
            35                  40                  45

Gly Leu Ile Asn Pro Tyr Asn Gly Asp Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Ala Leu Arg Val Ala Leu Asp Tyr Trp Gly Gln Gly Thr
                100                 105                 110

Leu Val Thr Val Ser Ser
            115

<210> SEQ ID NO 111
<211> LENGTH: 119
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 111

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Asn Phe Leu Pro Val Val Phe Asp Tyr Trp Gly Gln Gly
            100                 105                 110

Thr Leu Val Thr Val Ser Ser
        115

<210> SEQ ID NO 112
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Ser Tyr
            20                  25                  30

Asn Val His Trp Ile Arg Gln Pro Pro Gly Lys Ala Leu Glu Trp Leu
        35                  40                  45

Ala Val Ile Trp Ala Gly Gly Ser Thr Asn Tyr Asn Ser Ala Leu Met
    50                  55                  60

Ser Arg Leu Thr Ile Ser Lys Asp Thr Ser Lys Ser Gln Val Val Leu
65                  70                  75                  80

Thr Met Thr Asn Met Arg Ala Glu Asp Thr Ala Thr Tyr Tyr Cys Ala
                85                  90                  95

Arg Asp Gly Ile Arg Leu Arg Phe Ala Tyr Trp Gly Gln Gly Thr Leu
            100                 105                 110

Val Thr Val Ser Ser
        115

<210> SEQ ID NO 113
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gln Gly Thr Lys Val Glu Ile
                100                 105                 110

Lys

<210> SEQ ID NO 114
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Lys Ser
                20                  25                  30

Leu Ala Trp Tyr Gln Gln Lys Pro Gly Gln Ala Pro Arg Leu Leu Ile
        35                  40                  45

Tyr Thr Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Phe Arg Ala Pro Ile
                85                  90                  95

Thr Phe Gly Gln Gly Thr Lys Val Glu Ile Lys Lys
                100                 105

<210> SEQ ID NO 115
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Asn Val Ala Thr His
                20                  25                  30

Val Gly Trp Tyr Gln Gln Lys Pro Gly Gln Ala Pro Arg Leu Leu Ile
        35                  40                  45

Tyr Ser Ala Ser Tyr Arg Tyr Ser Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Arg Tyr Pro Tyr
                85                  90                  95

```
Thr Phe Gly Gln Gly Thr Lys Leu Glu Ile Lys
        100                 105

<210> SEQ ID NO 116
<211> LENGTH: 345
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Met Tyr Lys Asp Cys Ile Glu Ser Thr Gly Asp Tyr Phe Leu Leu Cys
1               5                   10                  15

Asp Ala Glu Gly Pro Trp Gly Ile Ile Leu Glu Ser Leu Ala Ile Leu
            20                  25                  30

Gly Ile Val Val Thr Ile Leu Leu Leu Ala Phe Leu Phe Leu Met
            35                  40                  45

Arg Lys Ile Gln Asp Cys Ser Gln Trp Asn Val Leu Pro Thr Gln Leu
    50                  55                  60

Leu Phe Leu Leu Ser Val Leu Gly Leu Phe Gly Leu Ala Phe Ala Phe
65                  70                  75                  80

Ile Ile Glu Leu Asn Gln Gln Thr Ala Pro Val Arg Tyr Phe Leu Phe
                85                  90                  95

Gly Val Leu Phe Ala Leu Cys Phe Ser Cys Leu Leu Ala His Ala Ser
            100                 105                 110

Asn Leu Val Lys Leu Val Arg Gly Cys Val Ser Phe Ser Trp Thr Thr
            115                 120                 125

Ile Leu Cys Ile Ala Ile Gly Cys Ser Leu Leu Gln Ile Ile Ile Ala
    130                 135                 140

Thr Glu Tyr Val Thr Leu Ile Met Thr Arg Gly Met Met Phe Val Asn
145                 150                 155                 160

Met Thr Pro Cys Gln Leu Asn Val Asp Phe Val Val Leu Leu Val Tyr
                165                 170                 175

Val Leu Phe Leu Met Ala Leu Thr Phe Phe Val Ser Lys Ala Thr Phe
            180                 185                 190

Cys Gly Pro Cys Glu Asn Trp Lys Gln His Gly Arg Leu Ile Phe Ile
            195                 200                 205

Thr Val Leu Phe Ser Ile Ile Ile Trp Val Val Trp Ile Ser Met Leu
    210                 215                 220

Leu Arg Gly Asn Pro Gln Phe Gln Arg Gln Pro Gln Trp Asp Asp Pro
225                 230                 235                 240

Val Val Cys Ile Ala Leu Val Thr Asn Ala Trp Val Phe Leu Leu Leu
            245                 250                 255

Tyr Ile Val Pro Glu Leu Cys Ile Leu Tyr Arg Ser Cys Arg Gln Glu
            260                 265                 270

Cys Pro Leu Gln Gly Asn Ala Cys Pro Val Thr Ala Tyr Gln His Ser
            275                 280                 285

Phe Gln Val Glu Asn Gln Glu Leu Ser Arg Ala Arg Asp Ser Asp Gly
    290                 295                 300

Ala Glu Glu Asp Val Ala Leu Thr Ser Tyr Gly Thr Pro Ile Gln Pro
305                 310                 315                 320

Gln Thr Val Asp Pro Thr Gln Glu Cys Phe Ile Pro Gln Ala Lys Leu
            325                 330                 335

Ser Pro Gln Gln Asp Ala Gly Gly Val
            340                 345
```

```
<210> SEQ ID NO 117
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Thr Tyr Ala Met Asn
1               5

<210> SEQ ID NO 118
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Arg Ile Arg Ser Lys Tyr Asn Asn Tyr Ala Thr Tyr Tyr Ala Ala Ser
1               5                   10                  15

Val Lys Gly

<210> SEQ ID NO 119
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

His Gly Asn Phe Gly Asn Ser Tyr Val Ser Trp Phe Ala Tyr
1               5                   10

<210> SEQ ID NO 120
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Ala
        50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125
```

```
<210> SEQ ID NO 121
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
            115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
            195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
```

-continued

```
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Leu Leu Tyr Ser Lys Leu Thr
                405                 410                 415

Val Asp Lys Ser Arg Trp Gln Glu Gly Asn Val Phe Ser Cys Ser Val
                420                 425                 430

Met His Glu Ala Leu His Asn His Tyr Thr Gln Lys Ser Leu Ser Leu
            435                 440                 445

Ser Leu Gly Lys
    450

<210> SEQ ID NO 122
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Arg Ser Ser Thr Gly Ala Val Thr Thr Ser Asn Tyr Ala Asn
1               5                   10

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gly Thr Asn Lys Arg Ala Pro
1               5

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ala Leu Trp Tyr Ser Asn Leu Trp Val
1               5

<210> SEQ ID NO 125
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30
```

-continued

```
Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
                100                 105
```

<210> SEQ ID NO 126
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

```
Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
                100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
                180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

-continued

```
Gly Gly Gly Ser Gly Gly Gly Ser
1               5

<210> SEQ ID NO 128
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Gly Gly Gly Ser Gly Gly Gly Ser Gly Gly Gly Ser
1               5                   10

<210> SEQ ID NO 129
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gly Gly Gly Ser Gly Gly Gly Ser Gly Gly Gly Ser Gly Gly Gly Ser
1               5                   10                  15

<210> SEQ ID NO 130
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Gly Gly Ser Gly Gly Gly Ser Gly Gly Gly Ser Gly Gly Gly Ser
1               5                   10                  15

Gly Gly Gly Ser
            20

<210> SEQ ID NO 131
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gly Gly Gly Gly Ser Gly Gly Gly Gly Ser Gly Gly Gly Gly Ser
1               5                   10                  15

<210> SEQ ID NO 132
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25
```

<210> SEQ ID NO 133
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Gly Ser Thr Ser Gly Ser Gly Lys Pro Gly Ser Gly Glu Gly Ser Thr
1               5                   10                  15

Lys Gly

<210> SEQ ID NO 134
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ile Arg Pro Arg Ala Ile Gly Gly Ser Lys Pro Arg Val Ala
1               5                   10

<210> SEQ ID NO 135
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gly Lys Gly Gly Ser Gly Lys Gly Gly Ser Gly Lys Gly Gly Ser
1               5                   10                  15

<210> SEQ ID NO 136
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gly Gly Lys Gly Ser Gly Gly Lys Gly Ser Gly Gly Lys Gly Ser
1               5                   10                  15

<210> SEQ ID NO 137
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gly Gly Gly Lys Ser Gly Gly Gly Lys Ser Gly Gly Gly Lys Ser
1               5                   10                  15

<210> SEQ ID NO 138
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 138

Gly Lys Gly Lys Ser Gly Lys Gly Lys Ser Gly Lys Gly Lys Ser
1               5                   10                  15

<210> SEQ ID NO 139
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gly Gly Gly Lys Ser Gly Gly Lys Gly Ser Gly Lys Gly Gly Ser
1               5                   10                  15

<210> SEQ ID NO 140
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gly Lys Pro Gly Ser Gly Lys Pro Gly Ser Gly Lys Pro Gly Ser
1               5                   10                  15

<210> SEQ ID NO 141
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gly Lys Pro Gly Ser Gly Lys Pro Gly Ser Gly Lys Pro Gly Ser Gly
1               5                   10                  15

Lys Pro Gly Ser
            20

<210> SEQ ID NO 142
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gly Lys Gly Lys Ser Gly Lys Gly Lys Ser Gly Lys Gly Lys Ser Gly
1               5                   10                  15

Lys Gly Lys Ser
            20

<210> SEQ ID NO 143
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

```
Ser Thr Ala Gly Asp Thr His Leu Gly Gly Glu Asp Phe Asp
1               5               10

<210> SEQ ID NO 144
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gly Glu Gly Gly Ser Gly Glu Gly Gly Ser Gly Glu Gly Gly Ser
1               5               10                  15

<210> SEQ ID NO 145
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gly Gly Glu Gly Ser Gly Gly Glu Gly Ser Gly Gly Glu Gly Ser
1               5               10                  15

<210> SEQ ID NO 146
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gly Glu Gly Glu Ser Gly Glu Gly Glu Ser Gly Glu Gly Glu Ser
1               5               10                  15

<210> SEQ ID NO 147
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gly Gly Gly Glu Ser Gly Gly Glu Gly Ser Gly Glu Gly Gly Ser
1               5               10                  15

<210> SEQ ID NO 148
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Glu Gly Glu Ser Gly Glu Gly Glu Ser Gly Glu Gly Glu Ser Gly
1               5               10                  15

Glu Gly Glu Ser
            20

<210> SEQ ID NO 149
```

-continued

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gly Ser Thr Ser Gly Ser Gly Lys Pro Gly Ser Gly Glu Gly Ser Thr
1               5                   10                  15

Lys Gly

<210> SEQ ID NO 150
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Pro Arg Gly Ala Ser Lys Ser Gly Ser Ala Ser Gln Thr Gly Ser Ala
1               5                   10                  15

Pro Gly Ser

<210> SEQ ID NO 151
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gly Thr Ala Ala Ala Gly Ala Gly Ala Ala Gly Gly Ala Ala Ala Gly
1               5                   10                  15

Ala Ala Gly

<210> SEQ ID NO 152
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gly Thr Ser Gly Ser Ser Gly Ser Gly Ser Gly Gly Ser Gly Ser Gly
1               5                   10                  15

Gly Gly Gly

<210> SEQ ID NO 153
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Gly Lys Pro Gly Ser Gly Lys Pro Gly Ser Gly Lys Pro Gly Ser Gly
1               5                   10                  15

Lys Pro Gly Ser
            20
```

```
<210> SEQ ID NO 154
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Gly Ser Gly Ser
1

<210> SEQ ID NO 155
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ala Pro Ala Pro Ala Pro Ala Pro Ala Pro
1               5                   10

<210> SEQ ID NO 156
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ala Pro Ala Pro Ala Pro Ala Pro Ala Pro Ala Pro Ala Pro Ala Pro
1               5                   10                  15

Ala Pro Ala Pro
            20

<210> SEQ ID NO 157
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Ala Glu Ala Ala Ala Lys Glu Ala Ala Ala Lys Glu Ala Ala Ala Ala
1               5                   10                  15

Lys Glu Ala Ala Ala Ala Lys Glu Ala Ala Ala Ala Lys Ala Ala Ala
            20                  25                  30

<210> SEQ ID NO 158
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

-continued

```
Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330
```

```
<210> SEQ ID NO 159
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Ala Ala Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Ser Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 160
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Ala Ser Thr Lys Gly Pro Ser Val Phe Pro Leu Ala Pro Cys Ser Arg
1                   5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys

```
                        85                  90                  95

Arg Val Glu Ser Lys Tyr Gly Pro Pro Cys Pro Pro Cys Pro Ala Pro
                100                 105                 110

Glu Ala Ala Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 161
<211> LENGTH: 14
<212> TYPE: PRT
<213> ORGANISM: Homo sapiens

<400> SEQUENCE: 161

```
Gln Asp Gly Asn Glu Glu Met Gly Gly Ile Thr Gln Thr Pro
1                   5                   10
```

<210> SEQ ID NO 162
<211> LENGTH: 10
<212> TYPE: PRT
<213> ORGANISM: Homo sapiens

<400> SEQUENCE: 162

```
Leu Leu His Ala Cys Ile Pro Cys Gln Leu
1                   5                   10
```

<210> SEQ ID NO 163
<211> LENGTH: 20
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 163

Gly Gly Gly Gly Ser Gly Gly Gly Ser Gly Gly Gly Gly Ser Gly
1               5                   10                  15

Gly Gly Gly Ser
            20

<210> SEQ ID NO 164
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ser Ile Tyr Tyr Ser Gly Arg Thr Tyr Tyr Asn Pro Ser Leu Lys Ser
1               5                   10                  15

<210> SEQ ID NO 165
<211> LENGTH: 2229
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 165
atggccagga agtccgctct gctcgctctg gcacttctgc ttctgggatt tggacctgct      60
tgggctcagg tgcagctgca gcagtctggc cctagactcg tgcggccttc ccagaccctg     120
tctctgacct gtgccatctc cggcgactcc gtgttcaaca caacgccgc ctggtcctgg      180 atccggcagt ctccatctcg cggtctggag tggctcggtc gcacctacta ccgctctaaa     240
tggctgtacg actacgccgt gtccgtgaag tcccggatca ccgtgaaccc tgacacctcc     300
cggaaccagt tcaccctgca gctgaactcc gtgacccctg aggacaccgc cctgtactac     360
tgcgccagag gctactcctc ctccttcgac tattggggcc aaggcaccct cgtgaccgtg     420
tcctctgcct ccaccaaggg cccatcggtc ttccccctgg caccctcctc caagagcacc     480
tctgggggca gcgcggccct gggctgcctg gtcaaggact acttccccga accggtgacg     540
gtgtcgtgga actcaggcgc cctgaccagc ggcgtgcaca ccttccccgg tgtcctacag     600
tcctcaggac tctactccct cagcagcgtg gtgaccgtgc cctccagcag cttgggcacc     660
cagacctaca tctgcaacgt gaatcacaag cccagcaaca ccaaggtgga caagaaagtt     720
gagcccaaat cttgtgacaa aactcacaca tgcccaccgt gcccagcacc tgaagccgcc     780
gggggaccgt cagtcttcct cttccccca aaacccaagg acaccctcat gatctcccgg     840
acccctgagg tcacatgcgt ggtggtgagc gtgagccacg aagaccctga ggtcaagttc     900
aactggtacg tggacggcgt ggaggtgcat aatgccaaga caaagccgcg ggaggagcag     960
tacaacagca cgtaccgtgt ggtcagcgtc ctcaccgtcc tgcaccagga ctggctgaat    1020
ggcaaggagt acaagtgcaa ggtgtcgaac aaagccctcc cagcccccat cgagaaaacc    1080
atctccaaag ccaaagggca gccccgagaa ccacaggtgt acaccctgcc cccatcccgg    1140
gaggagatga ccaagaacca ggtcagcctg tcctgcgccg tcaaaggctt ctatcccagc    1200
gacatcgccg tggagtggga gagcaatggg cagccggaga acaactacaa gaccacgcct    1260
cccgtgctgg actccgacgg ctccttcttc ctcgtgagca agctcaccgt ggacaagagc    1320
agatggcagc aggggaacgt cttctcatgc tccgtgatgc atgaggctct gcacaaccgg    1380
ttcacgcaga agtctctctc cctgtctccg ggaaaaggag cggaggatc tggcggaggt    1440

-continued

```
ggaagtggcg gaggcggttc tggtggtggt ggatctgaca tcgtgatgac ccagacacct    1500
ctgagcagcc ccgttacatt gggccagcct gcctccatct cctgcagatc ctctcagtcc    1560
ctggtgcact ctgacggcaa cacctacctc tcttggctgc agcagaggcc tggacagcct    1620
cctagactgc tgatctacaa gatctccaac cggttcttcg gcgtgcccga cagattttct    1680
ggatctggcg ctggcaccga cttcaccctg aagatttcca gagtggaagc cgaggacgtg    1740
ggcgtgtact actgtatgca ggccacacag ttccctcaca cctttggcca gggcaccaag    1800
ctggaaatca agggcggatc tgagggaaag tccagcggct ccggcagcga aagcaagtcc    1860
accggcggaa gccaagtgac cctgaaagaa agcggccctg tgctggtcaa gcccaccgaa    1920
acactgaccc tgacctgtac cgtgtccggc ttctccctga ccaatatccg gatgtccgtg    1980
tcctggatca gacagcctcc tggcaaggct ctggaatggc tggcccacat cttctccaac    2040
gacgagaagt cctactccac cagcctgaag tcccggctga ccatctccag agacacctcc    2100
aagtctcagg tggtgctgac actgaccaac gtggaccctg tggataccgc cacctactac    2160
tgcgccagaa tgagactgcc ctacggcatg gatgtgtggg gccagggaac aaccgtgacc    2220
gtttcttct                                                            2229
```

<210> SEQ ID NO 166
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 166

```
atggctagat ccgcactgct cattctggct ctgcttctgc ttggactgtt ctctcctgga     60
gcatggggac agtctgctct gacccagcct gcctccgtgt ctggctctcc cggccagtcc    120
atcaccatca gctgtaccgg cacctcctcc aacatcggca cctacaagtt cgtgtcctgg    180
tatcagcaac accccgacaa ggcccccaaa gtgctgctgt acgaggtgtc caagcggccc    240
tctggcgtgt cctccagatt ctccggctcc aagtctggca caccgcctc cctgaccatc     300 agcggactgc aggctgagga ccaggccgac taccactgtg tgtcctacgc tggctctggc    360
accctgctgt ttggcggagg caccaagctg actgtcctgg gtcagcccaa ggctgcaccc    420
agtgtcactc tgttcccgcc ctcctctgag gagcttcaag ccaacaaggc cacactggtg    480
tgtctcataa gtgacttcta cccgggagcc gtgacagtgg cctggaaggc cgatagcagc    540
cccgtcaagg cgggagtcga aaccaccaca ccctccaaac aaagcaacaa caagtacgcg    600
gccagcagct atctgagcct gacgcctgag cagtggaagt cccacagaag ctacagctgc    660
caggtcacgc atgaagggag caccgtggag aagacagtgg cccctacaga atgttca       717
```

<210> SEQ ID NO 167
<211> LENGTH: 1518
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 167

```
atggccagga gtccgctct gctcgctctg gcacttctgc ttctgggatt tggacctgct      60
tgggctgaga tcgtgctgac ccagtctcct ggcacactgt cactgtctcc aggcgagaga    120
```

-continued

```
gctaccctgt cctgtagagc cagccagtct atctcctcct ccttcctgac ctggtatcag    180
cagaagcctg gacaggcccc tcggctgttg atctacggtg cttcttccag agccacaggc    240
atccctgaca gattctctgg cggcggatct ggcaccgact tcaccctgac aatctcccgg    300
ctggaacctg aggacttcgc cgtgtactac tgccagcact acggcagcag ccccatgtac    360
acatttggcc agggcaccaa gctggaaatc aagggcggat ctgagggaaa gtccagcggc    420
tccggcagcg aaagcaagtc caccggcgga agcgaggttc agctgctgga atctggcgga    480
ggattggttc agcctggcgg ttctctgaga ctgtcttgtg ccgcttccgg cttcaccttc    540
tccagctacg ctatgtcctg ggtccgacag gctcctggca aaggactgga atgggtgtcc    600
gccatctctg gctctggcgg cagcacctac tacgccgatt ctgtgaaggg cagattcacc    660
atcagccggg acaactccaa gaacaccctg tacctgcaga tgaactccct gagagccgag    720
gacaccgccg tgtactactg tgctaaggac gagggctact cctccggcca ctactacgga    780
atggatgtgt ggggccaggg caccacagtg acagtctctt ctgagcccaa atctagcgac    840
aaaactcaca catgcccacc gtgcccagca cctgaagccg ccggggggacc gtcagtcttc    900 ctcttccccc caaaacccaa ggacaccctc atgatctccc ggacccctga ggtcacatgc    960
gtggtggtga gcgtgagcca cgaagaccct gaggtcaagt tcaactggta cgtggacggc   1020
gtggaggtgc ataatgccaa gacaaagccg cgggaggagc agtacaacag cacgtaccgt   1080
gtggtcagcg tcctcaccgt cctgcaccag gactggctga atggcaagga gtacaagtgc   1140
aaggtgtcga acaaagccct cccagccccc atcgagaaaa ccatctccaa agccaaaggg   1200
cagccccgag aaccacaggt gtacaccctg cccccatccc gggaggagat gaccaagaac   1260
caggtcagcc tgtggtgcct ggtcaaaggc ttctatccca gcgacatcgc cgtggagtgg   1320
gagagcaatg ggcagccgga gaacaactac aagaccacgc ctcccgtgct ggactccgac   1380
ggctccttct tcctctacag caagctcacc gtggacaaga gcagatggca gcaggggaac   1440
gtcttctcat gctccgtgat gcatgaggct ctgcacaacc actacacgca gaagtctctc   1500
tccctgtctc cgggaaaa                                                 1518
```